United States Patent
Karra

(10) Patent No.: US 10,676,433 B2
(45) Date of Patent: *Jun. 9, 2020

(54) INDOLE DERIVATIVES AND THEIR USE IN NEURODEGENERATIVE DISEASES

(71) Applicant: Merck Patent GmbH, Darmstadt (DE)

(72) Inventor: Srinivasa R. Karra, Pembroke, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/264,097

(22) Filed: Jan. 31, 2019

(65) Prior Publication Data

US 2019/0161447 A1  May 30, 2019

Related U.S. Application Data

(62) Division of application No. 14/969,328, filed on Dec. 15, 2015, now Pat. No. 10,323,000.

(60) Provisional application No. 62/117,128, filed on Feb. 17, 2015, provisional application No. 62/091,855, filed on Dec. 15, 2014.

(51) Int. Cl.

| | |
|---|---|
| C07D 209/42 | (2006.01) |
| C07D 405/12 | (2006.01) |
| C07D 417/12 | (2006.01) |
| C07D 409/12 | (2006.01) |
| C07D 403/06 | (2006.01) |
| C07D 405/04 | (2006.01) |
| C07D 405/14 | (2006.01) |
| C07D 409/14 | (2006.01) |
| C07D 417/06 | (2006.01) |
| C07D 403/04 | (2006.01) |
| C07D 413/06 | (2006.01) |
| C07D 401/06 | (2006.01) |
| C07D 471/04 | (2006.01) |
| C07D 405/06 | (2006.01) |

(52) U.S. Cl.
CPC ......... *C07D 209/42* (2013.01); *C07D 401/06* (2013.01); *C07D 403/04* (2013.01); *C07D 403/06* (2013.01); *C07D 405/04* (2013.01); *C07D 405/06* (2013.01); *C07D 405/12* (2013.01); *C07D 405/14* (2013.01); *C07D 409/12* (2013.01); *C07D 409/14* (2013.01); *C07D 413/06* (2013.01); *C07D 417/06* (2013.01); *C07D 417/12* (2013.01); *C07D 471/04* (2013.01)

(58) Field of Classification Search
None
See application file for complete search history.

(56) References Cited

U.S. PATENT DOCUMENTS

2013/0197046 A1  8/2013  Boes

FOREIGN PATENT DOCUMENTS

| WO | 200209706 A1 | 2/2002 |
| WO | 2009023623 A1 | 2/2009 |
| WO | 09108551 A2 | 9/2009 |
| WO | 2009108551 A2 | 9/2009 |
| WO | 12163792 A1 | 12/2012 |
| WO | 2012163792 A1 | 12/2012 |

OTHER PUBLICATIONS

Berge et al., J. Pharmaceutical Sciences, 1977, 66(1): 1-19.
Deuchars et al., J. Neurosci., 2001, 21: 7143-7152.
Foster, Adv. Drug Res., 1985, 14:1-40.
Gillette et al., Biochemistry, 1994, 33(10): 2927-2937.
Griffiths et al., J. Immunology, 1995, 154: 2821-2828.
Hanzlik et al., J. Org. Chem., 1990, 55(13): 3992-3997.
Jarman et al., Carcinogenesis, 1995, 16(4): 683-688.
Kanjhan et al., J. Comp. Neurol., 1997, 407: 11-32.
Le et al., Neuroscience, 1998, 83: 177-190.
Reider et al., J. Org. Chem., 1987,52: 3326-3334.
Solle et al., J. Biol. Chemistry, 2001, 276: 125-132.
Smith M.B. and March J., "March's Advanced Organic Chemistry", 5th Ed., Ed., John Wiley & Sons, New York, 2001.
Sorrell Thomas Organic Chemistry, University Science Books, Sausalito, 1999.
Periodic Table of the Elements, CAS version, Handbook of Chemistry and Physics, 75th Ed.
American Psychiatric Association: Diagnostic and Statistical Manual of Mental Disorders (DSM-IV-TR), Fourth Edition, Text Revision. Washingtion, D.C., American Psychiatric Association, pp. 345-428, 2000.
Office action in corresponding JP 2017-550102 dated Jul. 18, 2019 (pp. 1-4).

*Primary Examiner* — Alicia L Otton
(74) *Attorney, Agent, or Firm* — Millen White Zelano and Branigan, PC; John Sopp

(57) ABSTRACT

The present invention relates to indole compounds, and pharmaceutically acceptable compositions thereof, useful as antagonists of P2X7, and for the treatment of P2X7-related disorders.

11 Claims, No Drawings

INDOLE DERIVATIVES AND THEIR USE IN NEURODEGENERATIVE DISEASES

RELATED APPLICATIONS

This application claims the benefit of U.S. Provisional Application Ser. No. 62/091,855, filed on Dec. 15, 2014, and U.S. Provisional Application Ser. No. 62/117,128, filed on Feb. 17, 2015. The contents of the aforementioned applications are hereby incorporated by reference in their entireties.

TECHNICAL FIELD OF THE INVENTION

The present invention relates to indole compounds useful as antagonists of P2X7. The invention also provides pharmaceutically acceptable compositions comprising compounds of the present invention and methods of using said compositions in the treatment of various disorders.

BACKGROUND OF THE INVENTION

The P2X7 receptor is a ligand-gated ion channel that belongs to the Purinergic Receptor Family. The receptor is expressed on many cell types related to the immune and nervous systems. In the nervous system P2X7 is expressed on microglia, oligodendrocytes and astrocytes. Brief activation of the P2X7 receptor channel with its endogenous ligand ATP leads to several downstream events including the processing and release of the proinflammatory cytokine IL1-β from monocytes and macrophages. P2X7 activation also plays an important role in regulating the glutamate release/uptake in astrocytes.

P2X7 receptors are ionotropic receptors activated by ATP, which may regulate neurotransmission in the CNS by activating presynaptic and/or postsynaptic P2X7 receptors on central and peripheral neurons and glia (Deuchars S. A. et al., J. Neurosci. 21:7143-7152, (2001), Kanjhan R. et al., J. Comp. Neurol. 407:11-32 (1997), Le K. T. et al., Neuroscience 83:177-190 (1998)). Activation of the P2X7 receptor on cells of the immune system (macrophages, mast cells and lymphocytes) leads to release of interleukin-1β (IL-1β), giant cell formation, degranulation, and L-selectin shedding. ATP is able to increase local release and process of IL-1 in rats through a P2X7 receptor mediated mechanism following lipopolysaccharide (LPS) intraperitoneal injections (Griffiths et al., J. Immunology Vol. 154, pages 2821-2828 (1995); Solle et al., J. Biol. Chemistry, Vol. 276, pages 125-132, (2001)).

Antagonism of the P2X7 receptor is considered to be an attractive therapeutic approach for the treatment of multiple sclerosis and Alzheimer's disease, due to its significant role in dampening the CNS inflammation and supporting neuroprotection.

SUMMARY OF THE INVENTION

It has now been found that compounds of this invention, and pharmaceutically acceptable compositions thereof, are effective as antagonists of P2X7. Such compounds have general formula I:

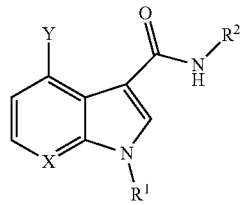

or a pharmaceutically acceptable salt thereof, wherein each of X, Y, R and $R^2$ is as defined and described in embodiments herein.

Compounds of the present invention, and pharmaceutically acceptable compositions thereof, are useful for treating a variety of diseases, disorders or conditions, associated with P2X7 activity. Such diseases, disorders, or conditions include those described herein.

DETAILED DESCRIPTION OF CERTAIN EMBODIMENTS

1. General Description of Compounds of the Invention

In certain embodiments, the present invention provides antagonists of P2X7. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_7$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl) alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group. The term "alkynylene" refers to a bivalent alkynyl group. A substituted alkynylene chain is a group containing at least one triple bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydropyranyl, tetrahydrothiophenyl pyrrolidinyl, piperidinyl, pyrrolinyl, morpholinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

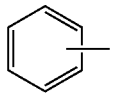

refers to at least

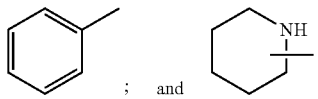

and refers to at least

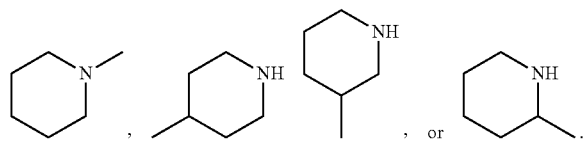

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; $-(CH_2)OR^\circ$; $-(CH_2)_{0-4}OR^\circ$; $-O(CH_2)_{0-4}R^\circ$, $-O-(CH_2)_{0-4}C(O)OR$; $-(CH_2)_{0-4}CH(OR^\circ)_2$; $-(CH_2)_{0-4}SR^\circ$; $-(CH_2)_{0-4}Ph$, which are optionally substituted with $R^\circ$; $-(CH_2)_{0-4}O(CH_2)_{0-1}Ph$ which is optionally substituted with $R^\circ$; $-CH=CHPh$, which is optionally substituted with $R^\circ$; $-(CH_2)_{1-4}O(CH_2)_{0-1}$-pyridyl which is optionally substituted with $R^\circ$; $-NO_2$; $-CN$; $-N_3$; $-(CH_2)_{1-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}C(O)R^\circ$; $-OC(O)(CH_2)_{0-4}SR^\circ$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ is optionally substituted as defined below and is independently hydrogen, $C_{1-6}$ aliphatic, $-CH_2Ph$, $-O(CH_2)_{0-1}Ph$, $-NH(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on $R^\circ$ (or the ring formed by taking two independent occurrences of $R^\circ$ together with their intervening atoms), are independently deuterium, halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, $-(haloR^\bullet)$, $-OH$, $-OR^\bullet*$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which is optionally substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,
—OH, protected hydroxy, alkoxy, oxo, thiooxo,
—NO$_2$, —CN, CF$_3$, N$_3$,
—NH$_2$, protected amino, —NH alkyl, —NH alkenyl, —NH alkynyl, —NH cycloalkyl, —NH— aryl, —NH-heteroaryl, —NH-heterocyclic, -dialkylamino, -diarylamino, -diheteroarylamino,
—O— alkyl, —O— alkenyl, —O— alkynyl, —O— cycloalkyl, —O-aryl, —O-heteroaryl, —O— heterocyclic,
—C(O)— alkyl, —C(O)— alkenyl, —C(O)— alkynyl, —C(O)— carbocyclyl, —C(O)-aryl, —C(O)— heteroaryl, —C(O)-heterocyclyl,
—CONH$_2$, —CONH— alkyl, —CONH— alkenyl, —CONH— alkynyl, —CONH-carbocyclyl, —CONH-aryl, —CONH-heteroaryl, —CONH-heterocyclyl,
—OCO$_2$— alkyl, —OCO$_2$— alkenyl, —OCO$_2$— alkynyl, —OCO$_2$— carbocyclyl, —OCO$_2$-aryl, —OCO$_2$-heteroaryl, —OCO$_2$-heterocyclyl, —OCONH$_2$, —OCONH— alkyl, —OCONH— alkenyl, —OCONH— alkynyl, —OCONH— carbocyclyl, —OCONH— aryl, —OCONH— heteroaryl, —OCONH— heterocyclyl,
—NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO$_2$— alkyl, —NHCO$_2$— alkenyl, —NHCO$_2$— alkynyl, —NHCO$_2$— carbocyclyl, —NHCO$_2$— aryl, —NHCO$_2$— heteroaryl, —NHCO$_2$— heterocyclyl, —NHC(O)NH$_2$, —NHC(O)NH— alkyl, —NHC(O)NH— alkenyl, —NHC(O)NH— alkenyl, —NHC(O)NH— carbocyclyl, —NHC(O)NH-aryl, —NHC(O)NH-heteroaryl, —NHC(O)NH— heterocyclyl, NHC(S)NH$_2$, —NHC(S)NH— alkyl, —NHC(S)NH— alkenyl, —NHC(S)NH— alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH— alkyl, —NHC(NH)NH—-alkenyl, —NHC(NH)NH— alkenyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC (NH)— carbocyclyl, —NHC(NH)-aryl, —NHC(NH)-heteroaryl, —NHC(NH)-heterocyclyl,
—C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl,
—S(O)— alkyl, —S(O)— alkenyl, —S(O)— alkynyl, —S(O)— carbocyclyl, —S(O)-aryl, —S(O)— heteroaryl, —S(O)-heterocyclyl —SO$_2$NH$_2$, —SO$_2$NH— alkyl, —SO$_2$NH— alkenyl, —SO$_2$NH— alkynyl, —SO$_2$NH— carbocyclyl, —SO$_2$NH— aryl, —SO$_2$NH— heteroaryl, —SO$_2$NH— heterocyclyl,
—NHSO$_2$— alkyl, —NHSO$_2$— alkenyl, —NHSO$_2$— alkynyl, —NHSO$_2$— carbocyclyl, —NHSO$_2$— aryl, —NHSO$_2$-heteroaryl, —NHSO$_2$-heterocyclyl,
—CH$_2$NH$_2$, —CH$_2$SO$_2$CH$_3$,
-mono-, di-, or tri-alkyl silyl,
-alkyl, -alkenyl, -alkynyl, -aryl, -arylalkyl, -heteroaryl, -heteroarylalkyl, heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S— alkynyl, —S— carbocyclyl, —S— aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}\text{-alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, tautomers, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^{3}H$ or $^{14}C$, has been incorporated, is suitable for medicament and/or substrate tissue distribution assays. These radioisotopes, i.e. tritium ($^{3}H$) and carbon-14 ($^{14}C$), are particularly preferred owing to simple preparation and excellent detectability. Incorporation of heavier isotopes, for example deuterium ($^{2}H$), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant. Compounds of the invention may be substituted by $^{18}F$, for use as PET imaging agents.

Deuterium ($^{2}H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a corn-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 µM. In certain embodiments, a modulator has an $IC_{50}$ and/or binding constant of less than about 5 µM. In certain embodiments, a modulator has an $IC_{50}$ and/or binding constant of between about 1 to about 5 µM. In certain embodiments, a modulator has an $IC_{50}$ and/or binding constant of less than about 1 µM. In certain embodiments, a modulator has an IC$_{50}$ and/or binding constant of between about 500 to about 1000 nM. In certain embodiments, a modulator has an IC$_{50}$ and/or binding constant of less than about 500 nM. In certain embodiments, a modulator has an IC$_{50}$ and/or binding constant of between about 100 to about 500 nM. In certain embodiments, a modulator has an IC$_{50}$ and/or binding constant of less than about 100 nM. In certain embodiments, a modulator has an IC$_{50}$ and/or binding constant of between about 10 to about 100 nM. In certain embodiments, a modulator has an IC$_{50}$ and/or binding constant of less than about 10 nM.

The terms "measurable affinity" and "measurably inhibit," as used herein, means a measurable change in P2X7 activity between a sample comprising a compound of the present invention, or composition thereof, and P2X7, and an equivalent sample comprising P2X7, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

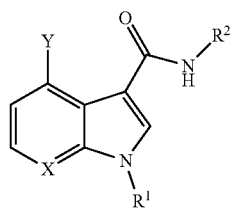

I or a pharmaceutically acceptable salt thereof, wherein:
X is CR or N;
Y is Cl or CF$_3$;
R$^1$ is C$_{1-6}$ aliphatic, C$_{5-10}$ aryl, a 3-8 membered saturated or partially unsaturated carbocyclic ring, a 3-7 membered heterocyclic ring having 1-4 heteroatoms independently selected from nitrogen, oxygen, or sulfur, a 5-6 membered monocyclic heteroaryl ring having 1-4 heteroatoms independently selected from nitrogen, oxygen, or sulfur, a fused 7-10 membered bicyclic saturated, partially unsaturated ring, aryl, or heteroaryl ring; each of which is optionally substituted by 1-5 of R$^A$; or R$^1$ is —SO$_2$R, —SOR, —C(O)R, —CO$_2$R, or —C(O)N(R)$_2$; each of which is optionally substituted by 1-5 of R$^A$;
R$^2$ is C$_{1-6}$ aliphatic, C$_{5-10}$ aryl, a 3-8 membered saturated or partially unsaturated carbocyclic ring, a 3-7 membered heterocyclic ring having 1-4 heteroatoms independently selected from nitrogen, oxygen, or sulfur, a 5-6 membered monocyclic heteroaryl ring having 1-4 heteroatoms independently selected from nitrogen, oxygen, or sulfur, a fused 7-10 membered bicyclic saturated, partially unsaturated ring, aryl, or heteroaryl ring; each of which is optionally substituted by 1-5 of R$^A$; or R$^2$ is —SO$_2$R, —SOR, —C(O)R, —CO$_2$R, or —C(O)N(R)$_2$;
each R$^A$ is independently —R, halogen, -haloalkyl, -hydroxyalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
each R is independently hydrogen, C$_{1-6}$ aliphatic, C$_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or
two R groups on the same atom are taken together with the atom to which they are attached to form a C$_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, R$^1$ is C$_{1-6}$ aliphatic which is optionally substituted by 1-5 of R$^A$. In certain embodiments, R$^1$ is C$_{1-6}$ alkyl. In certain embodiments, R$^1$ is C$_{1-6}$ alkenyl. In certain embodiments, R$^1$ is C$_{1-6}$ alkynyl.

In certain embodiments, R$^1$ is methyl, ethyl, n-propyl, i-propyl, n-butyl, s-butyl, t-butyl, straight chain or branched pentyl, straight chain or branched hexyl, each of which is optionally substituted by 1-5 of R$^A$. In certain embodiments, R$^1$ is ethenyl, n-propenyl, i-propenyl, n-butenyl, s-butenyl, t-butenyl, straight chain or branched pentenyl, straight chain or branched hexenyl, each of which is optionally substituted by 1-5 of R$^A$. In certain embodiments, R$^1$ is ethynyl, n-propynyl, i-propynyl, n-butynyl, s-butynyl, t-butynyl, straight chain or branched pentynyl, straight chain or branched hexynyl, each of which is optionally substituted by 1-5 of R$^A$.

In certain embodiments, R$^1$ is a C$_{5-10}$ aryl, a 3-8 membered saturated or partially unsaturated carbocyclic ring, a 3-7 membered heterocyclic ring having 1-4 heteroatoms independently selected from nitrogen, oxygen, or sulfur, a 5-6 membered monocyclic heteroaryl ring having 1-4 heteroatoms independently selected from nitrogen, oxygen, or sulfur, a fused 7-10 membered bicyclic saturated, partially unsaturated ring, aryl, or heteroaryl ring; each of which is optionally substituted by 1-5 of R$^A$;

In certain embodiments, R$^1$ is a 3-7 membered heterocyclic ring having 1-4 heteroatoms independently selected from nitrogen, oxygen, or sulfur, which is optionally substituted by 1-5 of R$^A$.

In certain embodiments, R$^1$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, 2-azaspiro[3.3]heptane, or xanthenyl; each of which is optionally substituted by 1-5 of $R^4$.

In certain embodiments, $R^1$ is pyrrolidinyl, tetrahydrofuranyl, azetidinyl, or 2-azaspiro[3.3]heptane xanthenyl; each of which is optionally substituted by 1-5 of $R^4$.

In certain embodiments, $R^1$ is —SO$_2$R, —SOR, —C(O)R, —CO$_2$R, or —C(O)N(R)$_2$; each of which is optionally substituted by 1-5 of $R^4$.

In certain embodiments, $R^1$ is —C(O)R, —CO$_2$R, or —C(O)N(R)$_2$; each of which is optionally substituted by 1-5 of $R^4$.

In certain embodiments, $R^1$ is

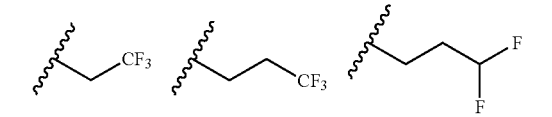

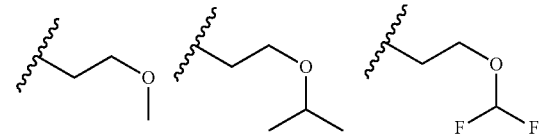

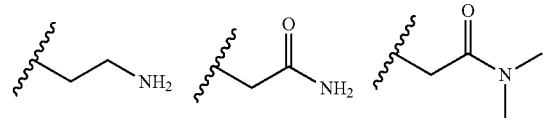

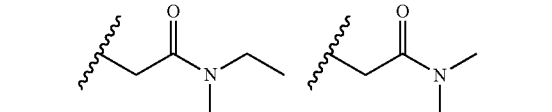

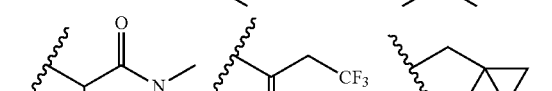

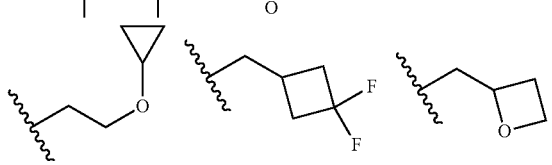

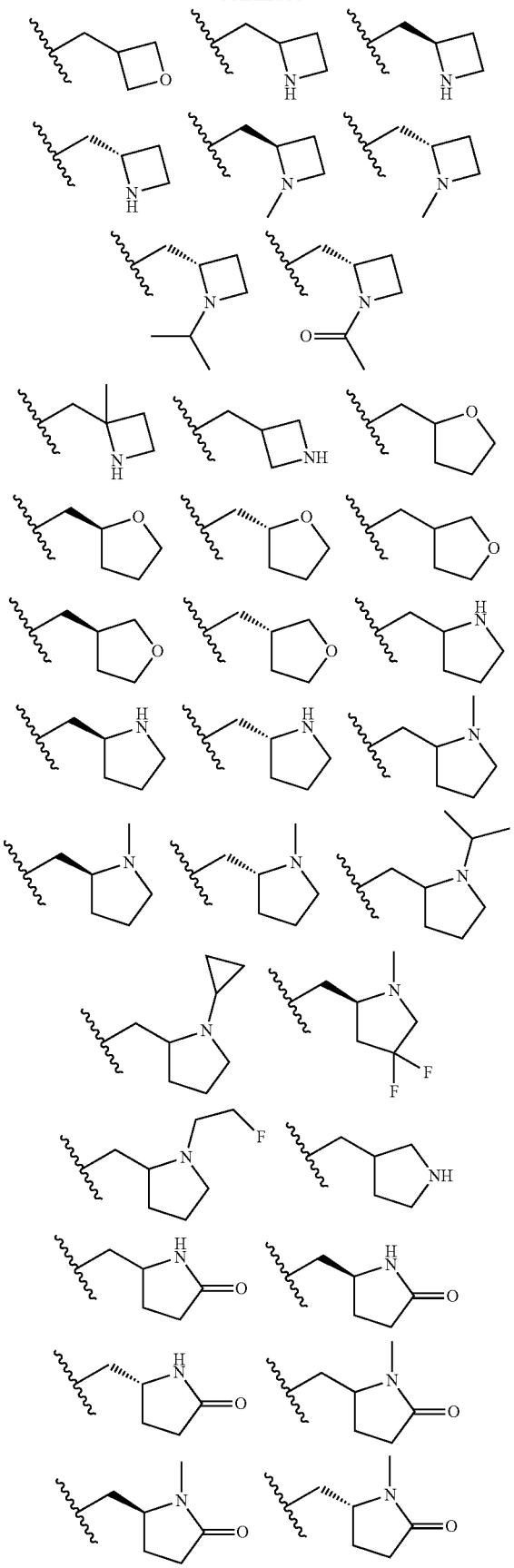

-continued

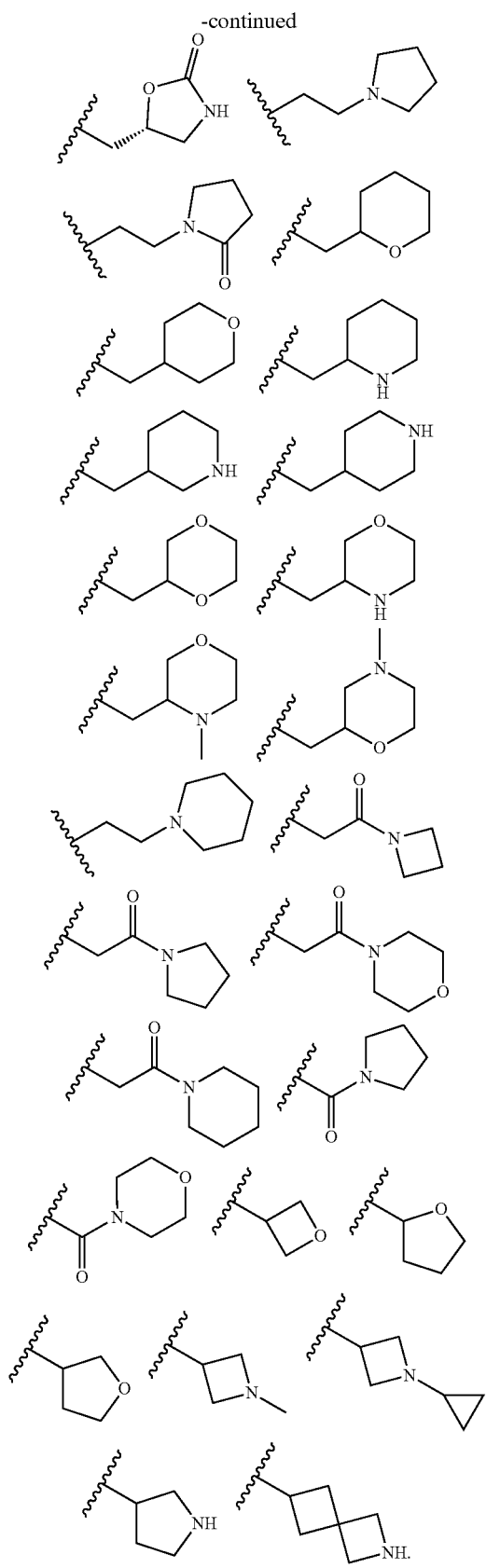

In certain embodiments, $R^2$ is $C_{1-6}$ aliphatic, which is optionally substituted by 1-5 of $R^A$. In certain embodiments, $R^1$ is $C_{1-6}$ alkyl. In certain embodiments, $R^1$ is $C_{1-6}$ alkenyl. In certain embodiments, $R^1$ is $C_{1-6}$ alkynyl.

In certain embodiments, $R^2$ is methyl, ethyl, n-propyl, i-propyl, n-butyl, s-butyl, t-butyl, straight chain or branched pentyl, straight chain or branched hexyl, each of which is optionally substituted by 1-5 of $R^A$.

In certain embodiments, $R^2$ is $C_{5-10}$ aryl, a 3-8 membered saturated or partially unsaturated carbocyclic ring, a 3-7 membered heterocylic ring having 1-4 heteroatoms independently selected from nitrogen, oxygen, or sulfur, a 5-6 membered monocyclic heteroaryl ring having 1-4 heteroatoms independently selected from nitrogen, oxygen, or sulfur, a fused 7-10 membered bicyclic saturated, partially unsaturated ring, aryl, or heteroaryl ring; each of which is optionally substituted by 1-5 of $R^A$.

In certain embodiments, $R^2$ is a 3-8 membered saturated or partially unsaturated carbocyclic ring, or a 3-7 membered heterocylic ring having 1-4 heteroatoms independently selected from nitrogen, oxygen, or sulfur, each of which is optionally substituted by 1-5 of $R^A$.

In certain embodiments, $R^2$ is —SO$_2$R, —SOR, —C(O)R, —CO$_2$R, or —C(O)N(R)$_2$.

In certain embodiments, $R^2$ is

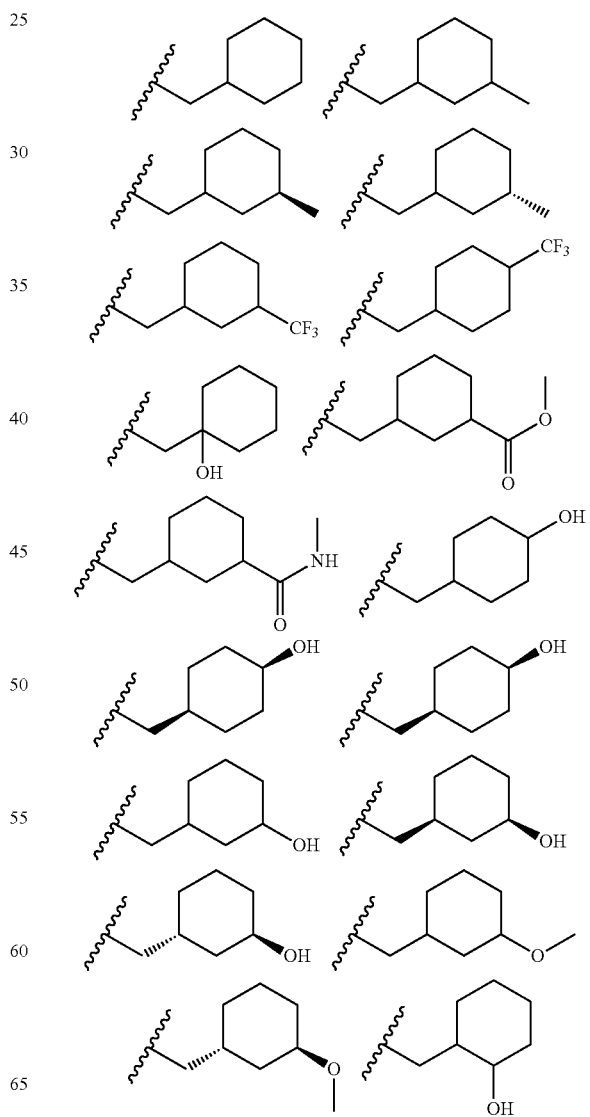

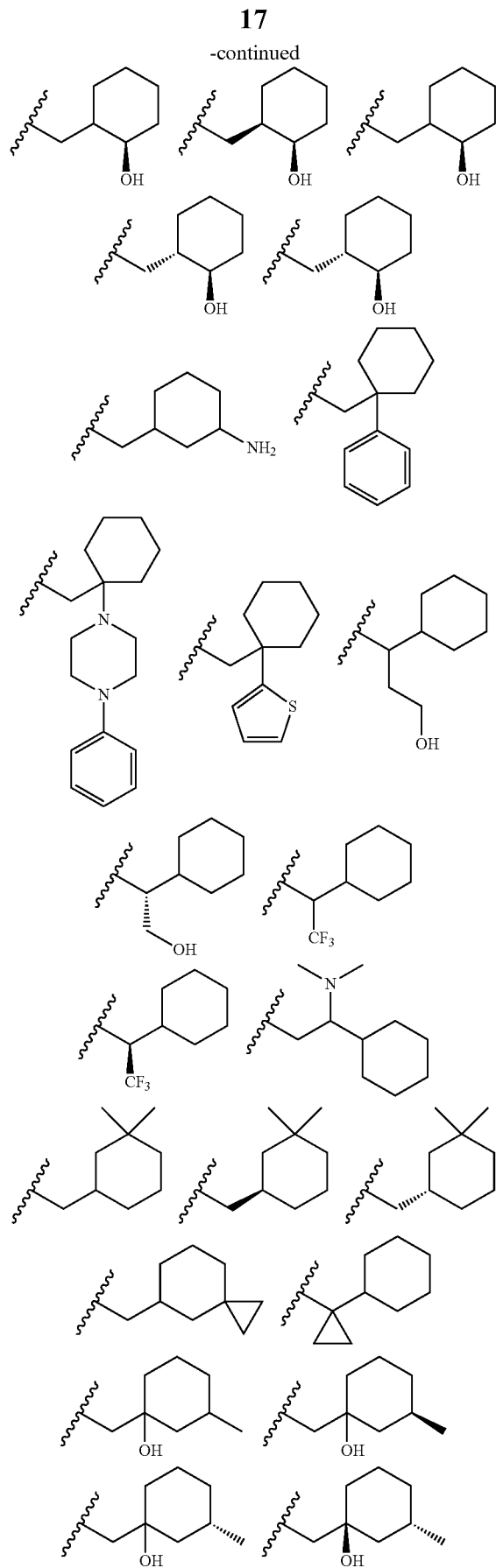
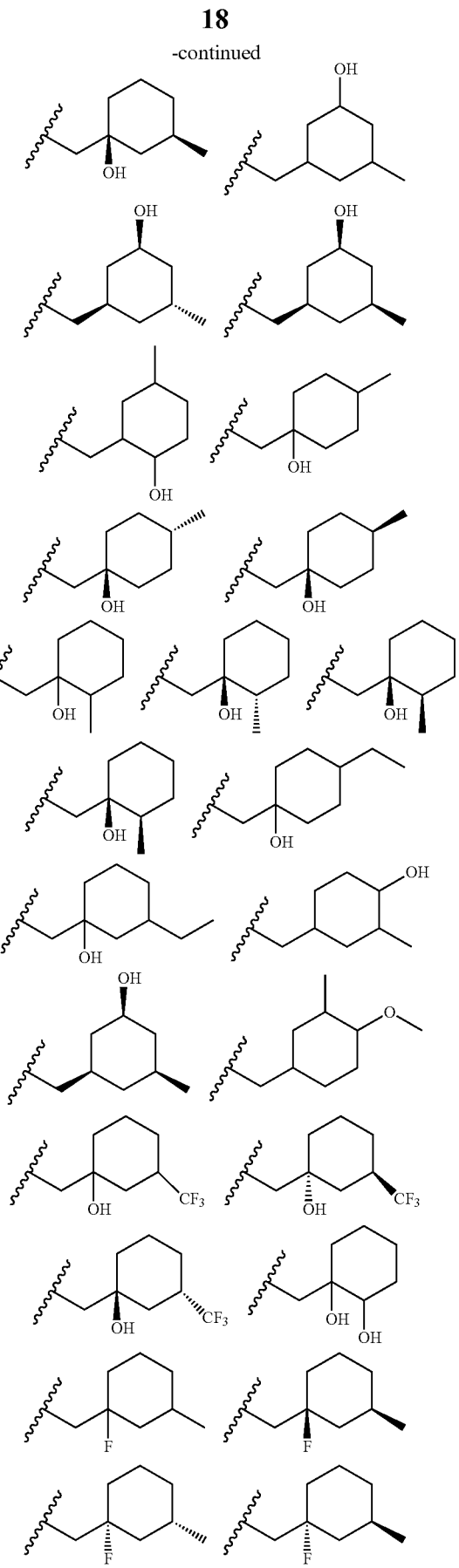

-continued
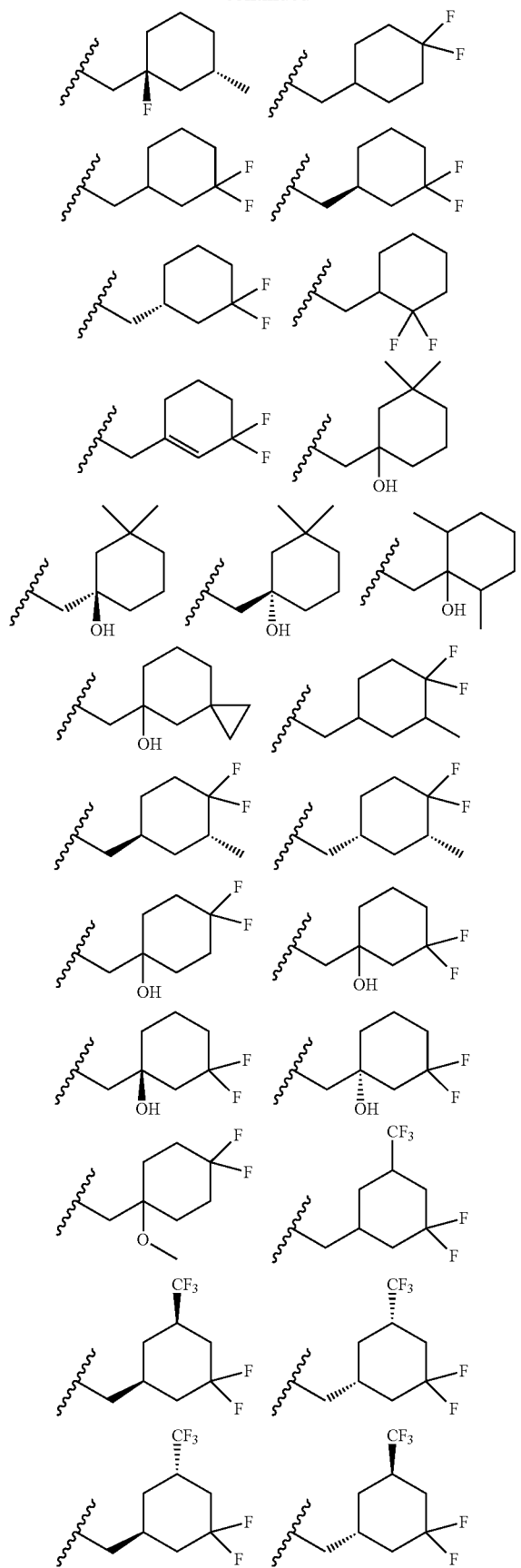
-continued
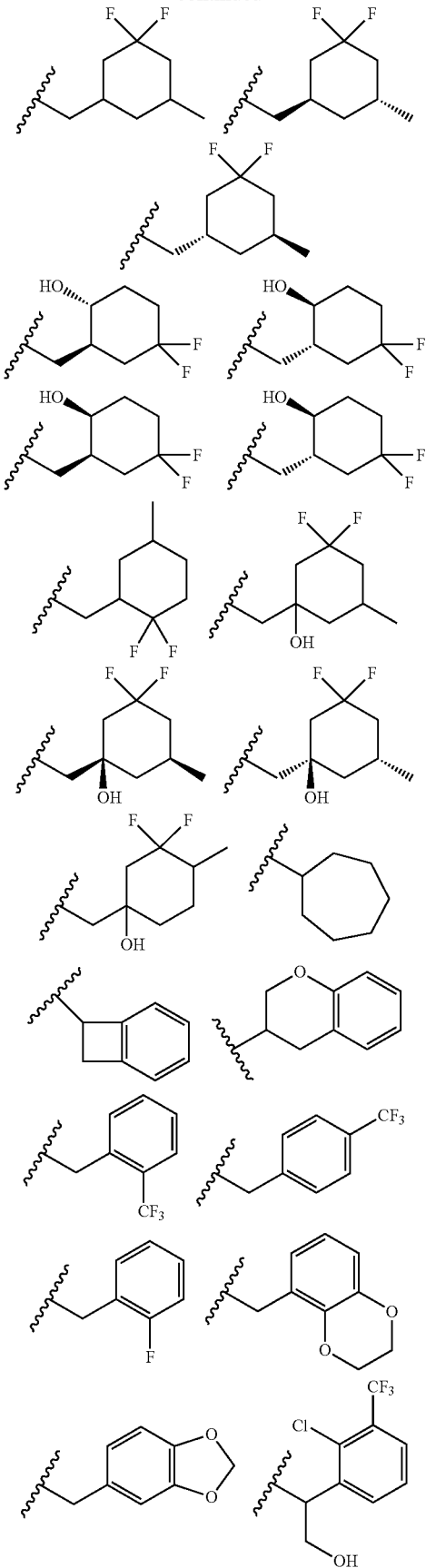

-continued

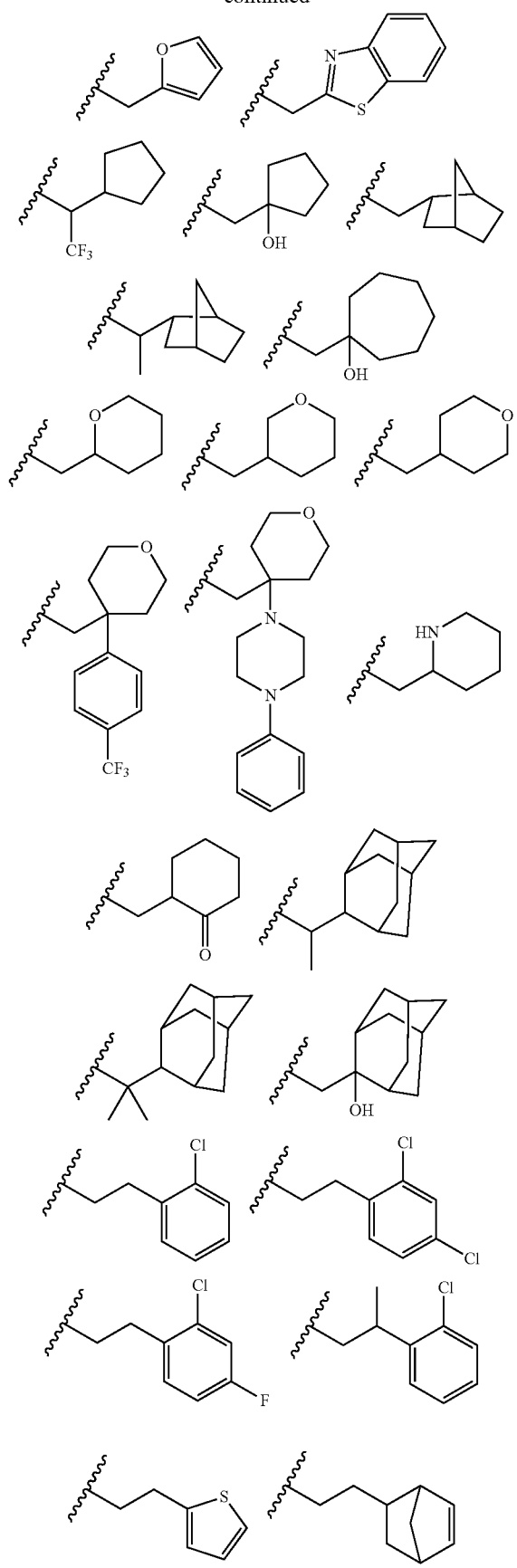
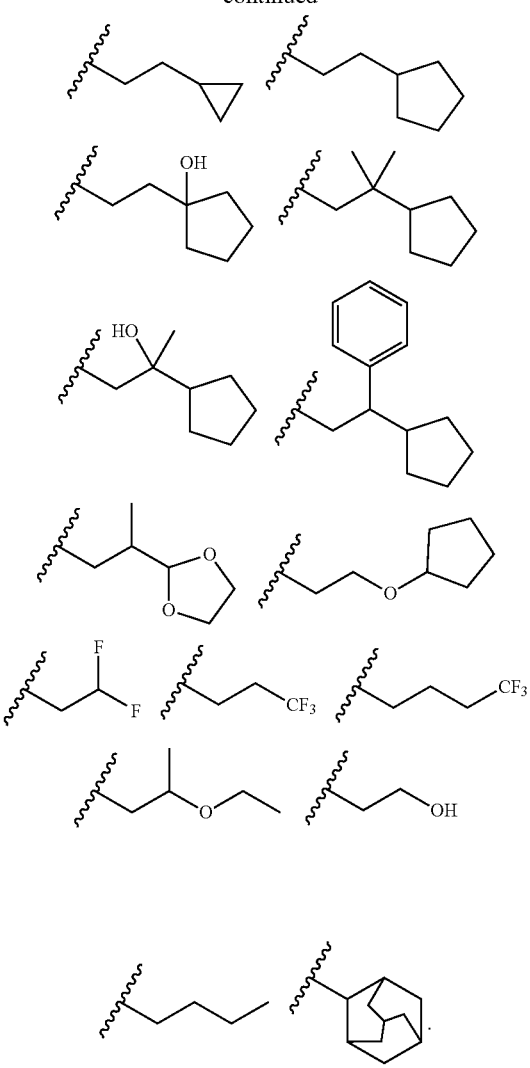

In certain embodiments, each of $R^1$, $R^2$, and $R^A$, is as defined above and described in embodiments, classes and subclasses above and herein, singly or in combination.

In certain embodiments, the present invention provides a compound of formula II,

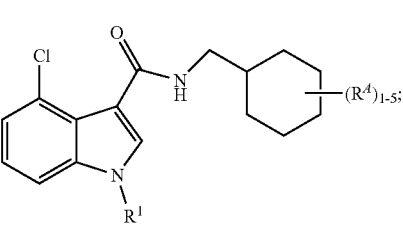

or a pharmaceutically acceptable salt thereof, wherein each of $R^1$ and $R^A$ is as defined above and described in embodiments, classes and subclasses above and herein, singly or in combination.

In certain embodiments, the present invention provides a compound of formula III:

III

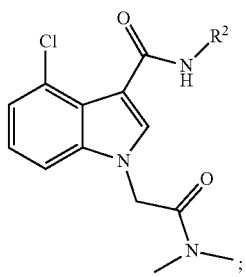

or a pharmaceutically acceptable salt thereof, wherein $R^2$ is as defined above and described in embodiments, classes and subclasses above and herein, singly or in combination.

In certain embodiments, the present invention provides a compound of formula IV:

IV

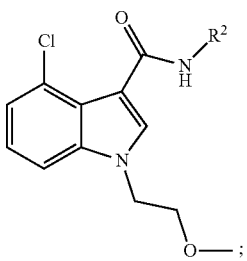

or a pharmaceutically acceptable salt thereof, wherein $R^2$ is as defined above and described in embodiments, classes and subclasses above and herein, singly or in combination.

In certain embodiments, the present invention provides a compound of formula V:

V

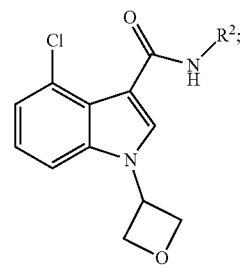

or a pharmaceutically acceptable salt thereof, wherein $R^2$ is as defined above and described in embodiments, classes and subclasses above and herein, singly or in combination.

In certain embodiments, the present invention provides a compound of formula VI:

VI

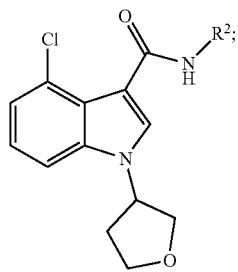

or a pharmaceutically acceptable salt thereof, wherein $R^2$ is as defined above and described in embodiments, classes and subclasses above and herein, singly or in combination.

In certain embodiments, the present invention provides a compound of formula VII:

VII

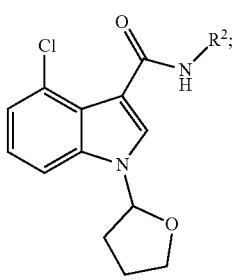

or a pharmaceutically acceptable salt thereof, wherein $R^2$ is as defined above and described in embodiments, classes and subclasses above and herein, singly or in combination.

In certain embodiments, the present invention provides a compound of formula VIII:

VIII

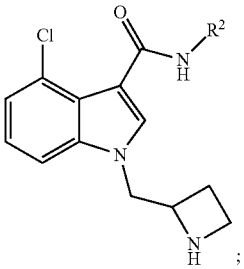

or a pharmaceutically acceptable salt thereof, wherein $R^2$ is as defined above and described in embodiments, classes and subclasses above and herein, singly or in combination.

In certain embodiments, the present invention provides a compound of formula IX:

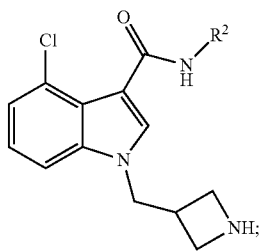

IX or a pharmaceutically acceptable salt thereof, wherein R² is as defined above and described in embodiments, classes and subclasses above and herein, singly or in combination.

In certain embodiments, the present invention provides a compound of formula X:

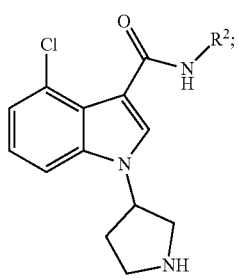

X or a pharmaceutically acceptable salt thereof, wherein R² is as defined above and described in embodiments, classes and subclasses above and herein, singly or in combination.

In certain embodiments, the present invention provides a compound of formula XI:

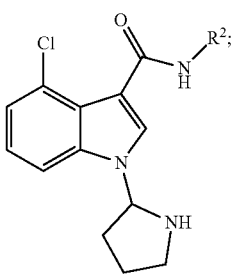

XI or a pharmaceutically acceptable salt thereof, wherein R² is as defined above and described in embodiments, classes and subclasses above and herein, singly or in combination.

In certain embodiments, the present invention provides a compound of formula XI:

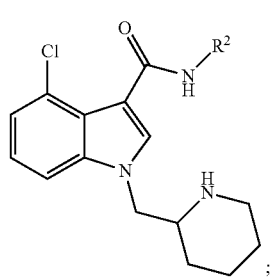

XI or a pharmaceutically acceptable salt thereof, wherein R² is as defined above and described in embodiments, classes and subclasses above and herein, singly or in combination.

In certain embodiments, the present invention provides a compound of formula XIII:

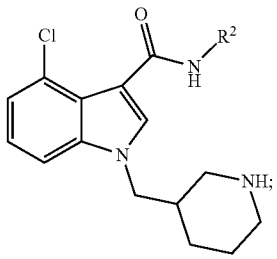

XIII or a pharmaceutically acceptable salt thereof, wherein R is as defined above and described in embodiments, classes and subclasses above and herein, singly or in combination.

In certain embodiments, the invention provides a compound selected from Table 1:

TABLE 1

| | |
|---|---|
| 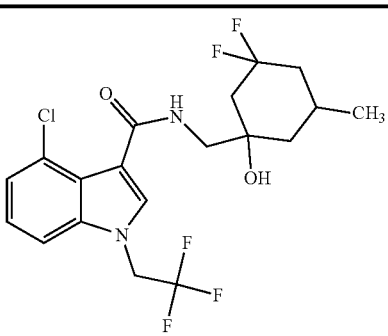 | 1 |
| 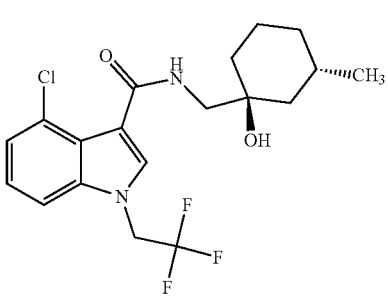 [SMILES: C[C@H]1CCC[C@@](O)(CNC(=O)c2cn(CC(F)(F)F)c3cccc(Cl)c23)C1] | 2 |

TABLE 1-continued
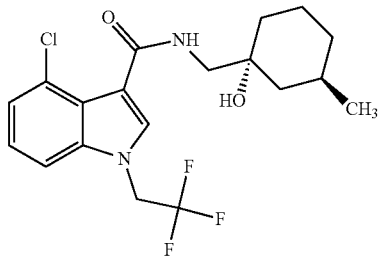 [SMILES: C[C@@H]1CCC[C@](O)(CNC(=O)c2cn(CC(F)(F)F)c3cccc(Cl)c23)C1] 3
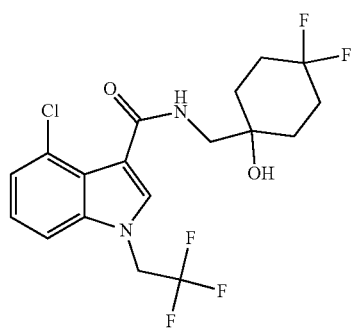 [SMILES: O=C(NCC1(O)CCC(F)(F)CC1)c1cn(CC(F)(F)F)c2cccc(Cl)c12] 4
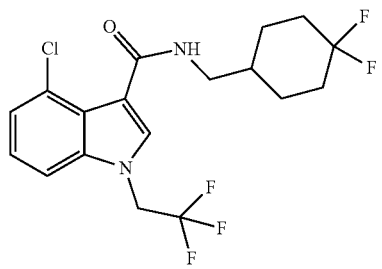 [SMILES: O=C(NCC1CCC(F)(F)CC1)c1cn(CC(F)(F)F)c2cccc(Cl)c12] 5
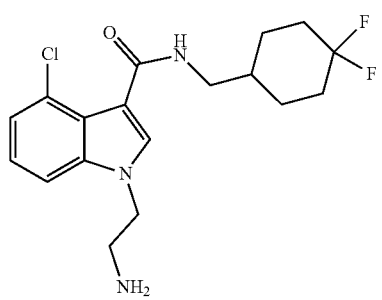 [SMILES: NCCn1cc(C(=O)NCC2CCC(F)(F)CC2)c2c(Cl)cccc21] 6
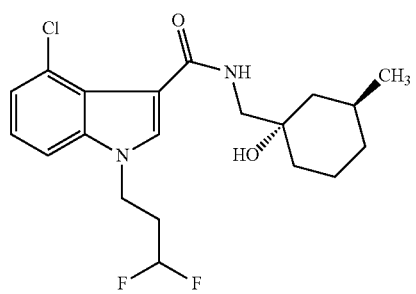 [SMILES: C[C@H]1CCC[C@@](O)(CNC(=O)c2cn(CCC(F)F)c3cccc(Cl)c23)C1] 7
TABLE 1-continued
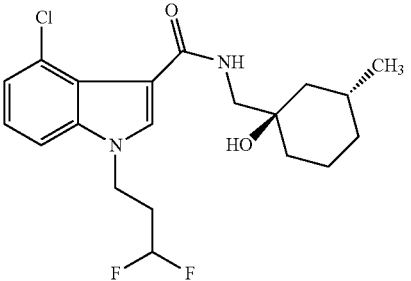 [SMILES: C[C@@H]1CCC[C@](O)(CNC(=O)c2cn(CCC(F)F)c3cccc(Cl)c23)C1] 8
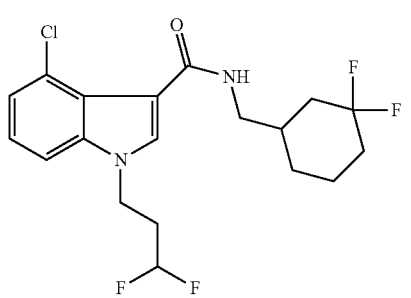 [SMILES: O=C(NCC1CCCC(F)(F)C1)c1cn(CCC(F)F)c2cccc(Cl)c12] 9
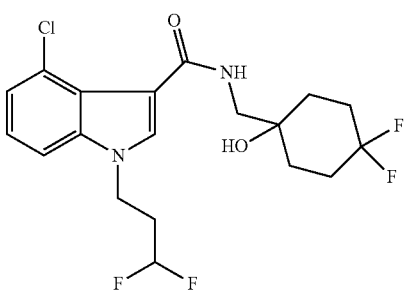 [SMILES: O=C(NCC1(O)CCC(F)(F)CC1)c1cn(CCC(F)F)c2cccc(Cl)c12] 10
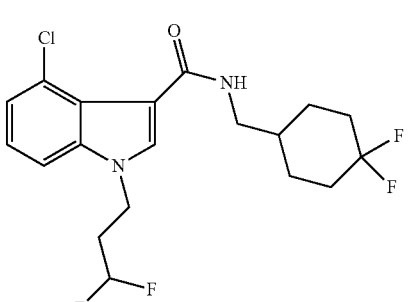 11
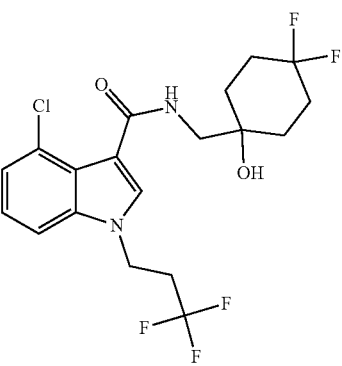 [SMILES: O=C(NCC1(O)CCC(F)(F)CC1)c1cn(CCC(F)(F)F)c2cccc(Cl)c12] 12

TABLE 1-continued
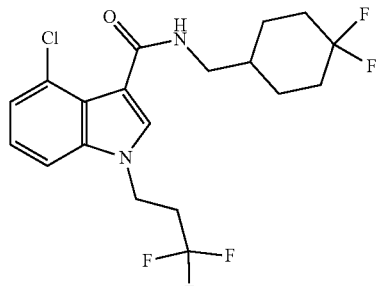 13
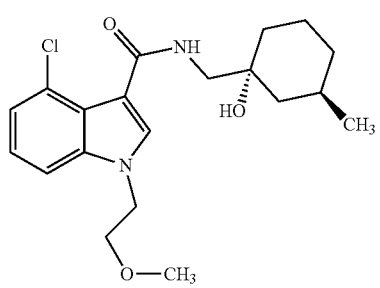 [SMILES: COCCn1cc(C(=O)NC[C@@]2(O)CCC[C@@H](C)C2)c2c(Cl)cccc21] 14
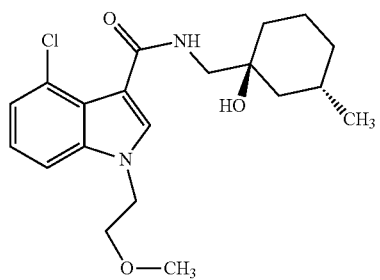 [SMILES: COCCn1cc(C(=O)NC[C@]2(O)CCC[C@H](C)C2)c2c(Cl)cccc21] 15
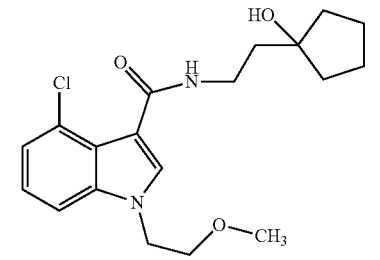 [SMILES: COCCn1cc(C(=O)NCCC2(O)CCCC2)c2c(Cl)cccc21] 16
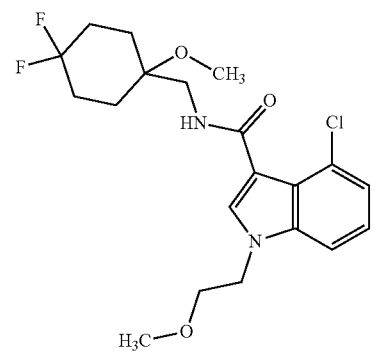 [SMILES: COCCn1cc(C(=O)NCC2(OC)CCC(F)(F)CC2)c2c(Cl)cccc21] 17
TABLE 1-continued
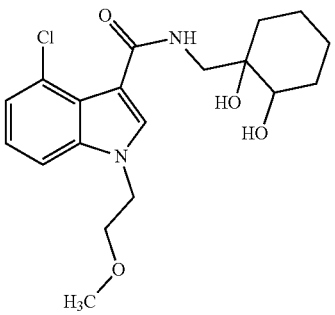 [SMILES: COCCn1cc(C(=O)NCC2(O)CCCCC2O)c2c(Cl)cccc21] 18
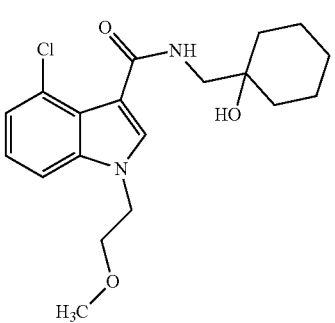 [SMILES: COCCn1cc(C(=O)NCC2(O)CCCCC2)c2c(Cl)cccc21] 19
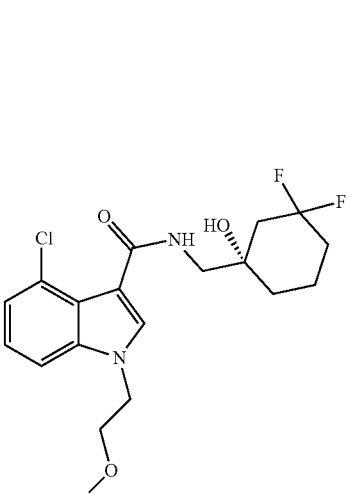 20
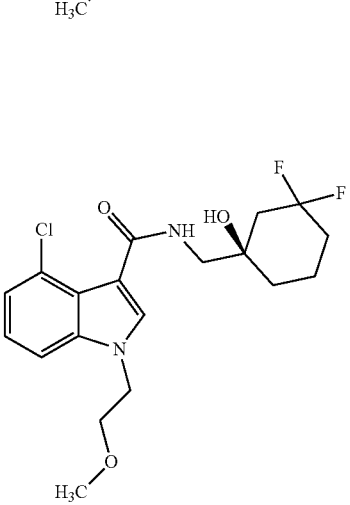 21

TABLE 1-continued
| | |
|---|---|
| 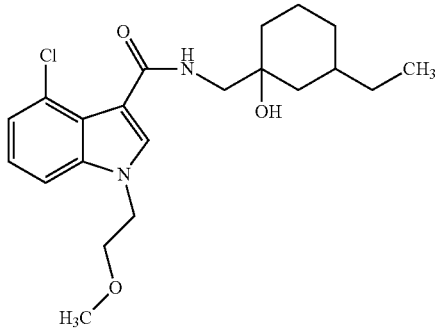 [SMILES: CCC1CCCC(O)(CNC(=O)c2cn(CCOC)c3cccc(Cl)c23)C1] 22 | 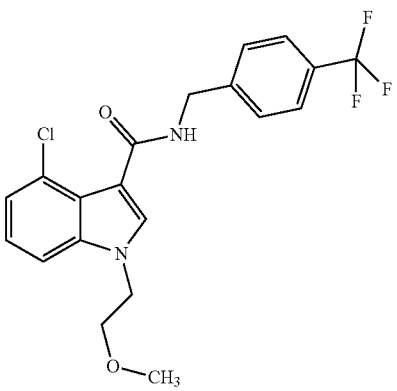 26 |
| 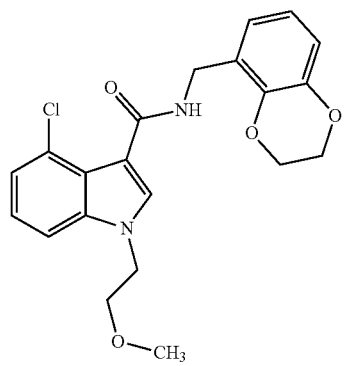 [SMILES: COCCn1cc(C(=O)NCc2cccc3c2OCCO3)c2c(Cl)cccc21] 23 | 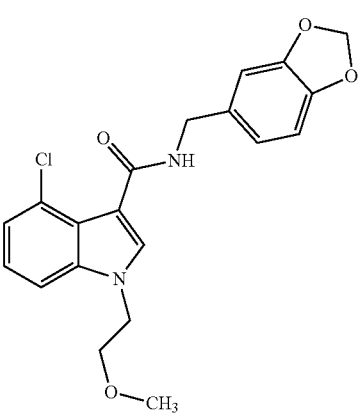 27 |
| 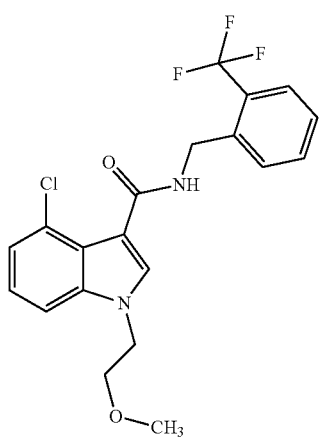 [SMILES: COCCn1cc(C(=O)NCc2ccccc2C(F)(F)F)c2c(Cl)cccc21] 24 | 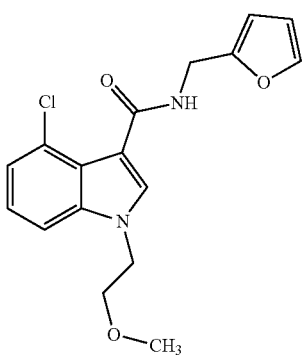 28 |
| 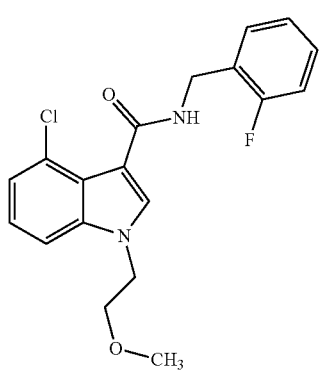 [SMILES: COCCn1cc(C(=O)NCc2ccccc2F)c2c(Cl)cccc21] 25 | 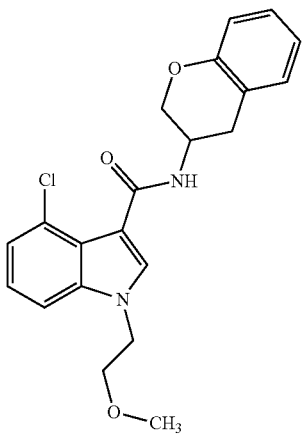 [SMILES: COCCn1cc(C(=O)NC2COc3ccccc3C2)c2c(Cl)cccc21] 29 |

TABLE 1-continued
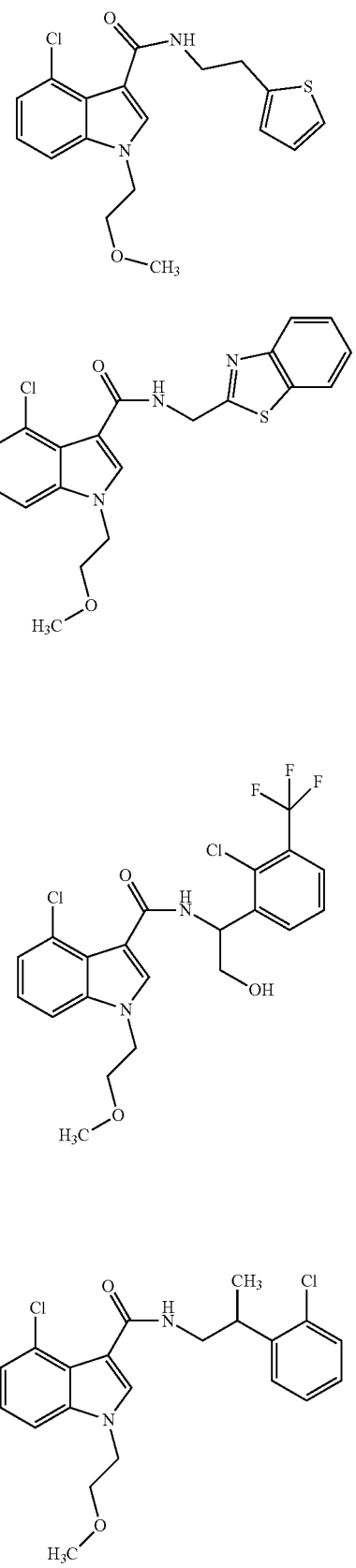
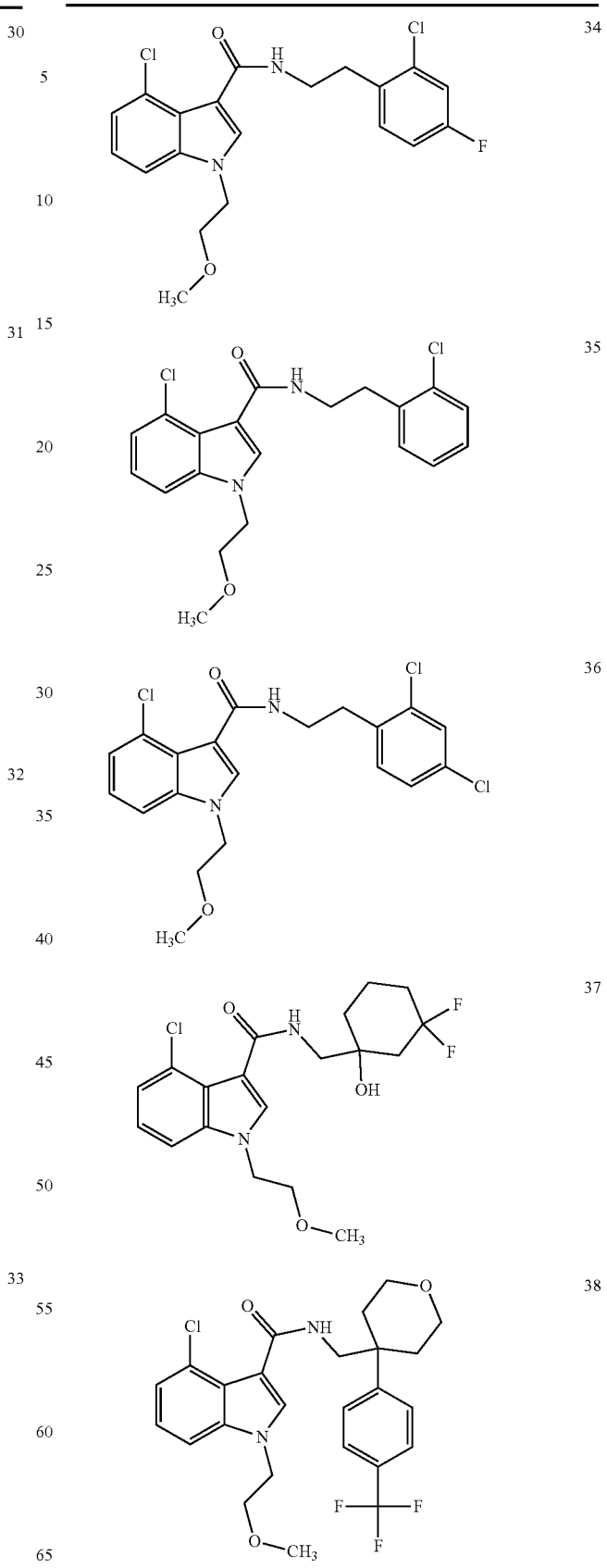

TABLE 1-continued
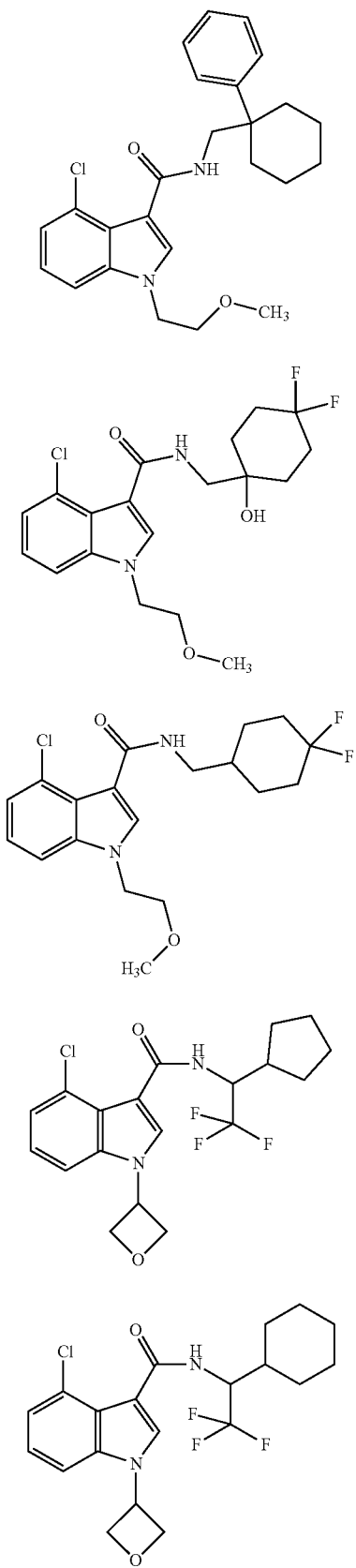
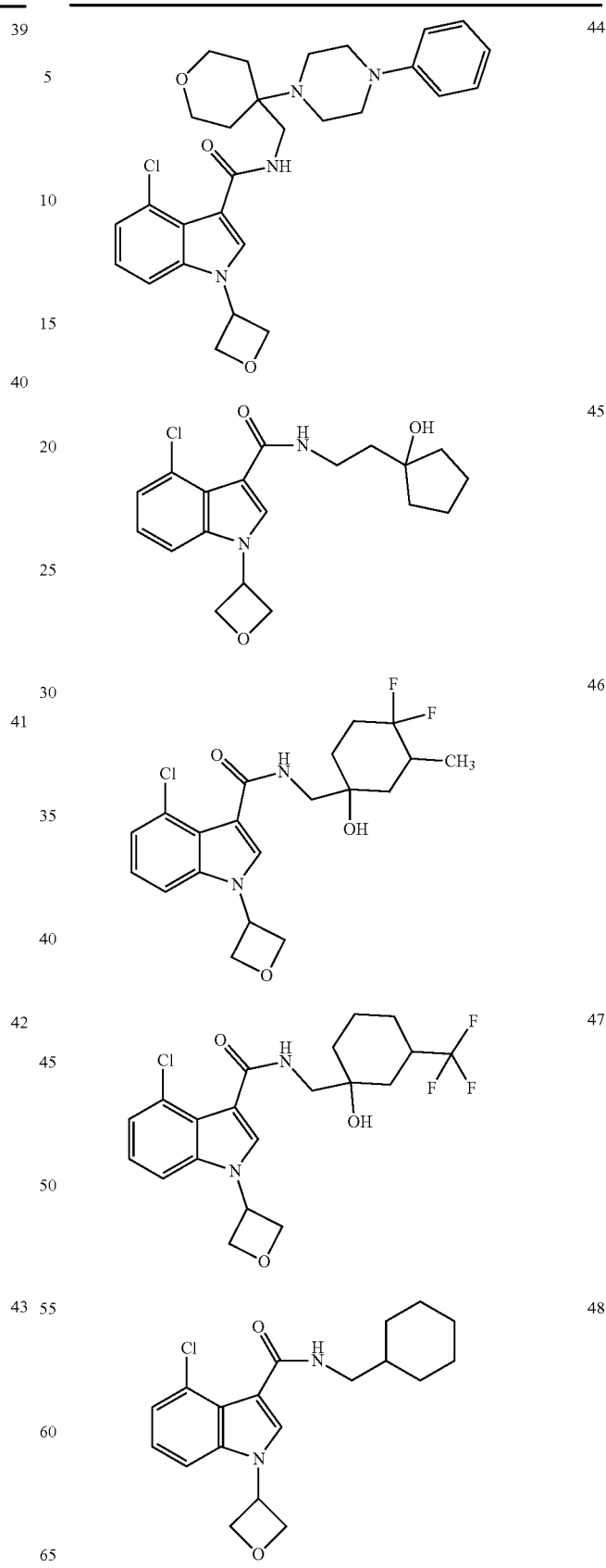

TABLE 1-continued
49 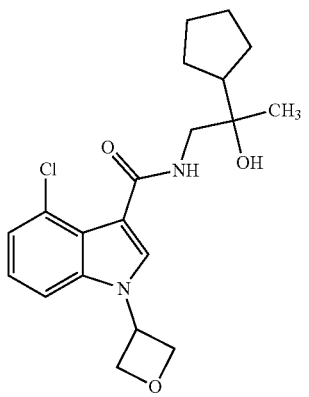 [SMILES: CC(O)(CNC(=O)c1cn(C2COC2)c2cccc(Cl)c12)C1CCCC1]
50 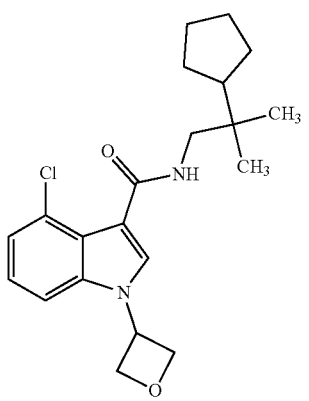 [SMILES: CC(C)(CNC(=O)c1cn(C2COC2)c2cccc(Cl)c12)C1CCCC1]
51 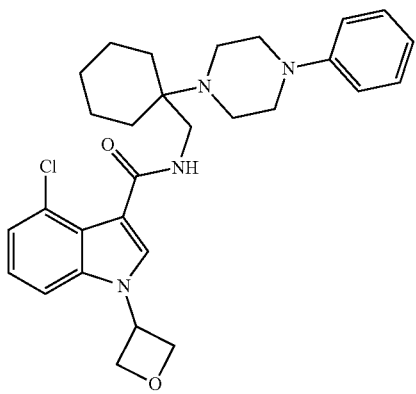 [SMILES: O=C(NCC1(N2CCN(c3ccccc3)CC2)CCCCC1)c1cn(C2COC2)c2cccc(Cl)c12]
52 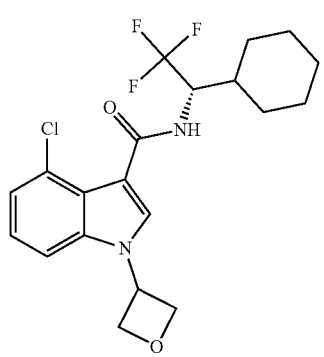 [SMILES: O=C(N[C@@H](C1CCCCC1)C(F)(F)F)c1cn(C2COC2)c2cccc(Cl)c12]
TABLE 1-continued
53 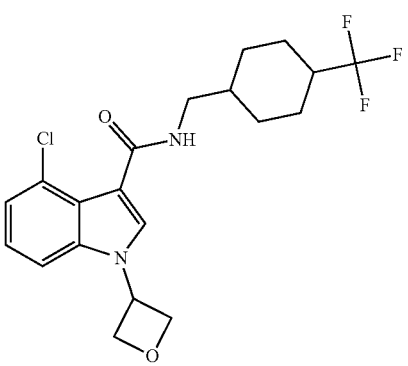 [SMILES: O=C(NCC1CCC(C(F)(F)F)CC1)c1cn(C2COC2)c2cccc(Cl)c12]
54 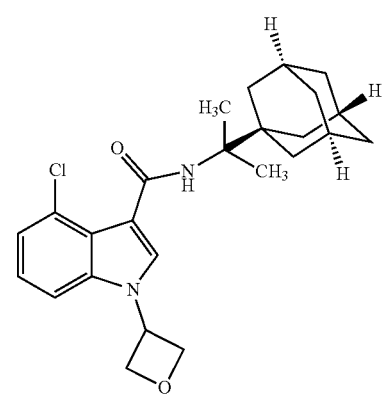 [SMILES: CC(C)(NC(=O)c1cn(C2COC2)c2cccc(Cl)c12)[C@]12C[C@H]3C[C@H](C[C@H](C3)C1)C2]
55 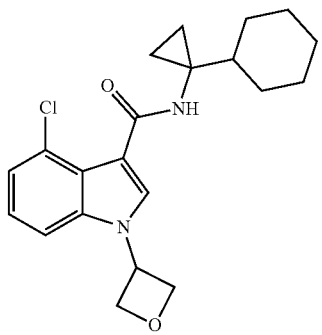 [SMILES: O=C(NC1(C2CCCCC2)CC1)c1cn(C2COC2)c2cccc(Cl)c12]
56 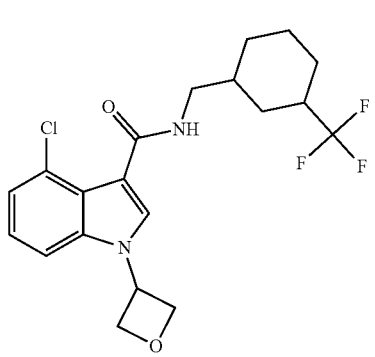 [SMILES: O=C(NCC1CCCC(C(F)(F)F)C1)c1cn(C2COC2)c2cccc(Cl)c12]

TABLE 1-continued
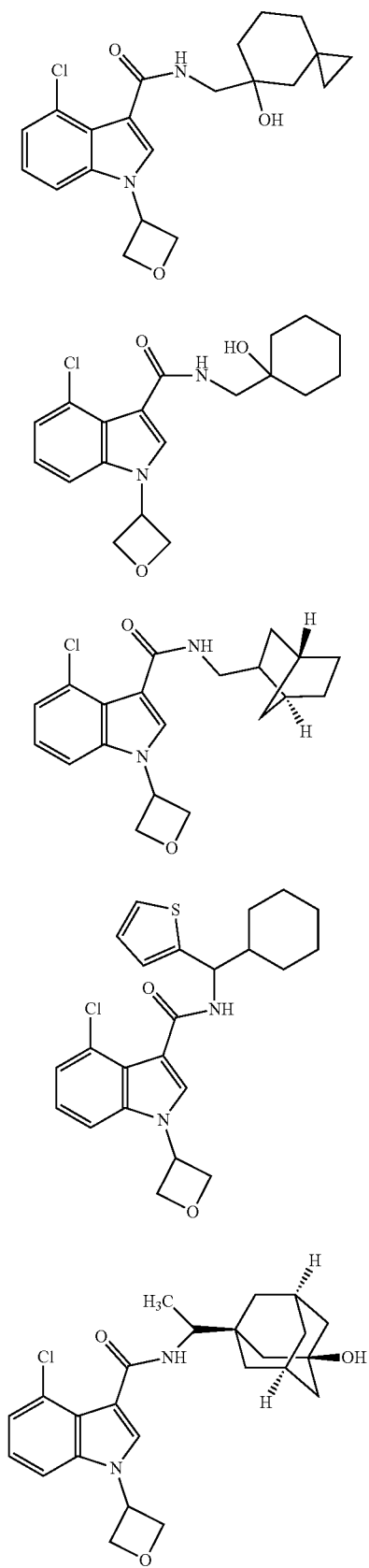
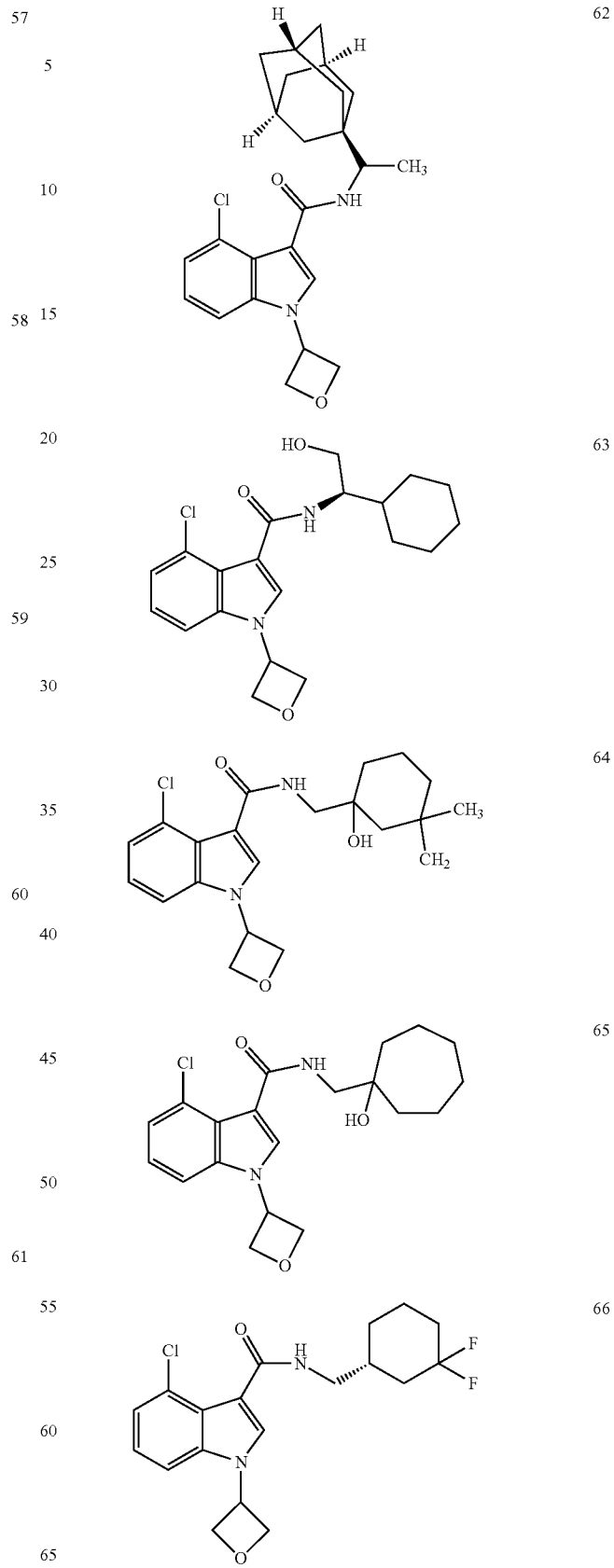

TABLE 1-continued
67 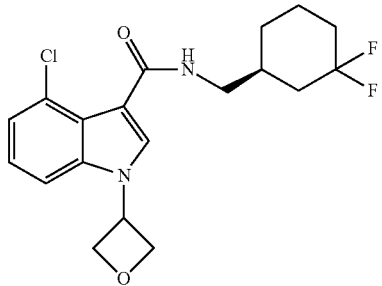 [SMILES: O=C(NC[C@H]1CCCC(F)(F)C1)c1cn(C2COC2)c2cccc(Cl)c12]
68 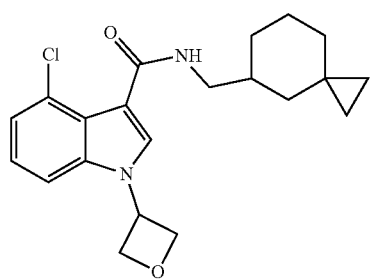 [SMILES: O=C(NCC1CCCC2(CC2)C1)c1cn(C2COC2)c2cccc(Cl)c12]
69 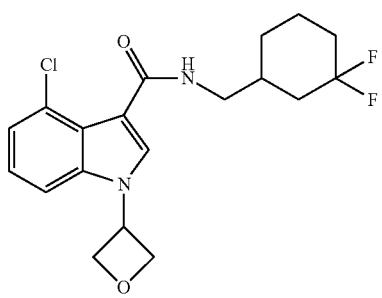 [SMILES: O=C(NCC1CCCC(F)(F)C1)c1cn(C2COC2)c2cccc(Cl)c12]
70 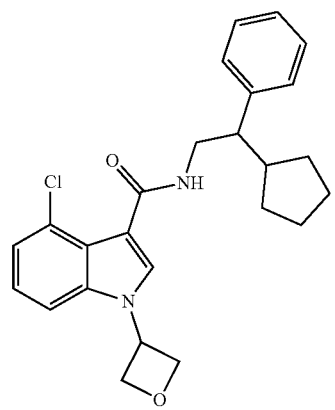 [SMILES: O=C(NCC(c1ccccc1)C1CCCC1)c1cn(C2COC2)c2cccc(Cl)c12]
TABLE 1-continued
71 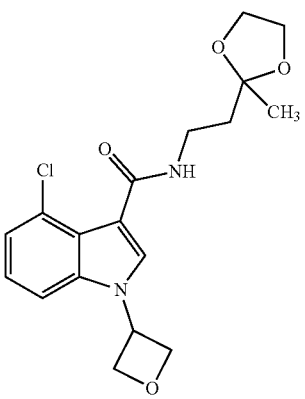 [SMILES: CC1(CCNC(=O)c2cn(C3COC3)c3cccc(Cl)c23)OCCO1]
72 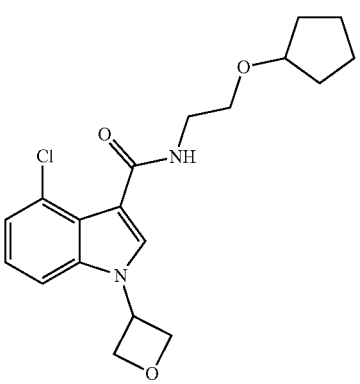 [SMILES: O=C(NCCOC1CCCC1)c1cn(C2COC2)c2cccc(Cl)c12]
73 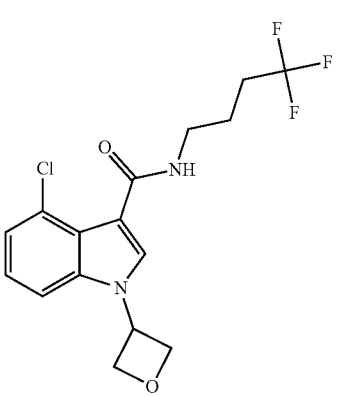 [SMILES: O=C(NCCCC(F)(F)F)c1cn(C2COC2)c2cccc(Cl)c12]
74 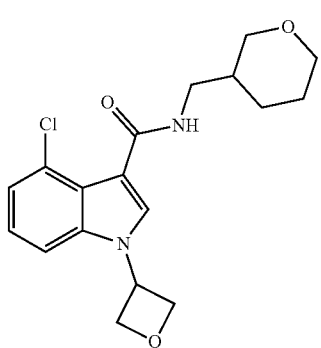 [SMILES: O=C(NCC1CCCOC1)c1cn(C2COC2)c2cccc(Cl)c12]

TABLE 1-continued
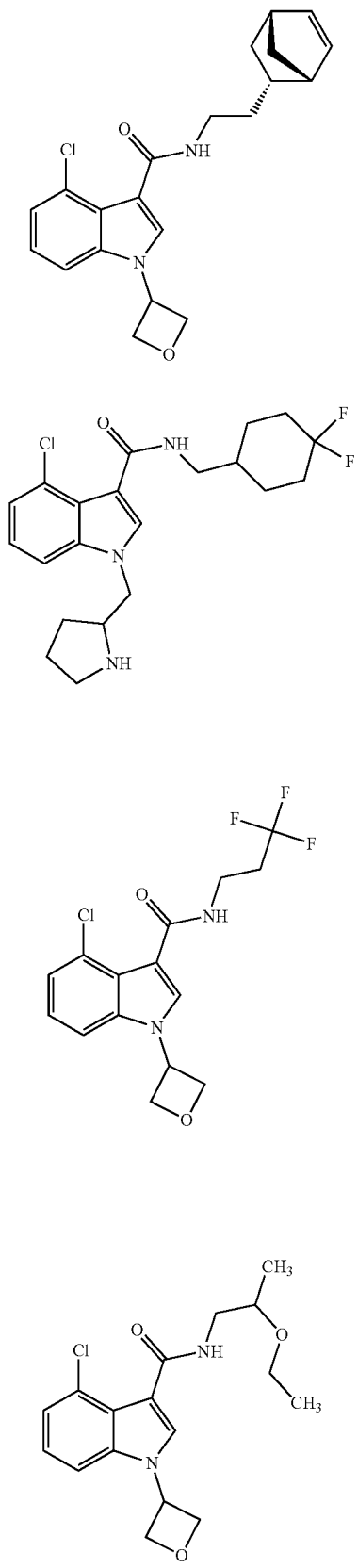
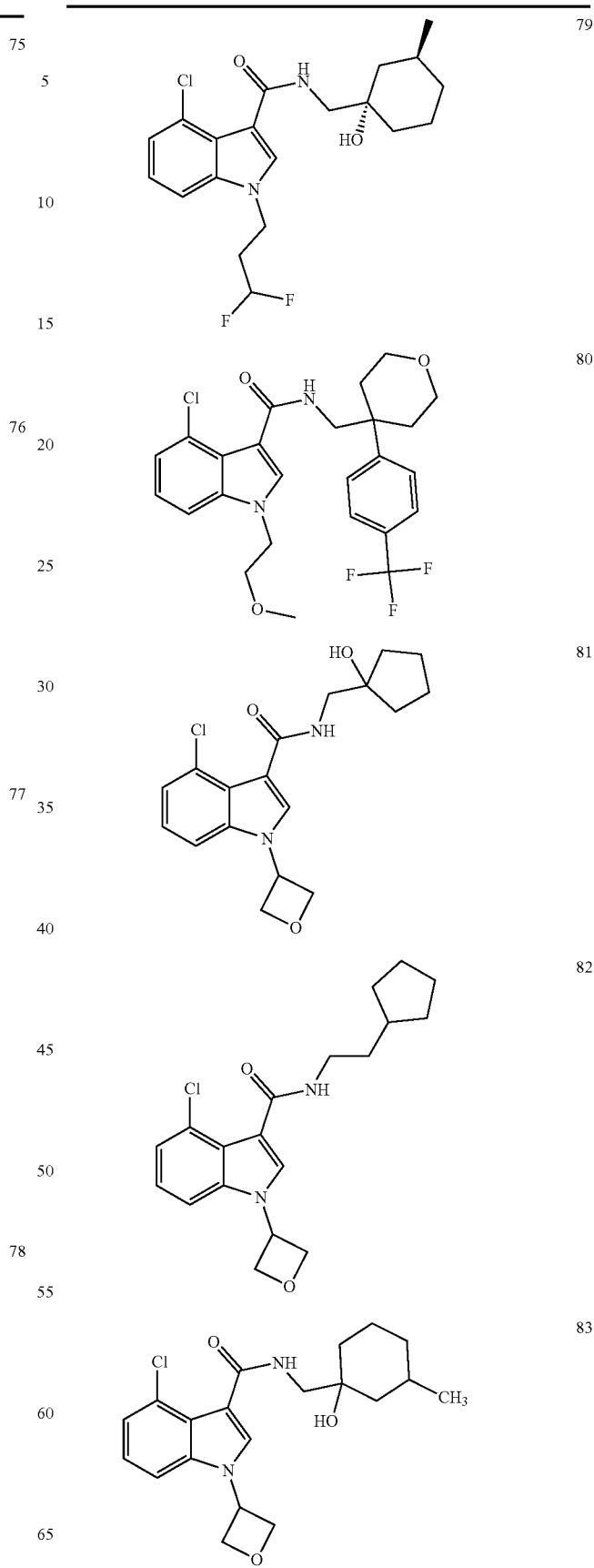

TABLE 1-continued
| | |
|---|---|
| 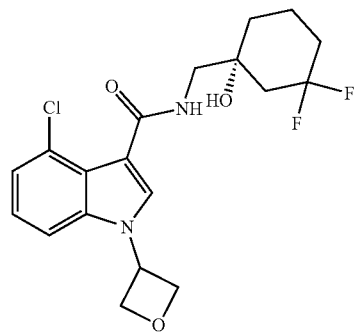 [SMILES: O=C(NC[C@@]1(O)CCCC(F)(F)C1)c1cn(C2COC2)c2cccc(Cl)c12] | 84 |
| 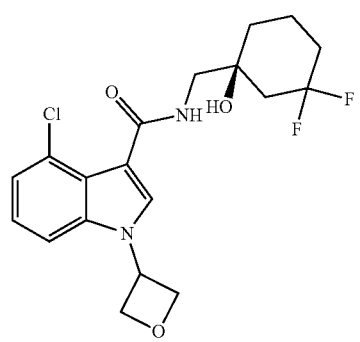 [SMILES: O=C(NC[C@]1(O)CCCC(F)(F)C1)c1cn(C2COC2)c2cccc(Cl)c12] | 85 |
| 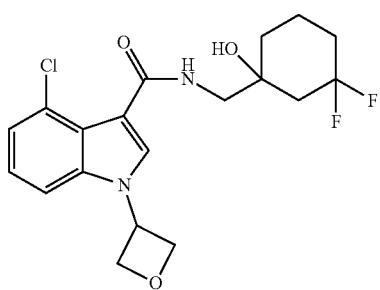 [SMILES: O=C(NCC1(O)CCCC(F)(F)C1)c1cn(C2COC2)c2cccc(Cl)c12] | 86 |
| 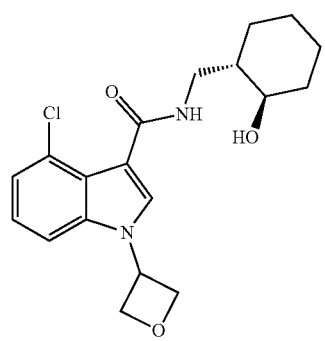 [SMILES: O=C(NC[C@@H]1CCCC[C@H]1O)c1cn(C2COC2)c2cccc(Cl)c12] | 87 |
TABLE 1-continued
| | |
|---|---|
| 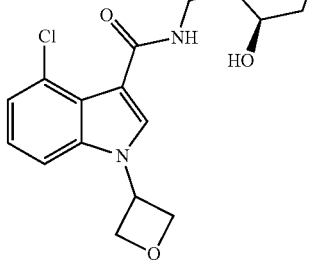 | 88 |
| 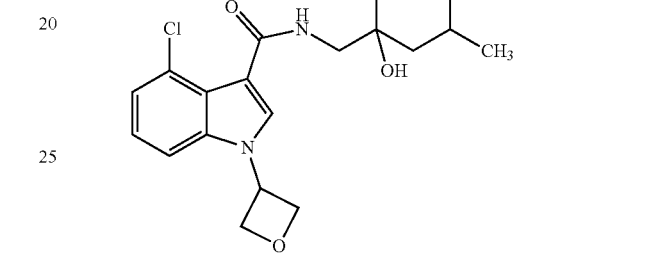 | 89 |
| | 90 |
| | 91 |
| 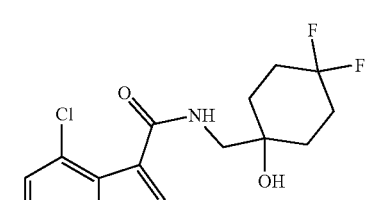 | 92 |

TABLE 1-continued
| | |
|---|---|
| 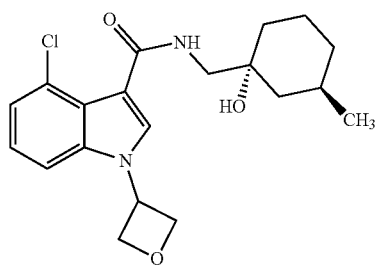 [SMILES: C[C@@H]1CCC[C@](O)(CNC(=O)c2cn(C3COC3)c3cccc(Cl)c23)C1] | 93 |
| 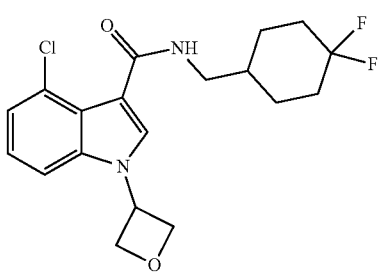 [SMILES: O=C(NCC1CCC(F)(F)CC1)c1cn(C2COC2)c2cccc(Cl)c12] | 94 |
| 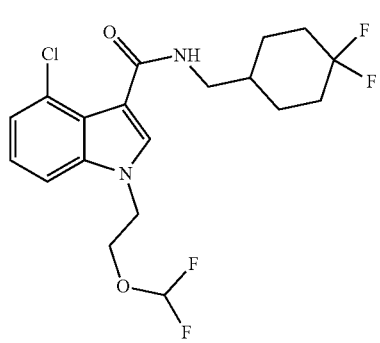 [SMILES: O=C(NCC1CCC(F)(F)CC1)c1cn(CCOC(F)F)c2cccc(Cl)c12] | 95 |
| 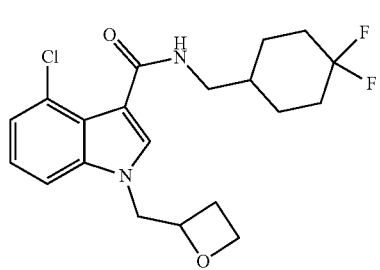 [SMILES: O=C(NCC1CCC(F)(F)CC1)c1cn(CC2CCO2)c2cccc(Cl)c12] | 96 |
| 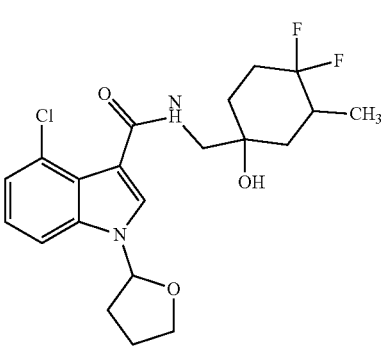 [SMILES: CC1CC(O)(CNC(=O)c2cn(C3CCCO3)c3cccc(Cl)c23)CCC1(F)F] | 97 |
TABLE 1-continued
| | |
|---|---|
| 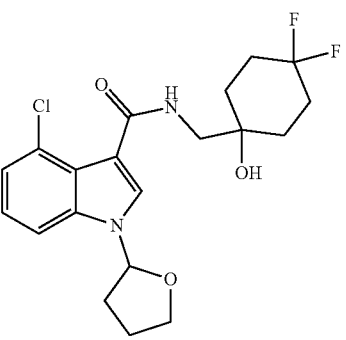 [SMILES: O=C(NCC1(O)CCC(F)(F)CC1)c1cn(C2CCCO2)c2cccc(Cl)c12] | 98 |
| 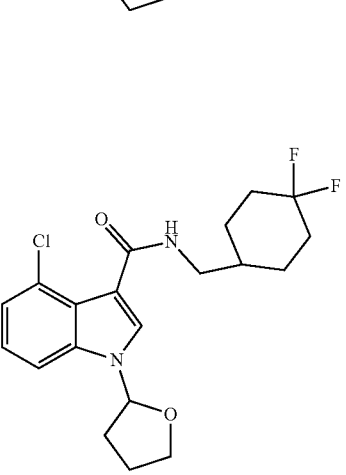 | 99 |
| 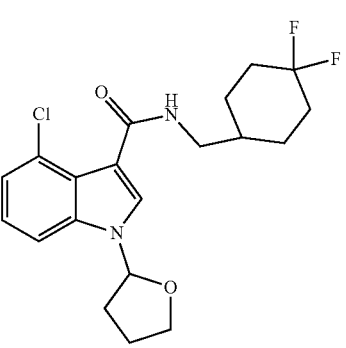 [SMILES: O=C(NCC1CCC(F)(F)CC1)c1cn(C2CCCO2)c2cccc(Cl)c12] | 100 |
| 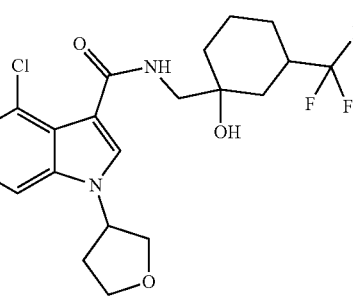 | 101 |

TABLE 1-continued
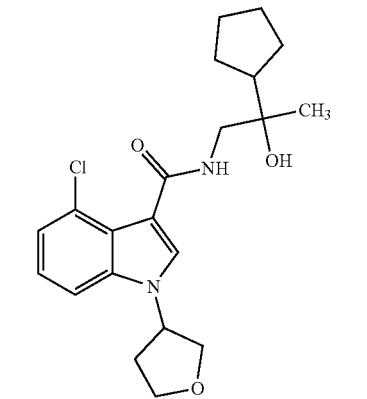 [SMILES: CC(O)(CNC(=O)c1cn(C2CCOC2)c2cccc(Cl)c12)C1CCCC1] 102
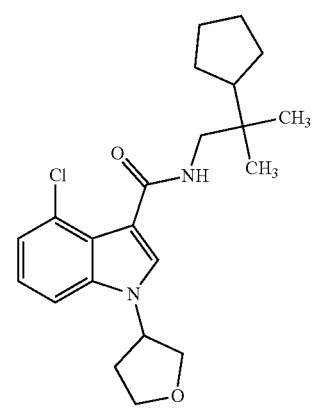 [SMILES: CC(C)(CNC(=O)c1cn(C2CCOC2)c2cccc(Cl)c12)C1CCCC1] 103
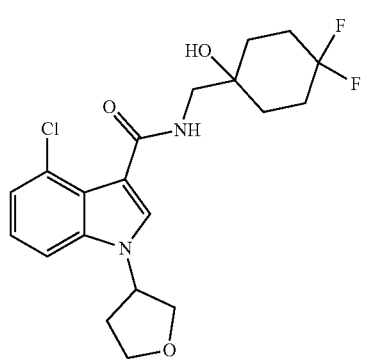 [SMILES: O=C(NCC1(O)CCC(F)(F)CC1)c1cn(C2CCOC2)c2cccc(Cl)c12] 104
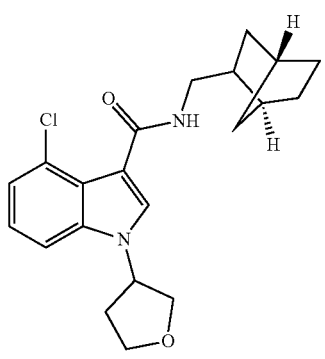 [SMILES: O=C(NCC1C[C@@H]2CC[C@H]1C2)c1cn(C2CCOC2)c2cccc(Cl)c12] 105
TABLE 1-continued
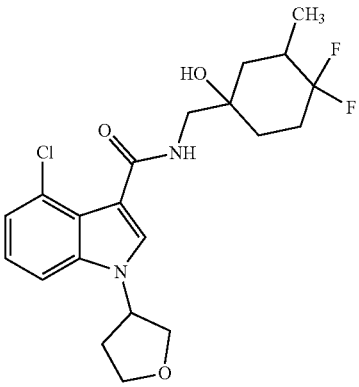 [SMILES: CC1CC(O)(CNC(=O)c2cn(C3CCOC3)c3cccc(Cl)c23)CCC1(F)F] 106
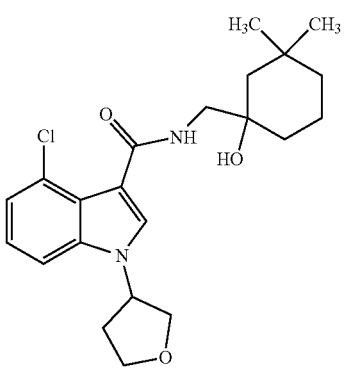 [SMILES: CC1(C)CCCC(O)(CNC(=O)c2cn(C3CCOC3)c3cccc(Cl)c23)C1] 107
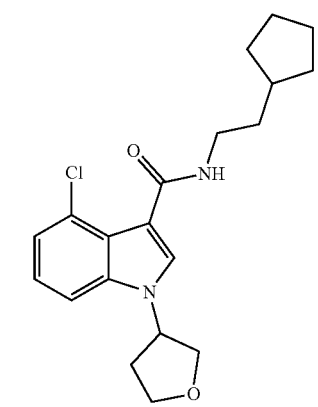 [SMILES: O=C(NCCC1CCCC1)c1cn(C2CCOC2)c2cccc(Cl)c12] 108
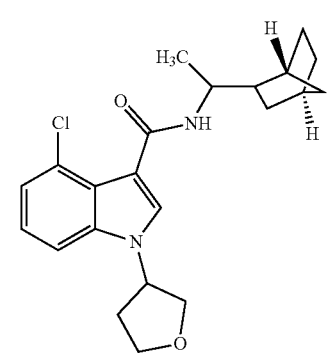 [SMILES: CC(NC(=O)c1cn(C2CCOC2)c2cccc(Cl)c12)C1C[C@H]2CC[C@@H]1C2] 109

TABLE 1-continued
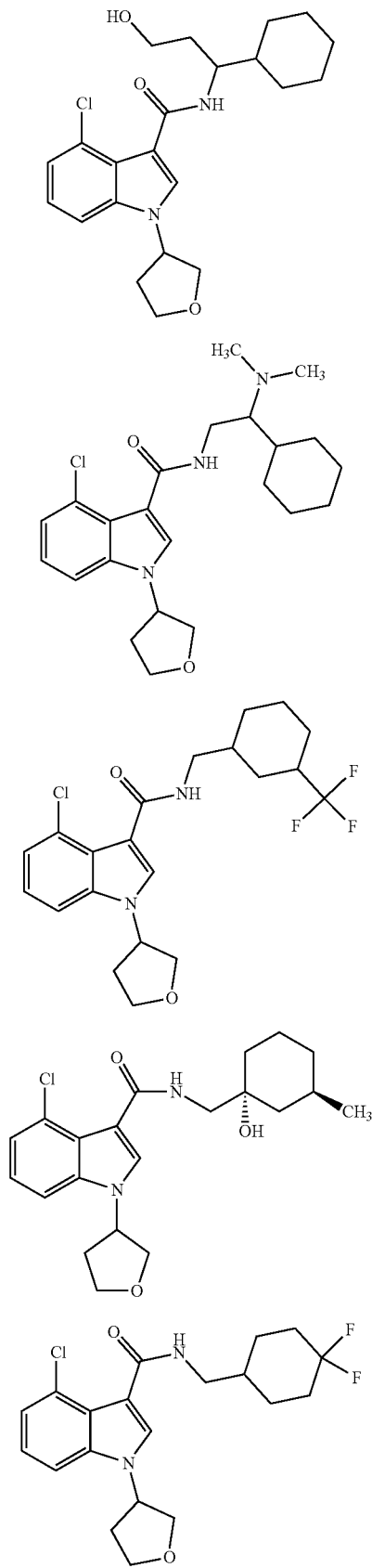
110
111
112
113
114
TABLE 1-continued
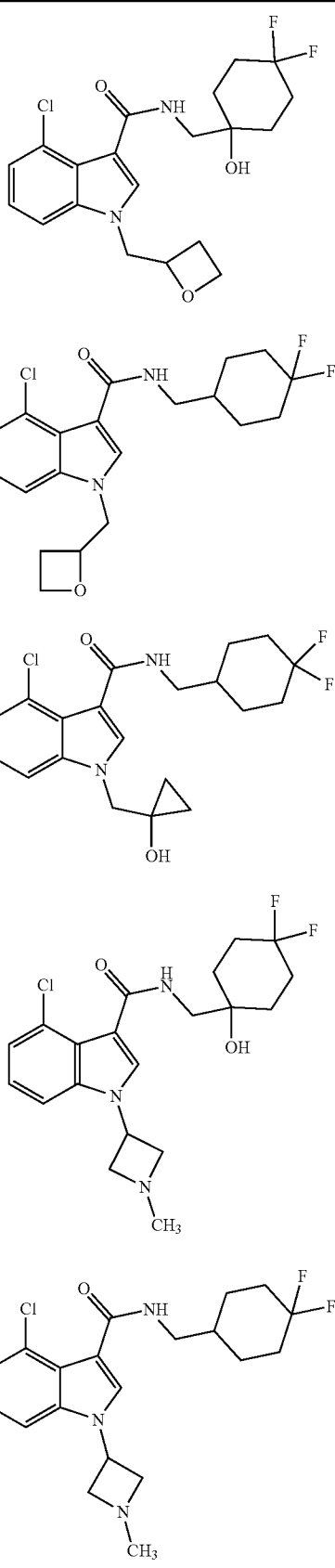
115
116
117
118
119

TABLE 1-continued
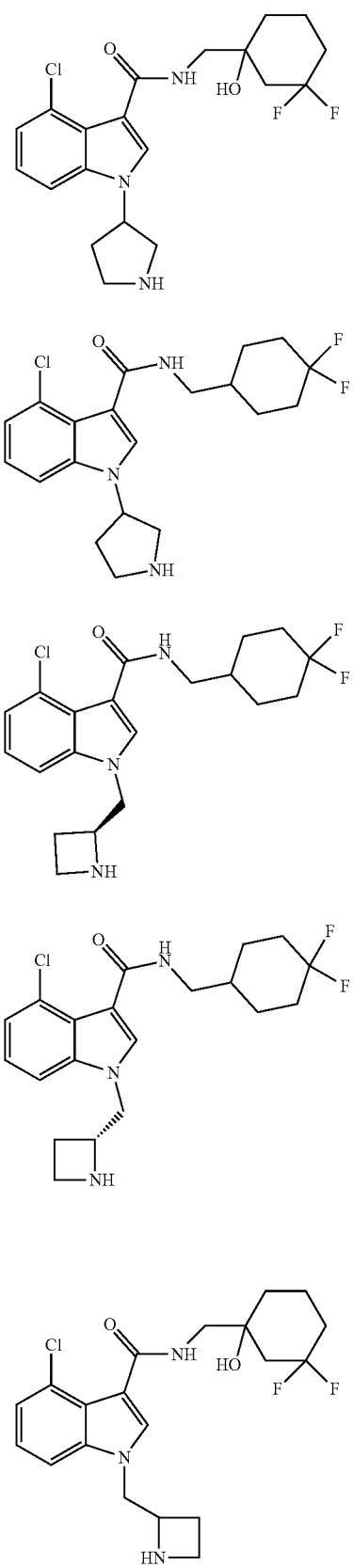
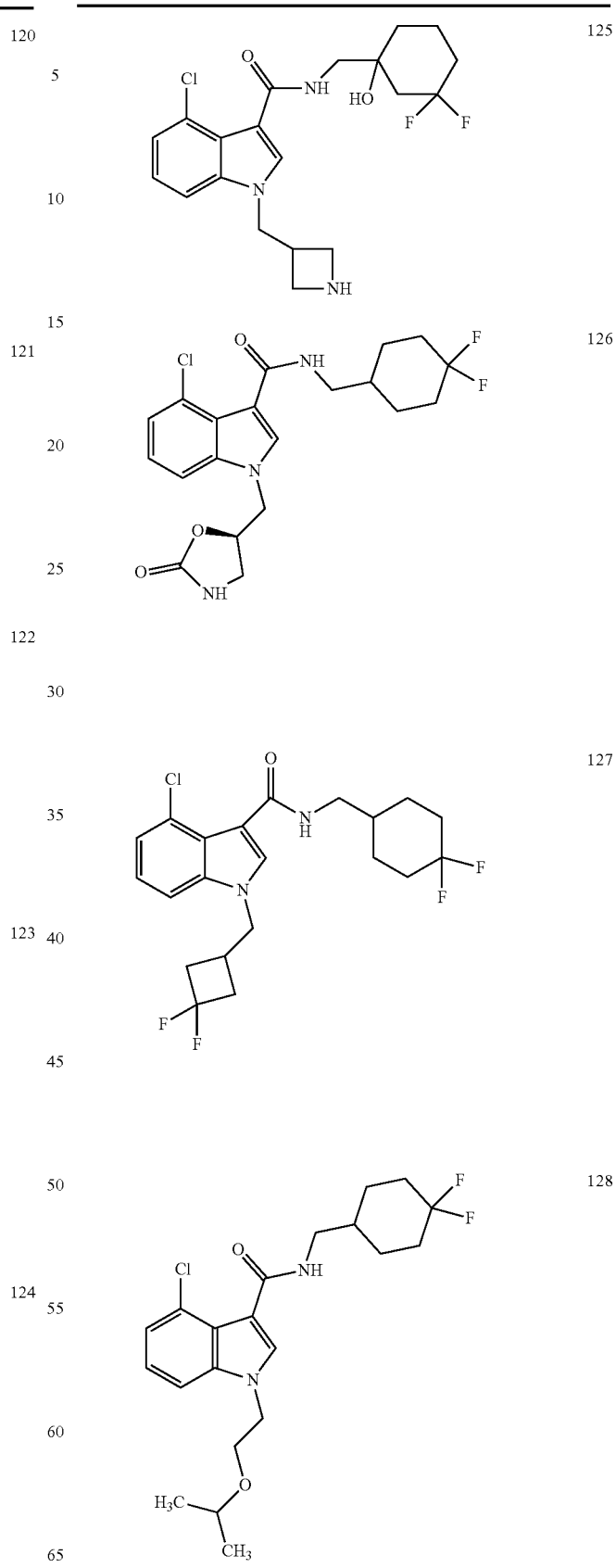

TABLE 1-continued
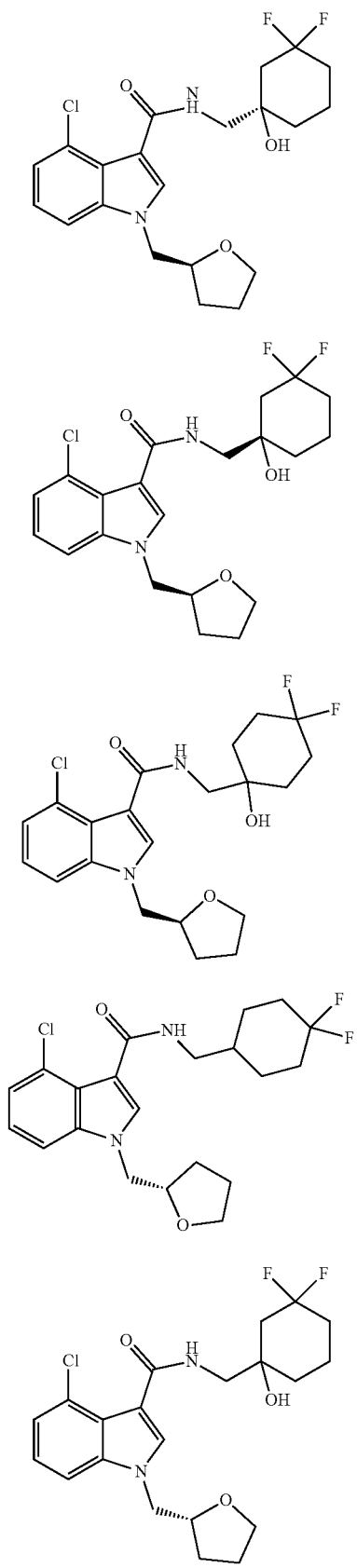
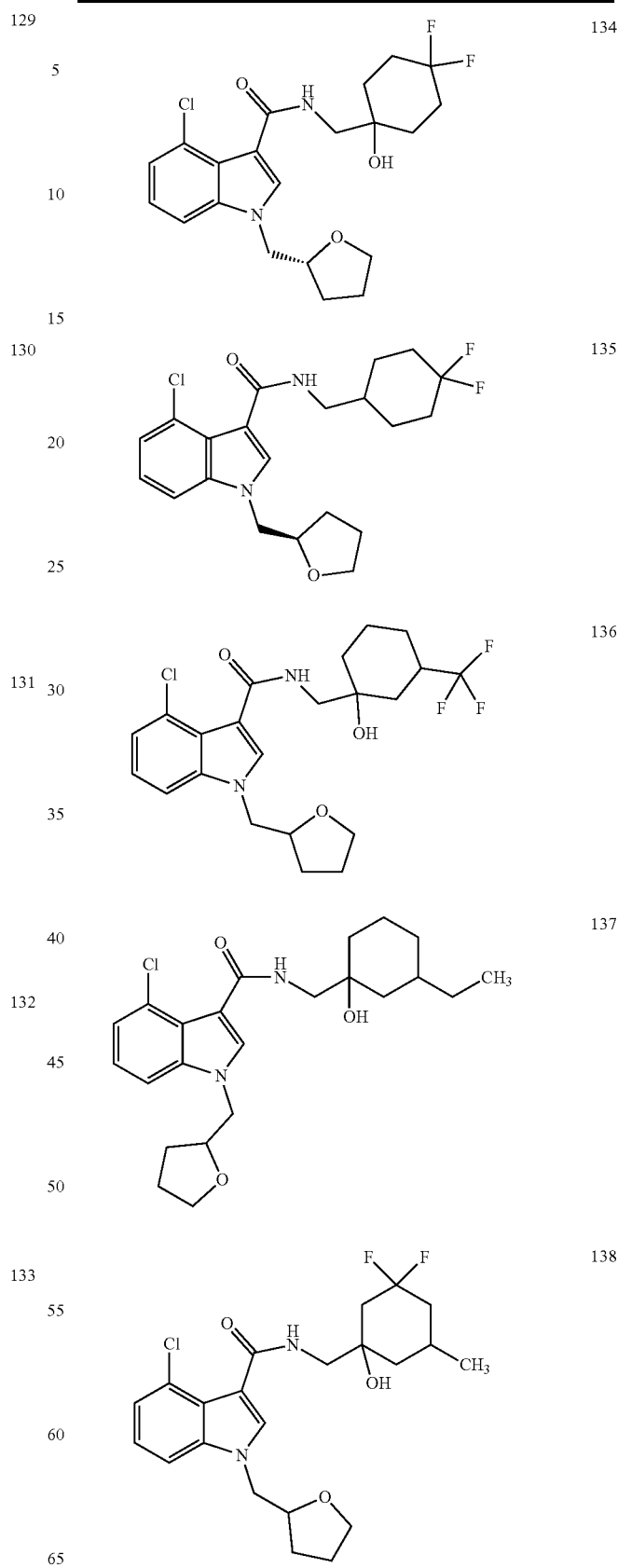

TABLE 1-continued
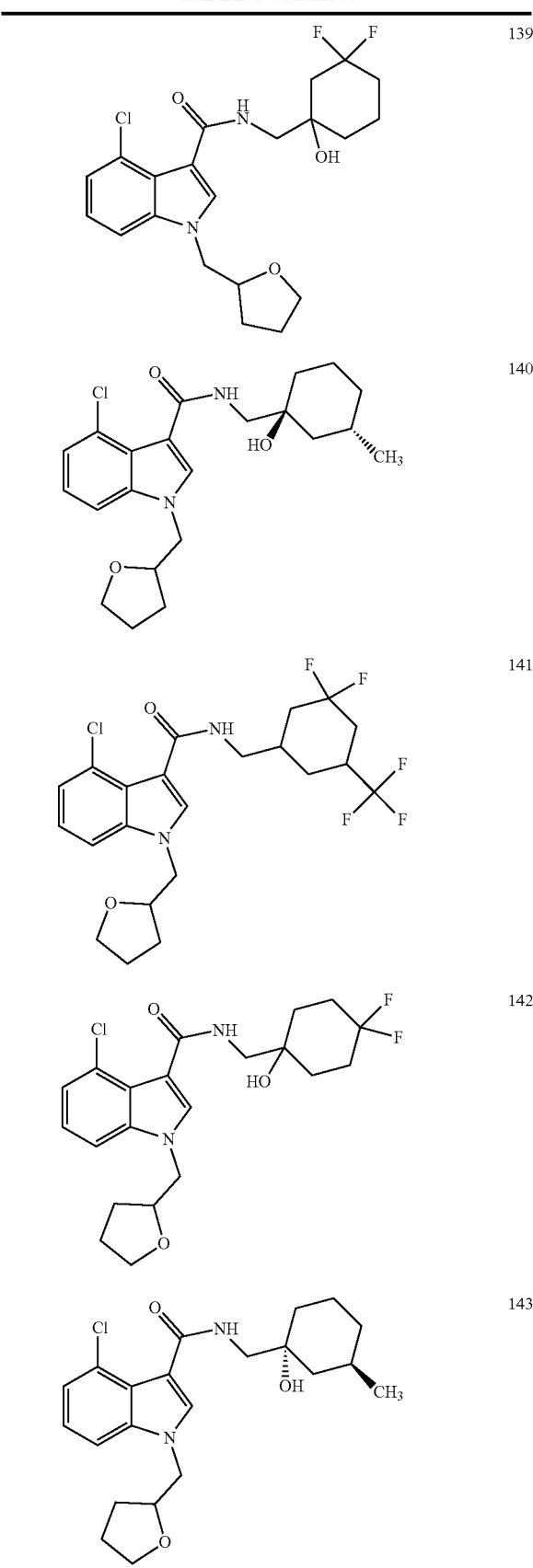
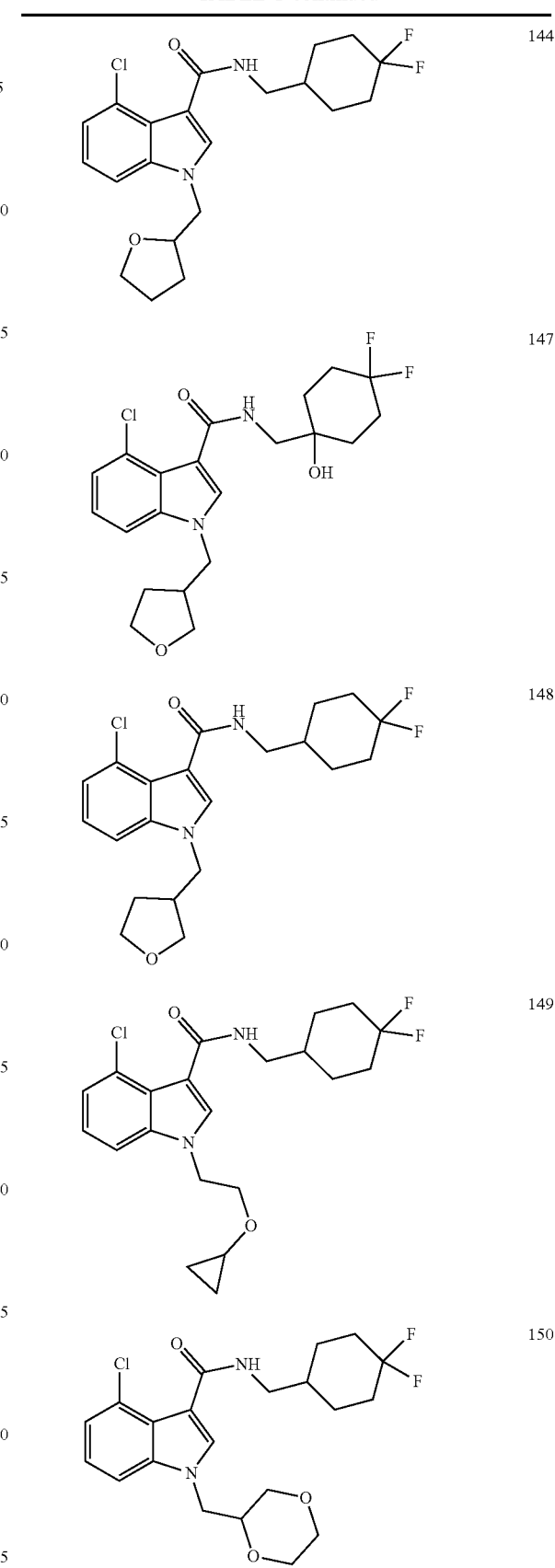

TABLE 1-continued
| | |
|---|---|
| 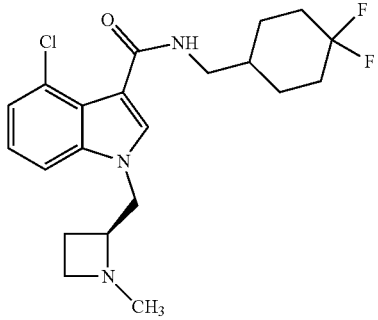 [SMILES: CN1CC[C@H]1Cn1cc(C(=O)NCC2CCC(F)(F)CC2)c2c(Cl)cccc21] | 151 |
| 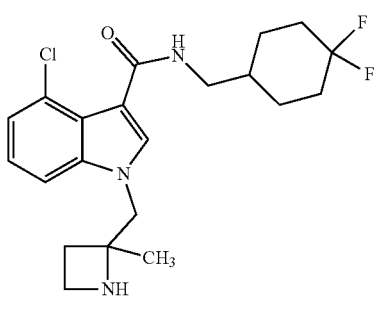 [SMILES: CC1(Cn2cc(C(=O)NCC3CCC(F)(F)CC3)c3c(Cl)cccc32)CCN1] | 152 |
| 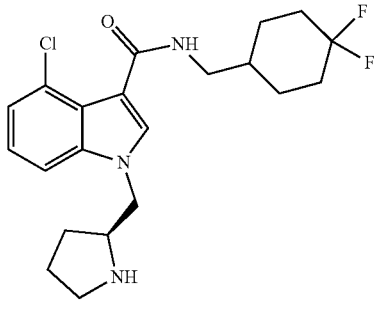 [SMILES: O=C(NCC1CCC(F)(F)CC1)c1cn(C[C@@H]2CCCN2)c2cccc(Cl)c12] | 153 |
| 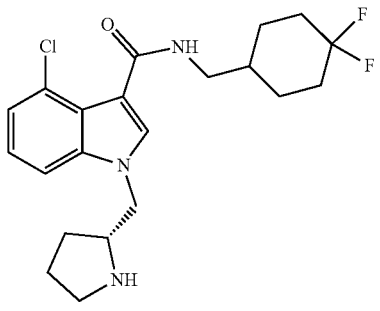 [SMILES: O=C(NCC1CCC(F)(F)CC1)c1cn(C[C@H]2CCCN2)c2cccc(Cl)c12] | 154 |
| 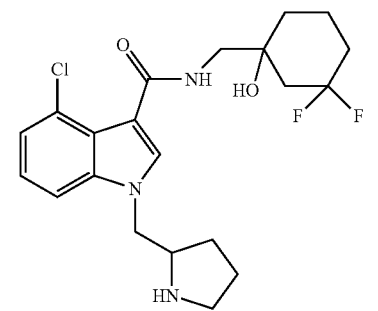 [SMILES: O=C(NCC1(O)CCCC(F)(F)C1)c1cn(CC2CCCN2)c2cccc(Cl)c12] | 155 |
TABLE 1-continued
| | |
|---|---|
| 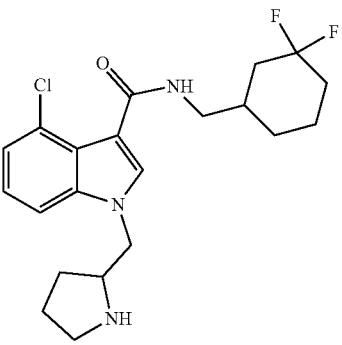 [SMILES: O=C(NCC1CCCC(F)(F)C1)c1cn(CC2CCCN2)c2cccc(Cl)c12] | 156 |
| 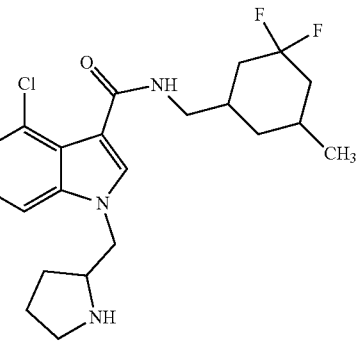 | 157 |
| 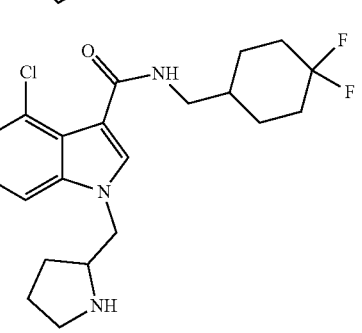 | 158 |
| 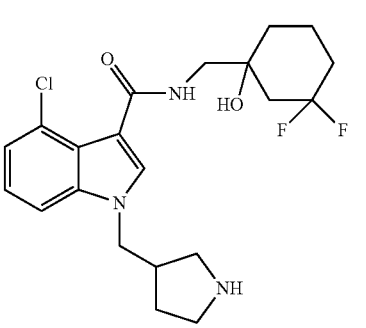 [SMILES: O=C(NCC1(O)CCCC(F)(F)C1)c1cn(CC2CCNC2)c2cccc(Cl)c12] | 159 |
| 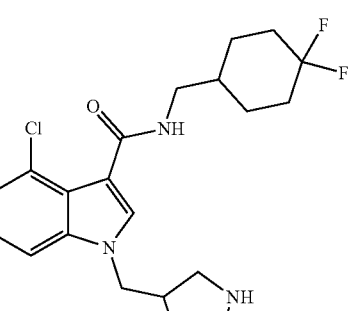 | 160 |

TABLE 1-continued
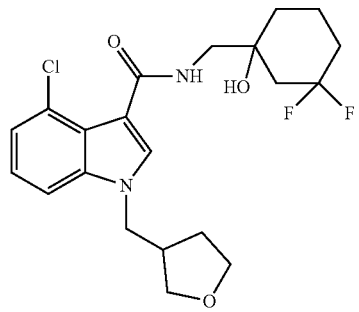 [SMILES: O=C(NCC1(O)CCCC(F)(F)C1)c1cn(CC2CCOC2)c2cccc(Cl)c12] 146
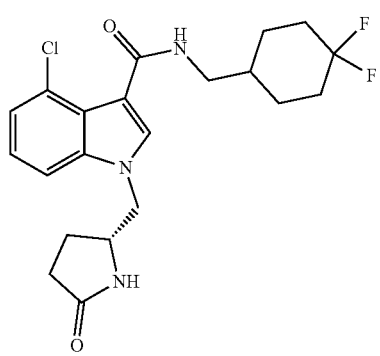 [SMILES: O=C1CC[C@H](Cn2cc(C(=O)NCC3CCC(F)(F)CC3)c3c(Cl)cccc32)N1] 162
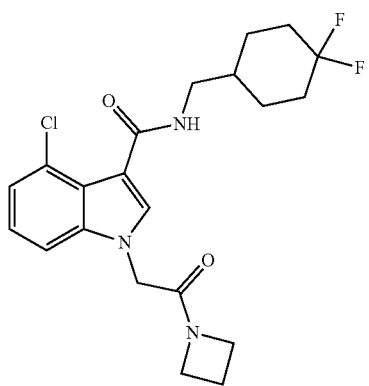 [SMILES: O=C(NCC1CCC(F)(F)CC1)c1cn(CC(=O)N2CCC2)c2cccc(Cl)c12] 163
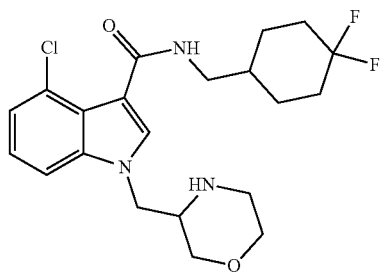 [SMILES: O=C(NCC1CCC(F)(F)CC1)c1cn(CC2COCCN2)c2cccc(Cl)c12] 164
TABLE 1-continued
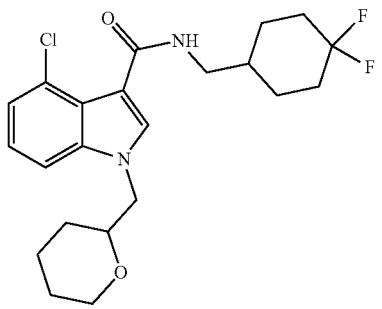 [SMILES: O=C(NCC1CCC(F)(F)CC1)c1cn(CC2CCCCO2)c2cccc(Cl)c12] 167
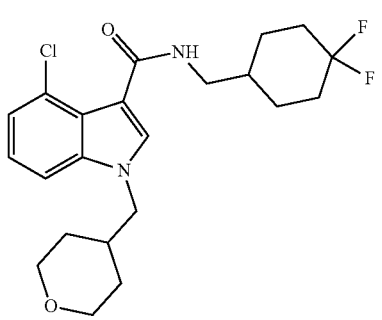 [SMILES: O=C(NCC1CCC(F)(F)CC1)c1cn(CC2CCOCC2)c2cccc(Cl)c12] 168
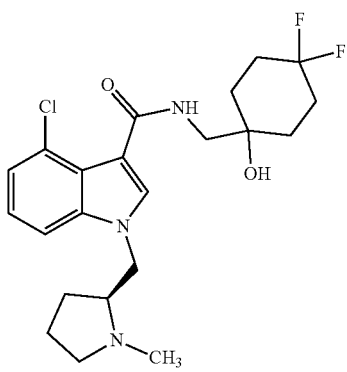 [SMILES: CN1CCC[C@H]1Cn1cc(C(=O)NCC2(O)CCC(F)(F)CC2)c2c(Cl)cccc21] 169
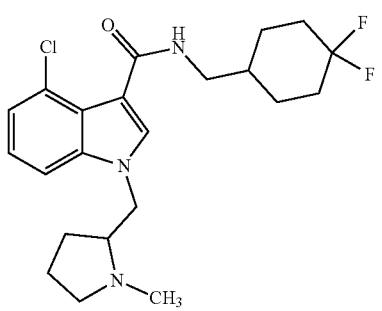 [SMILES: CN1CCCC1Cn1cc(C(=O)NCC2CCC(F)(F)CC2)c2c(Cl)cccc21] 170
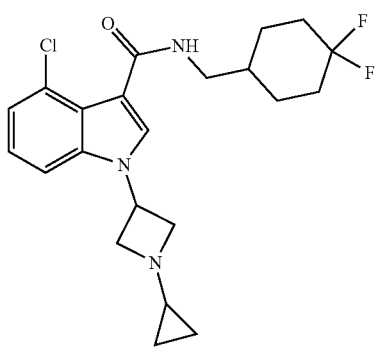 [SMILES: O=C(NCC1CCC(F)(F)CC1)c1cn(C2CN(C3CC3)C2)c2cccc(Cl)c12] 171

TABLE 1-continued
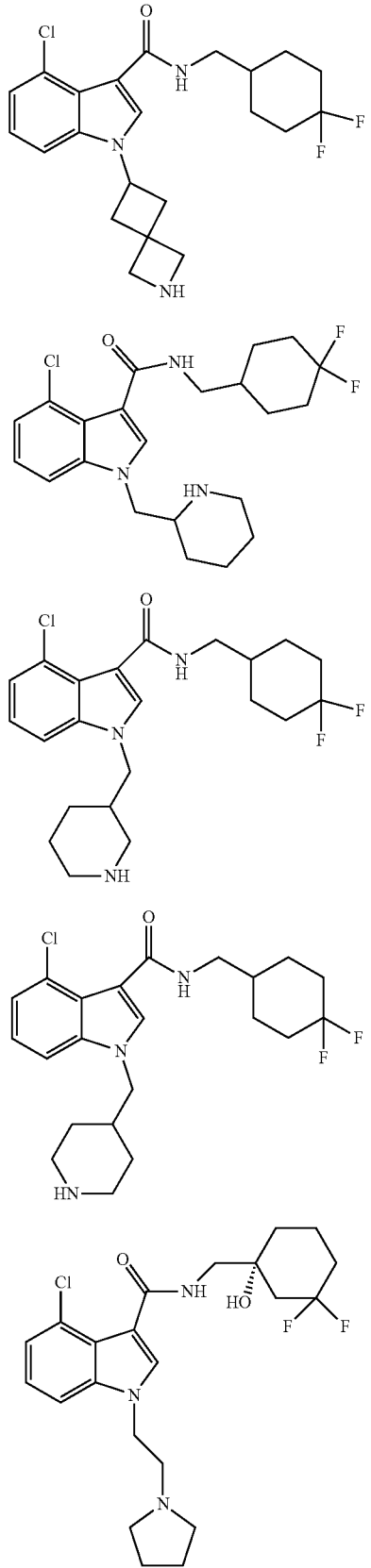
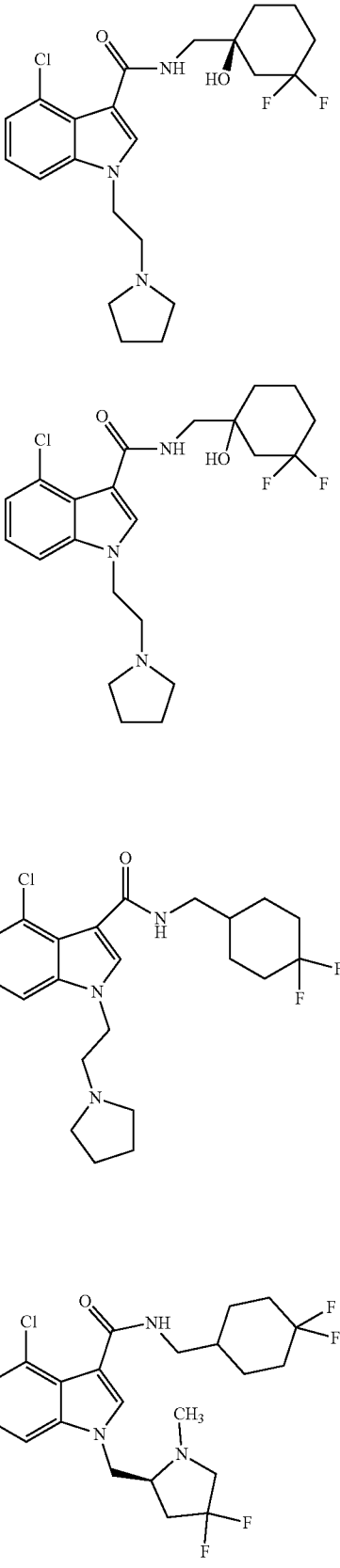

TABLE 1-continued
| | |
|---|---|
| 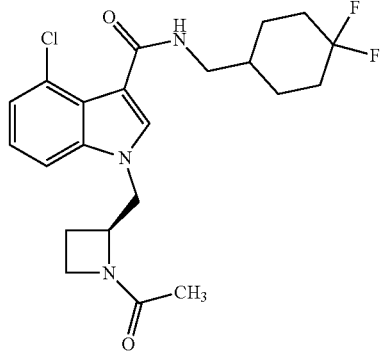 [SMILES: CC(=O)N1CC[C@H]1Cn1cc(C(=O)NCC2CCC(F)(F)CC2)c2c(Cl)cccc21] | 181 |
| 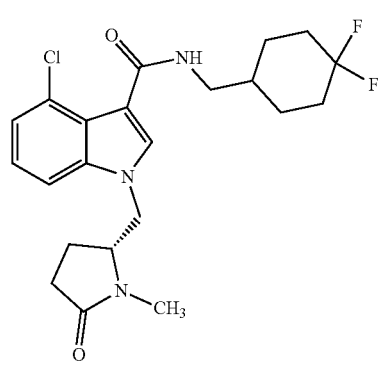 [SMILES: CN1C(=O)CC[C@@H]1Cn1cc(C(=O)NCC2CCC(F)(F)CC2)c2c(Cl)cccc21] | 182 |
| 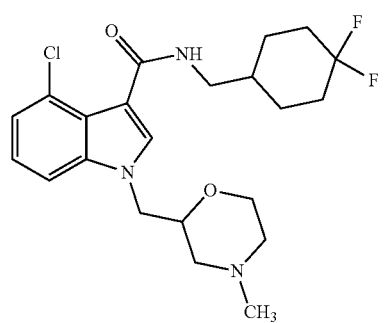 [SMILES: CN1CCOC(Cn2cc(C(=O)NCC3CCC(F)(F)CC3)c3c(Cl)cccc32)C1] | 183 |
| 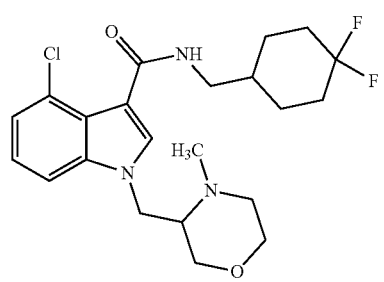 [SMILES: CN1CCOCC1Cn1cc(C(=O)NCC2CCC(F)(F)CC2)c2c(Cl)cccc21] | 184 |
TABLE 1-continued
| | |
|---|---|
| 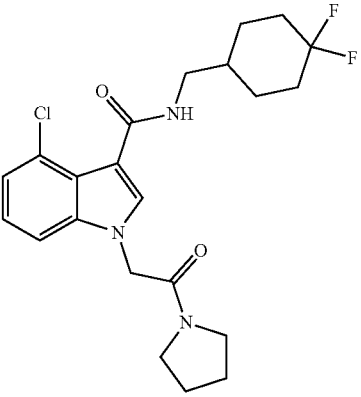 [SMILES: O=C(NCC1CCC(F)(F)CC1)c1cn(CC(=O)N2CCCC2)c2cccc(Cl)c12] | 185 |
|  | 186 |
| 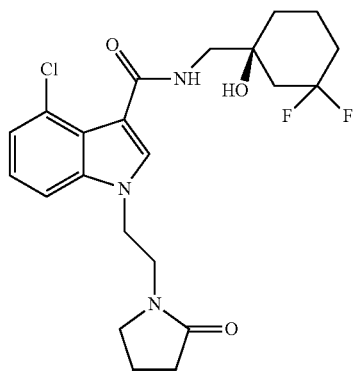 [SMILES: O=C(NC[C@]1(O)CCCC(F)(F)C1)c1cn(CCN2CCCC2=O)c2cccc(Cl)c12] | 187 |
| 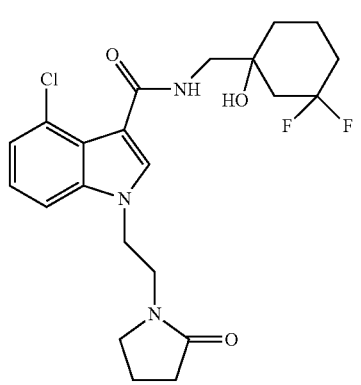 [SMILES: O=C(NCC1(O)CCCC(F)(F)C1)c1cn(CCN2CCCC2=O)c2cccc(Cl)c12] | 188 |

TABLE 1-continued
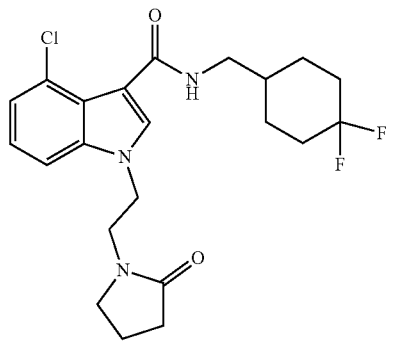 [SMILES: O=C(NCC1CCC(F)(F)CC1)c1cn(CCN2CCCC2=O)c2cccc(Cl)c12] 189
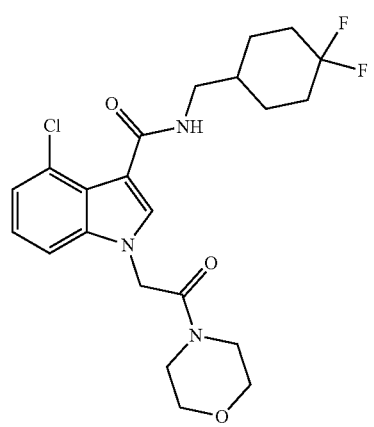 [SMILES: O=C(NCC1CCC(F)(F)CC1)c1cn(CC(=O)N2CCOCC2)c2cccc(Cl)c12] 190
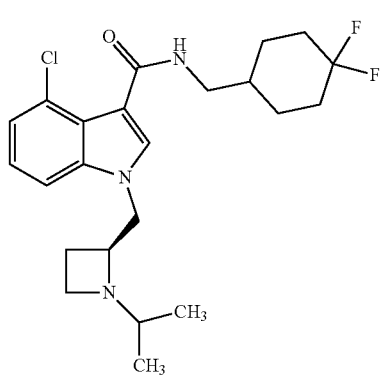 [SMILES: CC(C)N1CC[C@H]1Cn1cc(C(=O)NCC2CCC(F)(F)CC2)c2c(Cl)cccc21] 191
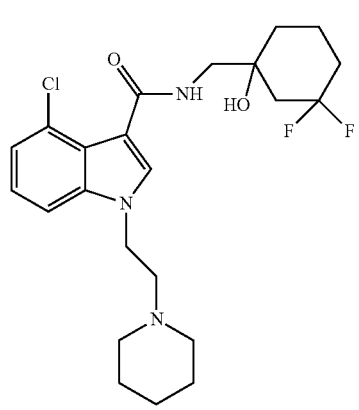 [SMILES: O=C(NCC1(O)CCCC(F)(F)C1)c1cn(CCN2CCCCC2)c2cccc(Cl)c12] 192
TABLE 1-continued
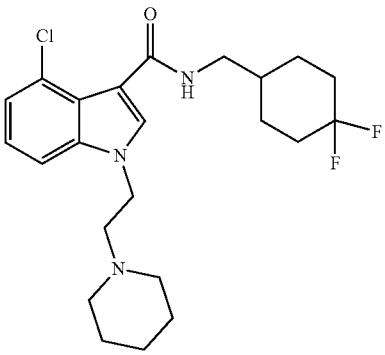 [SMILES: O=C(NCC1CCC(F)(F)CC1)c1cn(CCN2CCCCC2)c2cccc(Cl)c12] 193
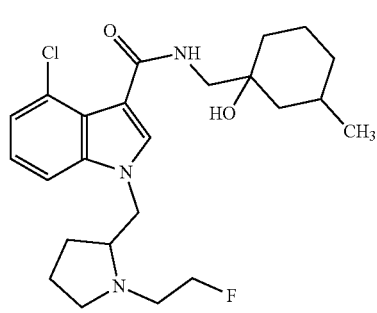 [SMILES: CC1CCCC(O)(CNC(=O)c2cn(CC3CCCN3CCF)c3cccc(Cl)c23)C1] 194
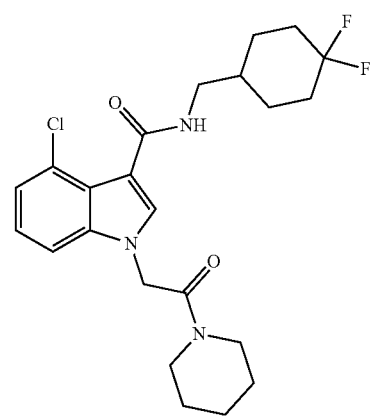 [SMILES: O=C(NCC1CCC(F)(F)CC1)c1cn(CC(=O)N2CCCCC2)c2cccc(Cl)c12] 195
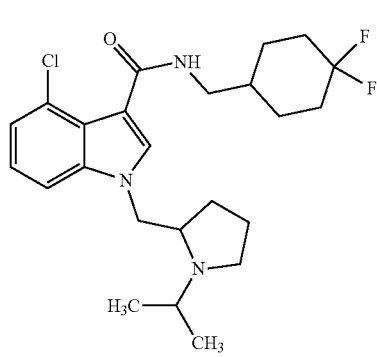 [SMILES: CC(C)N1CCCC1Cn1cc(C(=O)NCC2CCC(F)(F)CC2)c2c(Cl)cccc21] 196

TABLE 1-continued
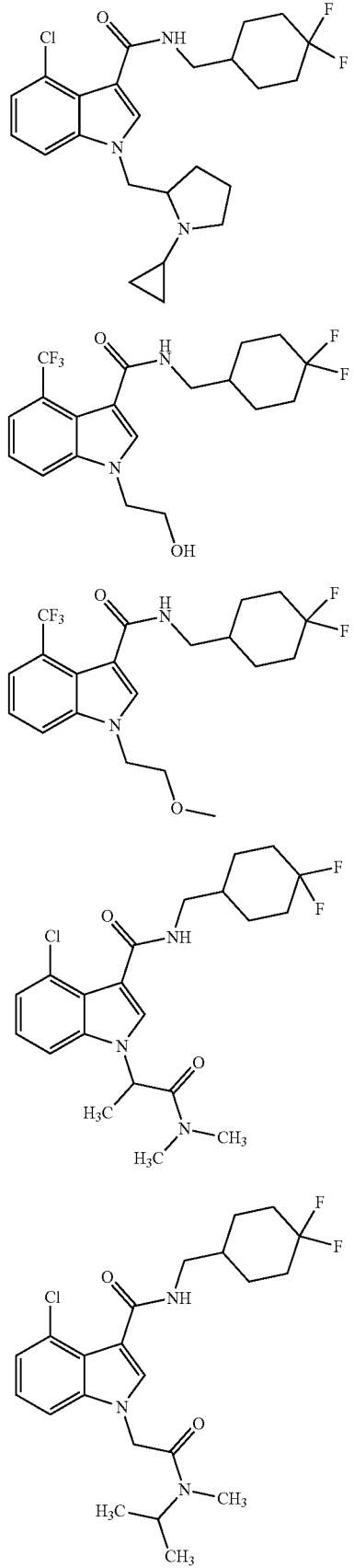
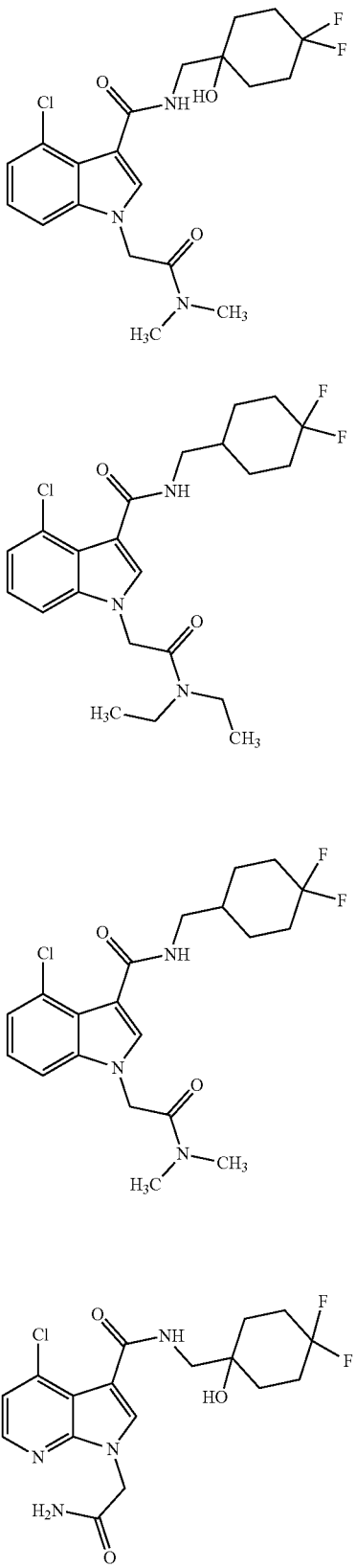

TABLE 1-continued
| | |
|---|---|
| 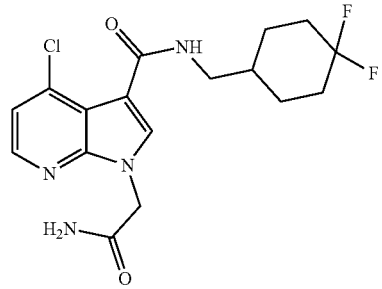 [SMILES: NC(=O)Cn1cc(C(=O)NCC2CCC(F)(F)CC2)c2c(Cl)ccnc21] | 210 |
| 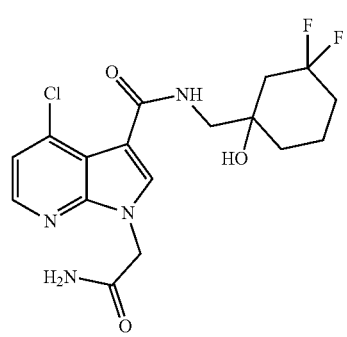 [SMILES: NC(=O)Cn1cc(C(=O)NCC2(O)CCCC(F)(F)C2)c2c(Cl)ccnc21] | 211 |
| 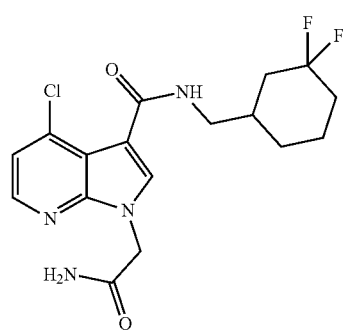 [SMILES: NC(=O)Cn1cc(C(=O)NCC2CCCC(F)(F)C2)c2c(Cl)ccnc21] | 212 |
| 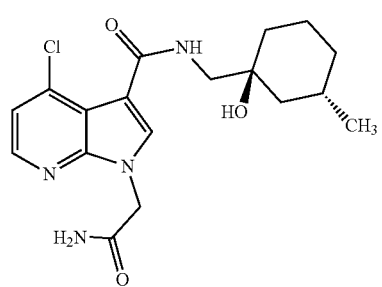 [SMILES: C[C@H]1CCC[C@@](O)(CNC(=O)c2cn(CC(N)=O)c3nccc(Cl)c23)C1] | 213 |
| 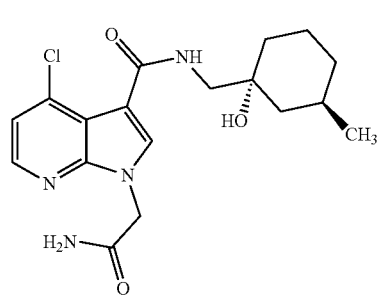 [SMILES: C[C@@H]1CCC[C@](O)(CNC(=O)c2cn(CC(N)=O)c3nccc(Cl)c23)C1] | 214 |
TABLE 1-continued
| | |
|---|---|
| 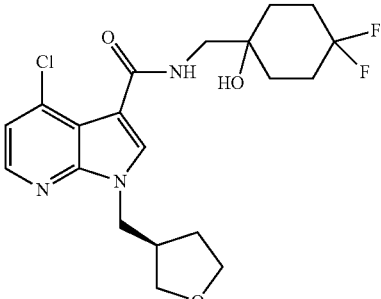 | 215 |
| 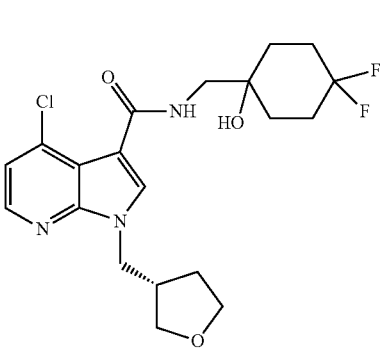 [SMILES: O=C(NCC1(O)CCC(F)(F)CC1)c1cn(C[C@@H]2CCOC2)c2nccc(Cl)c12] | 216 |
| 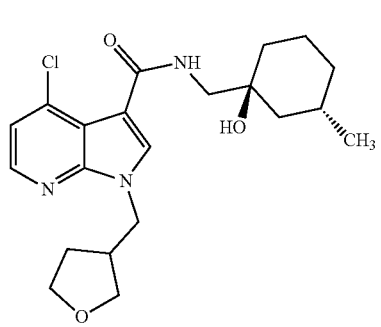 [SMILES: C[C@H]1CCC[C@@](O)(CNC(=O)c2cn(CC3CCOC3)c3nccc(Cl)c23)C1] | 217 |
| 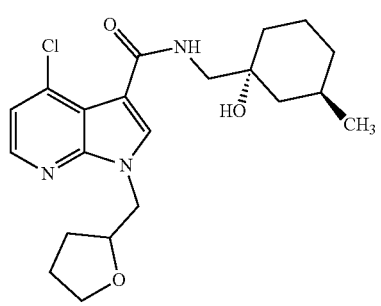 [SMILES: C[C@@H]1CCC[C@](O)(CNC(=O)c2cn(CC3CCCO3)c3nccc(Cl)c23)C1] | 218 |
| 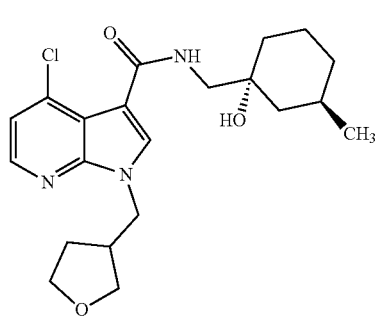 [SMILES: C[C@@H]1CCC[C@](O)(CNC(=O)c2cn(CC3CCOC3)c3nccc(Cl)c23)C1] | 219 |

TABLE 1-continued

TABLE 1-continued

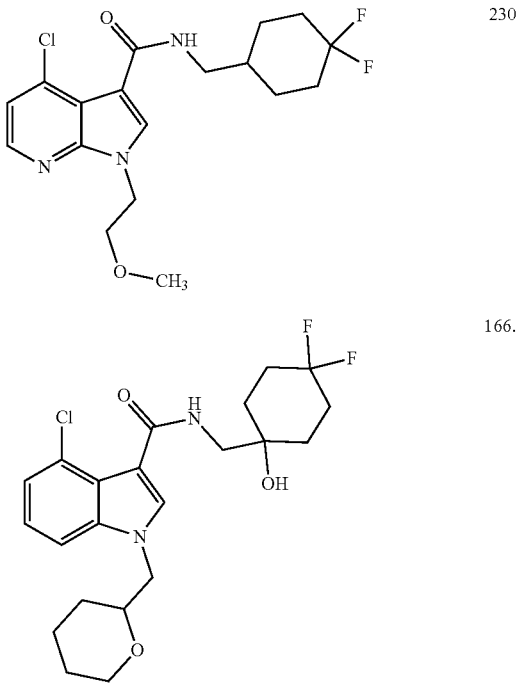

230

166.

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g.,

is understood to be

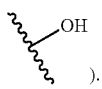

).

In certain embodiments, the compounds of the invention were synthesized in accordance with Schemes below. More specific examples of compounds made utilizing the Schemes are provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably modulate P2X7 in a biological sample or in a patient. In certain embodiments, the amount of compound in compositions of this invention is such that is effective to measurably modulate P2X7 in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation is also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In certain embodiments, the invention provides a method for antagonizing P2X7 in a positive manner in a patient or in a biological sample comprising the step of administering to said patient or contacting said biological sample with a compound according to the invention.

In certain embodiments, the invention is directed to the use of compounds of the invention and/or physiologically acceptable salts thereof, for antagonizing P2X7. The compounds are characterized by such a high affinity to P2X7, which ensures a reliable binding and preferably antagonization of P2X7. In certain embodiments, the substances are mono-specific in order to guarantee an exclusive and directed recognition with the single P2X7 target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is characterized by high affinity, high selectivity and minimal or even lacking cross-reactivity to other target molecules to exclude unhealthy and harmful impacts to the treated subject.

In certain embodiments, the present invention relates to a method for antagonizing P2X7 with at least one compound of formula (I) according to the invention and/or physiologically acceptable salts thereof, under conditions such that said P2X7 receptor is antagonized. In certain embodiments, the system is a cellular system. In other embodiments, the system is an in-vitro translation which is based on the protein synthesis without living cells. The cellular system is defined to be any subject provided that the subject comprises cells. Hence, the cellular system can be selected from the group of single cells, cell cultures, tissues, organs and animals. In certain embodiments, the method for antagonizing P2X7 is performed in-vitro. The prior teaching of the present specification concerning the compounds of formula (I), including any embodiments thereof, is valid and applicable without restrictions to the compounds according to formula (I) and their salts when used in the method for antagonizing P2X7. The prior teaching of the present specification concerning the compounds of formula (I), including any embodiments thereof, is valid and applicable without restrictions to the compounds according to formula (I) and their salts when used in the method for antagonizing P2X7.

In certain embodiments, the compounds according to the invention exhibit an advantageous biological activity, which is easily demonstrated in cell culture-based assays, for example assays as described herein or in prior art (cf. e.g. WO 2002/09706, which is incorporated herein by reference). In such assays, the compounds according to the invention preferably exhibit and cause an agonistic effect.

In certain embodiments, the invention provides a method for preventing, treating or ameliorating in a subject a disease, disorder, or condition that is causally related to the aberrant activity of P2X7 receptor, which comprises administering to the subject a therapeutically effective amount of a compound of any formulae herein, or a pharmaceutically acceptable salt thereof. In certain embodiments, the disease or disorder is an autoimmune, inflammatory or cardiovascular disease or disorder.

In certain embodiments, the disease or disorder is a neurodegenerative disease or disorder, including Parkinson's disease, multiple sclerosis (MS); Alzheimer's disease, diseases and disorders which are mediated by or result in neuroinflammation such as, for example traumatic brain injury, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; obesity; lipid disorders; cancer; blood pressure; spinal cord injury; and renal disorders.

In certain embodiments, the disease or disorder is pain, including acute, inflammatory and neuropathic pain, chronic pain, dental pain and headache including migraine, cluster headache and tension headache.

In certain embodiments, the disease or disorder is rheumatoid arthritis, osteoarthritis, psoriasis, allergic dermatitis, asthma, hyperresponsiveness of the airway, chronic obstructive pulmonary disease (COPD), bronchitis, septic shock, glomerulonephritis, irritable bowel disease, Crohn's disease, ulcerative colitis, atherosclerosis, growth and metastases of malignant cells, myoblastic leukaemia, diabetes, neurodegenerative disease, Alzheimer's disease, multiple sclerosis, meningitis, osteoporosis, burn injury, ischaemic heart disease, stroke, peripheral vascular disease, varicose veins, glaucoma, bipolar disorder, and neuropathic pain conditions such as diabetic neuropathy, post-herpetic neuralgia, low back pain, chemotherapy-induced neuropathic pain, fibromyalgia and spinal cord injury pain.

In certain embodiments, the present invention is used when the use of compounds which inhibit the P2X7 receptor are expected to improve pathological conditions. Such cases include, for example, prevention and therapy of swelling, exacerbation of pain and bone metabolism in rheumatoid arthritis, prevention and therapy of inflammatory bowel diseases, chronic obstructive pulmonary disease (COPD) and osteoarthritis, prevention and therapy of inflammatory pain and cancer pain and IL-1β-associated diseases such as Crohn's disease, emphysema, acute respiratory distress syndrome, adult respiratory distress syndrome, asthma, bronchitis, chronic pulmonary inflammatory diseases, silicosis, pulmonary sarcoidosis, allergic reactions, allergic contact hypersensitivity, eczema, contact dermatitis, psoriasis, sunburn, cancer, tissue ulceration, restenosis, periodontal disease, epidermolysis bullosa, osteoporosis, bone resorption disease, loosening of artificial joint implants, atherosclerosis, aortic aneurysm, congestive heart failure, myocardial infarction, stroke, cerebral ischemia, head trauma, neurotrauma, spinal cord injury, neurodegenerative disorder, Alzheimer's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, corneal scarring, scleritis, abnormal wound healing, burns, autoimmune diseases, Huntington's disease, diabetes, AIDS, cachexia, sepsis, septic shock, endotoxin shock, conjunctivitis shock, gram-negative sepsis, toxic shock syndrome, cerebral malaria, cardiac and renal reperfusion injury, thrombosis, glomerulonephritis, graft-versus-host reaction, homograft rejection, organ transplant toxicity, ulcerative colitis or muscle degeneration.

In certain embodiments, the present invention encompasses a method of treating a patient suffering from a mood disorder, including those suffering from a treatment resistant form of depression, comprising administering a therapeutically effective amount of a modulator of P2X7 receptor activity to a subject suffering from said affective disorder. It is understood that the mood disorder may be one among many of the disorders affecting mood and behavior. For example, mood disorders comprise depressive disorder (that includes major depressive disorder, dysthymic disorder), bipolar disorder (includes bipolar I disorder, bipolar II disorder, cyclothymic disorder), mood disorder due to a general medical condition and substance-induced mood disorder (American Psychiatric Association: Diagnostic and Statistical Manual of Mental Disorders (DSM-IV-TR), Fourth Edition, Text Revision. Washington, D.C., American Psychiatric Association, pages 345-428, 2000.). In certain embodiments, the disorder is a depressive disorder. The present invention also encompasses a method of treating a patient suffering from an anxiety disorder. Anxiety disorders include: panic attack, agoraphobia, specific phobia, social phobia, obsessive-compulsive disorder, posttraumatic stress disorder, acute stress disorder, and generalized anxiety disorder.

In certain embodiments, the disease or disorder is pain, selected from pain associated with postmastectomy pain syndrome, stump pain, phantom limb pain, oral neuropathic pain, Charcot's pain, toothache, venomous snake bite, spider bite, insect sting, postherpetic neuralgia, diabetic neuropathy, reflex sympathetic dystrophy, trigeminal neuralgia, osteoarthritis, rheumatoid arthritis, fibromyalgis, Guillain-Barre syndrome, meralgia paresthetica, burning-mouth syndrome, bilateral peripheral neuropathy, causalgia, sciatic neuritis, peripheral neuritis, polyneuritis, segmental neuritis, Gombault's neuritis, neuronitis, cervicobrachial neuralgia, cranial neuralgia, egniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia splenopalatine neuralgia, supraorbital neuralgia, vidian neuralgia, sinus headache, tension headache, labor, childbirth, intestinal gas, menstruation, cancer, and trauma.

In certain embodiments, the disease or disorder is associated with inflammation, including rheumatoid arthritis, osteoarthritis, uveitis, asthma, myocardial infarction, traumatic brain injury; septic shock, atherosclerosis, chronic pulmonary obstructive disease (COPD), acute spinal cord injury, inflammatory bowel disease and immune dysfunction In certain embodiments, the disease or disorder is associated with pain responses or imbalances in the maintenance of basal activity of sensory nerves. The amine compounds of the invention have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-mastectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In certain embodiments, the disease or disorder is arthritis, uveitis, asthma, myocardial infarction, traumatic brain injury, acute spinal cord injury, or inflammatory bowel disease.

In certain embodiments, the disease or disorder is MS.

In certain embodiments, the disease or disorder is Parkinson's disease.

In certain embodiments, the disease or disorder is rheumatoid arthritis.

In certain embodiments, the disease or disorder is traumatic brain injury.

In certain embodiments, the disease or disorder is pain.

In other embodiments, the invention provides compounds of the invention for use as a pharmaceutical especially in the treatment or prevention of the aforementioned conditions and diseases. Also provided herein is the use of the present compounds in the manufacture of a medicament for the treatment or prevention of one of the aforementioned conditions and diseases. The present invention also provides the use of a compound of the invention or a pharmaceutically acceptable salt thereof for the manufacture of a medicament for the treatment of conditions or diseases selected from P2X7 receptor mediated conditions or diseases.

When used to prevent the onset of a P2X7 related disease/disorder, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

A compound of Formula (I) of the present invention can be administered as sole active agent or can be adminstered in combination with other agents. These agents include non-steroidal anti-inflammatory drug (NSAIDS) such as celecoxib, rofecoxib, cimicoxib, etoricoxib, lumiracoxib, valdecoxib, deracoxib, N-(2-cyclohexyloxynitrophenyl) methane sulphonamide, COX189, ABT963, JTE-522, GW-406381, LAS-34475, CS-706, PAC-10649, SVT-2016, GW-644784, tenidap, acetylsalicylic acid (aspirin), amoxiprin, benorilate, choline magnesium salicylate, diflunisal, faislamine, methyl salicylate, magnesium salicylate, salicyl salicylate (salsalatee), diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, oxaprozin, tiaprofenic acid, suprofen, mefenamic acid, meclofenamic acid, phenylbutazone, azapropazone, metamizole, oxyphenbutazone, sulfinpyrazone, piroxicam, lornoxicam, meloxicam, tenoxicam, nimesulide, licofelone, or paracetamol.

A compound of Formula (I) of the present invention can be combined with agents such as TNFα inhibitors such as anti-TNF monoclonal antibodies (such as Remicade, CDP-870 and D2E7) and TNF receptor immunoglobulin molecules (such as Enbrel), low dose methotrexate, lefunomide; ciclesonide; hydroxychloroquine, d-penicillamine, auranofin or parenteral or oral gold.

A compound of Formula (I) of the present invention can also be administered in combination with an inhibitor of proTNFalpha convertase enzyme (TACE) such as 3-Amino-N-hydroxy-a-(2-methylpropyl)-3-[4-[(2-methyl-4-quinolinyl)methoxy]phenyl]-2-oxo-1-pyrrolidineacetamide, 2(S),3(S)-Piperidinedicarboxamide, N3-hydroxy-1-methyl-N2-[4-[(2-methyl-4-quinolinyl)methoxy]phenyl], 3-Thiomorpholinecarboxamide, 4-[[4-(2-butynyloxy)phenyl]sulfonyl]-N-hydroxy-2,2-dimethyl, 5-Hexenoic acid, 3-[(hydroxyamino)carbonyl]-2-(2-methylpropyl)-6-phenyl-,2-(2-methylpropyl)-2-(methylsulfonyl)hydrazide, (2R,3S,5E), 2-Piperidinecarboxamide, N,5-dihydroxy-1-[[4-(1-naphthalenylmethoxy)phenyl]sulfonyl]-, (2R,5R), Pentanamide, 3-(formylhydroxyamino)-4-methyl-2-(2-methylpropyl)-N-[(1S,2S)-2-methyl-1-[(2-pyridinylamino) carbonyl]butyl]-, (2R,3S),2-Propenamide, N-hydroxy-3-[3-[[(4-methoxyphenyl)sulfonyl](1-methylethyl)amino] phenyl]-3-(3-pyridinyl)-, (2E), Benzamide, N-(2,4-dioxo-1,3,7-triazaspiro[4.4]non-9-yl)-4-[(2-methyl-4-quinolinyl) methoxy], Benzamide, N-[(1-acetyl-4-piperidinyl)(2,5-dioxo-4-imidazolidinyl)methyl]-4-[(2-methyl-4-quinolinyl) methoxy], or 2,4-Imidazolidinedione, 5-methyl-5-[[[4-[(2-methyl-4-quinolinyl)methoxy]phenyl]sulfonyl]methyl].

A compound of Formula (I) of the present invention can also be administered in combination with a corticosteroid such as budesonide, corticosterone, cortisol, cortisone acetate, prednisone, prednisolone, methylprednisolone, dexamethasone, betamethasone, triamcinolone, beclometasone, fludrocortisone acetate, deoxycorticosterone acetate (doca), or aldosterone.

A compound of Formula (I) of the present invention can further be administered in combination with a b2-adrenergic receptor agonist such as formoterol, salbutamol (albuterol), levalbuterol, terbutaline, pirbuterol, procaterol, metaproterenol, fenoterol, bitolterol mesylate, salmeterol, bambuterol, or clenbuterol.

A compound of Formula (I) of the present invention can further be administered in combination with an antidepressant drug such as sertraline, escitalopram, fluoxetine, bupropion, paroxetine, venlafaxine, trazodone, amitriptyline, citalopram, duloxetine, mirtazapine, nortriptyline, imipramine, or lithium.

A compound of Formula (I) of the present invention can further be administered in combination with an antipsychotic drug such as chlorpromazine, fluphenazine, perphenazine, prochlorperazine, thioridazine, trifluoperazine, mesoridazine, promazine, triflupromazine, levomepromazine, promethazine, chlorprothixene, flupenthixol, thiothixene, zuclopenthixol, haloperidol, droperidol, pimozide, melperone, benperidol, triperidol, clozapine, olanzapine, risperidone, quetiapine, ziprasidone, amisulpride, paliperidone, bifeprunox, or aripiprazole.

A compound of Formula (I) of the present invention can also be administered in combination with a leukotriene biosynthesis inhibitor, 5-lipoxygenase (5-LO) inhibitor or 5-lipoxygenase activating protein (FLAP) antagonist, for example, zileuton; ABT-761; fenleuton; tepoxalin; nicaraven; VIA-2291; etalocib; ketoprofen, Abt-79175; Abt-85761; N-(5-substituted) thiophene-2-alkylsulfonamides; TDT-070; licofelone; PEP-03; tenoxicam; 2,6-di-tert-butylphenol hydrazones; methoxytetrahydropyrans such as Zeneca ZD-2138; the compound SB-210661; pyridinyl-substituted 2-cyanonaphthalene compounds such as L-739-010; 2-cyanoquinoline compounds such as L-746-530; indole and quinoline compounds such as MK-591, MK-886, and BAY×1005.

A compound of Formula (I) of the present invention can be administered in combination with a receptor antagonists for leukotrienes LTB4, LTC4, LTD4, and LTE, for example, phenothiazin-3-ones such as L-651.392; amidino compounds such as CGS-25019c; benzoxalamines such as ontezolast; benzenecarboximidamides such as BIIL 284/260; and compounds such as zafirlukast, ablukast, montelukast, praniukast, verlukast (MK-679), RG-12525, Ro-245913, iralukast (CGP 45715A), BAY×7195, and masilukast.

A compound of Formula (I) of the present invention can also be administered in combination with a PDE4 inhibitor including inhibitors of the isoform PDE4D.

A compound of Formula (I) of the present invention can also be administered in combination with a antihistaminic H1 receptor antagonists including cetirizine, loratadine, desloratadine, fexofenadine, astemizole, azelastine, and chlorpheniramine. A compound of Formula (I) of the present invention can further be administered in combination with a gastroprotective H2 receptor antagonist.

A compound of Formula (I) of the present invention can yet further be administered in combination with an a1- and a2-adrenoceptor agonist vasoconstrictor sympathomimetic agent, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

A compound of Formula (I) of the present invention can be administered in combination with anticholinergic agents including ipratropium bromide; tiotropium bromide; oxitropium bromide; pirenzepine; and telenzepine. The present invention still further relates to the combination of a compound of the invention together with a b1- to b4-adrenoceptor agonists including metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

A compound of Formula (I) of the present invention can be administered in combination with an insulin-like growth factor type I (IGF-1) mimetic.

A compound of Formula (I) of the present invention can be administered in combination with an inhaled glucocorticoid with reduced systemic side effects, including, prednisone, prednisolone, flunisolide, triamcinolone acetonide, beclomethasone dipropionate, budesonide, fluticasone propionate, and mometasone furoate.

A compound of Formula (I) of the present invention can be administered in combination with (a) tryptase inhibitors; (b) platelet activating factor (PAF) antagonists; (c) interleukin converting enzyme (ICE) inhibitors; (d) IMPDH inhibitors; (e) adhesion molecule inhibitors including VLA-4 antagonists; (f) cathepsins; (g) MAP kinase inhibitors; (h) glucose-6 phosphate dehydrogenase inhibitors; (i) kinin-B1- and B2-receptor antagonists; j) anti-gout agents, e.g., colchicine; (k) xanthine oxidase inhibitors, e.g., allopurinol; (l) uricosuric agents, e.g., probenecid, sulfinpyrazone, and benzbromarone; (m) growth hormone secretagogues; (n) transforming growth factor (TGFBβ); (o) platelet-derived growth factor (PDGF); (p) fibroblast growth factor, e.g., basic fibroblast growth factor (bFGF); (q) granulocyte macrophage colony stimulating factor (GM-CSF); (r) capsaicin cream; (s) Tachykinin NK1 and NK3 receptor antagonists such as NKP-608C; SB-233412 (talnetant); and D-4418; and (t) elastase inhibitors such as UT-77 and ZD-0892.

A compound of Formula (I) of the present invention can be administered in combination with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11).

A compound of Formula (I) of the present invention can be administered in combination with anticancer agents such as endostatin and angiostatin or cytotoxic drugs such as adriamycin, daunomycin, cis-platinum, etoposide, taxol, taxotere and farnesyl transferase inhibitors, VEGF inhibitors, COX-2 inhibitors and antimetabolites such as methotrexate antineoplastic agents, especially antimitotic drugs including the vinca alkaloids such as vinblastine and vincristine.

A compound of Formula (I) of the present invention can be administered in combination with antiviral agents such as Viracept, AZT, aciclovir and famciclovir, and antisepsis compounds such as Valant.

A compound of Formula (I) of the present invention can be administered in combination with cardiovascular agents such as calcium channel blockers, lipid lowering agents such as stating, fibrates, beta-blockers, ACE inhibitors, Angiotensin-2 receptor antagonists and platelet aggregation inhibitors.

A compound of Formula (I) of the present invention can be administered in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metrifonate.

A compound of Formula (I) of the present invention can be administered in combination with osteoporosis agents such as roloxifene, droloxifene, lasofoxifene or fosomax and immunosuppressant agents such as FK-506, rapamycin, cyclosporine, azathioprine, and methotrexate.

In certain embodiments, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX3CR1 for the C—X3-C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746, 530; or an indole or quinoline compound such as MK-591, MK-886, and BAY×1005.

The present invention further relates to the combination of a compound of the invention, or a pharmaceutically acceptable salt thereof, and a receptor antagonist for leukotrienes (LT) B4, LTC4, LTD4, and LTE4. Selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY×7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs, for example rosiglitazone.

The present invention further relates to the combination of a compound of the invention, or a pharmaceutically acceptable salt thereof with gabapentin, lidoderm, pregablin and equivalents and pharmaceutically active isomer(s) and metabolite(s) thereof.

The present invention further relates to the combination of a compound of the invention, or a pharmaceutically acceptable salt thereof with celecoxib, etoricoxib, lumiracoxib, rofecoxib, valdecoxib, diclofenac, loxoprofen, naproxen, paracetamol and equivalents and pharmaceutically active isomer(s) and metabolite(s) thereof.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, gabapentin, pregabalin, phenyloin, sodium valproate, amitryptiline or other anti-depressant agent-s, paracetamol, CB 1 agonist, muscarinic agonist, TRPV-1 antagonist, mGluR5 agonist or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B1- or B2-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK1 or NK3 receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), or (xxvi) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin); (ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride; (iii) an agent which inhibits cancer cell invasion (for example a metalloproteinase inhibitor like marimastat or an inhibitor of urokinase plasminogen activator receptor function); (iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI-1033)), an inhibitor of the platelet-derived growth factor family, or an inhibitor of the hepatocyte growth factor family; (v) an antiangiogenic agent such as one which inhibits the effects of vascular endothelial growth factor (for example the anti-vascular endothelial cell growth factor antibody bevacizumab, linomide, an inhibitor of integrin αvβ function or an angiostatin); (vi) a vascular damaging agent such as combretastatin A4; (vii) an agent used in antisense therapy, for example one directed to one of the targets listed above, such as ISIS 2503, an anti-ras antisense; (viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to antagonize P2X7 activity, usually between about one hour and one week. In-vitro treatment can be carried out using cultivated cells from a biopsy sample or cell line.

The host or subject can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, suitable models or model systems have been developed, for example cell culture models and models of transgenic animals. For the determination of certain stages in the signal transduction cascade, interacting compounds can be utilized in order to modulate the signal. The compounds according to the invention can also be used as reagents for testing P2X7-dependent signal transduction pathways in animals and/or cell culture models or in the clinical diseases mentioned in this application.

The use according to the previous paragraphs of the specification may be either performed in-vitro or in-vivo models. The modulation can be monitored by the techniques described in the course of the present specification. In certain embodiments, the in-vitro use is preferably applied to samples of humans suffering from P2X7-related disorders. Testing of several specific compounds and/or derivatives thereof makes the selection of that active ingredient possible that is best suited for the treatment of the human subject. The in-vivo dose rate of the chosen derivative is advantageously pre-adjusted to the P2X7 susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the antagonism of P2X7 activity if expedient.

The invention also relates to the use of compounds according to formula (I) and/or physiologically acceptable salts thereof for the prophylactic or therapeutic treatment and/or monitoring of diseases that are caused, mediated and/or propagated by P2X7 activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by P2X7 activity. In certain embodiments, the invention provides the use of a compound according to formula I or physiologically acceptable salts thereof, for the production of a medicament for the prophylactic or therapeutic treatment of a P2X7-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to booster the response and eradicate the pathogens and/or symptoms of the disease completely. Either the identical compound or different compounds can be applied. The methods of the invention can also be used to reducing the likelihood of developing a disorder or even prevent the initiation of disorders associated with P2X7 activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously passed disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with P2X7 activity, in such a way that a pathogenic modification of their overall condition or of the condition of particular regions of the organism could establish at least temporarily.

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention can also be utilized as commercial research reagents for various medical research and diagnostic uses. Such uses can include but are not limited to: use as a calibration standard for quantifying the activities of candidate P2X7 antagonists in a variety of functional assays; use as blocking reagents in random compound screening, i.e. in looking for new families of P2X7 receptor ligands, the compounds can be used to block recovery of the presently claimed P2X7 compounds; use in the co-crystallization with P2X7 receptor, i.e. the compounds of the present invention will allow formation of crystals of the compound bound to P2X7, enabling the determination of receptor/compound structure by x-ray crystallography; other research and diagnostic applications, etc.; use in assays as probes for determining the expression of P2X7 on the surface of cells; and developing assays for detecting compounds which bind to the same site as the P2X7 binding ligands.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Antagonism of P2X7 activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Compound numbers utilized in the Examples below correspond to compound numbers set forth supra.

$^1$H NMR was recorded on a Bruker 400 MHz spectrometer, using residual signal of deuterated solvent as internal reference. Chemical shifts (δ) are reported in ppm relative to the residual solvent signal (δ=2.49 ppm for 1H NMR in DMSO-d6). 1H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

LCMS-Analysis was performed under the following conditions:

Method A (Rapid LC): A Shimadzu Shim-pack XR-ODS, 3.0×30 mm, 2.2 μm, was used at a temperature of 50° C. and at a flow rate of 1.5 mL/min, 2 uL injection, mobile phase: (A) water with 0.1% formic acid and 1% acetonitrile, mobile phase (B) methanol with 0.1% formic acid; retention time given in minutes. Method details: (I) runs on a Binary Pump G1312B with UV/Vis diode array detector G1315C and Agilent 6130 mass spectrometer in positive and negative ion electrospray mode with UV-detection at 220 and 254 nm with a gradient of 15-95% (B) in a 2.2 min linear gradient (II) hold for 0.8 min at 95% (B) (III) decrease from 95-15% (B) in a 0.1 min linear gradient (IV) hold for 0.29 min at 15% (B).

Method B: A: 0.1% TFA in H$_2$O, B: 0.1% TFA in ACN:
Runtime: 6.5 min
Flow Rate: 1.0 mL/min
Gradient: 5-95% B in 4.5 min, wavelength 254 and 215 nM.
Column: Waters Sunfire C18, 3.0×50 mm, 3.5 um, +ve mode
Mass Scan: 100-900 Da Chiral analysis/separation condition:
Mobile Phase: Hexane:EtOH:DEA=70:30:0.1; Flow Rate: 1.0 mL/min; Runtime: 25 min
Column: CHIRALPAK AY-H (250×4.6 mm, 5 μm).

Chiral analysis/separation condition:
Column: AS-H (250*4.6 mm 5 μm)
Mobile Phase: Hexane:ETOH:DEA=90:10:0.1
Flow: 1 ml/min
Temperature: 40
Runtime: 30 min Chiral-HPLC conditions:
Co-Solvent: 30% MeOH; Column: AD-H (4.6*250 mm, 5 um); CO$_2$ Flow Rate: 2.1 mL/min
Co-Solvent Flow Rate: 0.9 mL/min; Total Flow: 3 mL/min; Runtime: 9 min Example 1: Preparation of 4-chloro-N-((4,4-difluorocyclohexyl)methyl)-1-(2,2,2-trifluoroethyl)-1H-indole-3-carboxamide (5)

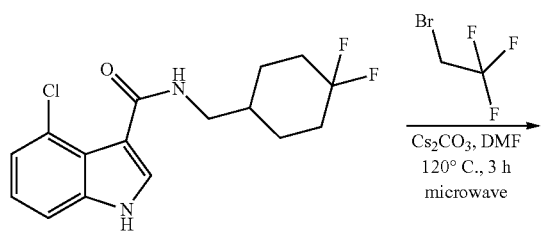

-continued

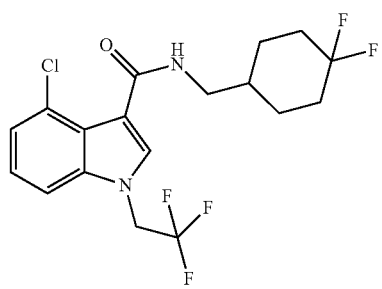

A mixture of 4-chloro-N-((4,4-difluorocyclohexyl)methyl)-1H-indole-3-carboxamide (0.163 g, 0.50 mmol), 2-bromo-1,1,1-trifluoroethane (0.204 g, 1.25 mmol) and Cs$_2$CO$_3$ (489 mg, 1.50 mmol) in anhydrous DMF (2 ml) was stirred at 120° C. for 30 min under microwave irradiation. The reaction mixture was diluted with EtOAc (20 mL) and washed with water (3×20 mL). The separated organic layer was dried over Na$_2$SO$_4$ and concentrated in vacuo. The residue was purified by Prep-HPLC to give 4-chloro-N-((4,4-difluorocyclohexyl)methyl)-1-(2,2,2-trifluoroethyl)-1H-indole-3-carboxamide (0.067 g, 33%) as white solid. $^1$H NMR (500 MHz, DMSO-d$_6$) δ 8.29-8.27 (m, 1H), 7.73 (s, 1H), 7.68-7.66 (m, 1H), 7.28-7.20 (m, 2H), 5.32-5.27 (m, 2H), 3.17-3.15 (m, 2H), 2.04-2.02 (m, 2H), 1.85-1.70 (m, 5H) 1.29-1.24 (m, 2H) ppm; [M+H]$^+$ 409.1; LC-MS (254 nm) Purity: 97.98%; $t_R$=2.10 min; HPLC (254 nm) Purity: >99%; $t_R$=10.10 min.

Example 2: Preparation of 4-chloro-N-((4,4-difluoro-1-hydroxycyclohexyl) methyl)-1-(2,2,2-trifluoroethyl)-1H-indole-3-carboxamide (4)

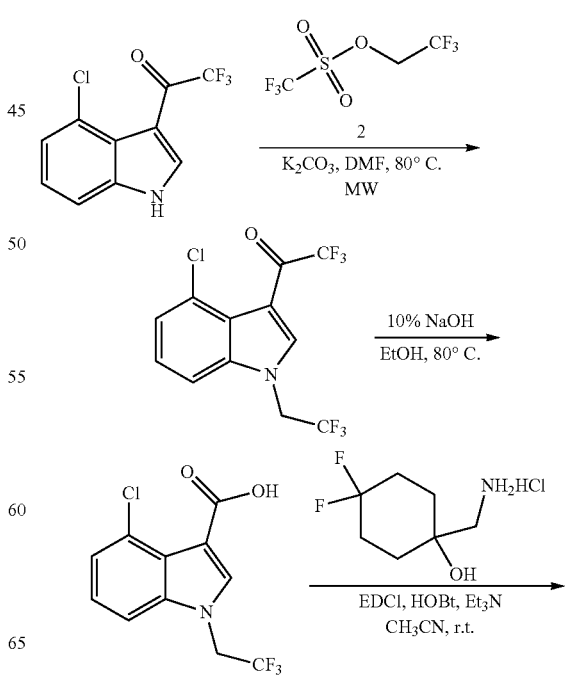

-continued

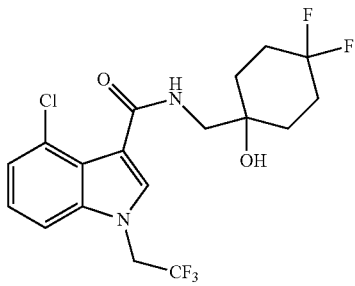

Step 1: Preparation of 1-(4-chloro-1-(2,2,2-trifluoroethyl)-1H-indol-3-yl)-2,2,2-trifluoro-ethanone

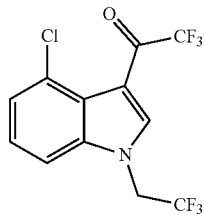 [SMILES: O=C(c1cn(CC(F)(F)F)c2cccc(Cl)c12)C(F)(F)F]

A mixture of 1-(4-chloro-1H-indol-3-yl)-2,2,2-trifluoroethanone (0.500 g, 2.0 mmol), 2,2,2-trifluoroethyl trifluoromethanesulfonate (0.57 mL, 4.0 mmol), K$_2$CO$_3$ (0.828 g, 6.0 mmol) and DMF (2 mL) was stirred at 80° C. for 50 min under microwave condition. The mixture was cooled to room temperature, partitioned between water (30 mL) and EtOAc (80 mL). The separated organic layer was dried over anhydrous Na$_2$SO$_4$, filtered and concentrated to give the title compound (0.600 g, 90%) as a green solid.

Step 2: Preparation of 4-chloro-1-(2,2,2-trifluoroethyl)-1H-indole-3-carboxylic acid

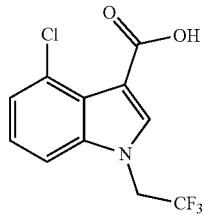 [SMILES: O=C(O)c1cn(CC(F)(F)F)c2cccc(Cl)c12]

A mixture of 1-(4-chloro-1-(2,2,2-trifluoroethyl)-1H-indol-3-yl)-2,2,2-trifluoroethanone (0.600 g, 1.8 mmol), EtOH (10 mL) and 10% NaOH (4 mL) was stirred at 80° C. for 2 h. The mixture was partitioned between water (50 mL) and EtOAc (30 mL). The aqueous phase was adjusted to pH 5 with 1 M HCl and then extracted with EtOAc (100 mL). The separated organic layer was dried over anhydrous Na$_2$SO$_4$, filtered and concentrated to give 4-chloro-1-(2,2,2-trifluoroethyl)-1H-indole-3-carboxylic acid (0.377 g, 75%) as a white solid.

Step 3: Preparation of 4-chloro-N-((4,4-difluoro-1-hydroxycyclohexyl)methyl)-1-(2,2,2-trifluoroethyl)-1H-indole-3-carboxamide

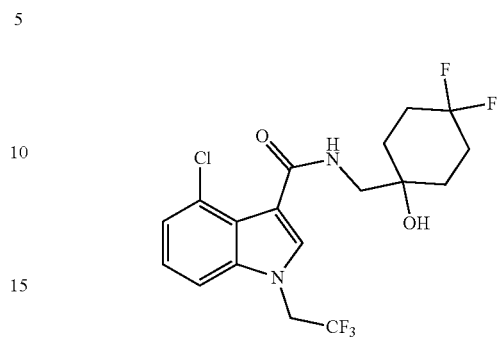

A mixture of 4-chloro-1-(2,2,2-trifluoroethyl)-1H-indole-3-carboxylic acid (0.100 g, 0.36 mmol), 1-(aminomethyl)-4,4-difluorocyclohexanol (0.060 g, 0.36 mmol), EDCI (0.084 g, 0.47 mmol), HOBt (0.064 g, 0.47 mmol) and Et$_3$N (1.5 mL) in CH$_3$CN (20 mL) was stirred at room temperature overnight. The reaction was quenched with water (20 mL) and extracted with DCM (100 mL). The separated organic layer was dried over MgSO$_4$, filtered, concentrated to dryness, and the residue was purified by column chromatography on silica gel (EtOAc:petroleum ether=2:1) to give 4-chloro-N-((4,4-difluoro-1-hydroxycyclohexyl)methyl)-1-(2,2,2-trifluoroethyl)-1H-indole-3-carboxamide (0.052 g, 35%) as a white solid.
$^1$H NMR (500 MHz, DMSO-d$_6$): δ 8.14 (t, J=6.0 Hz, 1H), 7.79 (s, 1H), 7.68 (d, J=8.0 Hz, 1H), 7.29-7.22 (m, 2H), 5.30 (q, J=9.0 Hz, 2H), 4.71 (s, 1H), 3.32 (s, 2H), 2.08-1.88 (m, 4H), 1.66-1.64 (m, 4H) ppm; [M+H]$^+$ 425.1; LC-MS: Purity (254 nm): 98%; t$_R$=1.44 min; HPLC Purity (254 nm): 99%; t$_R$=4.43 min.

Example 3: Preparation of 4-chloro-N-(((1R,3R)-1-hydroxy-3-methylcyclo-hexyl)methyl)-1-(2,2,2-trifluoroethyl)-1H-indole-3-carboxamide (3)

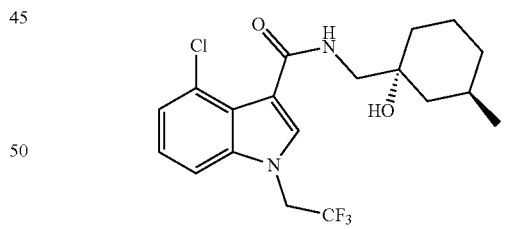

The title compound was synthesized according to the procedure described in Example 2 using a mixture of 4-chloro-1-(2,2,2-trifluoroethyl)-1H-indole-3-carboxylic acid (0.100 g, 0.36 mmol), (1S,3S)-1-(aminomethyl)-3-methylcyclohexanol (0.052 g, 0.36 mmol), EDCI (0.084 g, 0.47 mmol), HOBt (0.064 g, 0.47 mmol) and Et$_3$N (1.5 mL) in CH$_3$CN (2.0 mL), to provide 4-chloro-N-(((1R,3R)-1-hydroxy-3-methylcyclo-hexyl)methyl)-1-(2,2,2-trifluoroethyl)-1H-indole-3-carboxamide (0.060 g, 41%) as a white solid.
$^1$H NMR (500 MHz, DMSO-d$_6$) δ 7.95 (t, J=6.0 Hz, 1H), 7.79 (s, 1H), 7.67 (d, J=7.5 Hz, 1H), 7.29-7.21 (m, 2H), 5.33-5.27 (q, J=9.3 Hz, 2H), 4.23 (s, 1H), 3.20 (d, J=6.0 Hz, 2H), 1.73-1.71 (m, 1H), 1.61-1.45 (m, 5H), 1.27-1.21 (m, 1H), 0.99-0.95 (m, 1H), 0.83 (d, J=6.5 Hz, 3H), 0.80-0.75 (m, 1H) ppm; [M+H]⁺ 403.1; LC-MS Purity (254 nm): 98%; $t_R$=1.51 min; HPLC Purity (254 nm): 99%; $t_R$=4.74 min.

Example 4: Preparation of 4-chloro-N-(((1S,3S)-1-hydroxy-3-methylcyclohexyl) methyl)-1-(2,2,2-trifluoroethyl)-1H-indole-3-carboxamide (2)

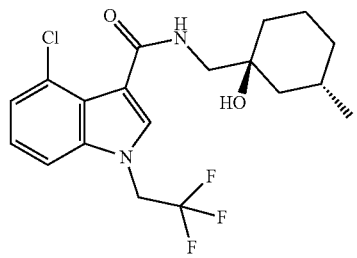 [SMILES: C[C@H]1CCC[C@@](O)(CNC(=O)c2cn(CC(F)(F)F)c3cccc(Cl)c23)C1]

The title compound was synthesized according to the procedure described in Example 2 using a mixture of 4-chloro-1-(2,2,2-trifluoroethyl)-1H-indole-3-carboxylic acid (0.100 g, 0.36 mmol), (1S,3S)-1-(aminomethyl)-3-methylcyclohexanol (0.052 g, 0.36 mmol), EDCI (0.083 g, 0.43 mmol), HOBt (0.059 g, 0.84 mmol), and DIPEA (0.186 g, 1.44 mmol) in DCM (10 mL) to provide 4-chloro-N-(((1S,3S)-1-hydroxy-3-methylcyclohexyl)methyl)-1-(2,2,2-trifluoroethyl)-1H-indole-3-carboxamide (0.085 g, 73%) as a white solid.

¹H NMR (500 MHz, DMSO-d₆) δ 7.96 (t, J=6.0 Hz, 1H), 7.79 (s, 1H), 7.67 (d, J=8.0 Hz, 1H), 7.29-7.21 (m, 2H), 5.33-5.27 (m, 2H), 4.23 (s, 1H), 3.20 (t, J=6.5 Hz, 2H), 1.73-1.45 (m, 6H), 1.28-1.20 (m, 1H), 1.00-0.94 (m, 1H), 0.84-0.82 (m, 3H), 0.80-0.74 (m, 1H) ppm; [M+H]⁺ 403.1.

Example 5: 4-chloro-N-((3,3-difluoro-1-hydroxy-5-methylcyclohexyl)methyl)-1-(2,2,2-trifluoroethyl)-1H-indole-3-carboxamide (1) (HATU Coupling Example)

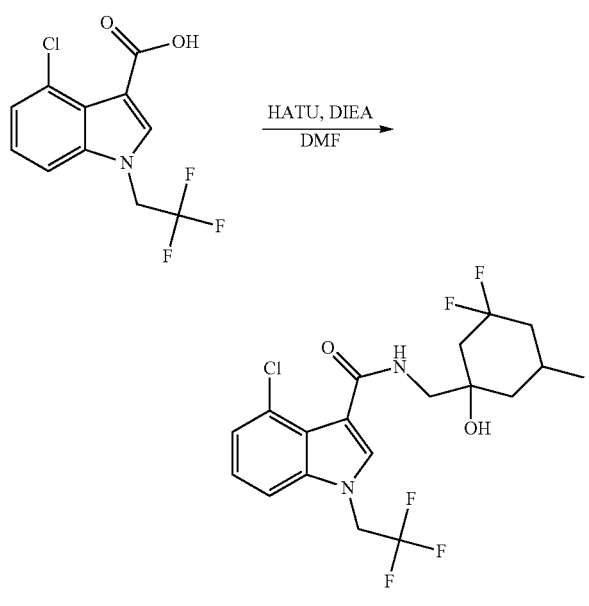

To a stirred solution of 4-Chloro-1-(2,2,2-trifluoro-ethyl)-1H-indole-3-carboxylic acid (200.00 mg; 0.72 mmol; 1.00 eq.), HATU (301.31 mg; 0.79 mmol; 1.10 eq.) and 1-Aminomethyl-3,3-difluoro-5-methyl-cyclohexanol (142.01 mg; 0.79 mmol; 1.10 eq.) in DMF (3 ml) was added DIEA (0.38 ml; 2.16 mmol; 3.00 eq.). The mixture was stirred at room temperature overnight. Then the reaction was quenched with water (15 mL), and extracted with DCM/methanol (10:1, 30 mL×3). The combined organic layer was washed with water (20 mL×2), brine (20 mL×2), dried over sodium sulfate, filtered and concentrated in vacuo. The residue was purified by column chromatography on silica gel (DCM:methanol=80:1) to obtain 4-chloro-N-((3,3-difluoro-1-hydroxy-5-methylcyclohexyl)methyl)-1-(2,2,2-trifluoroethyl)-1H-indole-3-carboxamide (62, 20%) as a white solid. [M+H]⁺ 439.

Example 6: Preparation of 4-chloro-N-((4,4-difluorocyclohexyl)methyl)-1-(3,3,3-trifluoropropyl)-1H-indole-3-carboxamide (37)

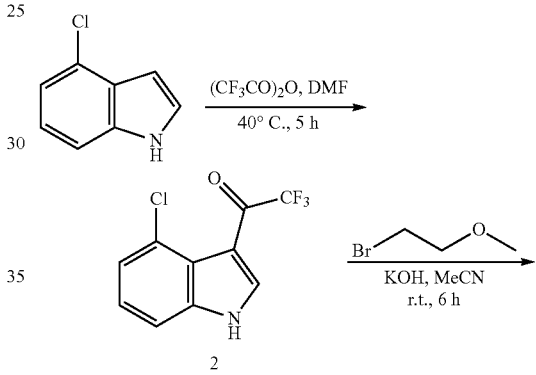

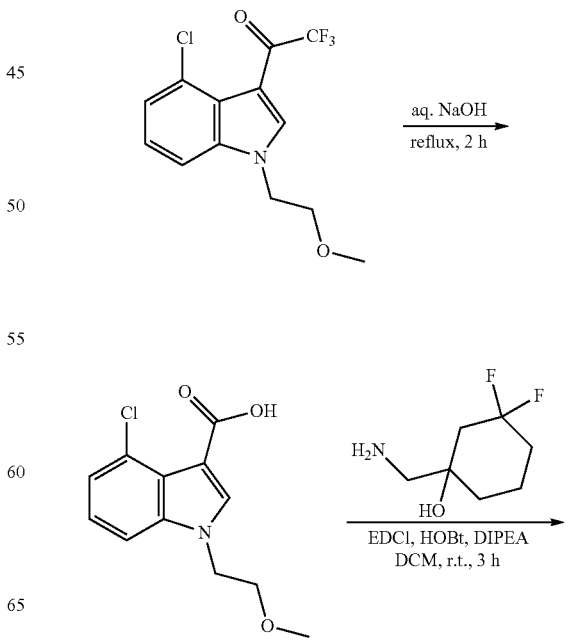

-continued

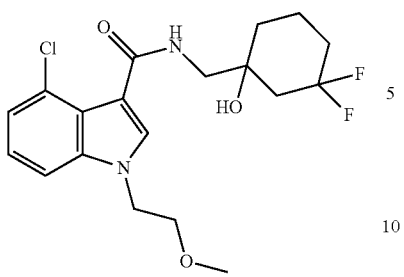

Step 1: Preparation of 1-(4-chloro-1H-indol-3-yl)-2,2,2-trifluoroethanone

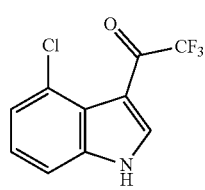 [SMILES: O=C(c1c[nH]c2cccc(Cl)c12)C(F)(F)F]

To a solution of 4-chloro-1H-indole (10.0 g, 66.2 mmol) in DMF (25 mL) was added 2,2,2-trifluoroacetic anhydride (14 ml, 100 mmol) at 0° C. The reaction was heated to 40° C. for 5 h, then cooled to room temperature and water (50 mL) was added. The precipitate was collected by filtration, dried in vacuo to give 1-(4-chloro-1H-indol-3-yl)-2,2,2-trifluoroethanone (12.8 g, 78.8%), which was used in the next run without further purification. LCMS m/z: 248.1 [M+H]$^+$.

Step 2: Preparation of 1-(4-chloro-1-(2-methoxyethyl)-1H-indol-3-yl)-2,2,2-trifluoro ethanone

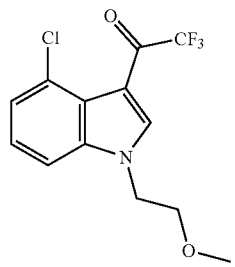 [SMILES: COCCn1cc(C(=O)C(F)(F)F)c2c(Cl)cccc21]

To a mixture of 1-(4-chloro-1H-indol-3-yl)-2,2,2-trifluoroethanone (5.00 g, 20.2 mmol), KOH (1.70 g, 29.8 mmol) in CH$_3$CN (20 mL) was added 1-bromo-2-methoxyethane (4.2 g, 30.4 mmol) at room temperature. The reaction was stirred at room temperature for 6 h, and then water (50 mL) was added. The precipitate was collected by filtration and dried in vacuo to give 1-(4-chloro-1-(2-methoxyethyl)-1H-indol-3-yl)-2,2,2-trifluoroethanone (6.4 g, 61.2%) as a white solid, which was used in the next step without further purification. LCMS m/z: 306.1 [M+H]$^+$.

Step 3: Preparation of 4-chloro-1-(2-methoxyethyl)-1H-indole-3-carboxylic acid

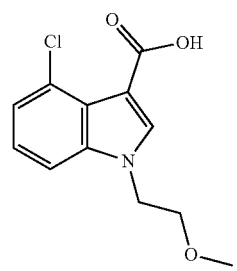 [SMILES: COCCn1cc(C(=O)O)c2c(Cl)cccc21]

A mixture of 1-(4-chloro-1-(2-methoxyethyl)-1H-indol-3-yl)-2,2,2-trifluoroethanone (0.100 g, 0.33 mmol) and 30% aqueous NaOH (5.0 mL) was heated to 105° C. for 2 h, and then cooled to room temperature. The aqueous solution was adjusted to pH 3 with concentrated HCl. The precipitate was collected, dried in vacuo to give 4-chloro-1-(2-methoxyethyl)-1H-indole-3-carboxylic acid (0.051 g, 61.0%) as a white solid, which was used in the next step without further purification. LCMS m/z: 254.1 [M+H]+.

Step 4: Preparation of 4-chloro-N-((3,3-difluoro-1-hydroxycyclohexyl)methyl)-1-(2-methoxyethyl)-1H-indole-3-carboxamide

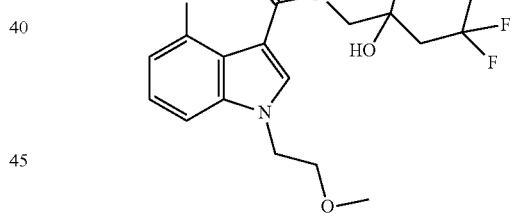

The title compound was synthesized according to the procedure described in Example 2 using 4-chloro-1-(2-methoxyethyl)-1H-indole-3-carboxylic acid (0.050 g, 0.198 mmol), EDCI (0.049 g, 0.257 mmol), HOBt (0.0347 g, 0.257 mmol), TEA (0.1 mL) and 1-(aminomethyl)-3,3-difluorocyclohexanol (0.0354 g, 0.198 mmol) in DCM to provide 4-chloro-N-((3,3-difluoro-1-hydroxycyclohexyl)methyl)-1-(2-methoxyethyl)-1H-indole-3-carboxamide (0.044 g, 50.6%) as a light-yellow solid.

$^1$H NMR (500 MHz, DMSO-d$_6$) δ 7.91 (t, J=6.0 Hz, 1H), 7.80 (s, 1H), 7.57 (d, J=8.0 Hz, 1H), 7.19 (t, J=8.0 Hz, 1H), 7.15 (d, J=7.5 Hz, 1H), 4.69 (s, 1H), 4.39 (t, J=5.0 Hz, 2H), 3.67 (t, J=5.0 Hz, 2H), 3.40-3.35 (m, 2H), 3.25 (s, 3H), 2.02-1.89 (m, 3H), 1.76-1.71 (m, 2H), 1.61-1.47 (m, 3H) ppm; [M+H]$^+$ 401.1.

Example 7: (R)-4-chloro-N-((3,3-difluoro-1-hydroxycyclohexyl)methyl)-1-(2-methoxyethyl)-1H-indole-3-carboxamide (21)

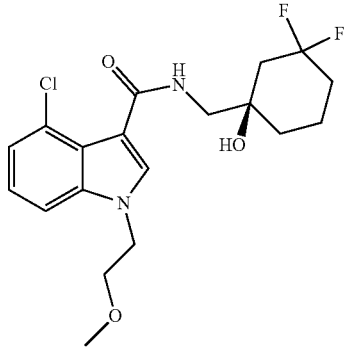 [SMILES: COCCn1cc(C(=O)NC[C@@]2(O)CCCC(F)(F)C2)c2c(Cl)cccc21]

130 mg of 4-chloro-N-((3,3-difluoro-1-hydroxycyclohexyl)methyl)-1-(2-methoxy ethyl)-1H-indole-3-carboxamide was separated to obtain 57 mg of the title compound. [M+H]⁺ 401.1. Chiral-HPLC conditions: Co-Solvent: 30% MeOH; Column: AD-H (4.6*250 mm, 5 um) CO₂ Flow Rate: 2.1 mL/min; Co-Solvent Flow Rate: 0.9 mL/min; Total Flow: 3 mL/min Runtime: 9 min.

Example 8: (S)-4-chloro-N-((3,3-difluoro-1-hydroxycyclohexyl)methyl)-1-(2-methoxyethyl)-1H-indole-3-carboxamide (20)

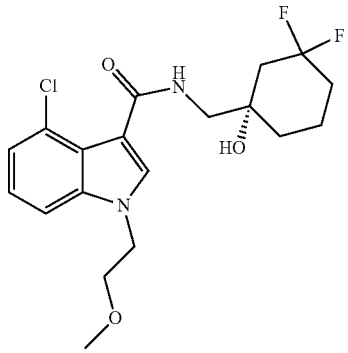 [SMILES: COCCn1cc(C(=O)NC[C@]2(O)CCCC(F)(F)C2)c2c(Cl)cccc21]

130 mg of 4-chloro-N-((3,3-difluoro-1-hydroxycyclohexyl)methyl)-1-(2-methoxy ethyl)-1H-indole-3-carboxamide was separated to obtain 56 mg of the title compound. [M+H]⁺ 401. (For separation, see example 7)

Example 9: Preparations of 4-chloro-N-((4,4-difluorocyclohexyl)methyl)-1-(2-methoxyethyl)-1H-indole-3-carboxamide (41)

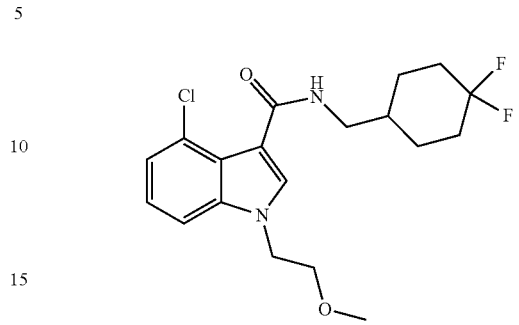

The title compound was synthesized according to the procedure described in Example 5 using 4-chloro-1-(2-methoxyethyl)-1H-indole-3-carboxylic acid (0.300 g, 1.18 mmol), HATU (0.450 g, 1.18 mmol), (4,4-difluorocyclohexyl)methanamine (0.177 g, 1.18 mmol) and DIPEA (0.306 g, 0.4 mL, 2.37 mmol) in DMF (4.0 mL) to afford 4-chloro-N-((4,4-difluorocyclohexyl)methyl)-1-(2-methoxyethyl)-1H-indole-3-carboxamide (0.330 g, 72%) as an off white solid.

¹H NMR (500 MHz, CDCl₃) δ 7.87 (s, 1H), 7.33 (d, J=8.0 Hz, 1H), 7.22-7.15 (m, 2H), 6.83 (brs, 1H), 4.28 (t, J=5.0 Hz, 2H), 3.71 (t, J=5.0 Hz, 2H), 3.40 (t, J=6.5 Hz, 2H), 3.30 (s, 3H), 2.14-2.09 (m, 2H), 1.91-1.89 (m, 2H), 1.78-1.66 (m, 3H), 1.43-1.35 (m, 2H) ppm; [M+H]⁺ 384.9.

Example 10: 4-chloro-N-((4,4-difluoro-1-hydroxycyclohexyl)methyl)-1-(2-methoxyethyl)-1H-indole-3-carboxamide (40)

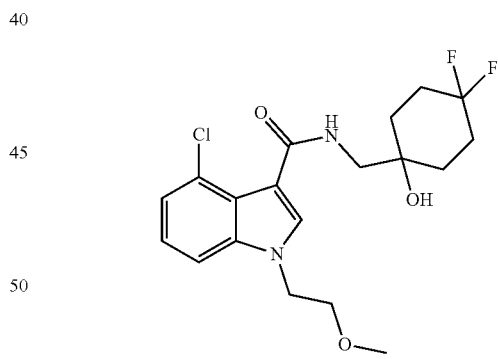

The title compound was synthesized according to the procedure described in Example 5 using 4-chloro-1-(2-methoxyethyl)-1H-indole-3-carboxylic acid and 1-(aminomethyl)-4,4-difluorocyclohexanol, HATU and DIEA.

¹H NMR (500 MHz, DMSO-d₆) δ 7.97 (t, J=6.0 Hz, 1H), 7.77 (s, 1H), 7.56 (d, J=8.0 Hz, 1H), 7.19-7.13 (m, 2H), 4.75 (s, 1H), 4.38 (t, J=5.0 Hz, 2H), 3.66 (t, J=5.5 Hz, 2H), 3.30 (d, J=7.0 Hz, 2H), 3.21 (s, 3H), 2.06-1.95 (m, 2H), 1.89-1.84 (m, 2H), 1.64-1.62 (m, 4H) ppm; [M+H]⁺ 400.8.

Example 11: Preparation of 4-Chloro-1-(2-methoxy-ethyl)-1H-indole-3-carboxylic acid (4,4-difluoro-1-methoxy-cyclohexylmethyl)-amide (17)

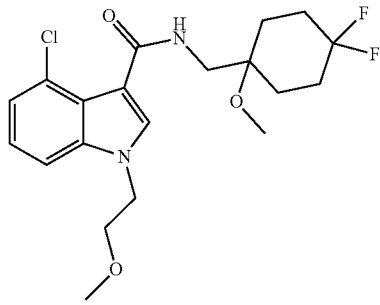 [SMILES: COCCn1cc(C(=O)NCC2(OC)CCC(F)(F)CC2)c2c(Cl)cccc21]

The title compound was synthesized according to the procedure described in Example 2 using 4-Chloro-1-(2-methoxy-ethyl)-1H-indole-3-carboxylic acid (90 mg, 0.35 mmol, 1.00 eq), C-(4,4-Difluoro-1-methoxy-cyclohexyl)-methylamine hydrochloride (114 mg, 0.53 mmol, 1.50 eq), EDC (115.62 mg, 0.60 mmol, 1.70 eq), Benzotriazol-1-ol (76 mg, 0.56 mmol, 1.60 eq) and DIPEA (0.33 mL, 1.93 mmol, 5.50 eq) in dry THF (10 mL, 111.11 V) to afford 4-Chloro-1-(2-methoxy-ethyl)-1H-indole-3-carboxylic acid (4,4-difluoro-1-methoxy-cyclohexylmethyl)-amide (41 mg, 0.10 mmol, 28.5%) as a white solid.

$^1$H NMR (400 MHz, DMSO-d$_6$): δ 7.92 (t, J=6.40 Hz, 1H), 7.72 (s, 1H), 7.54 (m, 1H), 7.19-7.12 (m, 2H), 4.37 (t, J=5.20 Hz, 2H), 3.65 (t, J=5.20 Hz, 2H), 3.40-3.37 (m, 2H), 3.21 (s, 3H), 3.18 (s, 3H), 1.90-1.83 (m, 6H), 1.59-1.54 (m, 2H) ppm; [M+H]$^+$ 415.2.

Example 12: Preparation of 4-Chloro-1-(2-methoxy-ethyl)-1H-indole-3-carboxylic acid (1-hydroxy-cyclohexyl methyl)-amide (19)

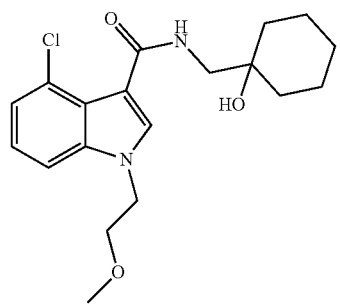 [SMILES: COCCn1cc(C(=O)NCC2(O)CCCCC2)c2c(Cl)cccc21]

The title compound was synthesized according to the procedure described in Example 2 using 4-Chloro-1-(2-methoxy-ethyl)-1H-indole-3-carboxylic acid (100 mg, 0.39 mmol, 1.00 eq), 1-Aminomethylcyclohexanol hydrochloride (97 mg, 0.59 mmol, 1.50 eq), EDC (128 mg, 0.66 mmol, 1.70 eq), Benzotriazol-1-ol (85 mg, 0.62 mmol, 1.60 eq) and DIPEA (0.37 mL, 2.15 mmol, 5.50 eq) in dry THF (10 mL, 100 V) to afford 4-Chloro-1-(2-methoxy-ethyl)-1H-indole-3-carboxylic acid (1-hydroxy-cyclohexyl methyl)-amide (60 mg, 0.16 mmol, 41.8%) as a white solid.

$^1$H NMR (400 MHz, DMSO-d$_6$): δ 7.78 (s, 1H), 7.73 (t, J=5.96 Hz, 1H), 7.55 (dd, J=1.24, 7.86 Hz, 1H), 7.19-7.12 (m, 2H), 4.39-4.36 (m, 3H), 3.67-3.64 (m, 2H), 3.25-3.21 (m, 5H), 1.57-1.51 (m, 2H), 1.48-1.37 (m, 7H), 2.26-1.24 (m, 1H), ppm; [M+H]$^+$ 365.2.

Example 13: Preparation of 4-Chloro-1-(2-methoxy-ethyl)-1H-indole-3-carboxylic acid ((1S,3S)-1-hydroxy-3-methyl-cyclohexylmethyl)-amide (14)

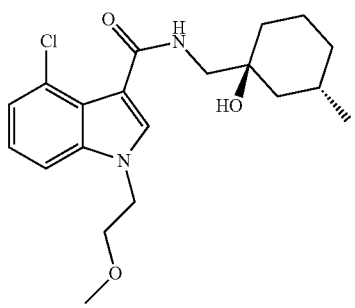 [SMILES: COCCn1cc(C(=O)NC[C@]2(O)CCC[C@H](C)C2)c2c(Cl)cccc21]

The title compound was synthesized according to the procedure described in Example 2 using of 4-Chloro-1-(2-methoxy-ethyl)-1H-indole-3-carboxylic acid (100 mg, 0.39 mmol, 1.00 eq), (1S,3S)-1-Aminomethyl-3-methyl-cyclohexanol (84 mg, 0.59 mmol, 1.50 eq), EDC (128 mg, 0.66 mmol, 1.70 eq), Benzotriazol-1-ol (85 mg, 0.62 mmol, 1.60 eq) and DIPEA (0.37 mL, 2.15 mmol, 5.50 eq) in dry THF (10 mL, 100 V) to afford 4-Chloro-1-(2-methoxy-ethyl)-1H-indole-3-carboxylic acid ((1S,3S)-1-hydroxy-3-methyl-cyclohexyl methyl)-amide (20 mg, 0.05 mmol, 13.5%) as a white solid.

$^1$H NMR (400 MHz, DMSO-d$_6$): δ 7.79-7.76 (m, 1H), 7.55 (dd, J=1.20, 8.00 Hz, 1H), 7.19-7.12 (m, 2H), 4.39-4.36 (m, 1H), 4.26 (s, 1H), 3.66 (t, J=5.20 Hz, 2H), 3.21-0.00 (m, 5H), 1.71-1.69 (m, 1H), 1.59-1.50 (m, 4H), 1.45-1.43 (m, 1H), 1.23-1.17 (m, 2H), 0.97-0.91 (m, 1H), 0.83-0.81 (m, 3H) ppm; [M+H]+ 379.2.

Example 14: Preparation of 4-Chloro-1-(2-methoxy-ethyl)-1H-indole-3-carboxylic acid ((1R,3R)-1-hydroxy-3-methyl-cyclohexylmethyl)-amide (15)

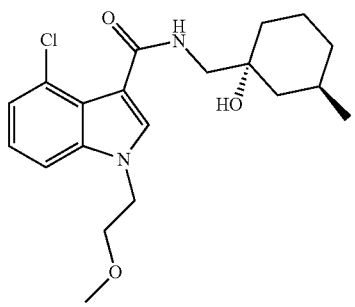 [SMILES: COCCn1cc(C(=O)NC[C@@]2(O)CCC[C@@H](C)C2)c2c(Cl)cccc21]

The title compound was synthesized according to the procedure described in Example 2 using 4-Chloro-1-(2-methoxy-ethyl)-1H-indole-3-carboxylic acid (100 mg, 0.39 mmol, 1.00 eq), (1R,3R)-1-Aminomethyl-3-methyl-cyclohexanol (84 mg, 0.59 mmol, 1.50 eq), EDC (128 mg, 0.66 mmol, 1.70 eq), Benzotriazol-1-ol (85 mg, 0.62 mmol, 1.60 eq) and DIPEA (0.37 mL, 2.15 mmol, 5.50 eq) in dry THF (10 mL, 100 V) to afford 4-Chloro-1-(2-methoxy-ethyl)-1H-indole-3-carboxylic acid ((1R,3R)-1-hydroxy-3-methyl-cyclohexylmethyl)-amide (12 mg, 0.04 mmol, 10.1%) as a white solid.

$^1$H NMR (400 MHz, DMSO-$d_6$): δ 7.79-7.76 (m, 1H), 7.55 (dd, J=1.20, 8.00 Hz, 1H), 7.19-7.12 (m, 2H), 4.39-4.36 (m, 1H), 4.26 (s, 1H), 3.66 (t, J=5.20 Hz, 2H), 3.21-3.00 (m, 5H), 1.71-1.69 (m, 1H), 1.59-1.50 (m, 4H), 1.45-1.43 (m, 1H), 1.23-1.17 (m, 2H), 0.97-0.91 (m, 1H), 0.83-0.81 (m, 3H) [M+H]+ 379.2.

Example 15: Preparation of 4-chloro-N-((3-ethyl-1-hydroxycyclohexyl)methyl)-1-(2-methoxyethyl)-1H-indole-3-carboxamide (22)

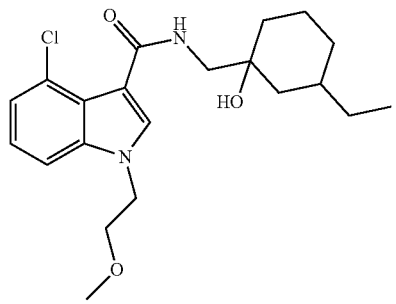 [SMILES: CCC1CCCC(O)(CNC(=O)c2cn(CCOC)c3cccc(Cl)c23)C1]

The title compound was synthesized according to the procedure described in Example 2 using 4-Chloro-1-(2-methoxy-ethyl)-1H-indole-3-carboxylic acid (50.00 mg; 0.20 mmol; 1.00 eq.), 1-(aminomethyl)-3-ethylcyclohexanol (37.19 mg; 0.24 mmol; 1.20 eq.), EDC (45.34 mg; 0.24 mmol; 1.20 eq.), Benzotriazol-1-ol (31.96 mg; 0.24 mmol; 1.20 eq.) and DIPEA (0.093 g, 0.72 mmol) in DMF (2.0 mL) to provide 4-chloro-N-((3-ethyl-1-hydroxycyclohexyl)methyl)-1-(2-methoxyethyl)-1H-indole-3-carboxamide.

$^1$H NMR (400 MHz, DMSO-$d_6$) δ ppm 9.00 (1H), 8.07 (m, 1H), 7.97 (1H), 7.86 (s, 1H), 7.58 (1H), 7.51 (1H), 7.43 (1H), 7.21 (2H), 4.85 (m, 2H), 4.41 (2H), 3.69 (2H), 3.27 (3H). m/z: 393 [M+H]

Example 16: Preparation of 4-Chloro-1-(2-methoxy-ethyl)-1H-indole-3-carboxylic acid (1,2-dihydroxy-cyclohexylmethyl)-amide (18)

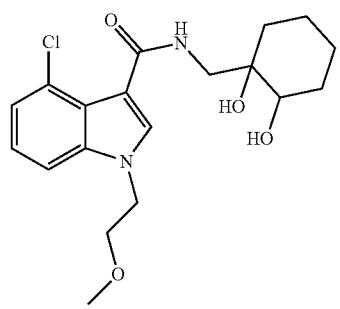 [SMILES: COCCn1cc(C(=O)NCC2(O)CCCCC2O)c2c(Cl)cccc21]

The title compound was synthesized according to the procedure described in Example 2 using 4-Chloro-1-(2-methoxy-ethyl)-1H-indole-3-carboxylic acid (200 mg, 0.78 mmol, 1.00 eq), 1-Aminomethylcyclohexane-1,2-diol (170 mg, 1.17 mmol, 1.50 eq), EDC (256 mg, 1.33 mmol, 1.70 eq), Benzotriazol-1-ol (170 mg, 1.25 mmol, 1.60 eq) and DIPEA (0.74 mL, 4.29 mmol, 5.50 eq) in dry THF (10 mL, 50 V) to afford 4-Chloro-1-(2-methoxy-ethyl)-1H-indole-3-carboxylic acid (1,2-dihydroxy-cyclohexylmethyl)-amide (120 mg, 0.31 mmol, 40.3%) as a white solid.

$^1$H NMR (400 MHz, DMSO-$d_6$): δ 8.05-7.85 (m, 1H), 7.82-7.77 (m, 1H), 7.57-7.54 (m, 1H), 7.20-7.13 (m, 2H), 4.83-4.60 (m, 1H), 4.59-4.06 (m, 3H), 3.67-3.64 (m, 2H), 3.53-3.45 (m, 1H), 3.10-3.05 (m, 4H), 1.59-1.25 (m, 8H) ppm; [M+H]+ 381.2.

Example 17: Preparation of 4-Chloro-1-(2-methoxy-ethyl)-1H-indole-3-carboxylic acid 2-fluoro-benzylamide (25)

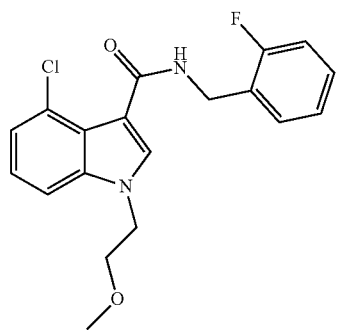 [SMILES: COCCn1cc(C(=O)NCc2ccccc2F)c2c(Cl)cccc21]

The title compound was synthesized according to the procedure described in Example 2 using 4-Chloro-1-(2-methoxy-ethyl)-1H-indole-3-carboxylic acid (150 mg, 0.59 mmol, 1.00 eq), 2-Fluoro-benzylamine (112 mg, 0.88 mmol, 1.50 eq), Et$_3$N (0.25 mL, 1.76 mmol, 3.00 eq), Benzotriazol-1-ol (142 mg, 0.88 mmol, 1.50 eq) and EDC (170 mg, 0.88 mmol, 1.50 eq) in dry THF to provide 4-Chloro-1-(2-methoxy-ethyl)-1H-indole-3-carboxylic acid 2-fluoro-benzylamide (50 mg, 0.14 mmol, 23.6%) as a white solid.

$^1$H NMR (400 MHz, DMSO-$d_6$): δ 8.57 (t, J=5.88 Hz, 1H), 7.79 (s, 1H), 7.56 (dd, J=8.00, 1.08 Hz, 1H), 7.47 (dd, J=10.86, 1.52 Hz, 1H), 7.33-7.29 (m, 1H), 7.21-7.13 (m, 4H), 4.49 (d, J=5.60 Hz, 2H), 4.39 (t, J=5.16 Hz, 2H), 3.67 (t, J=5.12 Hz, 2H), 3.22 (s, 3H) ppm; [M+H]$^+$361.2.

Example 18: Preparation of 4-Chloro-1-(2-methoxy-ethyl)-1H-indole-3-carboxylic acid 2-trifluoromethyl-benzylamide (24)

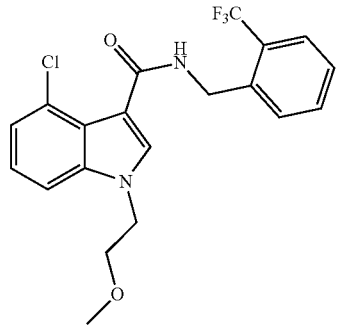 [SMILES: COCCn1cc(C(=O)NCc2ccccc2C(F)(F)F)c2c(Cl)cccc21]

The title compound was synthesized according to the procedure described in Example 2 using 4-Chloro-1-(2-methoxy-ethyl)-1H-indole-3-carboxylic acid (150 mg, 0.59 mmol, 1.00 eq), 2-Trifluoromethyl-benzylamine (156 mg, 0.88 mmol, 1.50 eq), Et$_3$N (0.25 mL, 1.76 mmol, 3.00 eq), Benzotriazol-1-ol (142 mg, 0.88 mmol, 1.50 eq) and EDC (170 mg, 0.88 mmol, 1.50 eq) in dry THF (5 mL, 33 V) to provide 4-Chloro-1-(2-methoxy-ethyl)-1H-indole-3-carboxylic acid 2-trifluoromethyl-benzylamide (60 mg, 0.15 mmol, 24.8%) as a white solid.

$^1$H NMR (400 MHz, DMSO-d$_6$): δ 8.68 (t, J=5.92 Hz, 1H), 7.86 (s, 1H), 7.74 (d, J=7.68 Hz, 1H), 7.69-7.65 (m, 2H), 7.58 (dd, J=7.94, 1.16 Hz, 1H), 7.51-7.47 (m, 1H), 7.22-7.15 (m, 2H), 4.64 (d, J=5.76 Hz, 2H), 4.41 (t, J=5.20 Hz, 2H), 3.68 (t, J=5.16 Hz, 2H), 3.23 (s, 3H) ppm; [M+H]$^+$ 411.0.

Example 19: Preparation of 4-Chloro-1-(2-methoxy-ethyl)-1H-indole-3-carboxylic acid 4-trifluoro methyl-benzylamide (26)

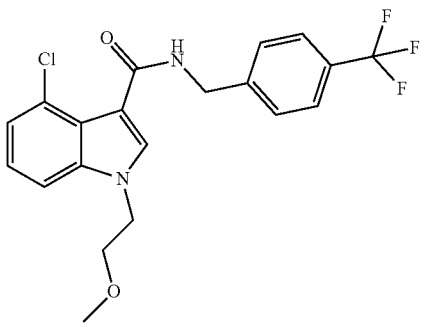 [SMILES: COCCn1cc(C(=O)NCc2ccc(C(F)(F)F)cc2)c2c(Cl)cccc21]

The title compound was synthesized according to the procedure described in Example 2 using 4-Chloro-1-(2-methoxy-ethyl)-1H-indole-3-carboxylic acid (150 mg, 0.59 mmol, 1.00 eq), 4-Trifluoromethyl-benzylamine (156 mg, 0.88 mmol, 1.50 eq), Benzotriazol-1-ol (142.95 mg, 0.88 mmol, 1.50 eq) and EDC (170 mg, 0.88 mmol, 1.50 eq) in dry THF (5 mL, 33V) to provide 4-Chloro-1-(2-methoxy-ethyl)-1H-indole-3-carboxylic acid 4-trifluoro methyl-benzyl amide (60 mg, 0.15 mmol, 24.9%) as a off-white solid.

$^1$H NMR (400 MHz, DMSO-d$_6$): δ 8.69 (t, J=6.08 Hz, 1H), 7.80 (s, 1H), 7.71 (d, J=8.08 Hz, 2H), 7.60-7.56 (m, 3H), 7.21-7.14 (m, 2H), 4.53 (d, J=5.96 Hz, 2H), 4.39 (t, J=5.20 Hz, 2H), 3.67 (t, J=5.12 Hz, 2H), 3.22 (s, 3H), [M+H]$^+$ 411.0.

Example 20: Preparation of 4-Chloro-1-(2-methoxy-ethyl)-1H-indole-3-carboxylic acid (2,3-dihydro-benzo[1,4]dioxin-5-ylmethyl)-amide (23)

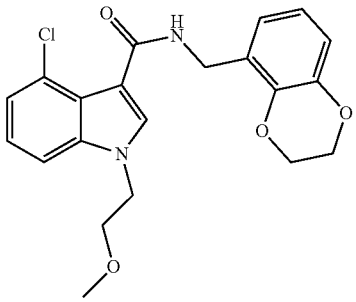 [SMILES: COCCn1cc(C(=O)NCc2cccc3c2OCCO3)c2c(Cl)cccc21]

The title compound was synthesized according to the procedure described in Example 2 using 4-Chloro-1-(2-methoxy-ethyl)-1H-indole-3-carboxylic acid (150 mg, 0.59 mmol, 1.00 eq), C-(2,3-Dihydro-benzo[1,4]dioxin-5-yl)-methylamine hydrochloride (186 mg, 0.88 mmol, 1.50 eq), Et$_3$N (0.25 mL, 1.76 mmol, 3.00 eq), Benzotriazol-1-ol (142.95 mg, 0.88 mmol, 1.50 eq) and EDC (170 mg, 0.88 mmol, 1.50 eq) in dry THF (5 mL, 33.33 V) to provide 4-Chloro-1-(2-methoxy-ethyl)-1H-indole-3-carboxylic acid (2,3-dihydro-benzo[1,4]dioxin-5-yl methyl)-amide (155 mg, 0.38 mmol, 65.7%) as a white solid.

$^1$H NMR (400 MHz, DMSO-d$_6$): δ 8.35 (t, J=5.88 Hz, 1H), 7.78 (s, 1H), 7.55 (d, J=7.36 Hz, 1H), 7.19-7.12 (m, 2H), 6.88 (dd, J=6.94, 2.00 Hz, 1H), 6.79-6.73 (m, 2H), 4.38 (t, J=4.56 Hz, 4H), 4.30-4.28 (m, 2H), 4.24-4.23 (m, 2H), 3.66 (t, J=5.12 Hz, 2H), 3.21 (s, 3H), ppm; [M+H]+ 401.2.

Example 21: Preparation of 4-Chloro-1-(2-methoxy-ethyl)-1H-indole-3-carboxylic acid (benzo[1,3] dioxol-5-ylmethyl)-amide (27)

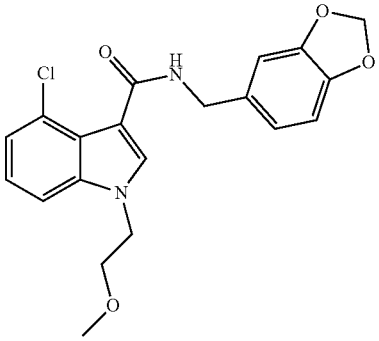 [SMILES: COCCn1cc(C(=O)NCc2ccc3c(c2)OCO3)c2c(Cl)cccc21]

The title compound was synthesized according to the procedure described in Example 2 using 4-Chloro-1-(2-methoxy-ethyl)-1H-indole-3-carboxylic acid (150 mg, 0.59 mmol, 1.00 eq), C-Benzo[1,3]dioxol-5-yl-ethylamine (136 mg, 0.88 mmol, 1.50 eq), Et$_3$N (0.25 mL, 1.76 mmol, 3.00 eq), Benzotriazol-1-ol (142 mg, 0.88 mmol, 1.50 eq) and EDC (170 mg, 0.88 mmol, 1.50 eq) in dry THF (5 mL, 33V) to provide 4-Chloro-1-(2-methoxy-ethyl)-1H-indole-3-carboxylic acid (benzo[1,3]dioxol-5-ylmethyl)-amide (105 mg, 0.27 mmol, 46.1%) as a white solid.

¹H NMR (400 MHz, DMSO-d₆): δ 8.52 (t, J=6.00 Hz, 1H), 7.75 (s, 1H), 7.55 (dd, J=7.98, 1.12 Hz, 1H), 7.20-7.12 (m, 2H), 6.94 (d, J=1.24 Hz, 1H), 6.88-6.82 (m, 2H), 5.99 (s, 2H), 4.39-4.34 (m, 4H), 3.66 (t, J=5.12 Hz, 2H), 3.22 (s, 3H).

Example 22: Preparation of 4-Chloro-1-(2-methoxy-ethyl)-1H-indole-3-carboxylic acid chroman-3-ylamide (29)

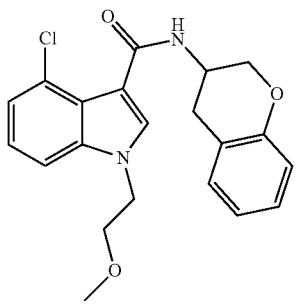 [SMILES: COCCn1cc(C(=O)NC2COc3ccccc3C2)c2c(Cl)cccc21]

The title compound was synthesized according to the procedure described in Example 2 using 4-Chloro-1-(2-methoxy-ethyl)-1H-indole-3-carboxylic acid (150 mg, 0.59 mmol, 1.00 eq), Chroman-3-ylamine hydrochloride (168.06 mg, 0.88 mmol, 1.50 eq), Et₃N (0.25 mL, 1.76 mmol, 3.00 eq), Benzotriazol-1-ol (142.95 mg, 0.88 mmol, 1.50 eq) and EDC (170.03 mg, 0.88 mmol, 1.50 eq) in dry THF (5 mL, 33.33 V) to provide 4-Chloro-1-(2-methoxy-ethyl)-1H-indole-3-carboxylic acid chroman-3-ylamide (30 mg, 0.08 mmol, 13.2%) as a white solid.

¹H NMR (400 MHz, DMSO-d₆): δ 8.13 (d, J=7.20 Hz, 1H), 7.76 (s, 1H), 7.56 (dd, J=1.20, 7.88 Hz, 1H), 7.20-7.08 (m, 4H), 6.88-6.84 (m, 1H), 6.80 (d, J=8.04 Hz, 1H), 4.35-4.32 (m, 2H), 4.31 (brs, 1H), 4.27-4.24 (m, 1H), 3.93-3.88 (m, 1H), 3.66 (t, J=5.12 Hz, 2H), 3.22 (s, 3H), 3.06 (dd, J=16.36, 5.12 Hz, 1H), 2.91-2.85 (m, 1H) ppm; [M+H]⁺ 385.2.

Example 23: N-(benzo[d]thiazol-2-ylmethyl)-4-chloro-1-(2-methoxyethyl)-1H-indole-3-carboxamide (31)

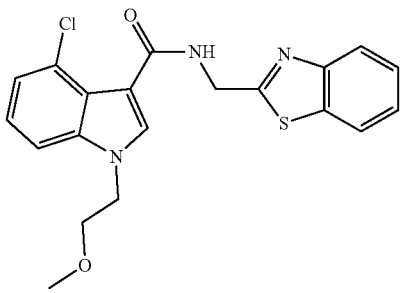 [SMILES: COCCn1cc(C(=O)NCc2nc3ccccc3s2)c2c(Cl)cccc21]

The title compound was synthesized according to the procedure described in Example 2 4-Chloro-1-(2-methoxy-ethyl)-1H-indole-3-carboxylic acid (50.00 mg; 0.20 mmol; 1.00 eq.), benzo[d]thiazol-2-ylmethanamine (46.61 mg; 0.24 mmol; 1.20 eq.), (3-Dimethylamino-propyl)-ethyl-carbodiimide hydrochloride (45.34 mg; 0.24 mmol; 1.20 eq.), Benzotriazol-1-ol (31.96 mg; 0.24 mmol; 1.20 eq.) and DIPEA (0.093 g, 0.72 mmol) in DMF (2.0 mL) to provide N-(benzo[d]thiazol-2-ylmethyl)-4-chloro-1-(2-methoxy-ethyl)-1H-indole-3-carboxamide.

¹H NMR (400 MHz, DMSO-d₆) δ ppm 9.00 (1H), 8.07 (m, 1H), 7.97 (1H), 7.86 (s, 1H), 7.58 (1H), 7.51 (1H), 7.43 (1H), 7.21 (2H), 4.85 (m, 2H), 4.41 (2H), 3.69 (2H), 3.27 (3H). m/z: 400 [M+H]

Example 24: Preparation of 4-Chloro-1-(2-methoxy-ethyl)-1H-indole-3-carboxylic acid (furan-2-ylmethyl)-amide (28)

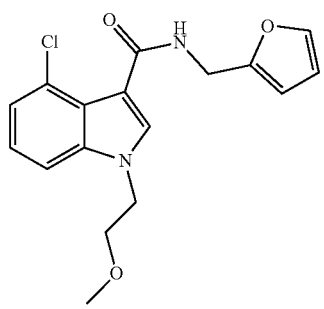 [SMILES: COCCn1cc(C(=O)NCc2ccco2)c2c(Cl)cccc21]

The title compound was synthesized according to the procedure described in Example 2 using 4-Chloro-1-(2-methoxy-ethyl)-1H-indole-3-carboxylic acid (150 mg, 0.59 mmol, 1.00 eq), C-Furan-2-yl-methylamine (86.14 mg, 0.88 mmol, 1.50 eq), Et₃N (0.25 mL, 1.76 mmol, 3.00 eq), Benzotriazol-1-ol (142.95 mg, 0.88 mmol, 1.50 eq) and EDC (170 mg, 0.88 mmol, 1.50 eq) in dry THF (5 mL, 33 V) to provide 4-Chloro-1-(2-methoxy-ethyl)-1H-indole-3-carboxylic acid (furan-2-ylmethyl)-amide (60 mg, 0.18 mmol, 30.8%) as a off-white solid.

¹H NMR (400 MHz, DMSO-d₆): δ 8.50 (t, J=5.72 Hz, 1H), 7.75 (s, 1H), 7.60-7.59 (m, 1H), 7.55 (dd, J=7.96, 1.08 Hz, 1H), 7.20-7.12 (m, 2H), 6.41 (dd, J=3.14, 1.84 Hz, 1H), 6.30 (dd, J=3.16, 0.68 Hz, 1H), 4.43 (d, J=5.76 Hz, 2H), 4.38 (t, J=5.20 Hz, 2H), 3.66 (t, J=5.12 Hz, 2H), 3.22 (s, 3H) ppm; [M+H]⁺ 333.2.

Example 25: Preparation of 4-Chloro-1-(2-methoxy-ethyl)-1H-indole-3-carboxylic acid (2-thiophen-2-yl-ethyl)-amide (30)

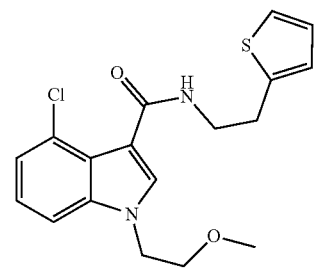 [SMILES: COCCn1cc(C(=O)NCCc2cccs2)c2c(Cl)cccc21]

The title compound was synthesized according to the procedure described in Example 2 using 4-Chloro-1-(2-methoxy-ethyl)-1H-indole-3-carboxylic acid (150 mg, 0.59 mmol, 1.00 eq), 2-Thiophen-2-yl-ethylamine (113.98 mg, 0.88 mmol, 1.50 eq), Et₃N (0.25 mL, 1.76 mmol, 3.00 eq), Benzotriazol-1-ol (142.95 mg, 0.88 mmol, 1.50 eq) and EDC (170.03 mg, 0.88 mmol, 1.50 eq) in dry THF (5 mL, 33.33 V) to provide 4-Chloro-1-(2-methoxy-ethyl)-1H-indole-3-carboxylic acid (2-thiophen-2-yl-ethyl)-amide (45 mg, 0.12 mmol, 21.2%) as a white solid.

¹H NMR (400 MHz, DMSO-d₆): δ 8.20 (t, J=5.60 Hz, 1H), 7.69 (s, 1H), 7.55 (dd, J=7.96, 1.16 Hz, 1H), 7.36 (dd, J=4.98, 1.32 Hz, 1H), 7.20-7.12 (m, 2H), 6.98-6.95 (m, 2H), 4.38 (t, J=5.16 Hz, 2H), 3.66 (t, J=5.08 Hz, 2H), 3.48 (m, 2H), 3.23 (s, 3H), 3.06 (t, J=7.36 Hz, 2H) ppm; [M+H]⁺ 363.3.

Example 26: 4-Chloro-1-(2-methoxy-ethyl)-1H-indole-3-carboxylic acid [2-(2-chloro-phenyl)-ethyl]-amide (35)

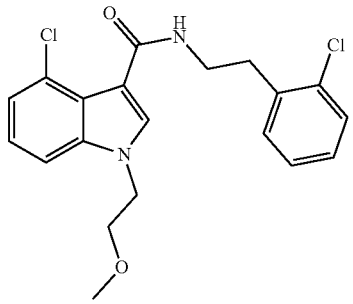 [SMILES: COCCn1cc(C(=O)NCCc2ccccc2Cl)c2c(Cl)cccc21]

The title compound was synthesized according to the procedure described in Example 2 using 4-Chloro-1-(2-methoxy-ethyl)-1H-indole-3-carboxylic acid (50.00 mg; 0.20 mmol; 1.00 eq.), 2-(2-chloro-phenyl)-ethylamine (36.81 mg; 0.24 mmol; 1.20 eq.), (3-Dimethylamino-propyl)-ethyl-carbodiimide hydrochloride (45.34 mg; 0.24 mmol; 1.20 eq.), Benzotriazol-1-ol (31.96 mg; 0.24 mmol; 1.20 eq.) and DIPEA (0.093 g, 0.72 mmol) in DMF (2.0 mL) to provide 4-Chloro-1-(2-methoxy-ethyl)-1H-indole-3-carboxylic acid [2-(2-chloro-phenyl)-ethyl]-amide.

¹H NMR (400 MHz, DMSO-d₆) δ ppm 8.14 (m, 1H), 7.67 (s, 1H), 7.56 (s, 1H), 7.42 (2H), 7.29 (2H), 7.14-7.18 (m, 2H), 4.37 (m, 2H), 3.66 (2H), 3.47 (2H), 3.24 (s, 3H), 2.97 (2H). m/z: 392 [M+H]

Example 27: 4-Chloro-1-(2-methoxy-ethyl)-1H-indole-3-carboxylic acid [2-(4-fluoro-2-chloro-phenyl)-ethyl]-amide (34)

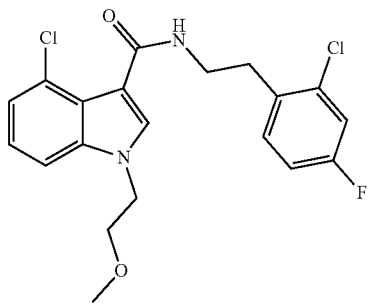 [SMILES: COCCn1cc(C(=O)NCCc2ccc(F)cc2Cl)c2c(Cl)cccc21]

The title compound was synthesized according to the procedure described in example 2 using a mixture of 4-Chloro-1-(2-methoxy-ethyl)-1H-indole-3-carboxylic acid (50.00 mg; 0.20 mmol; 1.00 eq.), 2-(4-fluoro-2-chloro-phenyl)-ethylamine (31.95 mg; 0.24 mmol; 1.20 eq.), (3-Dimethylamino-propyl)-ethyl-carbodiimide hydrochloride (45.34 mg; 0.24 mmol; 1.20 eq.), Benzotriazol-1-ol (31.96 mg; 0.24 mmol; 1.20 eq.) and DIPEA (0.093 g, 0.72 mmol) in DMF to provide 4-Chloro-1-(2-methoxy-ethyl)-1H-indole-3-carboxylic acid [2-(4-fluoro-2-chloro-phenyl)-ethyl]-amide.

¹H NMR (400 MHz, DMSO-d₆) δ ppm 8.11 (m, 1H), 7.67 (s, 1H), 7.56 (s, 1H), 7.42 (2H), 7.14-7.18 (m, 3H), 4.37 (m, 2H), 3.66 (2H), 3.47 (2H), 3.24 (s, 3H), 2.97 (2H). m/z: 410 [M+H]

Example 28: 4-chloro-N-(2-(2-chlorophenyl)propyl)-1-(2-methoxyethyl)-1H-indole-3-carboxamide (33)

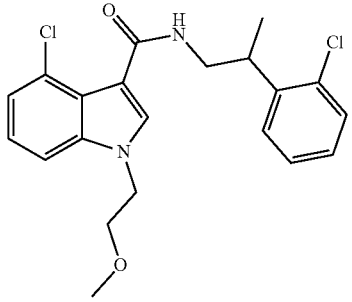 [SMILES: COCCn1cc(C(=O)NCC(C)c2ccccc2Cl)c2c(Cl)cccc21]

The title compound was synthesized according to the procedure described in Example 2 using 4-Chloro-1-(2-methoxy-ethyl)-1H-indole-3-carboxylic acid (50.00 mg; 0.20 mmol; 1.00 eq.), 2-(2-chlorophenyl) propan-1-amine (40.12 mg; 0.24 mmol; 1.20 eq.), (3-Dimethylamino-propyl)-ethyl-carbodiimide hydrochloride (45.34 mg; 0.24 mmol; 1.20 eq.), Benzotriazol-1-ol (31.96 mg; 0.24 mmol; 1.20 eq.) and DIPEA (0.093 g, 0.72 mmol) in DMF (2.0 mL) to obtain 4-chloro-N-(2-(2-chlorophenyl)propyl)-1-(2-methoxyethyl)-1H-indole-3-carboxamide.

¹H NMR (400 MHz, DMSO-d₆) δ ppm 8.10 (s, 1H), 7.65 (s, 1H), 7.54 (s, 1H), 7.48 (1H), 7.42 (1H), 7.34 (1H), 7.24 (1H), 7.16 (m, 1H), 7.12 (1H), 4.36 (m, 2H), 3.64 (2H), 3.56 (1H), 3.49 (2H), 3.24 (s, 3H), 1.25 (m, 3H). m/z: 405 [M+H]

Example 29: 4-chloro-N-(1-(2-chloro-3-(trifluoromethyl)phenyl)-2-hydroxyethyl)-1-(2-methoxyethyl)-1H-indole-3-carboxamide (32)

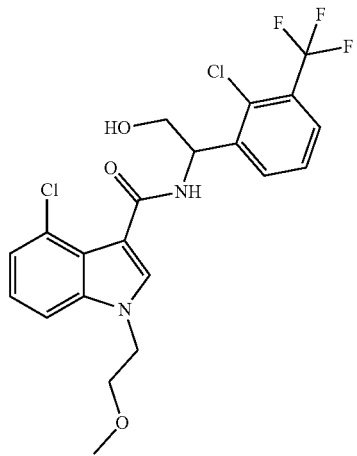 [SMILES: COCCn1cc(C(=O)NC(CO)c2cccc(C(F)(F)F)c2Cl)c2c(Cl)cccc21]

The title compound was synthesized according to the procedure described in Example 2 using 4-Chloro-1-(2-methoxy-ethyl)-1H-indole-3-carboxylic acid (50.00 mg; 0.20 mmol; 1.00 eq.), 2-amino-2-(2-chloro-3-(trifluoromethyl)phenyl)ethanol (58.12 mg; 0.24 mmol; 1.20 eq.), (3-Dimethylamino-propyl)-ethyl-carbodiimide hydrochloride (45.34 mg; 0.24 mmol; 1.20 eq.), Benzotriazol-1-ol (31.96 mg; 0.24 mmol; 1.20 eq.) and DIPEA (0.093 g, 0.72 mmol) in DMF (2.0 mL) to obtain the desired product.

$^1$H NMR (400 MHz, DMSO-d$_6$) δ ppm 8.56 (1H), 7.93 (2H), 7.78 (s, 1H), 7.79 (1H), 7.57 (2H), 5.55 (1H), 5.06 (1H), 4.41 (2H), 3.63 (4H), 3.24 (s, 3H), 3.19 (1H), 4.36 (m, 2H), 3.64 (2H), 3.56 (1H), 3.49 (2H), 3.24 (s, 3H). m/z: 475 [M+H]

Example 30: Preparation of 4-Chloro-1-(2-methoxy-ethyl)-1H-indole-3-carboxylic acid [2-(1-hydroxy-cyclopentyl)-ethyl]-amide (16)

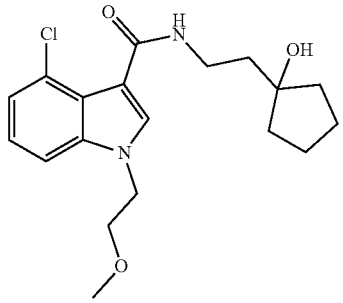 [SMILES: COCCn1cc(C(=O)NCCC2(O)CCCC2)c2c(Cl)cccc21]

The title compound was synthesized according to the procedure described in Example 2 using 4-Chloro-1-(2-methoxy-ethyl)-1H-indole-3-carboxylic acid (200 mg, 0.79 mmol, 1.00 eq), 1-(2-Aminoethyl)-cyclopentanol (199 mg, 1.18 mmol, 1.50 eq), DIPEA (0.42 mL, 2.37 mmol, 3.00 eq), EDC (457 mg, 2.37 mmol, 3.00 eq) and Benzotriazol-1-ol (192 mg, 1.18 mmol, 1.50 eq) in dry DMF (5 mL, 25 V) to provide 4-Chloro-1-(2-methoxy-ethyl)-1H-indole-3-carboxylic acid [2-(1-hydroxy-cyclopentyl)-ethyl]-amide (180 mg, 0.47 mmol, 60.2%) as a white solid.

$^1$H NMR (400 MHz, DMSO-d$_6$): δ 7.92 (t, J=5.48 Hz, 1H), 7.66 (s, 1H), 7.53 (dd, J=7.92, 1.16 Hz, 1H), 7.18-7.10 (m, 2H), 4.36 (t, J=5.20 Hz, 2H), 4.17 (s, 1H), 3.64 (t, J=5.12 Hz, 2H), 3.33-3.32 (m, 2H), 3.21 (s, 3H), 1.76-1.68 (m, 4H), 1.61-1.61 (m, 2H), 1.58-1.48 (m, 4H) ppm; [M+H]+ 365.2.

Example 31: Preparation of 4-chloro-1-(2-cyclopropoxyethyl)-N-((4,4-difluorocyclohexyl)methyl)-1H-indole-3-carboxamide (149)

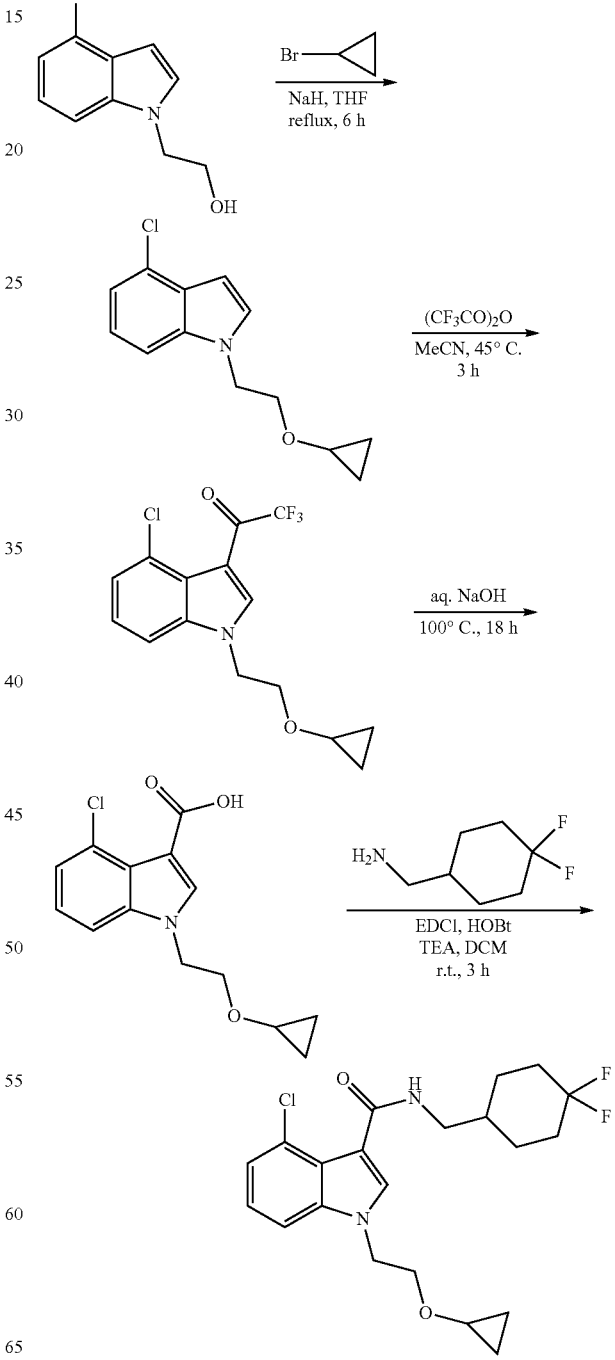

Step 1: Preparations of 4-chloro-1-(2-cyclopropoxyethyl)-1H-indole

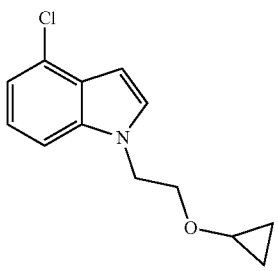 [SMILES: Clc1cccc2c1ccn2CCOC1CC1]

To a solution of 2-(4-chloro-1H-indol-1-yl)ethanol (1.95 g, 10 mmol) in THF (13 mL) was added NaH (0.80 g, 20 mmol, 60% in mineral oil) and bromocyclopropane (1.82 g, 15 mmol) at 0° C. The resulting reaction mixture was refluxed for 6 h, and then concentrated to dryness in vacuo. The residue was redissolved in EtOAc (20 mL) and washed with water (20 mL×2) twice and brine (20 mL). The organic layer was dried over MgSO$_4$, filtered and concentrated in vacuo. The residual oil was purified by column chromatography on silica gel (eluting with petroleum ether:ethyl acetate=5:1 to 2:1) to give 4-chloro-1-(2-cyclopropoxyethyl)-1H-indole (1.53 g, 65%) as a yellow solid. LC-MS Purity: >95%; $t_R$=1.73 min; [M+H]$^+$ 236.

Step 2: Preparation of 1-(4-chloro-1-(2-cyclopropoxyethyl)-1H-indol-3-yl)-2,2,2-trifluoroethanone

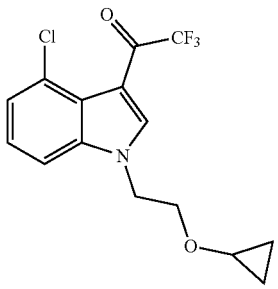 [SMILES: O=C(c1cn(CCOC2CC2)c2cccc(Cl)c12)C(F)(F)F]

A solution of 4-chloro-1-(2-cyclopropoxyethyl)-1H-indole (1.50 g, 6.3 mmol) and 2,2,2-trifluoroacetic anhydride (2.10 g, 10 mmol) in MeCN (15 mL) was stirred at 45° C. for 3 h. Then the reaction mixture was concentrated in vacuo and the residue was purified by column chromatography on silica gel (eluting with petroleum ether:ethyl acetate=2:1 to 1:2) to give 1-(4-chloro-1-(2-cyclopropoxyethyl)-1H-indol-3-yl)-2,2,2-trifluoroethanone (1.35 g, 65%) as a yellow solid. LC-MS Purity (254 nm): >95%; [M+H]$^+$ 332; $t_R$=1.24 min.

Step 3: Preparation of 4-chloro-1-(2-cyclopropoxyethyl)-1H-indole-3-carboxylic acid

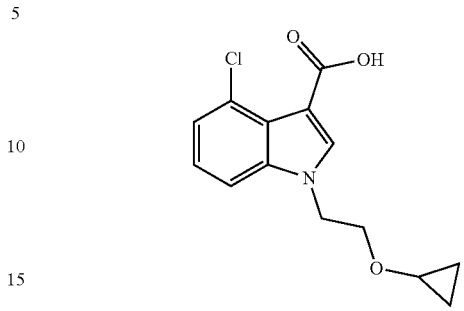

A mixture of 1-(4-chloro-1-(2-cyclopropoxyethyl)-1H-indol-3-yl)-2,2,2 trifluoroethanone (1.0 g, 3 mmol) and 10% aqueous sodium hydroxide (10 mL) was stirred at 100° C. for 18 h, then cooled to room temperature. The mixture was adjusted to pH 2 with 1 N HCl and extracted with DCM (15 mL×2). The combined organic layers were dried over MgSO$_4$, filtered and concentrated in vacuo to give 4-chloro-1-(2-cyclopropoxyethyl)-1H-indole-3-carboxylic acid (0.560 g, 66%) as a yellow solid, which was used in the next step without purification.

Step 4: Preparation of 4-chloro-1-(2-cyclopropoxyethyl)-N-((4,4-difluorocyclohexyl) methyl)-1H-indole-3-carboxamide

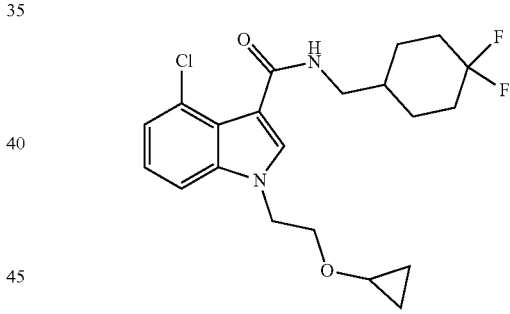

To a stirred solution of 4-chloro-1-(2-cyclopropoxyethyl)-1H-indole-3-carboxylic acid (0.560 g, 2.0 mmol), EDCI (0.800 g, 0.42 mmol) and HOBt (0.425 g, 3.1 mmol) in DCM (10 mL) were added Et$_3$N (0.525 g, 5.2 mmol) and (4,4-difluorocyclohexyl)methanamine (0.298 g, 2.0 mmol) at room temperature. After stirred at room temperature for 3 h, the reaction was quenched with water (10 mL) and extracted with DCM (20 mL×3). The combined organic layers were washed with water (10 mL), brine (10 mL), dried over Na$_2$SO$_4$ and concentrated to give a residue. The residue was purified by column chromatography on silica gel (DCM:MeOH=20:1) to afford 4-chloro-1-(2-cyclopropoxyethyl)-N-((4,4-difluorocyclohexyl)methyl)-1H-indole-3-carboxamide (0.150 g, 18%) as a white solid.

$^1$H NMR (500 MHz, DMSO-d$_6$) 8.09 (s, 1H), 7.69 (s, 1H), 7.53 (d, J=7.5 Hz, 1H), 7.17-7.12 (m, 2H), 4.35 (t, J=10.5 Hz, 2H), 3.76 (t, J=10.5 Hz, 2H), 3.30-3.27 (m, 1H), 3.15 (t, J=6.5 Hz, 2H), 2.00 (s, 2H), 1.84-1.72 (m, 5H), 1.25-1.22 (m, 2H), 0.38-0.36 (m, 4H) ppm; [M+Na]$^+$ 433.

Example 32: Preparation of 4-chloro-N-((4,4-difluorocyclohexyl)methyl)-1-(2-(difluoromethoxy)ethyl)-1H-indole-3-carboxamide (95)

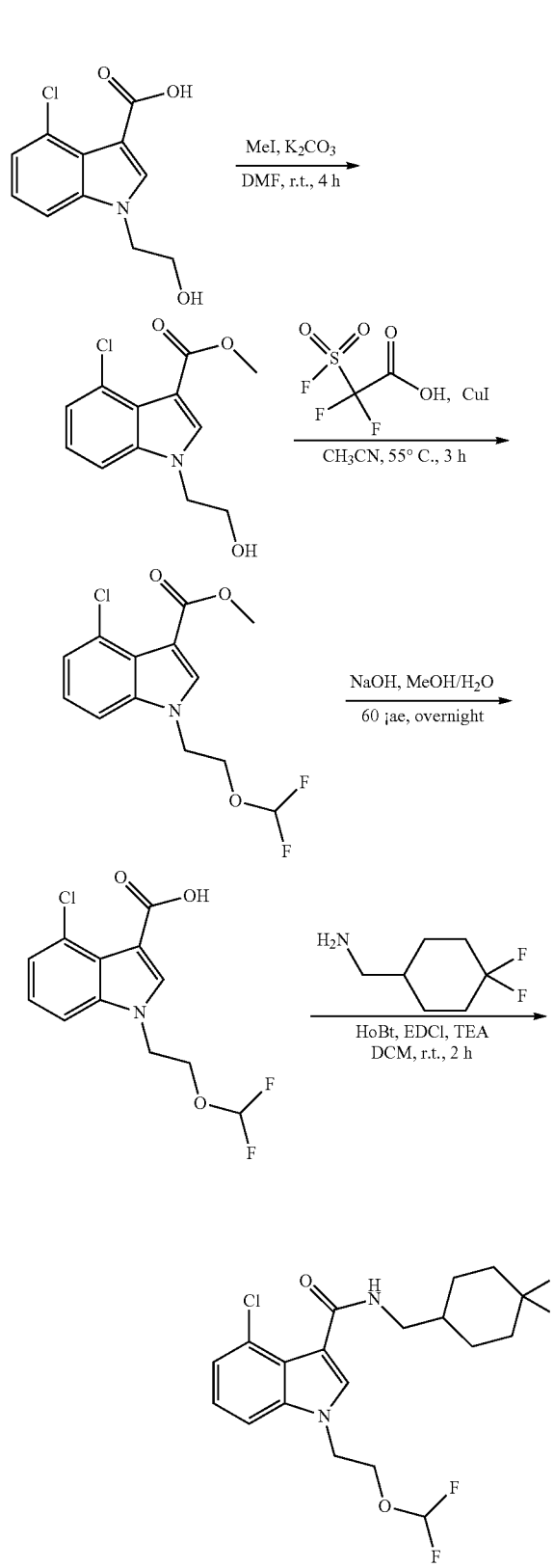

Step 1: Preparation of methyl 4-chloro-1-(2-hydroxyethyl)-1H-indole-3-carboxylate

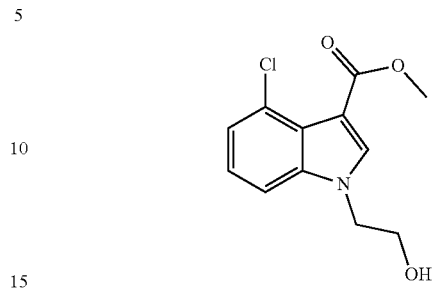

To a stirred mixture of 4-chloro-1-(2-hydroxyethyl)-1H-indole-3-carboxylic acid (2.00 g, 8.37 mmol) and potassium carbonate (4.62 g, 33.47 mmol) in anhydrous DMF (20 mL) was added iodomethane (1.18 g, 8.37 mmol) at room temperature and stirred for 4 h. The reaction mixture was quenched with brine (25 mL), extracted with ether (30 mL×3), the combined organic layer was washed with brine (20 mL), dried over anhydrous sodium sulfate, filtered and concentrated in vacuo, The reside was purified by column chromatography on silica gel (petroleum ether:EtOAc=4:1) to afford methyl 4-chloro-1-(2-hydroxyethyl)-1H-indole-3-carboxylate (1.50 g, 73%) as a white solid. $[M+H]^+$ 254.2.

Step 2: Preparation of methyl 4-chloro-1-(2-(difluoromethoxy)ethyl)-1H-indole-3-carboxylate

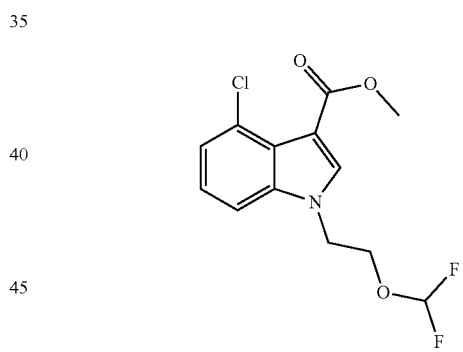

To a stirred solution of methyl 4-chloro-1-(2-hydroxyethyl)-1H-indole-3-carboxylate (0.500 g, 1.98 mmol) in acetonitrile (100 mL) was added copper(I) iodide (0.075 g, 0.4 mmol). The system was stirred at 55° C. under nitrogen atmosphere for a few minutes, then a solution of 2,2-difluoro-2-(fluorosulfonyl)acetic acid (1.407 g, 7.90 mmol) in acetonitrile (20 mL) was added dropwise thereto. The reaction was stirred at 55° C. for 3 h under nitrogen atmosphere, then the solvent was removed in vacuo. The residue was redissolved in dichloromethane (10 mL). The precipitate was filtered and washed with dichloromethane (10 mL×3). The filtrate was evaporated in vacuo. The residue was purified by column chromatography on silica gel (petroleum ether:EtOAc=5:1) to afford methyl 4-chloro-1-(2-(difluoromethoxy)ethyl)-1H-indole-3-carboxylate (0.120 g, 20%) as colorless oil. $[M+H]^+$ 304.1.

Step 3: Preparation of 4-chloro-1-(2-(difluoromethoxy)ethyl)-1H-indole-3-carboxylic acid

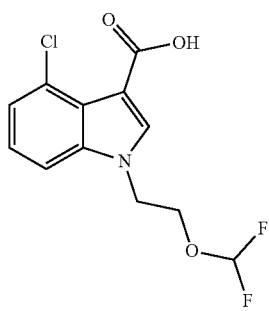 [SMILES: O=C(O)c1cn(CCOC(F)F)c2cccc(Cl)c12]

To a stirred solution of methyl 4-chloro-1-(2-(difluoromethoxy)ethyl)-1H-indole-3-carboxylate (0.100 g, 0.33 mmol) in methanol (50 mL) was added sodium hydroxide (10%, 5 mL). The mixture was stirred at 60° C. overnight, cooled to room temperature, the solvent was removed in vacuo. The pH value of the residue was adjusted to 1 with addition of hydrochloric acid (1N), and extracted with EtOAc (20 mL×3). The combined extracts was washed with brine (10 mL), dried over anhydrous sodium sulfate, filtered and concentrated in vacuo, The residue was purified by column chromatography on silica gel (petroleum ether: EtOAc=2:1) to afford 4-chloro-1-(2-(difluoromethoxy) ethyl)-1H-indole-3-carboxylic acid (0.090 g, 98%) as a yellow solid. [M+H]$^+$ 290.1.

Step 4: Preparation of 4-chloro-N-((4,4-difluorocyclohexyl)methyl)-1-(2-(difluoromethoxy) ethyl)-1H-indole-3-carboxamide

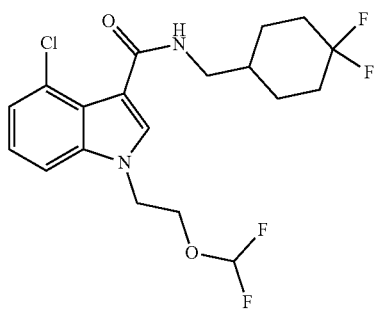 [SMILES: O=C(NCC1CCC(F)(F)CC1)c1cn(CCOC(F)F)c2cccc(Cl)c12]

A mixture of 4-chloro-1-(2-(difluoromethoxy)ethyl)-1H-indole-3-carboxylic acid (0.09 g, 0.31 mmol), (4,4-difluorocyclohexyl)methanamine (0.046 g, 0.31 mmol), HOBt (0.126 g, 0.93 mmol), EDCI (0.090 g, 0.47 mmol) and triethylamine (0.063 g, 0.62 mmol) in DCM (5 mL) was stirred at room temperature for 2 h, then quenched with water (10 mL), and extracted with EtOAc (20 mL×3). The combined extract was washed with brine (10 mL), dried over anhydrous sodium sulfate, filtered and concentrated in vacuo. The residue was purified by column chromatography on silica gel (hexane:EtOAc=2:1) to afford 4-chloro-N-((4, 4-difluorocyclohexyl) methyl)-1-(2-(difluoromethoxy) ethyl)-1H-indole-3-carboxamide (0.050 g, 38%) as a white solid.

$^1$H NMR (500 MHz, DMSO-d$_6$) δ 8.12 (t, J=6.0 Hz, 1H), 7.74 (s, 1H), 7.58 (d, J=8.0 Hz, 1H), 7.20 (t, J=7.5 Hz, 1H), 7.15 (d, J=7.5 Hz, 1H), 6.79-6.49 (m, 1H), 4.50 (t, J=5.0 Hz, 2H), 4.18 (t, J=5.0 Hz, 2H), 3.16 (t, J=6.5 Hz, 2H), 2.06-2.00 (m, 2H), 1.85-1.70 (m, 5H), 1.30-1.21 (m, 2H) ppm; [M+H]+ 421.0.

Example 33: Preparation of 4-chloro-N-((4,4-difluorocyclohexyl)methyl)-1-(((1-hydroxycyclopropyl)methyl)-1H-indole-3-carboxamide (117)

CMTP Reaction Example

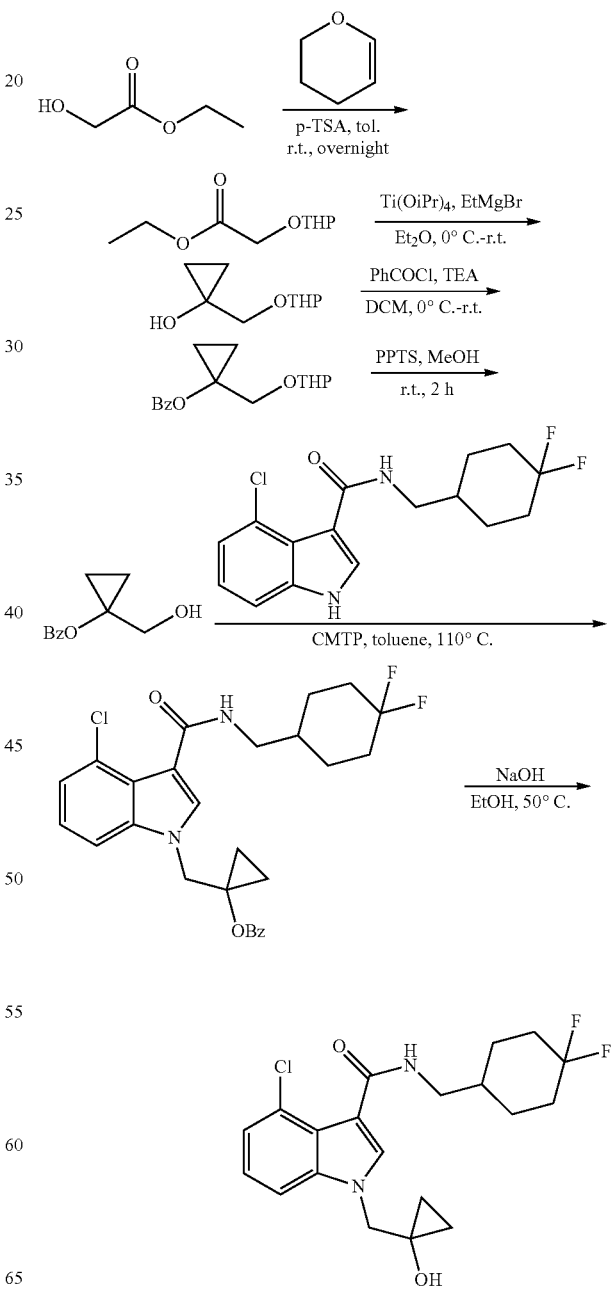

Step 1: Preparation of ethyl 2-(tetrahydro-2H-pyran-2-yloxy)acetate

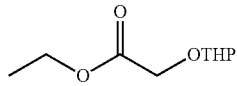

A mixture of 3,4-dihydro-2H-pyran (20.4 g, 242.3 mmol), ethyl 2-hydroxyacetate (24.0 g, 230.8 mmol) and TsOH (0.794 g, 4.6 mmol) in toluene (150 mL) was stirred at room temperature overnight. The resulting mixture was concentrated in vacuo and the residue was purified by column chromatography on silica gel (2% EtOAc in petroleum ether) to afford ethyl 2-(tetrahydro-2H-pyran-2-yloxy)acetate (25.2 g, 58%) as a colorless oil.

Step 2: Preparation of 1-((tetrahydro-2H-pyran-2-yloxy)methyl)cyclopropanol

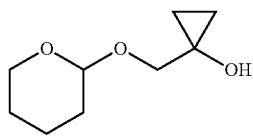 [SMILES: OC1(COC2CCCCO2)CC1]

To a stirred solution of ethyl 2-(tetrahydro-2H-pyran-2-yloxy)acetate (1.0 g, 5.32 mmol) in anhydrous Et$_2$O (30 mL) was added Ti(Oi-Pr)$_4$ (0.997 g, 3.51 mmol) and ethylmagnesium bromide (13.1 mmol, 1 M in Et$_2$O) dropwise at 0° C. After being stirred at room temperature for 2 h, the resulting mixture was quenched with water (10 mL) at 0° C. and extracted with EtOAc (50 mL×3). The combined organic layers were dried over Na$_2$SO$_4$, filtered and concentrated in vacuo. The residue was purified by silica gel column chromatography (4% EtOAc in petroleum ether) to afford 1-((tetrahydro-2H-pyran-2-yloxy)methyl)cyclopropanol (0.5 g, 54%) as a colorless oil.

Step 3: Preparation of 1-((tetrahydro-2H-pyran-2-yloxy)methyl)cyclopropyl benzoate

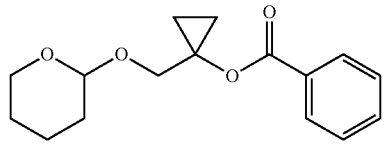 [SMILES: O=C(OC1(COC2CCCCO2)CC1)c1ccccc1]

To a stirred solution of 1-((tetrahydro-2H-pyran-2-yloxy)methyl)cyclopropanol (0.500 g, 2.9 mmol) in anhydrous DCM (15 mL) was added benzoyl chloride (0.494 g, 3.5 mmol) and TEA (0.879 g, 8.7 mmol) dropwise at 0° C. After being stirred at room temperature overnight, the resulting mixture was concentrated in vacuo and the residue was purified by column chromatography on silica gel (0-20% EtOAc in petroleum ether) to afford 1-((tetrahydro-2H-pyran-2-yloxy)methyl)cyclopropyl benzoate (0.6 g, 75%) as a yellow oil.

Step 4: Preparation of 1-(hydroxymethyl)cyclopropyl benzoate

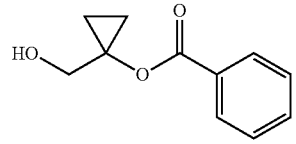 [SMILES: O=C(OC1(CO)CC1)c1ccccc1]

A mixture of 1-((tetrahydro-2H-pyran-2-yloxy)methyl)cyclopropyl benzoate (0.6 g, 2.17 mmol) and PPTS (0.055 g, 0.22 mmol) in methanol (50 mL) was stirred at room temperature for 2 h. The resulting mixture was concentrated in vacuo and the residue was purified by column chromatography on silica gel (0-10% EtOAc in petroleum ether) to afford 1-(hydroxymethyl)cyclopropyl benzoate (0.200 g, 47%) as a colorless oil.

Step 5: Preparation of 1-((4-chloro-3-((4,4-difluorocyclohexyl)methylcarbamoyl)-1H-indol-1-yl)methyl)cyclopropyl benzoate. (CMTP—Example)

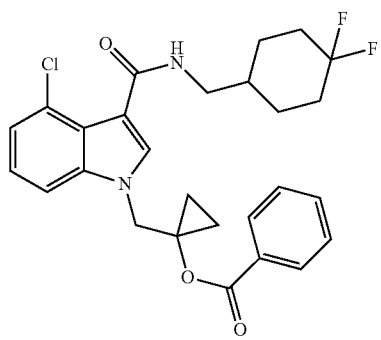 [SMILES: O=C(OC1(Cn2cc(C(=O)NCC3CCC(F)(F)CC3)c3c(Cl)cccc32)CC1)c1ccccc1]

A mixture of 1-(hydroxymethyl)cyclopropyl benzoate (0.100 g, 0.52 mmol), 4-chloro-N-((4,4-difluorocyclohexyl)methyl)-1H-indole-3-carboxamide (0.085 g, 0.26 mmol) and cyanomethylenetributylphosphorane (CMTP) (0.188 g, 0.78 mmol) in anhydrous toluene (4 mL) was stirred at 110° C. for 4 hour under nitrogen. The resulting mixture was concentrated in vacuo and the residue was purified by column chromatography on silica gel (0-5% MeOH in DCM) to afford 1-((4-chloro-3-((4,4-difluorocyclohexyl)methylcarbamoyl)-1H-indol-1-yl)methyl)-cyclopropyl benzoate (0.050 g, 38%) as a white solid.

Step 6: Preparation of 4-chloro-N-((4,4-difluorocyclohexyl)methyl)-1-((1-hydroxycyclopropyl)methyl)-1H-indole-3-carboxamide

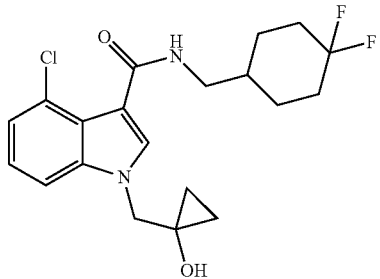 [SMILES: O=C(NCC1CCC(F)(F)CC1)c1cn(CC2(O)CC2)c2cccc(Cl)c12]

A solution of 1-((4-chloro-3-((4,4-difluorocyclohexyl)methylcarbamoyl)-1H-indol-1-yl) methyl)cyclopropyl benzoate (0.044 g, 0.088 mmol) and NaOH (1.0 mL, 2 M) in ethanol (2.0 mL) was stirred at 50° C. for 2 h. The resulting mixture was concentrated in vacuo and the residue was purified by column chromatography on silica gel purified by prep-HPLC to afford 4-chloro-N-((4,4-difluorocyclohexyl)methyl)-1-((1-hydroxycyclopropyl)methyl)-1H-indole-3-carboxamide (0.006 g, 17%) as a white solid.

$^1$H NMR (500 MHz, CDCl$_3$) δ 7.98 (s, 1H), 7.45-7.42 (m, 1H), 7.25-7.20 (m, 2H), 6.87-6.85 (m, 1H), 4.29 (s, 2H), 3.43 (t, J=8.3 Hz, 2H), 2.24-2.14 (m, 3H), 1.94-1.92 (m, 2H) 1.82-1.70 (m, 3H), 1.47-1.28 (m, 2H), 1.00-0.98 (m, 2H), 0.86-0.83 (m, 2H) ppm; [M+H]$^+$ 397.2.

Example 34: Preparation of 1-(2-aminoethyl)-4-chloro-N-((4,4-difluorocyclo-hexyl) methyl)-1H-indole-3-carboxamide (6)

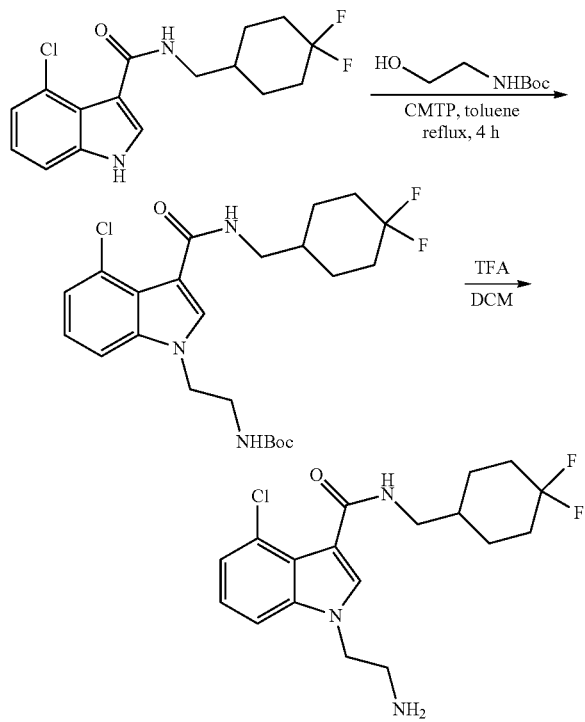

Step 1: Preparation of tert-butyl 2-(4-chloro-3-((4,4-difluorocyclohexyl) methyl carbamoyl)-1H-indol-1-yl)ethylcarbamate

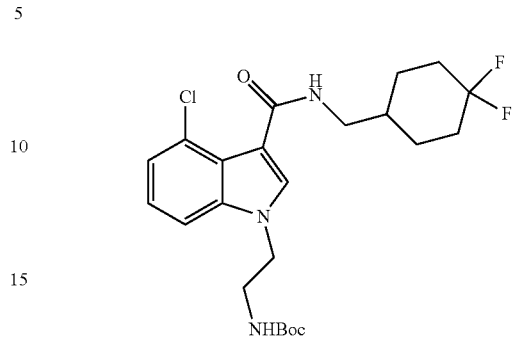

A solution of 4-chloro-N-((4,4-difluorocyclohexyl)methyl)-1H-indole-3-carboxamide (0.15 g, 0.46 mmol), tert-butyl 2-hydroxyethylcarbamate (0.148 g, 0.92 mmol) and cyanomethylenetributylphosphorane (CMTP) (0.443 g, 1.84 mmol) in toluene (2 mL) was heated at 110° C. under nitrogen for 4 h. The mixture was quenched with water (10 mL) and extracted with EtOAc (10 mL×3). The organic layers were washed with brine, dried over Na$_2$SO$_4$, filtrated and concentrated to give a residue, which was purified by Prep-TLC to afford tert-butyl 2-(4-chloro-3-((4,4-difluorocyclohexyl)methylcarbamoyl)-1H-indol-1-yl)ethylcarbamate (0.200 g, 80%) as a white solid.

Step 2: Preparation of 1-(2-aminoethyl)-4-chloro-N-((4,4-difluorocyclohexyl)methyl)-1H-indole-3-carboxamide

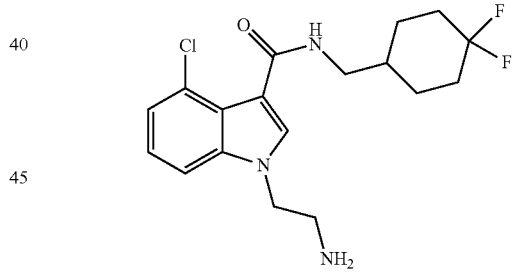

To a solution of tert-butyl 2-(4-chloro-3-((4,4-difluorocyclohexyl)methylcarbamoyl)-1H-indol-1-yl)ethylcarbamate (0.200 g, 0.43 mmol) in DCM (10 mL) was added TFA (10 mL). The reaction mixture was stirred at room temperature for 2 h. The volume was reduced in vacuo to approximately 2 mL. The residual liquid was partitioned between saturated aqueous NaHCO$_3$ (10 mL) and DCM (30 mL). The organic layer was dried over anhydrous Na$_2$SO$_4$, concentrated and purified by Prep-HPLC to provide 1-(2-aminoethyl)-4-chloro-N-((4,4-difluorocyclohexyl)methyl)-1H-indole-3-carboxamide (0.080 g, 51%) as a white solid.

$^1$H NMR (500 MHz, DMSO-d$_6$) 8.07 (t, J=5.5 Hz, 1H), 7.72 (s, 1H), 7.54 (d, J=7.5 Hz, 1H), 7.16 (t, J=7.5 Hz, 1H), 7.12 (d, J=7.0 Hz, 1H), 4.16 (t, J=6.5 Hz, 2H), 3.15 (t, J=6.5 Hz, 2H), 2.88 (t, J=6.5 Hz, 2H), 2.05-1.99 (m, 2H), 1.85-1.68 (m, 5H), 1.57-1.34 (m, 2H), 1.28-1.20 (m, 2H) ppm; [M+H]$^+$ 370.1.

Example 35. 4-chloro-N-((3,3-difluoro-1-hydroxy-cyclohexyl)methyl)-1-(2-(pyrrolidin-1-yl)ethyl)-1H-indole-3-carboxamide (178)

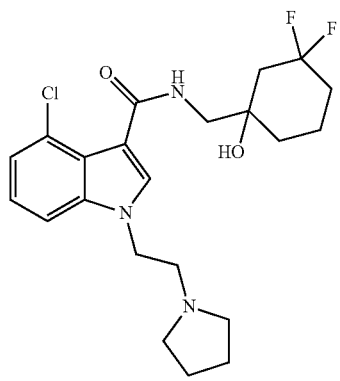 [SMILES: O=C(NCC1(O)CCCC(F)(F)C1)c1cn(CCN2CCCC2)c2cccc(Cl)c12]

The title compound was synthesized according to the procedure described in Example 33 using 4-chloro-N-((3,3-difluoro-1-hydroxycyclohexyl)methyl)-1H-indole-3-carboxamide (70.00 mg; 0.28 mmol; 1.00 eq.), 2-(pyrrolidin-1-yl)ethanol (35.28 mg; 0.31 mmol; 2.50 eq.) and (Tributyl-lambda5-phosphanylidene)-acetonitrile (147.72 mg; 0.61 mmol; 4.00 eq.) in Toluene (3 mL) by heating at 110° C. for 4 hours.

$^1$H NMR (400 MHz, DMSO-d$_6$) δ ppm 7.88 (2H), 7.55 (1H), 7.20 (2H), 4.67 (s, 1H), 4.30 (2H), 3.39 (1H), 3.21 (1H), 2.81 (2H), 2.03 (m, 3H), 1.75 (3H), 1.59 (4H). m/z: 440 [M+H]

Example 36: (R)-4-chloro-N-((3,3-difluoro-1-hydroxycyclohexyl)methyl)-1-(2-(pyrrolidin-1-yl)ethyl)-1H-indole-3-carboxamide (176)

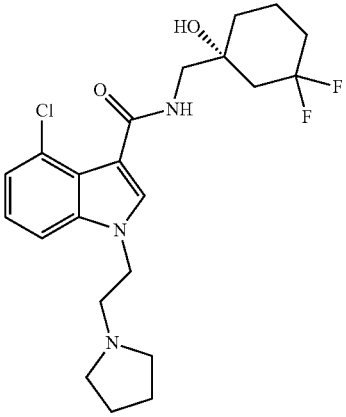 [SMILES: O=C(NC[C@@]1(O)CCCC(F)(F)C1)c1cn(CCN2CCCC2)c2cccc(Cl)c12]

The title compound was separated via chiral column from racemic 4-chloro-N-((3,3-difluoro-1-hydroxycyclohexyl)methyl)-1-(2-(pyrrolidin-1-yl)ethyl)-1H-indole-3-carboxamide. Chiral-HPLC conditions: Co-Solvent: 30% MeOH; Column: AD-H (4.6*250 mm, 5 um); CO$_2$ Flow Rate: 2.1 mL/min; Co-Solvent Flow Rate: 0.9 mL/min; Total Flow: 3 mL/min; Runtime: 9 min.

$^1$H NMR (400 MHz, DMSO-d$_6$) δ ppm 7.88 (2H), 7.55 (1H), 7.20 (2H), 4.67 (s, 1H), 4.30 (2H), 3.39 (1H), 3.21 (1H), 2.81 (2H), 2.03 (m, 3H), 1.75 (3H), 1.59 (4H). m/z: 440 [M+H]

Example 37: (S)-4-chloro-N-((3,3-difluoro-1-hydroxycyclohexyl)methyl)-1-(2-(pyrrolidin-1-yl)ethyl)-1H-indole-3-carboxamide (177)

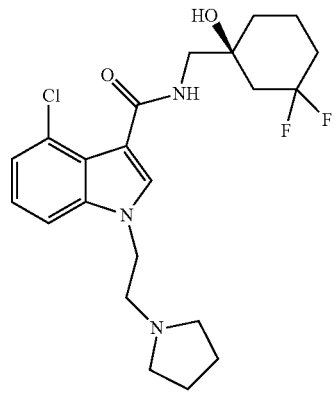 [SMILES: O=C(NC[C@]1(O)CCCC(F)(F)C1)c1cn(CCN2CCCC2)c2cccc(Cl)c12]

The title compound was separated (See example 36) from racemic 4-chloro-N-((3,3-difluoro-1-hydroxycyclohexyl)methyl)-1-(2-(pyrrolidin-1-yl)ethyl)-1H-indole-3-carboxamide.

$^1$H NMR (400 MHz, DMSO-d$_6$) δ ppm 7.88 (2H), 7.55 (1H), 7.20 (2H), 4.67 (s, 1H), 4.30 (2H), 3.39 (1H), 3.21 (1H), 2.81 (2H), 2.03 (m, 3H), 1.75 (3H), 1.59 (4H). m/z: 440 [M+H]

Example 38: Preparation of 4-chloro-N-((3,3-difluoro-1-hydroxycyclohexyl)methyl)-1-(2-(2-oxopyrrolidin-1-yl)ethyl)-1H-indole-3-carboxamide (188)

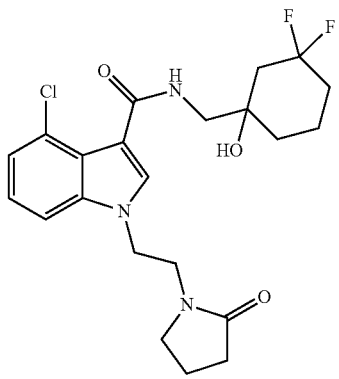 [SMILES: O=C(NCC1(O)CCCC(F)(F)C1)c1cn(CCN2CCCC2=O)c2cccc(Cl)c12]

The title compound was synthesized according to the procedure described in Example 33 using 4-chloro-N-((3,3-difluoro-1-hydroxycyclohexyl)methyl)-1H-indole-3-carboxamide (70.00 mg; 0.28 mmol; 1.00 eq.), 2-hydroxyethyl-pyrrolidin-2-one (39.56 mg; 0.31 mmol; 2.50 eq.) and (Tributyl-lambda5-phosphanylidene)-acetonitrile (147.72 mg; 0.61 mmol; 4.00 eq.) in Toluene (3 mL) stirred at 110° C. for 4 hours to provide the desired product.

$^1$H NMR (400 MHz, DMSO-d$_6$) δ ppm 8.05 (s, 1H), 7.74 (s, 1H), 7.52 (s, 1H), 7.21 (1H), 7.16 (m, 1H), 4.33 (m, 2H), 3.55 (2H), 3.14 (2H), 3.10 (2H), 2.12 (2H), 2.03 (m, 2H), 1.86-1.75 (6H), 1.45 (m, 2H), 1.23 (m, 2H), 0.89 (1H). m/z: 454 [M+H]

Example 39: (R)-4-chloro-N-((3,3-difluoro-1-hydroxycyclohexyl)methyl)-1-(2-(2-oxopyrrolidin-1-yl)ethyl)-1H-indole-3-carboxamide (186)

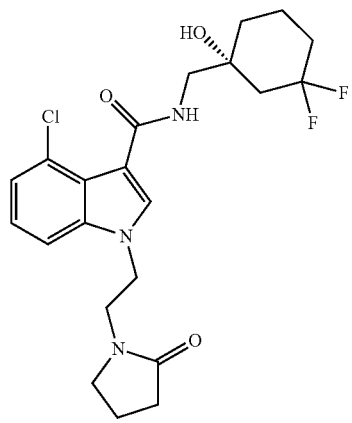 [SMILES: O=C(NC[C@@]1(O)CCCC(F)(F)C1)c1cn(CCN2CCCC2=O)c2cccc(Cl)c12]

The title compound was separated via chiral column from racemic 4-chloro-N-((3,3-difluoro-1-hydroxycyclohexyl)methyl)-1-(2-(2-oxopyrrolidin-1-yl)ethyl)-1H-indole-3-carboxamide. Chiral-HPLC conditions: Co-Solvent: 25% MeOH; Column: OD-H (4.6*250 mm, 5 um); CO2 Flow Rate: 2.25 mL/min; Co-Solvent Flow Rate: 0.75 mL/min; Total Flow: 3 mL/min; Runtime: 9 min.

$^1$H NMR (400 MHz, DMSO-d$_6$) δ ppm 8.05 (s, 1H), 7.74 (s, 1H), 7.52 (s, 1H), 7.21 (1H), 7.16 (m, 1H), 4.33 (m, 2H), 3.55 (2H), 3.14 (2H), 3.10 (2H), 2.12 (2H), 2.03 (m, 2H), 1.86-1.75 (6H), 1.45 (m, 2H), 1.23 (m, 2H), 0.89 (1H). m/z: 454 [M+H]

Example 40: (S)-4-chloro-N-((3,3-difluoro-1-hydroxycyclohexyl)methyl)-1-(2-(2-oxopyrrolidin-1-yl)ethyl)-1H-indole-3-carboxamide (187)

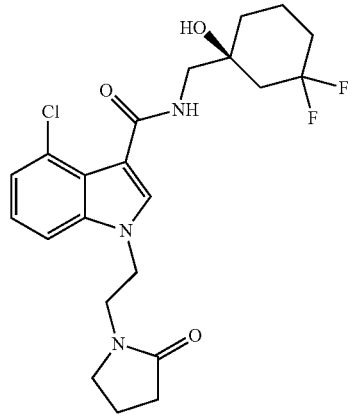 [SMILES: O=C(NC[C@]1(O)CCCC(F)(F)C1)c1cn(CCN2CCCC2=O)c2cccc(Cl)c12]

The title compound was separated (see example 39) from racemic 4-chloro-N-((3,3-difluoro-1-hydroxycyclohexyl)methyl)-1-(2-(2-oxopyrrolidin-1-yl)ethyl)-1H-indole-3-carboxamide.

$^1$H NMR (400 MHz, DMSO-d$_6$) δ ppm 8.05 (s, 1H), 7.74 (s, 1H), 7.52 (s, 1H), 7.21 (1H), 7.16 (m, 1H), 4.33 (m, 2H), 3.55 (2H), 3.14 (2H), 3.10 (2H), 2.12 (2H), 2.03 (m, 2H), 1.86-1.75 (6H), 1.45 (m, 2H), 1.23 (m, 2H), 0.89 (1H). m/z: 454 [M+H]

Example 41: Preparation of 4-chloro-N-((4,4-difluorocyclohexyl)methyl)-1-(2-(pyrrolidin-1-yl)ethyl)-1H-indole-3-carboxamide (179)

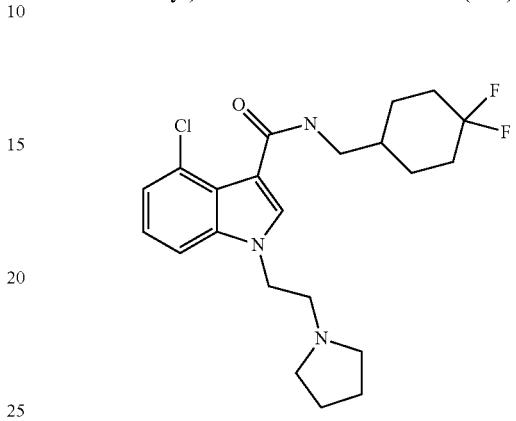

The title compound was synthesized according to the procedure described in Example 33 using 4-Chloro-1H-indole-3-carboxylic acid (4,4-difluoro-cyclohexyl methyl)-amide (50.00 mg; 0.15 mmol; 1.00 eq.), 2-Pyrrolidin-1-yl-ethanol (44.06 mg; 0.38 mmol; 2.50 eq.) and (Tributyl-lambda5-phosphanylidene)-acetonitrile (147.72 mg; 0.61 mmol; 4.00 eq.) in Toluene (3 mL).

$^1$H NMR (400 MHz, DMSO-d$_6$) δ 10.54 (m, 1H), 8.15 (s, 1H), 7.82 (s, 1H), 7.62 (s, 1H), 7.20-7.27 (m, 2H), 4.61 (m, 2H), 3.57-3.62 (4H), 3.19 (2H), 3.06 (2H), 2.02 (2H), 1.86 (2H), 1.71 (m, 1H), 1.25 (m, 1H). m/z: 424 [M+H]

Example 42: Preparation of 4-chloro-N-((4,4-difluorocyclohexyl)methyl)-1-(2-(2-oxopyrrolidin-1-yl)ethyl)-1H-indole-3-carboxamide (189)

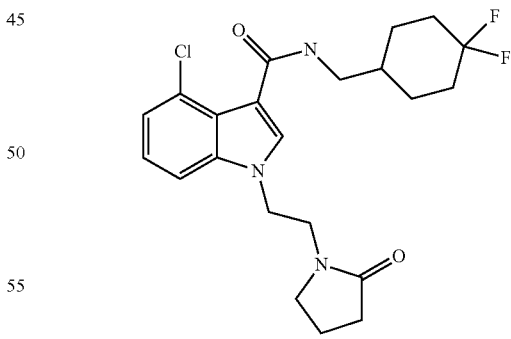

The title compound was synthesized according to the procedure described in Example 33 using 4-Chloro-1H-indole-3-carboxylic acid (4,4-difluoro-cyclohexyl methyl)-amide (50.00 mg; 0.15 mmol; 1.00 eq.), 2-hydroxyethyl-pyrrolidin-2-one (49.41 mg; 0.38 mmol; 2.50 eq.) and (Tributyl-lambda5-phosphanylidene)-acetonitrile (147.72 mg; 0.61 mmol; 4.00 eq.) in Toluene (3 mL).

$^1$H NMR (400 MHz, DMSO-d$_6$) δ ppm 8.05 (s, 1H), 7.74 (s, 1H), 7.52 (s, 1H), 7.21 (1H), 7.16 (m, 1H), 4.33 (m, 2H), 3.55 (2H), 3.14 (2H), 3.10 (2H), 2.12 (2H), 2.03 (m, 2H), 1.86-1.75 (6H), 1.45 (m, 2H), 1.23 (m, 2H), 0.89 (1H). m/z: 438 [M+H]

Example 43: Preparation of 4-chloro-N-((4,4-difluorocyclohexyl)methyl)-1-(2-(piperidin-1-yl)ethyl)-1H-indole-3-carboxamide (193)

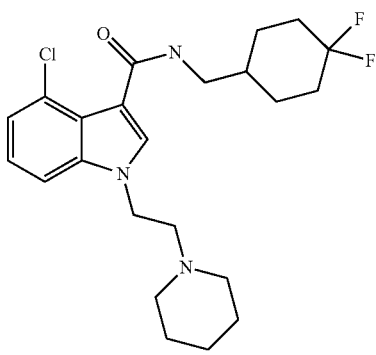 [SMILES: O=C(NCC1CCC(F)(F)CC1)c1cn(CCN2CCCCC2)c2cccc(Cl)c12]

The title compound was synthesized according to the procedure described in Example 33 using 4-Chloro-1H-indole-3-carboxylic acid (4,4-difluoro-cyclohexyl methyl)-amide (50.00 mg; 0.15 mmol; 1.00 eq.), 2-Piperidin-1-yl-ethanol (49.42 mg; 0.38 mmol; 2.50 eq.) and (Tributyl-lambda5-phosphanylidene)-acetonitrile (147.72 mg; 0.61 mmol; 4.00 eq.) in Toluene (3 mL).

$^1$H NMR (400 MHz, DMSO-d$_6$) δ ppm 10.54 (m, 1H), 8.15 (s, 1H), 7.82 (s, 1H), 7.62 (s, 1H), 7.20-7.27 (m, 2H), 4.61 (m, 2H), 3.57-3.62 (4H), 3.19 (2H), 3.06 (2H), 2.02 (2H), 1.86 (2H), 1.71 (m, 1H), 1.25 (m, 1H). m/z: 438 [M+H]

Example 44: Preparation of 4-chloro-N-((3,3-difluoro-1-hydroxycyclohexyl)methyl)-1-(2-(piperidin-1-yl)ethyl)-1H-indole-3-carboxamide (192)

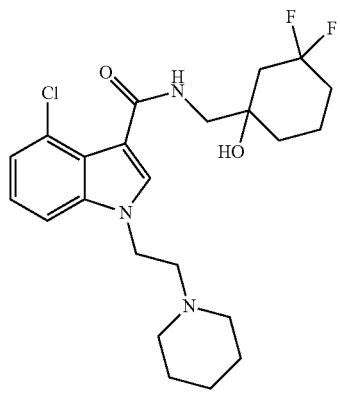 [SMILES: O=C(NCC1(O)CCCC(F)(F)C1)c1cn(CCN2CCCCC2)c2cccc(Cl)c12]

The title compound was synthesized according to the procedure described in Example 33 using 4-chloro-N-((3,3-difluoro-1-hydroxycyclohexyl)methyl)-1H-indole-3-carboxamide (70.00 mg; 0.28 mmol; 1.00 eq.), 2-Piperidin-1-yl-ethanol (39.56 mg; 0.31 mmol; 2.50 eq.) and (Tributyl-lambda5-phosphanylidene)-acetonitrile (147.72 mg; 0.61 mmol; 4.00 eq.) in Toluene (3 mL).

$^1$H NMR (400 MHz, DMSO-d$_6$) δ ppm 7.88 (m, 1H), 7.85 (s, 1H), 7.56 (1H), 7.19-7.15 (m, 2H), 4.61 (m, 2H), 3.57-3.62 (4H), 3.19 (2H), 3.06 (2H), 2.02 (2H), 1.86 (2H), 1.71 (m, 1H), 1.25 (m, 1H). m/z: 454 [M+H]

Example 45: Preparation of 4-chloro-N-((4,4-difluorocyclohexyl)methyl)-1-(3,3,3-trifluoropropyl)-1H-indole-3-carboxamide (12)

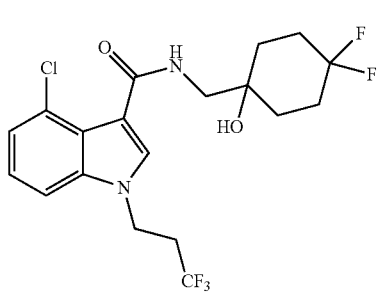 [SMILES: O=C(NCC1(O)CCC(F)(F)CC1)c1cn(CCC(F)(F)F)c2cccc(Cl)c12]

The title compound was synthesized according to the procedure described in Example 2 using 4-chloro-1-(3,3,3-trifluoropropyl)-1H-indole-3-carboxylic acid (0.050 g, 0.172 mmol), EDCI (0.049 g, 0.223 mmol), HOBt (0.0457 g, 0.223 mmol), TEA (0.1 mL), and 1-(aminomethyl)-4,4-difluorocyclohexanol hydrochloride (0.0219 mg, 0.172 mmol) in DCM to provide 4-chloro-N-((4,4-difluoro-1-hydroxycyclohexyl)methyl)-1-(3,3,3-trifluoropropyl)-1H-indole-3-carboxamide (40 mg, 55%) as a light-yellow solid.

$^1$H NMR (500 MHz, DMSO-d$_6$) δ 7.93 (t, J=6.0 Hz, 1H), 7.88 (s, 1H), 7.57 (d, J=8.0 Hz, 1H), 7.23 (t, J=7.5 Hz, 1H), 7.18 (d, J=7.0 Hz, 1H), 4.73 (s, 1H), 4.51 (t, J=7.0 Hz, 2H), 3.31 (t, J=5.5 Hz, 2H), 2.90-2.84 (m, 2H), 2.07-1.99 (m, 2H), 1.90-1.86 (m, 2H), 1.66-1.64 (m, 4H) ppm; [M+H]$^+$ 439.1.

Example 46: Preparation of 4-chloro-1-((3,3-difluorocyclobutyl)methyl)-N-((4,4-difluorocyclohexyl)methyl)-1H-indole-3-carboxamide (127)

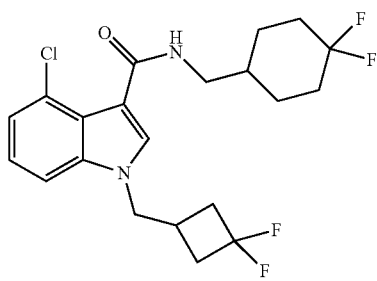 [SMILES: O=C(NCC1CCC(F)(F)CC1)c1cn(CC2CC(F)(F)C2)c2cccc(Cl)c12]

The title compound was synthesized according to the procedure described in Example 33 using 4-Chloro-1H-indole-3-carboxylic acid (4,4-difluoro-cyclohexyl methyl)-amide (50.00 mg; 0.15 mmol; 1.00 eq.), 3,3-difluorocyclobutyl-methanol (20.55 mg; 0.38 mmol; 2.50 eq.) and (Tributyl-lambda5-phosphanylidene)-acetonitrile (147.72 mg; 0.61 mmol; 4.00 eq.) in Toluene (3 mL).

$^1$H NMR (400 MHz, DMSO-d$_6$) δ ppm 10.54 (m, 1H), 8.10 (s, 1H), 7.78 (s, 1H), 7.60 (s, 1H), 7.15-7.19 (m, 2H), 4.31 (m, 2H), 3.17 (2H), 2.60 (2H), 2.03 (2H), 1.85 (2H), 1.71 (m, 1H), 1.60 (1H), 1.37 (1H), 1.25 (m, 1H). m/z: 432 [M+H]

Example 47: Preparation of 4-chloro-N-((4,4-difluorocyclohexyl)methyl)-1-(3,3,3-trifluoropropyl)-1H-indole-3-carboxamide (13)

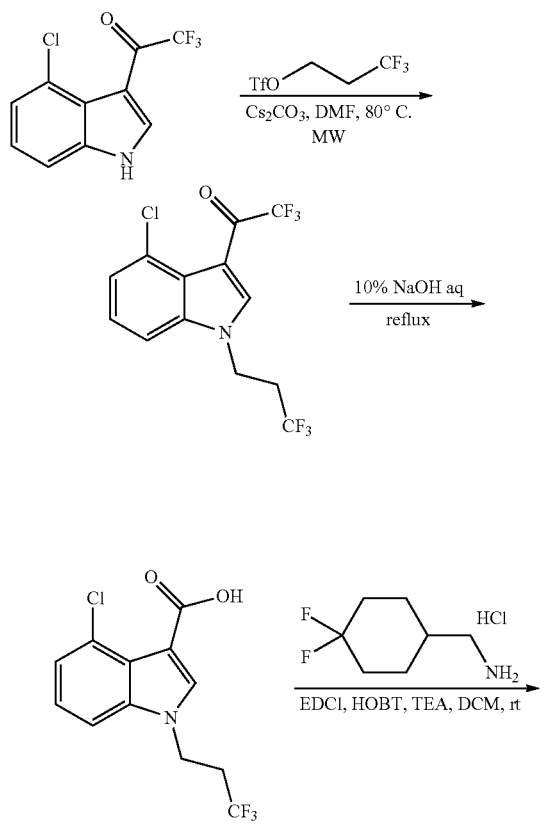

Step 1: Preparation of 3,3,3-trifluoropropyl trifluoromethanesulfonate

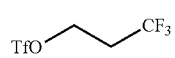

To a solution of 3,3,3-trifluoropropan-1-ol (0.684 g, 6 mmol) and pyridine (0.48 g, 6 mmol) in dry DCM (5 mL) at 0° C. was added trifluoromethanesulfonic anhydride (1.86 g, 6.6 mmol) dropwise. The reaction was stirred at 0° C. for 1 h, and then ice water (10 mL) was added. The pH value was adjusted to 7 with saturated aqueous NaHCO$_3$ and the solution was extracted with DCM (10 mL×3), dried over anhydrous Na$_2$SO$_4$, filtered and concentrated to give 3,3,3-trifluoropropyl trifluoromethanesulfonate (0.98 g, 66%) as pale yellow oil.

Step 2: Preparation of 1-(4-chloro-1-(3,3,3-trifluoropropyl)-1H-indol-3-yl)-2,2,2-trifluoro-ethanone

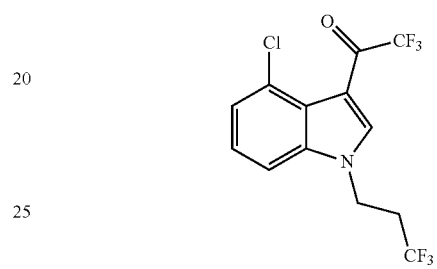

A mixture of 1-(4-chloro-1H-indol-3-yl)-2,2,2-trifluoroethanone (0.5 g, 2 mmol), Cs$_2$CO$_3$ (2.6 g, 8 mmol) and 3,3,3-trifluoropropyl trifluoromethanesulfonate (0.74 g, 3 mmol) in DMF (10 mL) was heated at 80° C. for 1 h under microwave condition. The reaction was diluted with water (10 mL), extracted with EtOAc (10 mL×3), dried over anhydrous Na$_2$SO$_4$, filtered and concentrated in vacuo. The residue was purified by column chromatography on silica gel (petroleum ether:EtOAc=20:1) to give 1-(4-chloro-1-(3,3,3-trifluoropropyl)-1H-indol-3-yl)-2,2,2-trifluoro-ethanone (1.20 g, 71%) as a light yellow solid.

Step 3: Preparation of 4-chloro-1-(3,3,3-trifluoropropyl)-1H-indole-3-carboxylic acid

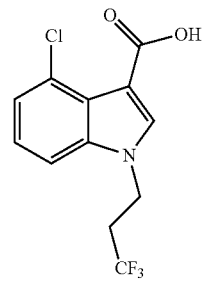 [SMILES: O=C(O)c1cn(CCC(F)(F)F)c2cccc(Cl)c12]

A mixture of 1-(4-chloro-1-(3,3,3-trifluoropropyl)-1H-indol-3-yl)-2,2,2-trifluoroethanone (0.650 g, 1.9 mmol) and 10% aqueous NaOH (6 mL) was refluxed for 1 h. Then the reaction was cooled to room temperature and the pH value was adjusted to 3 with conc. HCl. The formed precipitate was collected by filtration and dried to give 4-chloro-1-(3,3,3-trifluoropropyl)-1H-indole-3-carboxylic acid (0.320 g, 58%) as a white solid.

Step 4: Preparation of 4-chloro-N-((4,4-difluorocyclohexyl)methyl)-1-(3,3,3-trifluoropropyl)-1H-indole-3-carboxamide

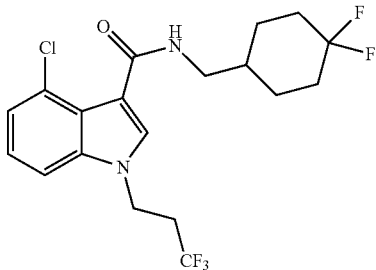 [SMILES: O=C(NCC1CCC(F)(F)CC1)c1cn(CCC(F)(F)F)c2cccc(Cl)c12]

A mixture of 4-chloro-1-(3,3,3-trifluoropropyl)-1H-indole-3-carboxylic acid (0.050 g, 0.17 mmol), EDCI (0.043 g, 0.22 mmol), HOBt (0.023 g, 0.22 mmol) and TEA (0.1 mL, 0.7 mmol) in DCM (1.0 mL) was stirred at room temperature for 1 h. Then cyclohexylmethanamine hydrochloride (0.032 g, 0.17 mmol) was added and the reaction was stirred at room temperature for 3 h. The mixture was diluted with DCM (10 mL) and washed with water (3 mL×3). The organic layer was dried over $Na_2SO_4$, filtered, concentrated to dryness, and the residue was purified by Prep-HPLC to give 4-chloro-N-((4,4-difluorocyclohexyl)methyl)-1-(3,3,3-trifluoropropyl)-1H-indole-3-carboxamide (0.020 g, 38%) as a white solid.

$^1$H NMR (500 MHz, DMSO-$d_6$): δ 8.09 (t, J=6.0 Hz, 1H), 7.81 (s, 1H), 7.55 (d, J=8.0 Hz, 1H), 7.21 (t, J=8.0 Hz, 1H), 7.16 (d, J=8.0 Hz, 1H), 4.49 (t, J=7.0 Hz, 2H), 3.31 (t, J=6.0 Hz, 2H), 2.83-2.89 (m, 2H), 2.01-2.04 (m, 2H), 1.69-1.85 (m, 5H), 1.26-1.28 (m, 2H) ppm; [M+H]$^+$ 423.1.

Example 48: Preparation of 4-Chloro-1-(3,3-difluoro-propyl)-1H-indole-3-carboxylic acid (4,4-di fluoro-cyclohexyl methyl)-amide (11)

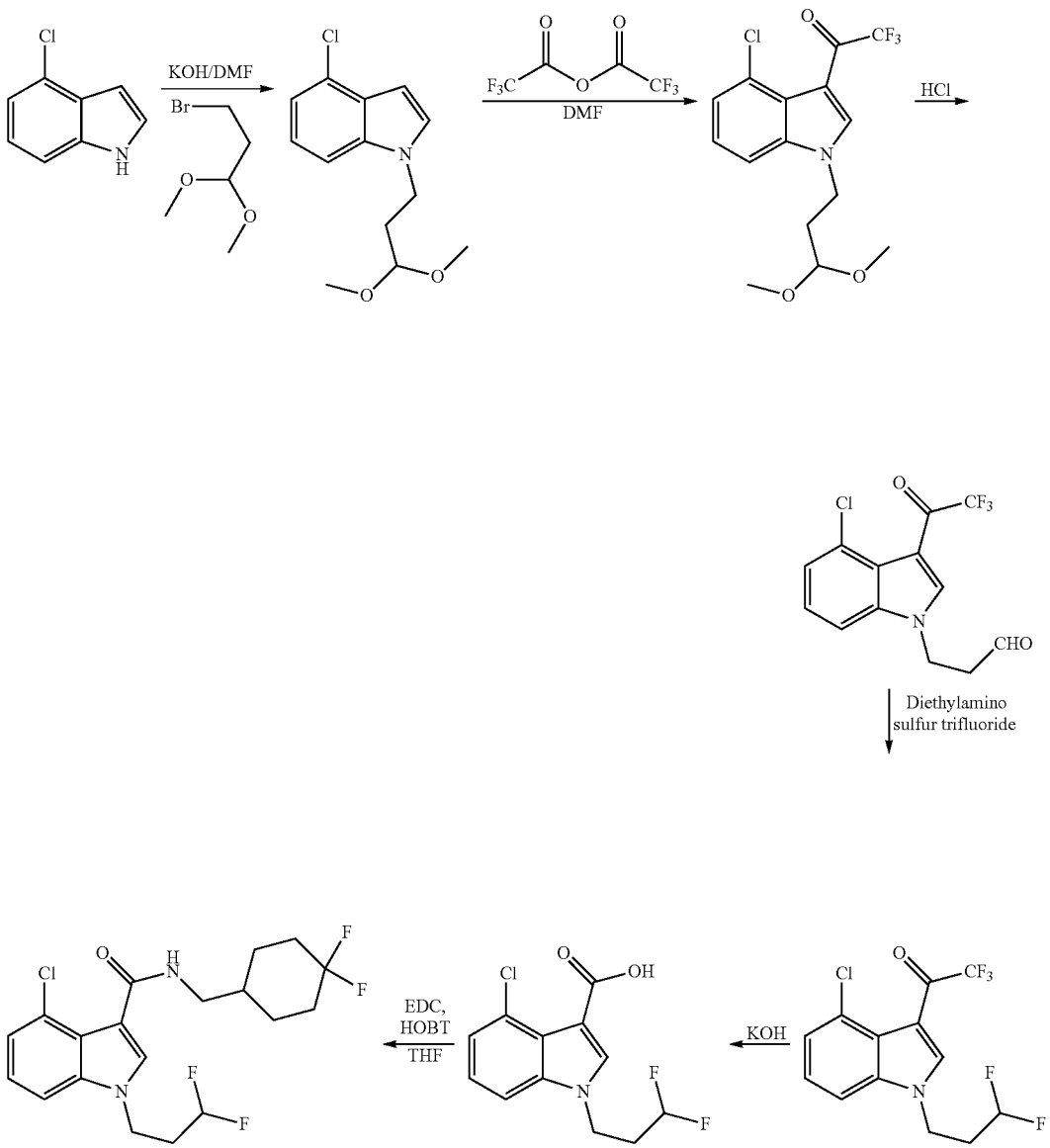

Step 1: Preparation of 4-Chloro-1-(3,3-dimethoxy-propyl)-1H-indole

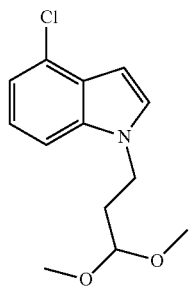 [SMILES: COC(CCn1ccc2c(Cl)cccc21)OC]

To a solution of 4-Chloro-1H-indole (1.50 g, 9.70 mmol, 1.00 eq) and 3-Bromo-1,1-dimethoxy-propane (3.75 g, 18.42 mmol, 1.90 eq) in dry DMF (15 mL, 10.00 V) was added KOH (2.56 g, 38.79 mmol, 4.00 eq) at room temperature. The mixture was stirred at 50° C. for 5 h, The completion of the reaction was confirmed by TLC and then quenched with water (1×50 mL) and extracted with EtOAc (1×100 mL). The combined extracts were washed with water (50 mL) and brine solution (50 mL), dried over $Na_2SO_4$, filtered and evaporated to afford the crude product. The crude product was further purified using column chromatography 15% ethyl acetate in petroleum ether to afford 4-Chloro-1-(3,3-dimethoxy-propyl)-1H-indole (2.45 g, 9.60 mmol, 99.0%) as a yellow liquid. $^1$H NMR (400 MHz, DMSO-d6): δ 7.49-7.43 (m, 2H), 7.15-7.07 (m, 2H), 6.47 (s, 2H), 4.26-4.19 (m, 3H), 3.20 (s, 6H), 2.03-1.98 (m, 2H) ppm.

Step 2: Preparation of 1-[4-Chloro-1-(3,3-dimethoxy-propyl)-1H-indol-3-yl]-2,2,2-trifluoro-ethanone

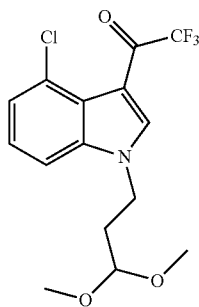 [SMILES: COC(CCn1cc(C(=O)C(F)(F)F)c2c(Cl)cccc21)OC]

To a solution of 4-Chloro-1-(3,3-dimethoxy-propyl)-1H-indole (2.45 g, 9.60 mmol, 1.00 eq) in DMF (20 mL) was added Trifluoroacetic anhydride (2.75 mL, 19.20 mmol, 2.00 eq) at room temperature. The reaction mixture was stirred at 45° C. for overnight. After the completion of the reaction as evidenced by TLC, the reaction mixture was quenched with water (1×50 mL) and extracted with EtOAc (1×100 mL). The combined extracts were washed with water (1×50 mL) and brine solution (lx 50 mL), dried over $Na_2SO_4$, filtered and evaporated to afford the crude product. 1-[4-Chloro-1-(3,3-dimethoxy-propyl)-1H-indol-3-yl]-2,2,2-trifluoro-ethanone (3.10 g, 6.16 mmol, 64.2%) as a pale yellow liquid. The crude product was used as such for the next step without further purification. [M+H]$^+$ 350.0.

Step 3: Preparation of 3-[4-Chloro-3-(2,2,2-trifluoro-acetyl)-indol-1-yl]-propionaldehyde

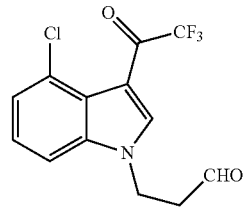 [SMILES: O=CCCn1cc(C(=O)C(F)(F)F)c2c(Cl)cccc21]

To a solution of 1-[4-Chloro-1-(3,3-dimethoxy-propyl)-1H-indol-3-yl]-2,2,2-trifluoro-ethanone (3.10 g, 6.16 mmol, 1.00 eq) in dry THF (20 mL) was added drop wise 1.5 M aqueous solution of hydrochloric acid (25 mL, 37.50 mmol, 6.09 eq). After stirred at 80° C. for 30 min, the reaction mixture was allowed to reach to RT, sat. aq. $NaHCO_3$ solution was added to the reaction mixture and solvent was removed under reduced pressure. The remaining aqueous layer was extracted with EtOAc (2×50 mL). The combined organic layers were dried over $Na_2SO_4$, filtered and the solvent was removed under reduced pressure to yield 3-[4-Chloro-3-(2,2,2-trifluoro-acetyl)-indol-1-yl]-propionaldehyde (1.80 g, 5.74 mmol, 93.2%) as a pale yellow solid, which was used in the next step without further purification. [M+H]$^+$ 322.2.

Step 4: Preparation of 1-[4-Chloro-1-(3,3-difluoro-propyl)-1H-indol-3-yl]-2,2,2-trifluoro-ethanone

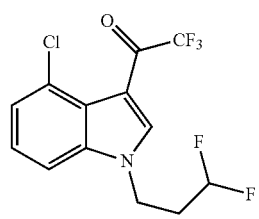 [SMILES: O=C(c1cn(CCC(F)F)c2cccc(Cl)c12)C(F)(F)F]

To a stirred solution of 3-[4-Chloro-3-(2,2,2-trifluoro-acetyl)-indol-1-yl]-propionaldehyde (1.80 g, 5.74 mmol, 1.00 eq) in DCM (20 mL) at −78° C. was added Diethylaminosulfur trifluoride (1.69 mL, 11.48 mmol, 2.00 eq) and allowed to stir for 3 h. After the completion of the reaction as evidenced by TLC, the reaction mixture was diluted with DCM (120 mL) and extracted with water (1×20 mL) and brine solution (1×20 mL). The separated organic layer was dried over $Na_2SO_4$ and concentrated under vacuum to get the crude product. which was further purified by column chromatography using silica gel (9:1) DCM and Methanol to afford 1-[4-Chloro-1-(3,3-difluoro-propyl)-1H-indol-3-yl]-2,2,2-trifluoro-ethanone (1.40 g, 4.30 mmol, 75%) as a yellow brown solid. $^1$H NMR (400 MHz, DMSO-d$_6$): δ 8.67 (s, 1H), 7.74-7.72 (m, 1H), 7.42-7.37 (m, 2H), 6.37-6.07 (m, 1H), 4.58 (t, J=7.00 Hz, 2H), 2.50-2.41 (m, 2H) ppm.

Step 5: Preparation of 4-Chloro-1-(3,3-difluoro-propyl)-1H-indole-3-carboxylic acid

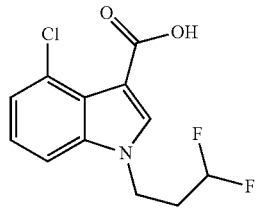 [SMILES: O=C(O)c1cn(CCC(F)F)c2cccc(Cl)c12]

A suspension of 1-[4-Chloro-1-(3,3-difluoro-propyl)-1H-indol-3-yl]-2,2,2-trifluoro-ethanone (1.40 g, 4.30 mmol, 1.00 eq,) and KOH 1N solution (20 mL) was stirred at 100° C. overnight. After the completion of the reaction as evidenced by TLC, the reaction mixture was acidified with aqueous hydrochloric acid (1.5 N, 10 mL) to pH 1~3. The formed precipitate was collected by filtration and dried to afford 4-Chloro-1-(3,3-difluoro-propyl)-1H-indole-3-carboxylic acid (0.90 g, 3.24 mmol, 75.4%) as an off-white solid. [M+H]$^+$ 274.0; LC-MS Purity (254 nm): 98.5%; $t_R$=3.37 min.

Step 6: Preparation of 4-Chloro-1-(3,3-difluoro-propyl)-1H-indole-3-carboxylic acid (4,4-di fluoro-cyclohexyl methyl)-amide

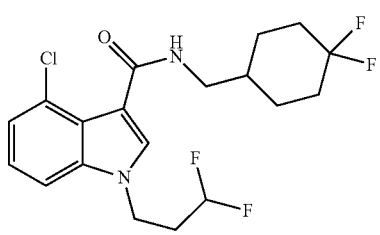 [SMILES: O=C(NCC1CCC(F)(F)CC1)c1cn(CCC(F)F)c2cccc(Cl)c12]

To a solution of 4-Chloro-1-(3,3-difluoro-propyl)-1H-indole-3-carboxylic acid (0.20 g, 0.72 mmol, 1.00 eq) and C-(4,4-Difluoro-cyclohexyl)-methylamine hydrochloride (0.16 g, 0.86 mmol, 1.20 eq) in THF (10 mL) were added Et$_3$N (0.30 mL, 2.16 mmol, 3.00 eq), EDC (0.28 g, 1.44 mmol, 2.00 eq) and Benzotriazol-1-ol (0.18 g, 1.08 mmol, 1.50 eq) at 0° C. The reaction mixture was stirred at RT for overnight. After the completion of the reaction as evidenced by TLC, the reaction mixture was diluted with ethyl acetate (1×10 mL) then washed with aq.NaHCO$_3$ solution (10%, 1×10 mL), and washed with water and brine solution, dried over Na$_2$SO$_4$ and concentrated under vacuum. The crude product was further purified using Column chromatography 45% ethyl acetate in petroleum ether to afford 4-Chloro-1-(3,3-difluoro-propyl)-1H-indole-3-carboxylic acid (4,4-difluoro-cyclohexylmethyl)-amide (0.15 g, 0.35 mmol, 49.0%) as a off-white solid. $^1$H NMR (400 MHz, DMSO-d$_6$): δ 8.10 (t, J=5.9 Hz, 1H), 7.76 (d, J=7.4 Hz, 1H), 7.53 (d, J=7.7 Hz, 1H), 7.19 (t, J=8.0 Hz, 1H), 7.14 (d, J=7.1 Hz, 1H), 6.28-5.98 (m, 1H), 4.37 (t, J=7.4 Hz, 2H), 3.13 (t, J=6.2 Hz, 2H), 2.38-2.32 (m, 2H), 2.01 (t, J=3.4 Hz, 2H), 1.84-1.67 (m, 5H), 1.27-1.18 (m, 2H), ppm; [M+H]$^+$ 405.1.

Example 49: Preparation of 4-Chloro-1-(3,3-difluoro-propyl)-1H-indole-3-carboxylic acid (3,3-difluoro-cyclohexylmethyl)-amide (9)

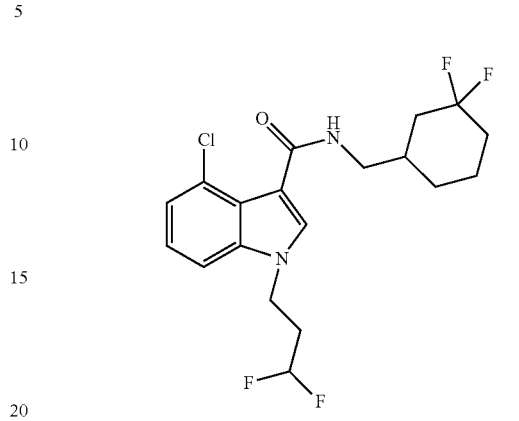

The title compound was synthesized according to the procedure described in Example 2 using 4-Chloro-1-(3,3-difluoro-propyl)-1H-indole-3-carboxylic acid (0.20 g, 0.72 mmol, 1.00 eq), C-(3,3-Difluoro-cyclohexyl)-methylamine hydrochloride (0.16 g, 0.86 mmol, 1.20 eq), Et$_3$N (0.30 mL, 2.16 mmol, 3.00 eq), EDC (0.28 g, 1.44 mmol, 2.00 eq) and Benzotriazol-1-ol (0.18 g, 1.08 mmol, 1.50 eq) to afford 4-Chloro-1-(3,3-difluoro-propyl)-1H-indole-3-carboxylic acid (3,3-difluoro-cyclohexylmethyl)-amide (0.09 g, 0.22 mmol, 30.6%) as a white solid.
$^1$H NMR (400 MHz, DMSO-d$_6$): δ 8.11 (t, J=5.84 Hz, 1H), 7.78 (s, 1H), 7.55-7.53 (m, 1H), 7.22-7.13 (m, 2H), 6.29-5.98 (m, 1H), 4.37 (d, J=7.36 Hz, 2H), 3.21-3.10 (m, 2H), 2.50-2.31 (m, 2H), 2.14 (d, J=9.08 Hz, 1H), 1.97 (s, 1H), 1.80-1.74 (m, 3H), 1.55-1.37 (m, 3H), 1.12-0.86 (m, 1H) ppm; [M+H]+ 405.2.

Example 50: Preparation of 4-Chloro-1-(3,3-difluoro-propyl)-1H-indole-3-carboxylic acid (4,4-difluoro-1-hydroxy-cyclohexylmethyl)-amide (10)

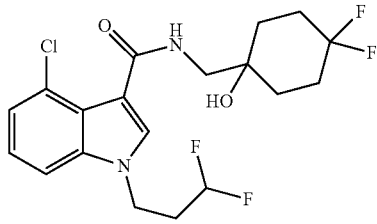 [SMILES: O=C(NCC1(O)CCC(F)(F)CC1)c1cn(CCC(F)F)c2cccc(Cl)c12]

The title compound was synthesized according to the procedure described in Example 2 using 4-Chloro-1-(3,3-difluoro-propyl)-1H-indole-3-carboxylic acid (0.20 g, 0.72 mmol, 1.00 eq), 1-Aminomethyl-4,4-difluoro-cyclohexanol (0.14 g, 0.86 mmol, 1.20 eq), Et$_3$N (0.30 mL, 2.16 mmol, 3.00 eq), EDC (0.28 gm 1.44 mmol, 2.00 eq) and Benzotriazol-1-ol (0.18 g, 1.08 mmol, 1.50 eq) to afford 4-Chloro-1-(3,3-difluoro-propyl)-1H-indole-3-carboxylic acid (4,4-difluoro-1-hydroxy-cyclohexyl methyl)-amide (0.25 mL, 0.59 mmol, 81.9%) as a white solid.
$^1$H NMR (400 MHz, DMSO-d$_6$): δ 7.96 (t, J=6.12 Hz, 1H), 7.83 (s, 1H), 7.56-7.54 (m, 1H), 7.23-7.14 (m, 2H), 6.29-5.99 (m, 1H), 4.72 (s, 1H), 4.38 (t, J=7.28 Hz, 2H),

Example 51: Preparation of 4-Chloro-1-(3,3-difluoro-propyl)-1H-indole-3-carboxylic acid ((1S,3S)-1-hydroxy-3-methyl-cyclohexylmethyl)-amide (79 MSC2526161)

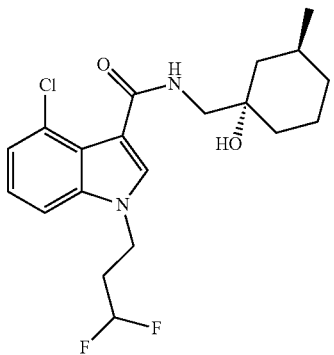 [SMILES: C[C@H]1CCC[C@@](O)(CNC(=O)c2cn(CCC(F)F)c3cccc(Cl)c23)C1]

The title compound was synthesized according to the procedure described in Example 2 using 4-Chloro-1-(3,3-difluoro-propyl)-1H-indole-3-carboxylic acid (150 mg, 0.54 mmol, 1.00 eq), (1S,3S)-1-Aminomethyl-3-methyl-cyclohexanol (77.41 mg, 0.54 mmol, 1.00 eq), Et$_3$N (0.23 mL, 1.62 mmol, 3.00 eq), HOBt (109.54 mg, 0.81 mmol, 1.50 eq), EDC (209.30 mg, 1.08 mmol, 2.00 eq) in dry THF to afford 4-Chloro-1-(3,3-difluoro-propyl)-1H-indole-3-carboxylic acid ((1S,3S)-1-hydroxy-3-methyl-cyclohexylmethyl)-amide (65 mg, 0.19 mmol, 34.4%) as a white solid.

$^1$H NMR (400 MHz, DMSO-d$_6$): δ 8.83-8.80 (m, 1H), 7.96 (d, J=9.2 Hz, 1H), 4.29 (d, J=9.3 Hz, 1H), 7.71 (d, J=9.0 Hz, 1H), 7.15 (d, J=9.1 Hz, 1H), 4.55-4.52 (m, 2H), 3.72-3.70 (m, 2H), 3.31 (d, J=7.2 Hz, 3H), 3.26 (t, J=12.4 Hz, 2H), 2.04-1.98 (m, 2H), 1.86-1.73 (m, 5H), 1.32-1.23 (m, 2H) ppm; [M+H]+ 413.2.

Example 52: Preparation of 4-Chloro-1-(3,3-difluoro-propyl)-1H-indole-3-carboxylic acid ((1R,3R)-1-hydroxy-3-methyl-cyclohexylmethyl)-amide (8)

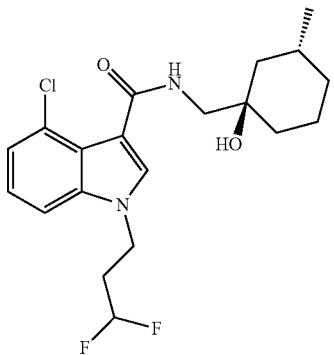 [SMILES: C[C@@H]1CCC[C@](O)(CNC(=O)c2cn(CCC(F)F)c3cccc(Cl)c23)C1]

The title compound was synthesized according to the procedure described in Example 2 using 4-Chloro-1-(3,3-difluoro-propyl)-1H-indole-3-carboxylic acid (150 mg 0.54 mmol, 1.00 eq), (1R,3R)-1-Aminomethyl-3-methyl-cyclohexanol (77.41 mg, 0.54 mmol, 1.00 eq), Et$_3$N (0.23 mL, 1.62 mmol, 3.00 eq), HOBt (109.54 mg, 0.81 mmol, 1.50 eq), and EDC (209 mg, 1.08 mmol, 2.00 eq) to afford 4-Chloro-1-(3,3-difluoro-propyl)-1H-indole-3-carboxylic acid ((1R,3R)-1-hydroxy-3-methyl-cyclohexylmethyl)-amide (75.00 mg, 0.19 mmol, 34.4%) as a white solid.

$^1$H NMR (400 MHz, DMSO-d$_6$): δ 7.83 (s, 1H), 7.79-7.76 (m, 1H), 7.54 (dd, J=8.9, Hz, 1H), 7.22-7.14 (m, 1H), 6.29-5.99 (m, 1H), 4.38-4.36 (m, 2H), 4.24 (s, 1H), 3.18 (d, J=6.1 Hz, 2H), 2.41-2.31 (m, 2H), 1.71-1.69 (m, 1H), 1.60-1.50 (m, 4H), 1.44 (d, J=10.00 Hz, 1H), 1.24-1.17 (m, 1H), 0.94 (t, J=8 Hz, 1H), 0.82 (d, J=6.60 Hz, 3H), 0.77-0.73 (m, 1H), ppm; [M+H]+ 399.0.

Example 53: Preparation of 4-Chloro-1-dimethylcarbamoylmethyl-1H-indole-3-carboxylic acid (4,4-difluoro-cyclohexylmethyl)-amide (208)

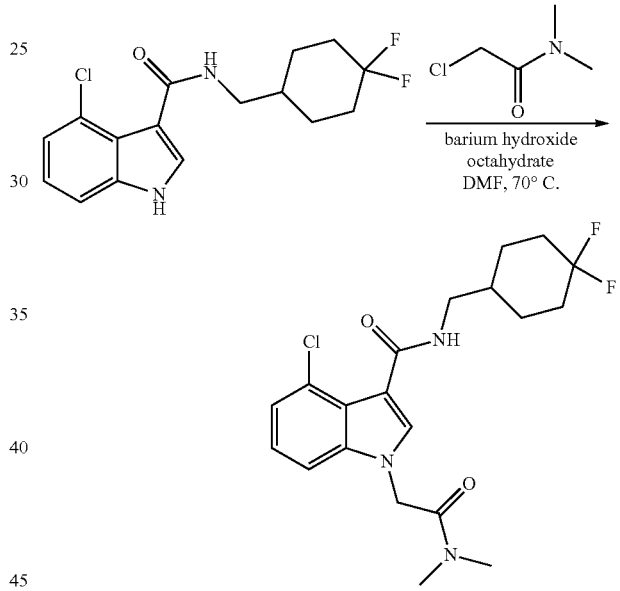

Barium hydroxide octahydrate (241.35 mg; 0.77 mmol; 2.00 eq.) was added to a solution of 4-chloro-N-((4,4-difluorocyclohexyl)methyl)-1H-indole-3-carboxamide (125.00 mg; 0.38 mmol; 1.00 eq.), and 2-chloro-N,N-dimethylacetamide (58.13 mg; 0.48 mmol; 1.25 eq.) in DMF (3.90 ml; 50.54 mmol; 132.13 eq.). The reaction mixture was stirred overnight at 70° C. The reaction mixture was diluted with DMSO (1 ml) and water (1 ml) then submitted to medium pressure liquid chromatography purification (Instrument: Yamazen, Column: Interchim 100 g polymeric Reverse Phase column, basic buffer) to afford the desired product 4-Chloro-1-dimethylcarbamoylmethyl-1H-indole-3-carboxylic acid (4,4-difluoro-cyclohexylmethyl)-amide (130.00 mg; 0.32 mmol) as a white solid.

$^1$H NMR (400 MHz, DMSO-d$_6$) δ 7.73 (s, 1H), 7.25 (s, 1H), 7.02 (d, J=5.4 Hz, 1H), 6.87-6.68 (m, 2H), 4.85 (s, 2H), 2.87-2.67 (m, 5H), 2.14 (s, 4H), 1.66 (d, J=8.0 Hz, 2H), 1.42 (dd, J=45.8, 12.7 Hz, 5H), 0.99-0.75 (m, 2H) ppm; [M+H]+ 412.1. LC-MS (254 nm) t$_R$=4.37 min; HPLC (254 nm) Purity: 97.6%; t$_R$=4.24 min.

Example 54: Preparation of 4-Chloro-1-dimethyl-carbamoylmethyl-1H-indole-3-carboxylic acid (4,4-difluoro-1-hydroxy-cyclohexylmethyl)-amide (205)

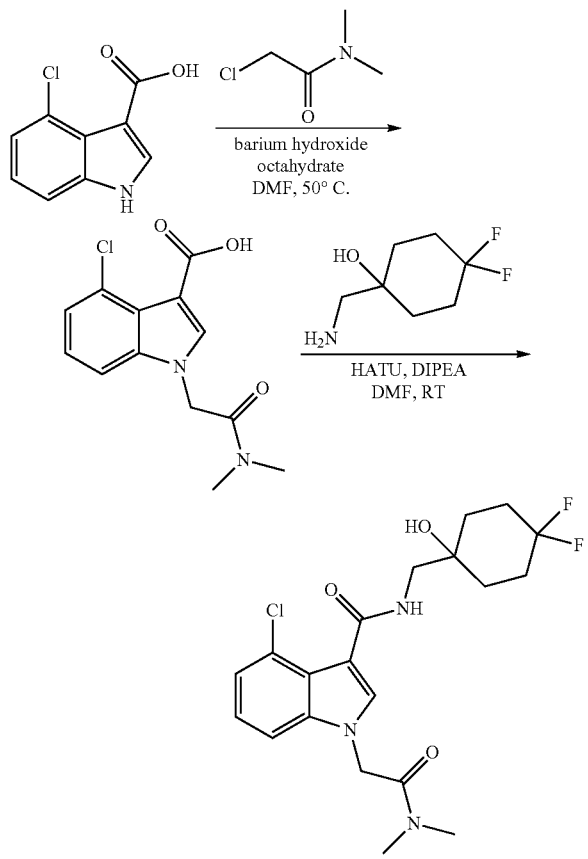

Step 1: Preparation of 4-Chloro-1-dimethylcarbamoylmethyl-1H-indole-3-carboxylic acid

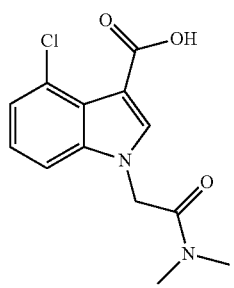 [SMILES: CN(C)C(=O)Cn1cc(C(=O)O)c2c(Cl)cccc21]

2-chloro-N,N-dimethylacetamide (0.19 ml; 1.84 mmol; 1.20 eq.) was added to a solution of 4-Chloro-1H-indole-3-carboxylic acid (300.00 mg; 1.53 mmol; 1.00 eq.) and barium hydroxide octahydrate (967.67 mg; 3.07 mmol; 2.00 eq.) in DMF (15.63 ml; 202.65 mmol; 132.13 eq.) at 50° C. The reaction mixture was stirred overnight. The reaction mixture was diluted with DMSO (1 ml) and water (1 ml) then submitted to MPLC purification (Yamazen, Interchim 100 g polymeric Reverse Phase column, basic buffer) to afford the desired product 4-Chloro-1-dimethylcarbamoyl-methyl-1H-indole-3-carboxylic acid (426.00 mg; 1.52 mmol) as a white solid.

$^1$H NMR (400 MHz, MeOD) δ 7.42 (s, 1H), 6.89-6.79 (m, 1H), 6.78-6.64 (m, 2H), 4.73 (s, 2H), 2.73 (s, 3H), 2.57-2.49 (m, 4H) ppm; [M+H]$^+$ 281.1. LC-MS (254 nm) $t_R$=3.47 min; HPLC (254 nm) Purity: >99%; $t_R$=2.68 min.

Step 2: Preparation of 4-Chloro-1-dimethylcarbamoylmethyl-1H-indole-3-carboxylic acid

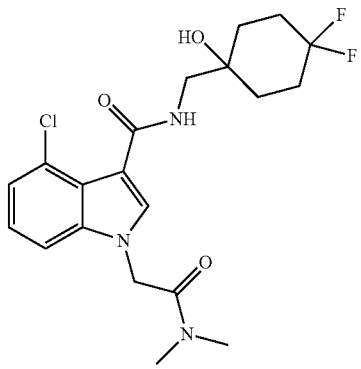 [SMILES: CN(C)C(=O)Cn1cc(C(=O)NCC2(O)CCC(F)(F)CC2)c2c(Cl)cccc21]

o-(7-azabenzotriazol-1-yl)-N,N,N',N'-tetramethyluronium hexafluoro-phosphate (84.66 mg; 0.22 mmol; 1.25 eq.) (HATU) was added to a solution of 4-Chloro-1-dimethyl-carbamoylmethyl-1H-indole-3-carboxylic acid (50.00 mg; 0.18 mmol; 1.00 eq.), 1-Aminomethyl-4,4-difluoro-cyclohexanol (32.36 mg; 0.20 mmol; 1.10 eq.) and n,n-diisopropylethylamine (0.12 ml; 0.71 mmol; 4.00 eq.) in DMF (1.81 ml; 23.54 mmol; 132.13 eq.) at 25° C. The reaction mixture was stirred overnight and evaporated to dryness under high vacuum. The residue was dissolved in Methanol (8 ml) and water (2 ml) and this solution was submitted to Medium Pressure Liquid Chromatography purification (Yamazen, Interchim 150 g polymeric Reverse Phase column, basic buffer) to afford the desired product 4-Chloro-1-dimethyl-carbamoylmethyl-1H-indole-3-carboxylic acid (4,4-difluoro-1-hydroxy-cyclohexylmethyl)-amide (30.00 mg; 0.07 mmol). $^1$H NMR [M+H]$^+$ 428.1. LC-MS (254 nm) $t_R$=3.94 min; HPLC (254 nm) Purity: >99%; $t_R$=3.40 min.

Example 55: Preparation of 4-Chloro-1-diethylcarbamoylmethyl-1H-indole-3-carboxylic acid (4,4-difluoro-cyclohexylmethyl)-amide (207)

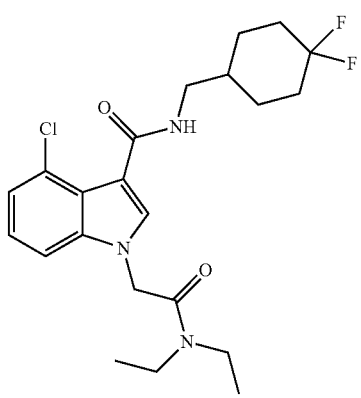 [SMILES: CCN(CC)C(=O)Cn1cc(C(=O)NCC2CCC(F)(F)CC2)c2c(Cl)cccc21]

The title compound was synthesized according to the procedure described in Example 53 using a N,N-diethyl-chloroacetamide (41.21 mg; 0.28 mmol; 1.20 eq.) and 4-chloro-N-((4,4-difluorocyclohexyl)methyl)-1H-indole-3-carboxamide (75.00 mg; 0.23 mmol; 1.00 eq.) to afford 4-Chloro-1-diethylcarbamoylmethyl-1H-indole-3-carboxylic acid (4,4-difluoro-cyclohexylmethyl)-amide (100.80 mg; 0.23 mmol) as a white amorphous solid.

$^1$H NMR (400 MHz, CDCl$_3$) δ 7.72 (s, 1H), 7.31-7.05 (m, 3H), 6.76 (s, 1H), 4.88 (s, 2H), 3.52-3.29 (m, 5H), 2.20-2.01 (m, 2H), 1.97-1.50 (m, 6H), 1.38 (dd, J=23.7, 11.1 Hz, 2H), 1.27 (t, J=7.2 Hz, 3H), 1.13 (t, J=7.1 Hz, 3H) ppm; [M+H]$^+$ 440.1. LC-MS (254 nm) $t_R$=4.77 min; HPLC (254 nm) Purity: 98%

Example 56: Preparation of 4-Chloro-1-[(isopropyl-methyl-carbamoyl)-methyl]-1H-indole-3-carboxylic acid (4,4-difluoro-cyclohexylmethyl)-amide (203)

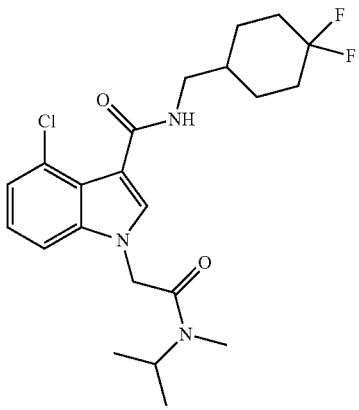 [SMILES: CC(C)N(C)C(=O)Cn1cc(C(=O)NCC2CCC(F)(F)CC2)c2c(Cl)cccc21]

The title compound was synthesized according to the procedure described in Example 54 using a mixture of 2-chloro-N-isopropyl-n-methylacetamide (41.21 mg; 0.28 mmol; 1.20 eq.) and (4,4-difluorocyclohexyl) methanamine (75.00 mg; 0.23 mmol; 1.00 eq.) to afford the desired product 4-Chloro-1-[(isopropyl-methyl-carbamoyl)-methyl]-1H-indole-3-carboxylic acid (4,4-difluoro-cyclohexylmethyl)-amide (35.00 mg; 0.08 mmol). [M+H]$^+$ 440.2 LC-MS (254 nm) $t_R$=3.94 min; HPLC (254 nm) Purity: 99.0%; $t_R$=4.46 min.

Example 57: Preparation of 4-chloro-N-((4,4-difluorocyclohexyl)methyl)-1-(1-(dimethylamino)-1-oxopropan-2-yl)-1H-indole-3-carboxamide (200)

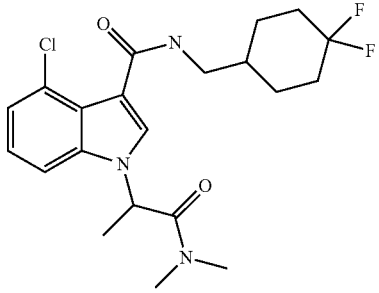 [SMILES: CC(C(=O)N(C)C)n1cc(C(=O)NCC2CCC(F)(F)CC2)c2c(Cl)cccc21]

The title compound was synthesized according to the procedure described in example 53 using a mixture of 2-Bromo-N,N-dimethyl-propionamide (60.61 mg; 0.37 mmol; 1.20 eq.), 4-Chloro-1H-indole-3-carboxylic acid (4,4-difluoro-cyclohexylmethyl)-amide (100.00 mg; 0.31 mmol; 1.00 eq.) and barium hydroxide octahydrate (193.08 mg; 0.61 mmol; 2.00 eq.) in DMF (10 mL) at 50° C. to provide the desired product as a white solid.

$^1$H NMR (400 MHz, DMSO-d$_6$) δ ppm 8.10 (1H), 7.72 (s, 1H), 7.53 (1H), 7.19 (m, 2H), 5.85 (1H), 3.15 (1H), 3.04 (3H), 2.86 (3H), 2.03 (2H), 1.85 (2H), 1.71 (m, 1H), 1.60 (2H), 1.25 (m, 2H). m/z: 426 [M+H]

Example 58: Preparation of 1-(2-Azetidin-1-yl-2-oxo-ethyl)-4-chloro-1H-indole-3-carboxylic acid (4,4-difluoro-cyclohexylmethyl)-amide (201)

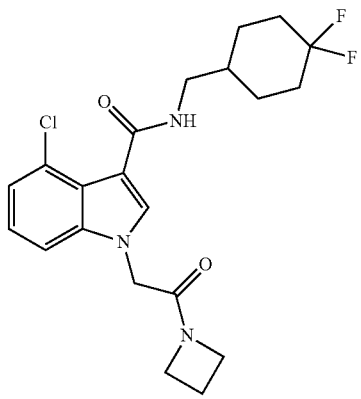 [SMILES: O=C(NCC1CCC(F)(F)CC1)c1cn(CC(=O)N2CCC2)c2cccc(Cl)c12]

The title compound was synthesized according to the procedure described in Example 54 using 1-azetidin-1-yl-2-chloro-ethanone (33.72 mg; 0.25 mmol; 1.10 eq.) and (4,4-difluorocyclohexyl)methanamine (75.00 mg; 0.23 mmol; 1.00 eq.) to afford the desired product 1-(2-Azetidin-1-yl-2-oxo-ethyl)-4-chloro-1H-indole-3-carboxylic acid (4,4-difluoro-cyclohexylmethyl)-amide (34.50 mg; 0.08 mmol). [M+H]$^+$ 424.1 LC-MS (254 nm) $t_R$=3.54 min; HPLC (254 nm) Purity: 99.4%; $t_R$=3.97 min.

Example 59: Preparation of 4-Chloro-1-(2-oxo-2-pyrrolidin-1-yl-ethyl)-1H-indole-3-carboxylic acid (4,4-difluoro-cyclohexylmethyl)-amide (185)

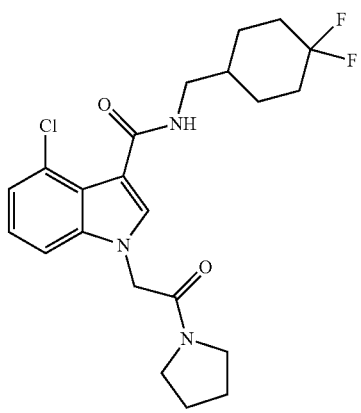 [SMILES: O=C(NCC1CCC(F)(F)CC1)c1cn(CC(=O)N2CCCC2)c2cccc(Cl)c12]

The title compound was synthesized according to the procedure described in Example 54 using a mixture of 2-chloro-1-pyrrolidin-1-yl-ethanone (37.27 mg; 0.25 mmol; 1.10 eq.) and (4,4-difluorocyclohexyl)methanamine (75.00 mg; 0.23 mmol; 1.00 eq.) to afford the desired product 4-Chloro-1-(2-oxo-2-pyrrolidin-1-yl-ethyl)-1H-indole-3-carboxylic acid (4,4-difluoro-cyclohexylmethyl)-amide (65.00 mg; 0.15 mmol). [M+H]$^+$ 438.1. LC-MS (254 nm) $t_R$=3.74 min; HPLC (254 nm) Purity: 99.5%; $t_R$=4.18 min.

Example 60: Preparation of 4-Chloro-1-(2-morpholin-4-yl-2-oxo-ethyl)-1H-indole-3-carboxylic acid (4,4-difluoro-cyclohexylmethyl)-amide (190)

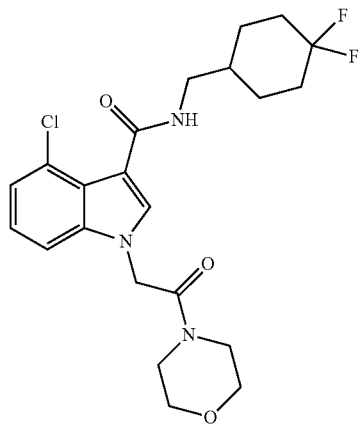 [SMILES: O=C(NCC1CCC(F)(F)CC1)c1cn(CC(=O)N2CCOCC2)c2cccc(Cl)c12]

The title compound was synthesized according to the procedure described in example 53 using a mixture of 4-(bromoacetyl)morpholine (57.30 mg; 0.28 mmol; 1.20 eq.) and 4-chloro-N-((4,4-difluorocyclohexyl)methyl)-1H-indole-3-carboxamide (75.00 mg; 0.23 mmol; 1.00 eq.) to afford 4-Chloro-1-(2-morpholin-4-yl-2-oxo-ethyl)-1H-indole-3-carboxylic acid (4,4-difluoro-cyclohexylmethyl)-amide (54.00 mg; 0.12 mmol) as a white amorphous solid. $^1$H NMR (400 MHz, CDCl$_3$) δ 7.69-7.46 (m, 1H), 7.23 (t, J=34.2 Hz, 1H), 4.95 (s, 1H), 3.89-2.96 (m, 1H), 2.13 (s, 1H), 1.83 (d, J=72.4 Hz, 1H), 1.40 (s, 1H), 0.12--0.11 (m, 1H) ppm; [M+H]$^+$454.1. LC-MS (254 nm) $t_R$=4.35 min; HPLC (254 nm) Purity: 98.7%; $t_R$=3.97 min.

Example 61: Preparation of 4-Chloro-1-(2-oxo-2-piperidin-1-yl-ethyl)-1H-indole-3-carboxylic acid (4,4-difluoro-cyclohexylmethyl)-amide (195)

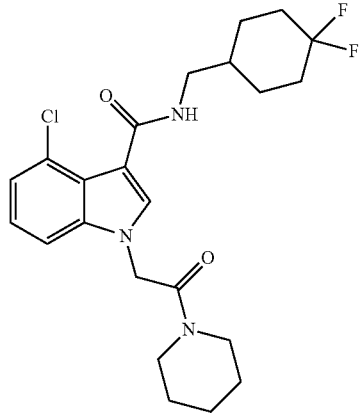 [SMILES: O=C(NCC1CCC(F)(F)CC1)c1cn(CC(=O)N2CCCCC2)c2cccc(Cl)c12]

The title compound was synthesized according to the procedure described in example 54 using a mixture of 2-chloro-1-piperidin-1-yl-ethanone (40.81 mg; 0.25 mmol; 1.10 eq.) and (4,4-difluorocyclohexyl)methanamine (75.00 mg; 0.23 mmol; 1.00 eq.) to afford the desired product 4-Chloro-1-(2-oxo-2-piperidin-1-yl-ethyl)-1H-indole-3-carboxylic acid (4,4-difluoro-cyclohexylmethyl)-amide (95.00 mg; 0.21 mmol). [M+H]$^+$ 452.1 LC-MS (254 nm) $t_R$=4.83 min; HPLC (254 nm) Purity: 99.2%; $t_R$=4.53 min.

Example 62: Preparation of 4-chloro-1-(2-methoxyethyl)-N-((1-phenylcyclohexyl) methyl)-1H-indole-3-carboxamide (39)

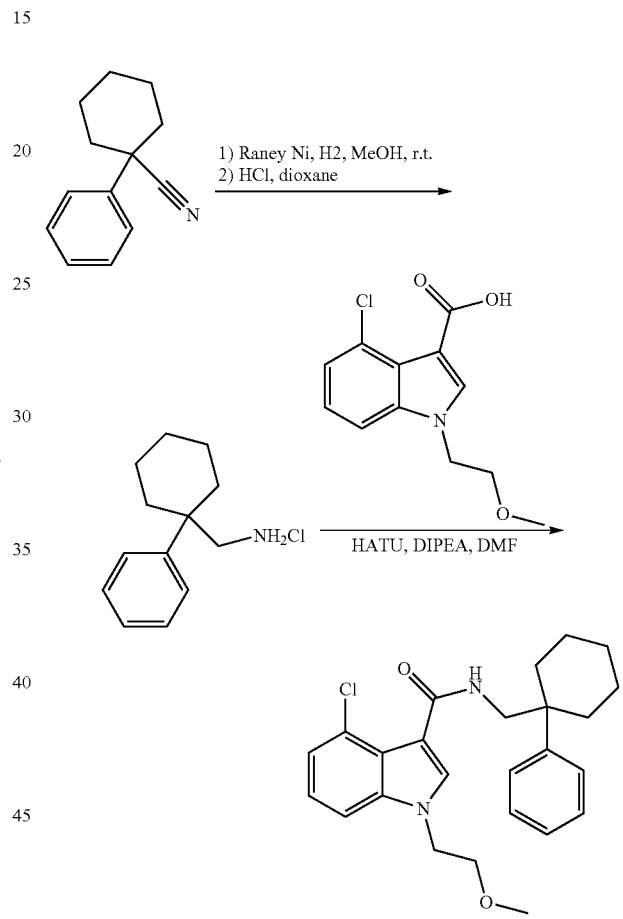

Step 1: Preparation of (1-phenylcyclohexyl) methanamine hydrochloride

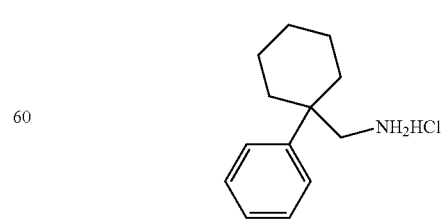

To a stirred solution of 1-phenylcyclohexanecarbonitrile (0.500 g, 2.70 mmol) in methanol (10 mL) was added Raney Ni (0.100 g). The resulting mixture was stirred at room temperature under hydrogen atmosphere for 16 h, and then filtered through celite. To the filtrate was added hydrochloric acid (5 mL, 20 mmol, 4 M in dioxane), and the mixture was stirred at room temperature for 30 min, then concentrated in vacuo. The residue was triturated by EtOAc (20 mL) and the precipitate was filtered to afford (1-phenylcyclohexyl) methanamine hydrochloride (0.400 g, 65.8%) as white solid.

Step 2: Preparation of 4-chloro-1-(2-methoxyethyl)-N-((1-phenylcyclohexyl) methyl)-1H-indole-3-carboxamide

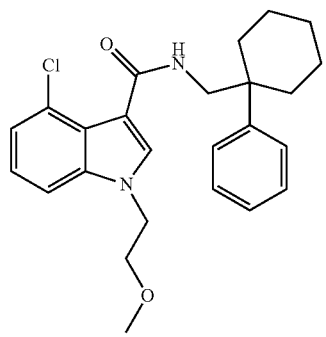 [SMILES: COCCn1cc(C(=O)NCC2(c3ccccc3)CCCCC2)c2c(Cl)cccc21]

The title compound was synthesized according to the procedure described in Example 5 using 4-chloro-1-(2-methoxyethyl)-1H-indole-3-carboxylic acid (0.100 g, 0.40 mmol), HATU (0.225 g, 0.59 mmol) and (1-phenylcyclohexyl) methanamine hydrochloride (0.116 g, 0.51 mmol) in DMF (5 mL) to afford 4-chloro-1-(2-methoxyethyl)-N-((1-phenylcyclohexyl)methyl)-1H-indole-3-carboxamide (0.130 g, 77%) as a white solid.

$^1$H NMR (500 MHz, DMSO-d$_6$): δ 7.63 (s, 1H), 7.52 (d, J=8.0 Hz, 1H), 7.47 (t, J=6.0 Hz, 1H), 7.43-7.41 (d, J=8.0 Hz, 2H), 7.34 (t, J=7.5 Hz, 2H), 7.19 (t, J=7.5 Hz, 1H), 7.15 (t, J=7.5 Hz, 1H), 7.09 (d, J=7.5 Hz, 1H), 4.35 (t, J=5.0 Hz, 2H), 3.64 (t, J=5.5 Hz, 2H), 3.33 (d, J=6.5 Hz, 2H), 3.22 (s, 3H), 2.13-2.10 (m, 2H), 1.73-1.69 (m, 2H), 1.58-1.55 (m, 2H), 1.44 (brs, 1H), 1.36-1.23 (m, 3H) ppm; [M+H]$^+$ 425.1.

Example 63: Preparation of 4-chloro-1-(2-methoxyethyl)-N-((4-(4-(trifluoromethyl) phenyl)-tetrahydro-2H-pyran-4-yl) methyl)-1H-indole-3-carboxamide (80)

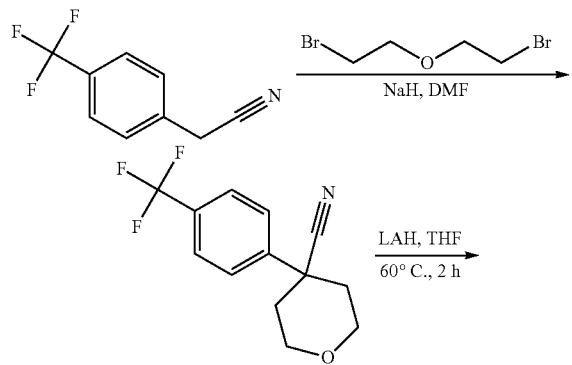

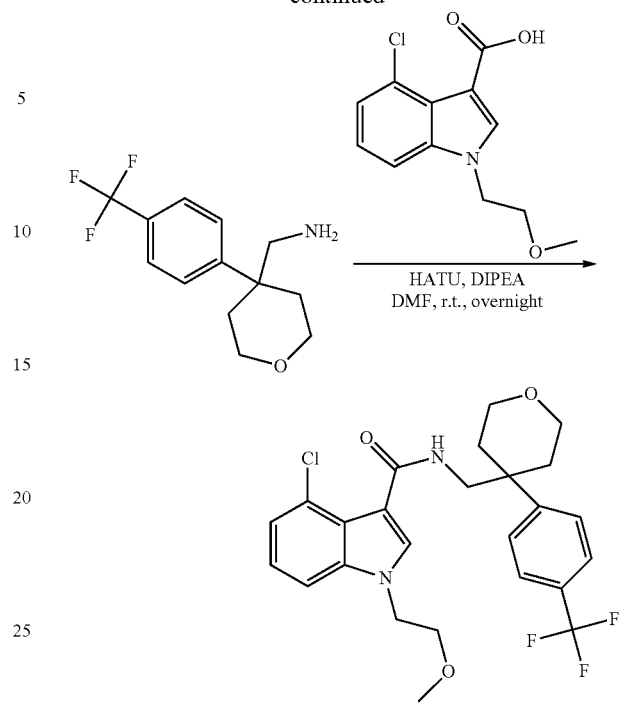

Step 1: Preparation of 4-(4-(trifluoromethyl) phenyl)-tetrahydro-2H-pyran-4-carbonitrile

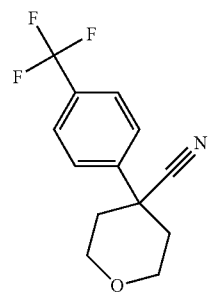 [SMILES: N#CC1(c2ccc(C(F)(F)F)cc2)CCOCC1]

To a stirred solution of 2-(4-(trifluoromethyl)phenyl)acetonitrile (2.0 g, 10.8 mmol) in DMF (10 mL) was slowly added a suspension of NaH (60%, 0.95 g, 23.7 mmol) in DMF (10 mL) at 0° C. under N$_2$ atmosphere over 10 min, the reaction was allowed to warm to room temperature and stirred for 0.5 h. Then the reaction was cooled to 0° C. and 2,2'-dibromodiethyl ether (1.5 mL, 11.8 mmol) in DMF (20 mL) was added dropwise over 60 min. The reaction was allowed to warm to room temperature and stirred for 1 h. The mixture was quenched with water (30 mL) and extracted with EtOAc (30 mL×3). The combined organic layer was washed with water (10 mL) and brine (10 mL), dried over sodium sulfate, filtered and concentrated in vacuo. The residue was purified with column chromatography on silica gel (petroleum ether:EtOAc=100:1) to afford 4-(4-(trifluoromethyl)phenyl)-tetrahydro-2H-pyran-4-carbonitrile (2.30 g, 83%) as red oil. GC-MS: [M]$^+$ 255; t$_R$=10.39 min.

Step 2: Preparation of (4-(4-(trifluoromethyl) phenyl)-tetrahydro-2H-pyran-4-yl) methanamine

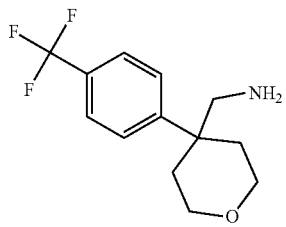 [SMILES: NCC1(c2ccc(C(F)(F)F)cc2)CCOCC1]

To a stirred solution of 4-(4-(trifluoromethyl)phenyl)-tetrahydro-2H-pyran-4-carbonitrile (1.0 g, 3.9 mmol) in THF (20 mL) was added lithium aluminium hydride (0.3 g, 7.8 mmol) in proportions at 0° C., then the reaction was stirred at 60° C. for 2 h. After the mixture was cooled to 0° C., methanol (2 mL) was added slowly to quench the reaction. Magnesium sulfate (0.500 g) was added and the system was stirred at room temperature for 0.5 h. The mixture was filtered off through celite and the filtrate was concentrated to afford (4-(4-(trifluoromethyl) phenyl)-tetrahydro-2H-pyran-4-yl) methanamine (0.55 g, 48%) as red oil. $[M+H]^+$ 260.1; LC-MS Purity (254 nm): >99%; $t_R$=1.16 min.

Step 3: Preparation of 4-chloro-1-(2-methoxyethyl)-N-((4-(4-(trifluoromethyl) phenyl)-tetrahydro-2H-pyran-4-yl) methyl)-1H-indole-3-carboxamide

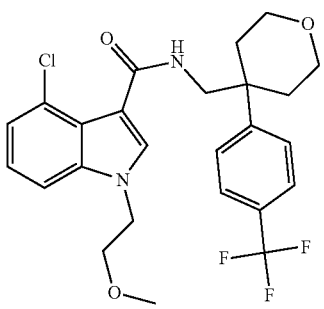 [SMILES: COCCn1cc(C(=O)NCC2(c3ccc(C(F)(F)F)cc3)CCOCC2)c2c(Cl)cccc21]

The title compound was synthesized according to the procedure described in Example 5 using of 4-chloro-1-(2-methoxyethyl)-1H-indole-3-carboxylic acid (0.150 g, 0.59 mmol), HATU (0.247 g, 0.65 mmol), (4-(4-(trifluoromethyl) phenyl)-tetrahydro-2H-pyran-4-yl) methanamine (0.168 g, 0.65 mmol), DIPEA (0.3 mL, 1.77 mmol), to afford 4-chloro-1-(2-methoxyethyl)-N-((4-(4-(trifluoromethyl) phenyl)-tetrahydro-2H-pyran-4-yl)methyl)-1H-indole-3-carboxamide (0.205 g, 70%) as an off white solid.

$^1$H NMR (500 MHz, DMSO-$d_6$) δ 7.77 (t, J=6.0 Hz, 1H), 7.70-7.68 (m, 2H), 7.65-7.64 (m, 2H), 7.59 (s, 1H), 7.52 (d, J=8.0 Hz, 1H), 7.15 (t, J=8.0 Hz, 1H), 7.09 (t, J=8.0 Hz, 1H), 4.35 (t, J=5.0 Hz, 2H), 3.81-3.77 (m, 2H), 3.65 (t, J=5.0 Hz, 2H), 3.52 (d, J=6.0 Hz, 2H), 3.42 (t, J=8.5 Hz, 2H), 3.22 (s, 3H), 2.10-2.07 (m, 2H), 2.03-1.96 (m, 2H) ppm; $[M+H]^+$ 495.1.

Example 64: Preparation of 4-chloro-N-((4,4-difluorocyclohexyl)methyl)-1-(oxetan-3-yl)-1H-indole-3-carboxamide (94)

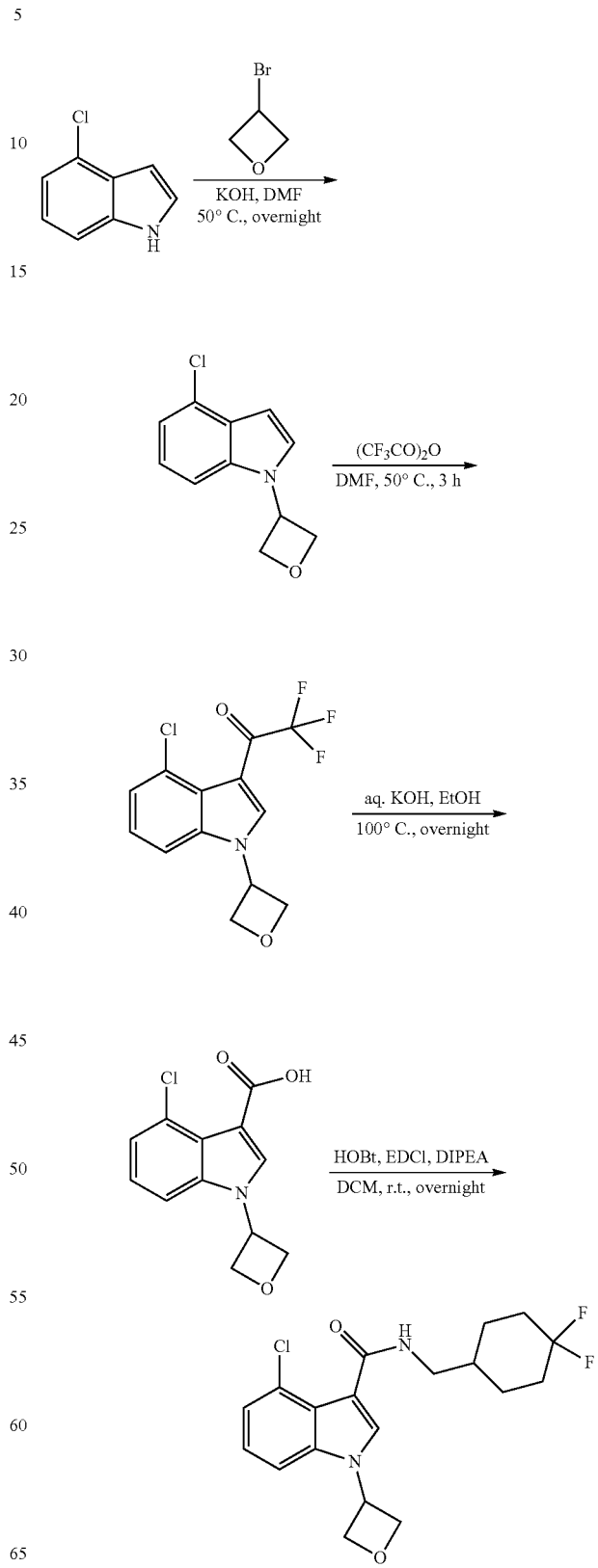

Step 1: Preparation of 4-chloro-1-(oxetan-3-yl)-1H-indole

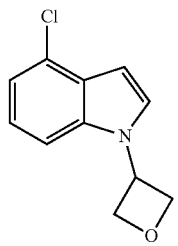 [SMILES: Clc1cccc2c1ccn2C1COC1]

To a stirred solution of 4-chloro-1H-indole (0.90 g, 5.93 mmol) and compound 3-bromooxetane (1.22 g, 8.90 mmol) in DMF (10.0 mL) was added potassium hydroxide (1.00 g, 17.81 mmol) at room temperature. The mixture was stirred at 50° C. overnight. Water (30 mL) was added and the mixture was extracted with EtOAc (30 mL×3). The combined extracts were collected and washed with water (10 mL) and brine (10 mL), dried over $Na_2SO_4$, concentrated in vacuo to give 4-chloro-1-(oxetan-3-yl)-1H-indole (0.70 g, 47%) as a brown oil, which was used in the next step without further purification. $[M+H]^+$ 208.0.

Step 2: Preparation of 1-(4-chloro-1-(oxetan-3-yl)-1H-indol-3-yl)-2,2,2-trifluoro ethanone

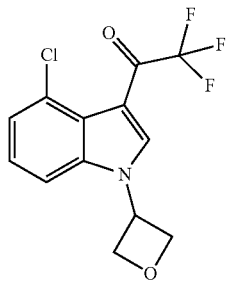 [SMILES: O=C(c1cn(C2COC2)c2cccc(Cl)c12)C(F)(F)F]

To a stirred solution of 4-chloro-1-(oxetan-3-yl)-1H-indole (0.70 g, 3.37 mmol) in DMF (10.0 mL) was added trifluoroacetic anhydride (1.06 g, 5.05 mmol) at room temperature. The mixture was stirred at 50° C. for 3 h. Water (30 mL) was added and the mixture was extracted with EtOAc (30 mL×3). The combined extracts were washed with water (10 mL) and brine (10 mL), dried over $Na_2SO_4$, concentrated in vacuo to give 1-(4-chloro-1-(oxetan-3-yl)-1H-indol-3-yl)-2,2,2-trifluoroethanone (0.90 g, 87%) as a purple oil, which was used to next step without further purification. $[M+H]^+$ 304.0.

Step 3: Preparation of 4-chloro-1-(oxetan-3-yl)-1H-indole-3-carboxylic acid

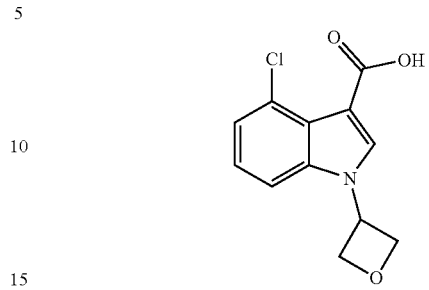

To a stirred solution of 1-(4-chloro-1-(oxetan-3-yl)-1H-indol-3-yl)-2,2,2-trifluoroethanone (0.90 g, 2.96 mmol) in ethanol (5.0 mL) was added 20% aqueous potassium hydroxide (10 mL) at room temperature. The mixture was stirred at 100° C. overnight. After being cooled to room temperature, the mixture was extracted with EtOAc (10 mL×2). The aqueous layer was acidified with concentrated hydrochloric acid (3.0 mL) to pH 2~3, and then extracted with EtOAc (20 mL×3). The combined organic layer was washed with brine (10 mL), dried over $Na_2SO_4$, concentrated in vacuo to give 4-chloro-1-(oxetan-3-yl)-1H-indole-3-carboxylic acid (0.60 g, 80%) as a off-white solid, which was used to next step without further purification. $[M+H]^+$ 252.0.

Step 4: Preparation of 4-chloro-N-((4,4-difluorocyclohexyl)methyl)-1-(oxetan-3-yl)-1H-indole-3-carboxamide

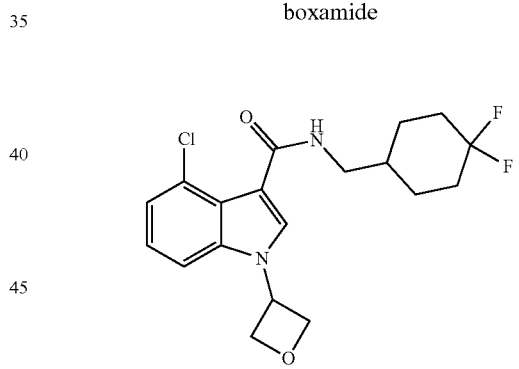

A mixture of 4-chloro-1-(oxetan-3-yl)-1H-indole-3-carboxylic acid (0.120 g, 0.47 mmol), HOBt (0.070 g, 0.52 mmol), EDCI (0.100 g, 0.52 mmol) and TEA (0.144 g, 1.43 mmol) in DCM (20 mL) was stirred at room temperature for 1 h, and then (4,4-difluorocyclohexyl)methanamine (0.71 g, 0.47 mmol) was added thereto. The mixture was stirred at room temperature overnight, and then the volatiles were removed in vacuo. The residue was dispersed in $H_2O$ (10 mL) and extracted with DCM/MeOH (10:1, 30 mL×3). The combined organic layers were washed with brine (10 mL), dried over $Na_2SO_4$, and concentrated in vacuo. The residue was purified by column chromatography on silica gel (DCM:MeOH=100:1) to afford 4-chloro-N-((4,4-difluorocyclohexyl)methyl)-1-(oxetan-3-yl)-1H-indole-3-carboxamide (0.110 g, 60%) as a white solid.

$^1$H NMR (500 MHz, DMSO-$d_6$) δ 8.18 (t, J=5.5 Hz, 1H), 8.10 (s, 1H), 7.56 (d, J=8.0 Hz, 1H), 7.22-7.16 (m, 2H), 5.83-5.77 (m, 1H), 5.05 (t, J=7.5 Hz, 2H), 4.92 (t, J=7.5 Hz,

2H), 3.16 (t, J=6.5 Hz, 2H), 2.05-1.98 (m, 2H), 1.86-1.69 (m, 5H), 1.29-1.17 (m, 2H) ppm; [M+H]⁺ 383.1; LC-MS Purity (254 nm): >99%; $t_R$=4.15 min; HPLC Purity (254 nm): >99%; $t_R$=4.31 min.

Example 65: 4-chloro-N-(cyclohexylmethyl)-1-(oxetan-3-yl)-1H-indole-3-carboxamide (48)

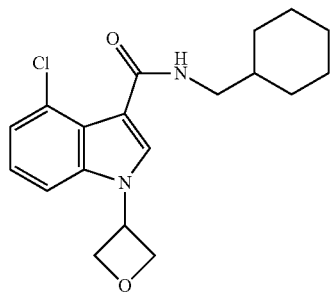 [SMILES: O=C(NCC1CCCCC1)c1cn(C2COC2)c2cccc(Cl)c12]

The title compound was synthesized according to the procedure described in Example 2 using 4-Chloro-1-oxetan-3-yl-1H-indole-3-carboxylic acid (200.00 mg; 0.79 mmol; 1.00 eq.), C-Cyclohexyl-methylamine (103.46 mg; 0.91 mmol; 1.15 eq.), EDC (198.05 mg; 1.03 mmol; 1.30 eq.), Benzotriazol-1-ol (139.60 mg; 1.03 mmol; 1.30 eq.) and Ethyl-diisopropyl-amine (0.39 ml; 2.38 mmol; 3.00 eq.) in DCM (20 mL) to provide 4-chloro-N-(cyclohexylmethyl)-1-(oxetan-3-yl)-1H-indole-3-carboxamide (215, 78%).

¹H NMR (400 MHz, Chloroform-d) δ 8.11 (s, 1H), 7.40 (d, J=8.0 Hz, 1H), 7.32-7.16 (m, 2H), 6.72 (s, 1H), 5.57 (p, J=6.9 Hz, 1H), 5.19 (t, J=7.4 Hz, 2H), 5.06 (t, J=6.7 Hz, 2H), 3.38 (t, J=6.3 Hz, 2H), 1.89-1.59 (m, 6H), 1.37-1.14 (m, 4H), 1.05 (qd, J=11.7, 3.1 Hz, 3H). [M+H]+: 347.

Example 66: Preparation of 4-Chloro-1-oxetan-3-yl-1H-indole-3-carboxylic acid (2,2-difluoro-ethyl)-amide (76)

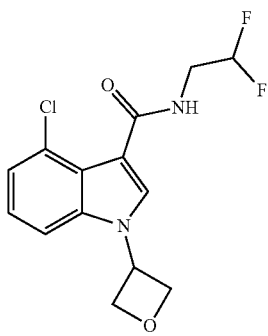 [SMILES: O=C(NCC(F)F)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 2,2-difluoroethylamine hydrochloride (52.54 mg; 0.45 mmol; 1.5 eq.) to afford the desired product 4-Chloro-1-oxetan-3-yl-1H-indole-3-carboxylic acid (2,2-difluoro-ethyl)-amide (89 mg; 0.28 mmol). [M+H]⁺ 315.1 LC-MS (254 nm) $t_R$=3.22 min; HPLC (254 nm) Purity: >99%; $t_R$=3.27 min.

Example 66: Preparation of 4-Chloro-1-oxetan-3-yl-1H-indole-3-carboxylic acid (3,3,3-trifluoro-propyl)-amide (77)

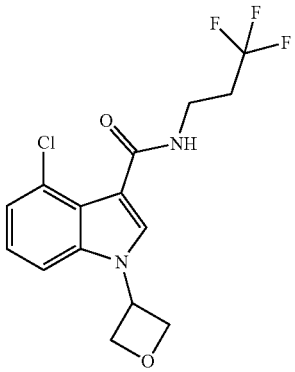 [SMILES: O=C(NCCC(F)(F)F)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 3,3,3-trifluoropropylamine (37.07 mg; 0.33 mmol; 1.1 eq.) to afford the desired product 4-Chloro-1-oxetan-3-yl-1H-indole-3-carboxylic acid (3,3,3-trifluoro-propyl)-amide (10 mg; 0.03 mmol). [M+H]⁺ 347.1 LC-MS (254 nm) $t_R$=3.52 min; HPLC (254 nm) Purity: 95.79%; $t_R$=3.76 min.

Example 67: Preparation of 4-Chloro-1-oxetan-3-yl-1H-indole-3-carboxylic acid (4,4,4-trifluoro-butyl)-amide (73)

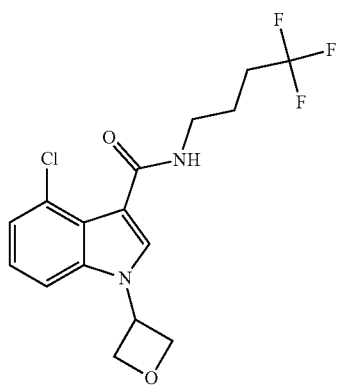 [SMILES: O=C(NCCCC(F)(F)F)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 4,4,4-trifluorobutylamine (45.46 mg; 0.36 mmol; 1.20 eq.) to afford the desired product 4-Chloro-1-oxetan-3-yl-1H-indole-3-carboxylic acid (4,4,4-trifluoro-butyl)-amide (59.0 mg; 0.16 mmol). [M+H]⁺ 361.1 LC-MS (254 nm) $t_R$=4.48 min; HPLC (254 nm) Purity: 99.82%; $t_R$=4.03 min.

Example 68: Preparation of 4-Chloro-1-oxetan-3-yl-1H-indole-3-carboxylic acid (2-ethoxy-propyl)-amide (78)

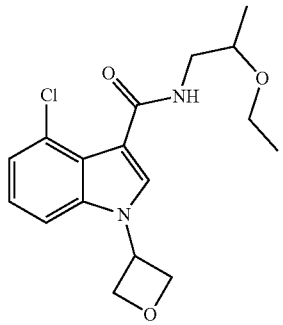 [SMILES: CCOC(C)CNC(=O)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (100.00 mg; 0.40 mmol; 1.00 eq.) and 2-Ethoxy-propylamine hydrochloride (27.74 mg; 0.2 mmol; 0.5 eq.) to afford the desired product 4-Chloro-1-oxetan-3-yl-1H-indole-3-carboxylic acid (2-ethoxy-propyl)-amide (8.00 mg; 0.02 mmol). [M+H]$^+$ 337.1 LC-MS (254 nm) $t_R$=4.14 min; HPLC (254 nm) Purity: 96.69%; $t_R$=3.50 min.

Example 69: Preparation of 4,4-Chloro-1-oxetan-3-yl-1H-indole-3-carboxylic acid (tetrahydro-pyran-3-ylmethyl)-amide (74)

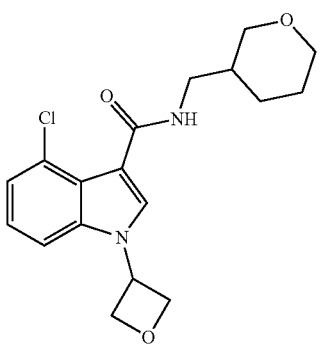 [SMILES: O=C(NCC1CCCOC1)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and C-(Tetrahydro-pyran-3-yl)-methylamine hydrochloride (54.23 mg; 0.36 mmol; 1.20 eq.) to afford the desired product 4-Chloro-1-oxetan-3-yl-1H-indole-3-carboxylic acid (tetrahydro-pyran-3-ylmethyl)-amide (72.0 mg; 0.21 mmol). [M+H]$^+$ 349.1 LC-MS (254 nm) $t_R$=3.83 min; HPLC (254 nm) Purity: >99%; $t_R$=3.18 min.

Example 70: Preparation of 4-Chloro-1-oxetan-3-yl-1H-indole-3-carboxylic acid (1-hydroxy-cyclopentylmethyl)-amide (81)

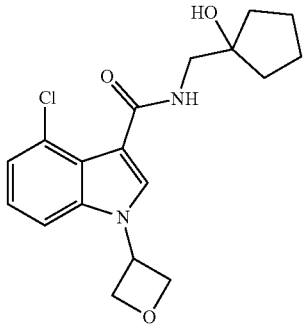 [SMILES: O=C(NCC1(O)CCCC1)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (100.00 mg; 0.40 mmol; 1.00 eq.) and 1-(aminomethyl) cyclopentanol (22.88 mg; 0.2 mmol; 0.5 eq.) to afford the desired product 4-Chloro-1-oxetan-3-yl-1H-indole-3-carboxylic acid (1-hydroxy-cyclopentylmethyl)-amide (40.0 mg; 0.11 mmol). [M+H]$^+$ 349.1 LC-MS (254 nm) $t_R$=3.12 min; HPLC (254 nm) Purity: 97.70%; $t_R$=3.20 min.

Example 71: Preparation of 4-Chloro-1-oxetan-3-yl-1H-indole-3-carboxylic acid [2-(2-methyl-[1,3]dioxolan-2-yl)-ethyl]-amide (71)

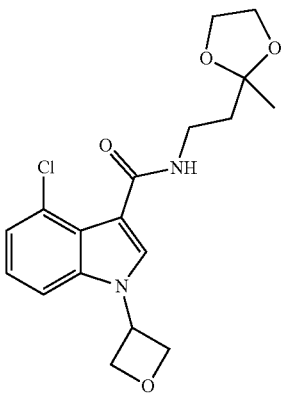 [SMILES: CC1(CCNC(=O)c2cn(C3COC3)c3cccc(Cl)c23)OCCO1]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 2-methyl-1,3-dioxolane-2-ethanamine (46.91 mg; 0.36 mmol; 1.20 eq.) to afford the desired product 4-Chloro-1-oxetan-3-yl-1H-indole-3-carboxylic acid [2-(2-methyl-[1,3]dioxolan-2-yl)-ethyl]-amide (26.0 mg; 0.07 mmol). [M+H]$^+$ 365.2 LC-MS (254 nm) $t_R$=3.87 min; HPLC (254 nm) Purity: 98.94%; $t_R$=3.22 min.

Example 72: Preparation of 4-Chloro-1-oxetan-3-yl-1H-indole-3-carboxylic acid (2-cyclopentyl-ethyl)-amide (82)

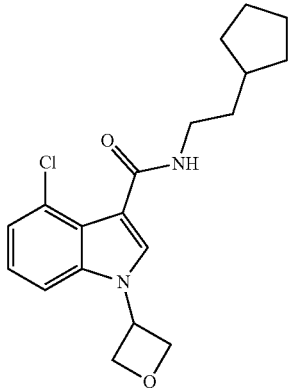 [SMILES: O=C(NCCC1CCCC1)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (100.00 mg; 0.40 mmol; 1.00 eq.) and 2-cyclopentyl-ethyl-amine (22.49 mg; 0.2 mmol; 0.5 eq.) to afford the desired product 4-Chloro-1-oxetan-3-yl-1H-indole-3-carboxylic acid (2-cyclopentyl-ethyl)-amide (35.0 mg; 0.1 mmol). [M+H]$^+$ 347.2 LC-MS (254 nm) $t_R$=4.23 min; HPLC (254 nm) Purity: 95.97%; $t_R$=4.65 min.

Example 73: Preparation of trans-4-Chloro-1-oxetan-3-yl-1H-indole-3-carboxylic acid-2-hydroxy-cyclohexylmethyl)-amide (87)

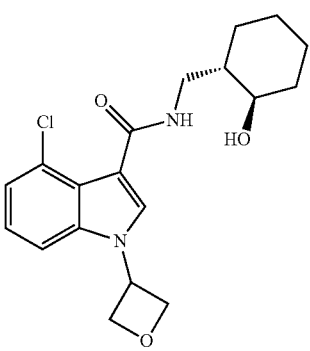 [SMILES: O=C(NC[C@@H]1CCCC[C@H]1O)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (100.00 mg; 0.40 mmol; 1.00 eq.) and trans-2-aminomethyl-1-cyclohexanol (61.61 mg; 0.48 mmol; 1.20 eq.) to afford the desired product trans-4-Chloro-1-oxetan-3-yl-1H-indole-3-carboxylic acid-2-hydroxy-cyclohexylmethyl)-amide (121.50 mg; 0.33 mmol). $^1$H NMR (400 MHz, DMSO) δ 8.12 (s, 1H), 8.03 (t, J=5.8 Hz, 1H), 7.64-7.51 (m, 1H), 7.29-7.12 (m, 2H), 5.88-5.72 (m, 1H), 5.07 (t, J=7.3 Hz, 2H), 4.93 (td, J=6.6, 3.3 Hz, 2H), 4.75 (d, J=4.8 Hz, 1H), 3.43 (dt, J=13.2, 4.6 Hz, 1H), 3.36-3.26 (m, 1H), 3.19 (dt, J=14.2, 4.7 Hz, 1H), 1.83 (m, 2H), 1.74-1.55 (m, 2H), 1.40 (m, 1H), 1.28-0.92 (m, 4H); [M+H]$^+$ 363.1 LC-MS (254 nm) $t_R$=3.30 min; HPLC (254 nm) Purity: >99%; $t_R$=3.55 min.

Example 74: Step 4: Preparation of cis-4-Chloro-1-oxetan-3-yl-1H-indole-3-carboxylic acid ((1R,2R)-2-hydroxy-cyclohexylmethyl)-amide (88)

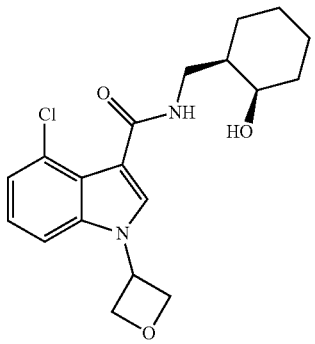 [SMILES: O=C(NC[C@H]1CCCC[C@H]1O)c1cn(C2COC2)c2cccc(Cl)c12]

The title compound was synthesized according to the procedure described in Example 5 using 4-Chloro-1-oxetan-3-yl-1H-indole-3-carboxylic acid (100.00 mg; 0.40 mmol; 1.00 eq.), cis-2-aminomethyl-cyclohexanol hydrochloride (65.83 mg; 0.40 mmol; 1.00 eq.) and HATU (188.86 mg; 0.50 mmol; 1.25 eq.), and N,N-diisopropylethylamine (0.20 ml; 1.19 mmol; 3.00 eq.) in DMF (4.05 ml; 52.50 mmol; 132.13 eq.) to afford the desired product cis-4-Chloro-1-oxetan-3-yl-1H-indole-3-carboxylic acid ((1R,2R)-2-hydroxy-cyclohexylmethyl)-amide (86.50 mg; 0.24 mmol). $^1$H NMR (400 MHz, DMSO) δ 8.12 (s, 1H), 8.07 (t, J=5.9 Hz, 1H), 7.64-7.52 (m, 1H), 7.28-7.12 (m, 2H), 5.87-5.72 (m, 1H), 5.06 (t, J=7.3 Hz, 2H), 4.93 (td, J=6.7, 1.7 Hz, 2H), 4.36 (t, J=7.3 Hz, 1H), 3.85 (s, 1H), 3.35-3.23 (m, 1H), 3.19-3.04 (m, 1H), 1.77-1.48 (m, 4H), 1.46-1.29 (m, 4H), 1.27-1.09 (m, 1H); [M+H]$^+$ 363.1 LC-MS (254 nm) $t_R$=3.36 min; HPLC (254 nm) Purity: 98.8%; $t_R$=3.57 min

Example 75: Preparation of 4-Chloro-1-oxetan-3-yl-1H-indole-3-carboxylic acid (2-cyclopentyloxy-ethyl)-amide (72)

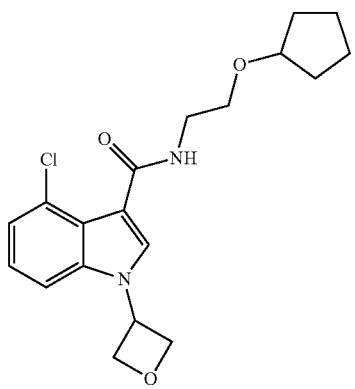 [SMILES: O=C(NCCOC1CCCC1)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 2-(cyclopentyloxy)ethylamine (46.20 mg; 0.36 mmol; 1.20 eq.) to afford the desired product 4-Chloro-1-oxetan-3-yl-1H-indole-3-carboxylic acid (2-cyclopentyloxy-ethyl)-amide (37.0 mg; 0.10 mmol).

[M+H]⁺ 363.2 LC-MS (254 nm) t_R=4.86 min; HPLC (254 nm) Purity: >99%; t_R=4.11 min.

Example 76: Preparation of 4-Chloro-1-oxetan-3-yl-1H-indole-3-carboxylic acid (1-hydroxy-cyclohexyl-methyl)-amide (58)

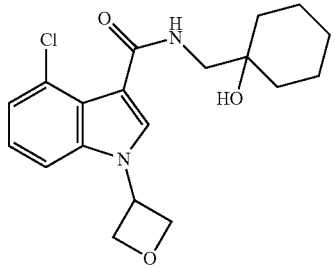 [SMILES: O=C(NCC1(O)CCCCC1)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 1-(aminomethyl)cyclohexanol (42.35 mg; 0.33 mmol; 1.10 eq.) to afford the desired product 4-Chloro-1-oxetan-3-yl-1H-indole-3-carboxylic acid (1-hydroxy-cyclohexylmethyl)-amide (49.0 mg; 0.14 mmol). [M+H]⁺ 363.2 LC-MS (254 nm) t_R=4.12 min; HPLC (254 nm) Purity: >99%; t_R=3.53 min.

Example 77: Preparation of 4-Chloro-1-oxetan-3-yl-1H-indole-3-carboxylic acid ((1S,4R)-1-bicyclo[2.2.1]hept-2-ylmethyl)-amide (59)

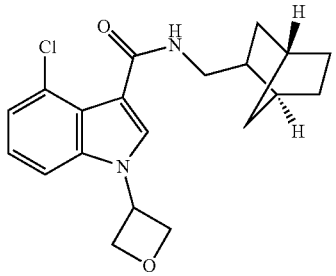 [SMILES: O=C(NCC1C[C@@H]2CC[C@H]1C2)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and c-bicyclo[2.2.1]hept-2-yl-methylamine hydrobromide (67.57 mg; 0.33 mmol; 1.10 eq.) to afford the desired product 4-Chloro-1-oxetan-3-yl-1H-indole-3-carboxylic acid ((1S,4R)-1-bicyclo[2.2.1]hept-2-ylmethyl)-amide (65.0 mg; 0.18 mmol). [M+H]⁺ 360.2 LC-MS (254 nm) t_R=5.14 min; HPLC (254 nm) Purity: >99%; t_R=4.67 min.

Example 78: Preparation of 4-Chloro-1-oxetan-3-yl-1H-indole-3-carboxylic acid ((S)-1-cyclohexyl-2,2,2-trifluoro-ethyl)-amide (52)

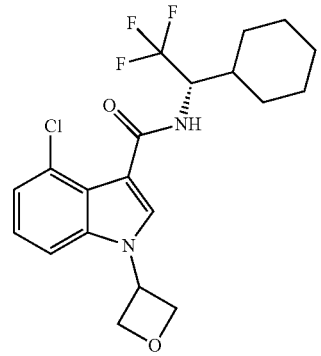 [SMILES: O=C(N[C@@H](C1CCCCC1)C(F)(F)F)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 1-(aminomethyl)cyclohexanol (56.70 mg; 0.31 mmol; 1.05 eq.) to afford the desired product 4-Chloro-1-oxetan-3-yl-1H-indole-3-carboxylic acid ((S)-1-cyclohexyl-2,2,2-trifluoro-ethyl)-amide (19.7 mg; 0.05 mmol). [M+H]⁺ 415.0 LC-MS (254 nm) t_R=5.61 min; HPLC (254 nm) Purity: >99%; t_R=5.27 min.

Example 79: Preparation of 4-Chloro-1-oxetan-3-yl-1H-indole-3-carboxylic acid (4-trifluoromethyl-cyclohexylmethyl)-amide (53)

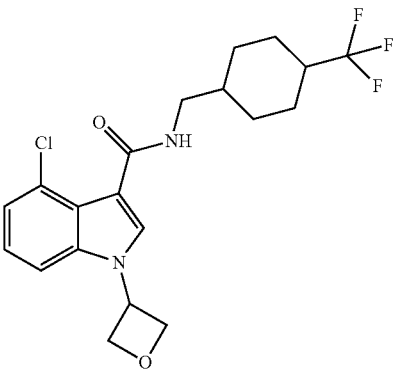 [SMILES: O=C(NCC1CCC(C(F)(F)F)CC1)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 1-aminomethyl-4-trifluoromethylcyclohexane (56.70 mg; 0.31 mmol; 1.05 eq.) to afford the desired product 4-Chloro-1-oxetan-3-yl-1H-indole-3-carboxylic acid (4-trifluoromethyl-cyclohexylmethyl)-amide (85.5 mg; 0.21 mmol). [M+H]⁺ 415.0 LC-MS (254 nm) t_R=5.11 min; HPLC (254 nm) Purity: >99%; t_R=4.79 min

Example 80: Preparation of 4-Chloro-1-oxetan-3-yl-1H-indole-3-carboxylic acid (3-trifluoromethyl-cyclohexylmethyl)-amide (56)

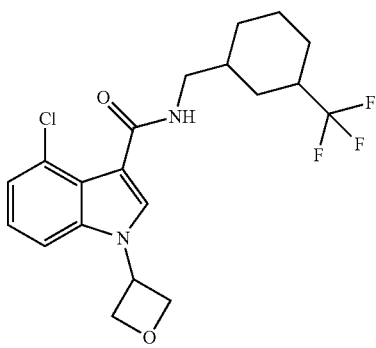 [SMILES: O=C(NCC1CCCC(C(F)(F)F)C1)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and [3-(trifluoromethyl)cyclohexyl]methanamine (56.70 mg; 0.31 mmol; 1.05 eq.) to afford the desired product 4-Chloro-1-oxetan-3-yl-1H-indole-3-carboxylic acid (3-trifluoromethyl-cyclohexylmethyl)-amide (93.3 mg; 0.22 mmol). [M+H]$^+$ 415.0 LC-MS (254 nm) $t_R$=5.13 min; HPLC (254 nm) Purity: >99%; $t_R$=4.01 min.

Example 81: Preparation of 4-Chloro-1-oxetan-3-yl-1H-indole-3-carboxylic acid ((R)-1-cyclohexyl-2-hydroxy-ethyl)-amide (63)

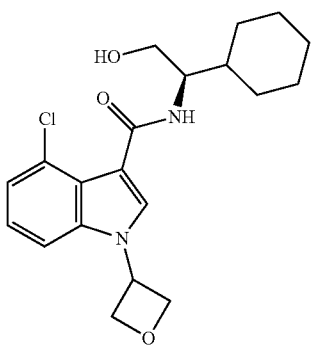 [SMILES: O=C(N[C@@H](CO)C1CCCCC1)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and d-cyclohexylglycinol (46.95 mg; 0.33 mmol; 1.10 eq.) to afford the desired product 4-Chloro-1-oxetan-3-yl-1H-indole-3-carboxylic acid ((R)-1-cyclohexyl-2-hydroxy-ethyl)-amide (75.0 mg; 0.20 mmol). [M+H]$^+$ 377.2 LC-MS (254 nm) $t_R$=4.39 min; HPLC (254 nm) Purity: >99%; $t_R$=3.94 min.

Example 82: Preparation of 4-Chloro-1-oxetan-3-yl-1H-indole-3-carboxylic acid (2-cyclopentyl-2-hydroxy-propyl)-amide (49)

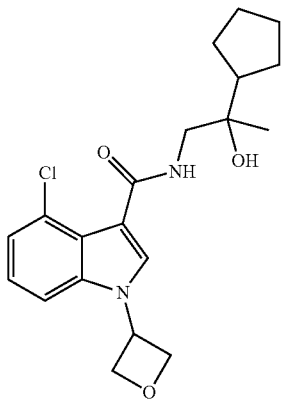 [SMILES: CC(O)(CNC(=O)c1cn(C2COC2)c2cccc(Cl)c12)C1CCCC1]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 1-amino-2-cyclopentylpropan-2-ol (42.68 mg; 0.30 mmol; 1.00 eq.) to afford the desired product 4-Chloro-1-oxetan-3-yl-1H-indole-3-carboxylic acid (2-cyclopentyl-2-hydroxy-propyl)-amide (86.6 mg; 0.23 mmol). [M+H]$^+$ 377.1 LC-MS (254 nm) $t_R$=3.63 min; HPLC (254 nm) Purity: >99%; $t_R$=3.90 min.

Example 83: Preparation of 4-Chloro-1-oxetan-3-yl-1H-indole-3-carboxylic acid (1-hydroxy-cycloheptylmethyl)-amide (65)

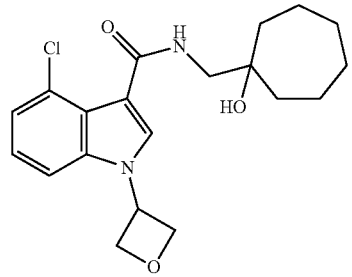 [SMILES: O=C(NCC1(O)CCCCCC1)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 1-Aminomethyl-cycloheptanol hydrochloride (64.26 mg; 0.36 mmol; 1.20 eq.) to afford the desired product 4-Chloro-1-oxetan-3-yl-1H-indole-3-carboxylic acid (2-cyclopentyl-2-phenyl-ethyl)-amide (24.0 mg; 0.06 mmol). [M+H]$^+$ 377.1 LC-MS (254 nm) $t_R$=4.37 min; HPLC (254 nm) Purity: >99%; $t_R$=3.81 min.

Example 84: Preparation of 4-Chloro-1-oxetan-3-yl-1H-indole-3-carboxylic acid ((1S,2S,4S)-2-bicyclo[2.2.1]hept-5-en-2-yl-ethyl)-amide (75)

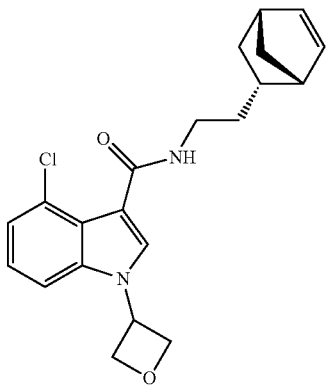 [SMILES: O=C(NCC[C@@H]1C[C@@H]2C=C[C@H]1C2)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 2-[(1s,2s,4s)-bicyclo[2.2.1]hept-5-en-2-yl]ethanamine (46.20 mg; 0.36 mmol; 1.20 eq.) to afford the desired product 4-Chloro-1-oxetan-3-yl-1H-indole-3-carboxylic acid ((1S,2S,4S)-2-bicyclo[2.2.1]hept-5-en-2-yl-ethyl)-amide (53.0 mg; 0.14 mmol). [M+H]+ 371.2 LC-MS (254 nm) $t_R$=5.16 min; HPLC (254 nm) Purity: 97.14%; $t_R$=4.75 min.

Example 85: Preparation of 4-Chloro-1-oxetan-3-yl-1H-indole-3-carboxylic acid (2-cyclopentyl-2-methyl-propyl)-amide (50)

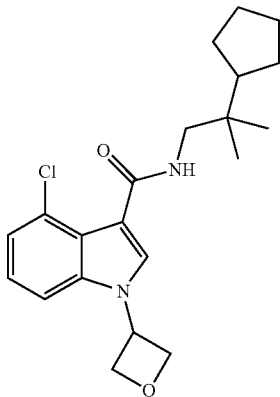 [SMILES: CC(C)(CNC(=O)c1cn(C2COC2)c2cccc(Cl)c12)C1CCCC1]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 2-cyclopentyl-2-methylpropan-1-amine (42.10 mg; 0.30 mmol; 1.00 eq.) to afford the desired product 4-Chloro-1-oxetan-3-yl-1H-indole-3-carboxylic acid (2-cyclopentyl-2-methyl-propyl)-amide (76.4 mg; 0.20 mmol). [M+H]+ 375.2 LC-MS (254 nm) $t_R$=4.69 min; HPLC (254 nm) Purity: >99%; $t_R$=5.21 min.

Example 86: Preparation of 4-Chloro-1-oxetan-3-yl-1H-indole-3-carboxylic acid (1-cyclohexyl-cyclopropyl)-amide (55)

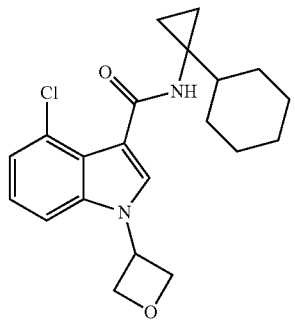 [SMILES: O=C(NC1(C2CCCCC2)CC1)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 1-Cyclohexyl-cyclopropylamine hydrochloride (57.6 mg; 0.33 mmol; 1.10 eq.) to afford the desired product 4-Chloro-1-oxetan-3-yl-1H-indole-3-carboxylic acid (1-cyclohexyl-cyclopropyl)-amide (42.5 mg; 0.11 mmol). [M+H]+ 473.2 LC-MS (254 nm) $t_R$=5.39 min; HPLC (254 nm) Purity: >99%; $t_R$=4.84 min.

Example 87: Preparation of 4-Chloro-1-oxetan-3-yl-1H-indole-3-carboxylic acid (1-hydroxy-3,3-dimethyl-cyclohexylmethyl)-amide (64)

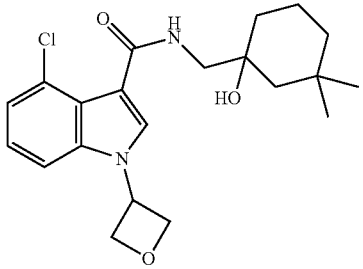 [SMILES: CC1(C)CCCC(O)(CNC(=O)c2cn(C3COC3)c3cccc(Cl)c23)C1]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 1-Aminomethyl-3,3-dimethyl-cyclohexanol (56.24 mg; 0.36 mmol; 1.20 eq.) to afford the desired product 4-Chloro-1-oxetan-3-yl-1H-indole-3-carboxylic acid (1-hydroxy-3,3-dimethyl-cyclohexylmethyl)-amide (105.9 mg; 0.27 mmol). [M+H]+ 391.2 LC-MS (254 nm) $t_R$=4.77 min; HPLC (254 nm) Purity: >99%; $t_R$=4.28 min.

Example 88: Preparation of 4-Chloro-1-oxetan-3-yl-1H-indole-3-carboxylic acid (1-adamantan-1-yl-ethyl)-amide (62)

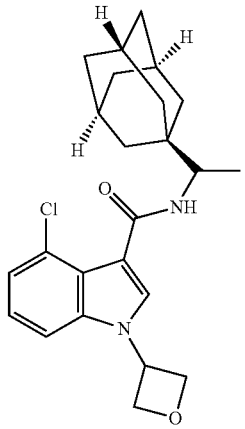 [SMILES: CC(NC(=O)c1cn(C2COC2)c2cccc(Cl)c12)[C@]12C[C@H]3C[C@H](C[C@H](C3)C1)C2]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and rimantadine hydrochloride (70.73 mg; 0.33 mmol; 1.10 eq.) to afford the desired product 4-Chloro-1-oxetan-3-yl-1H-indole-3-carboxylic acid (1-adamantan-1-yl-ethyl)-amide (84.0 mg; 0.20 mmol). [M+H]$^+$ 413.2 LC-MS (254 nm) $t_R$=5.98 min; HPLC (254 nm) Purity: >99%; $t_R$=5.45 min.

Example 89: Preparation of 4-Chloro-1-oxetan-3-yl-1H-indole-3-carboxylic acid [(3-hydroxy-adamantan-1-yl)-ethyl]-amide (61)

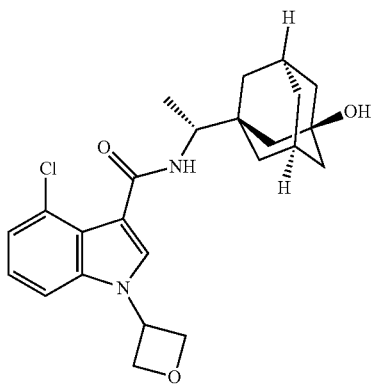 [SMILES: C[C@@H](NC(=O)c1cn(C2COC2)c2cccc(Cl)c12)[C@@]12C[C@@H]3C[C@@H](C[C@@](O)(C3)C1)C2]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and (1S,3R,5R,7S)-3-(1-Amino-ethyl)-adamantan-1-ol hydrochloride (75.98 mg; 0.33 mmol; 1.10 eq.) to afford the desired product 4-Chloro-1-oxetan-3-yl-1H-indole-3-carboxylic acid [(3-hydroxy-adamantan-1-yl)-ethyl]-amide (96.0 mg; 0.22 mmol). [M+H]$^+$ 429.2 LC-MS (254 nm) $t_R$=4.24 min; HPLC (254 nm) Purity: >99%; $t_R$=3.75 min.

Example 90: Preparation of 4-Chloro-1-oxetan-3-yl-1H-indole-3-carboxylic acid (1-adamantan-1-yl-1-methyl-ethyl)-amide (54)

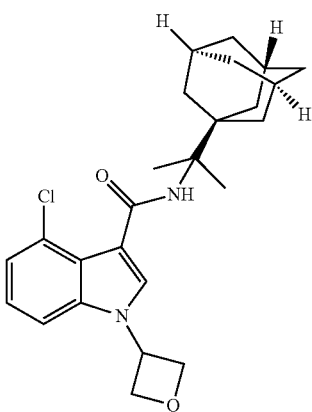 [SMILES: CC(C)(NC(=O)c1cn(C2COC2)c2cccc(Cl)c12)[C@]12C[C@H]3C[C@H](C[C@H](C3)C1)C2]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and 1-Adamantan-1-yl-1-methyl-ethylamine hydrochloride (75.33 mg; 0.33 mmol; 1.1 eq.) to afford the desired product 4-Chloro-1-oxetan-3-yl-1H-indole-3-carboxylic acid (1-adamantan-1-yl-1-methyl-ethyl)-amide (78.0 mg; 0.18 mmol). [M+H]$^+$ 427.2 LC-MS (254 nm) $t_R$=5.30 min; HPLC (254 nm) Purity: >99%; $t_R$=5.84 min.

Example 91: Preparation of 4-Chloro-1-oxetan-3-yl-1H-indole-3-carboxylic acid (cyclohexyl-thiophen-2-yl-methyl)-amide (60)

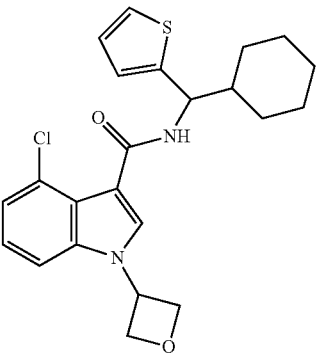 [SMILES: O=C(NC(c1cccs1)C1CCCCC1)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and C-Cyclohexyl-C-thiophen-2-yl-methylamine hydrochloride (75.98 mg; 0.33 mmol; 1.10 eq.) to afford the desired product 4-Chloro-1-oxetan-3-yl-1H-indole-3-carboxylic acid (cyclohexyl-thiophen-2-yl-methyl)-amide (98.0 mg; 0.23 mmol). [M+H]$^+$ 429.1 LC-MS (254 nm) $t_R$=5.69 min; HPLC (254 nm) Purity: >99%; $t_R$=5.32 min.

Example 92: Preparation of 4-Chloro-1-oxetan-3-yl-1H-indole-3-carboxylic acid (2-cyclopentyl-2-phenyl-ethyl)-amide (70)

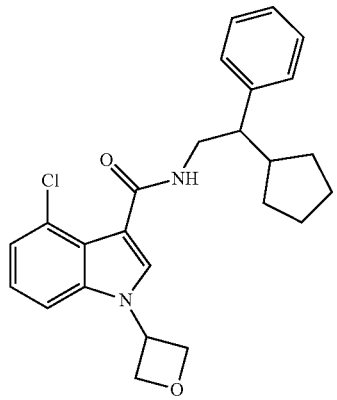 [SMILES: O=C(NCC(c1ccccc1)C1CCCC1)c1cn(C2COC2)c2cccc(Cl)c12]

The title compound was synthesized according to the procedure described in Example 5 using a mixture of 4-Chloro-1-oxetan-3-yl-1H-indole-3-carboxylic acid (75.00 mg; 0.30 mmol; 1.00 eq.) and (2-cyclopentyl-2-phenylethyl)amine (67.70 mg; 0.36 mmol; 1.20 eq.) to afford the desired product 4-Chloro-1-oxetan-3-yl-1H-indole-3-carboxylic acid (2-cyclopentyl-2-phenyl-ethyl)-amide (24.0 mg; 0.06 mmol). [M+H]$^+$ 423.2 LC-MS (254 nm) $t_R$=5.71 min; HPLC (254 nm) Purity: >99%; $t_R$=5.35 min.

Example 93: 4-chloro-N-(2-(1-hydroxycyclopentyl)ethyl)-1-(oxetan-3-yl)-1H-indole-3-carboxamide (45)

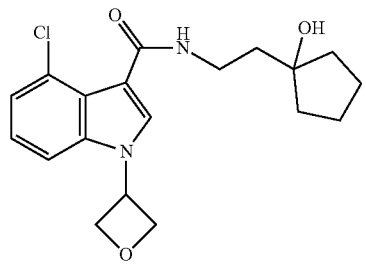 [SMILES: O=C(NCCC1(O)CCCC1)c1cn(C2COC2)c2cccc(Cl)c12]

The title compound was synthesized according to the procedure described in Example 2 using 4-Chloro-1-oxetan-3-yl-1H-indole-3-carboxylic acid (200.00 mg; 0.79 mmol; 1.00 eq.), 1-(2-Amino-ethyl)-cyclopentanol (118.08 mg; 0.91 mmol; 1.15 eq.), 3-Dimethylamino-propyl)-ethyl-carbodiimide hydrochloride (198.05 mg; 1.03 mmol; 1.30 eq.), Benzotriazol-1-ol (139.60 mg; 1.03 mmol; 1.30 eq.) and Ethyl-diisopropyl-amine (0.39 ml; 2.38 mmol; 3.00 eq.) to obtain the title compound (230, 80%).

$^1$H NMR (400 MHz, DMSO-d6) δ 8.10 (s, 1H), 8.01 (t, J=5.6 Hz, 1H), 7.56 (d, J=7.5 Hz, 1H), 7.35-7.07 (m, 2H), 5.80 (p, J=6.9 Hz, 1H), 5.06 (t, J=7.2 Hz, 2H), 4.92 (t, J=6.6 Hz, 2H), 3.50-3.31 (m, 2H), 2.02-1.39 (m, 10H). [M+H]+: 363.

Example 94: 4-chloro-N-(1-cyclopentyl-2,2,2-trifluoroethyl)-1-(oxetan-3-yl)-1H-indole-3-carboxamide (42)

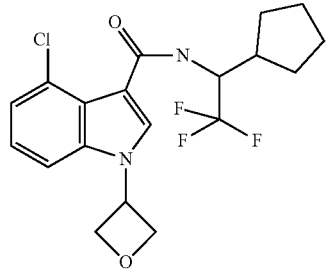 [SMILES: O=C(NC(C1CCCC1)C(F)(F)F)c1cn(C2COC2)c2cccc(Cl)c12]

The title compound was synthesized according to the procedure described in Example 2 using 4-Chloro-1-oxetan-3-yl-1H-indole-3-carboxylic acid (175.00 mg; 0.70 mmol; 1.00 eq.), 1-Cyclopentyl-2,2,2-trifluoro-ethylamine hydrochloride (162.84 mg; 0.80 mmol; 1.15 eq.), EDC (173.29 mg; 0.90 mmol; 1.30 eq.), Benzotriazol-1-ol (122.15 mg; 0.90 mmol; 1.30 eq.), and Ethyl-diisopropyl-amine (0.34 ml; 2.09 mmol; 3.00 eq.) in N,N-Dimethyl-formamide (3.00 ml) to obtain 4-chloro-N-(1-cyclopentyl-2,2,2-trifluoroethyl)-1-(oxetan-3-yl)-1H-indole-3-carboxamide (47, 17%).

$^1$H NMR (400 MHz, Chloroform-d) δ 8.21 (s, 1H), 7.41 (d, J=8.1 Hz, 1H), 7.32-7.04 (m, 3H), 5.56 (m, 1H), 5.29-4.82 (m, 6H), 2.33 (m, 1H), 1.93 (m, 2H), 1.79-1.33 (m, 5H) [M+H]+: 401.

Example 95: 4-chloro-N-(1-cyclohexyl-2,2,2-trifluoroethyl)-1-(oxetan-3-yl)-1H-indole-3-carboxamide (43)

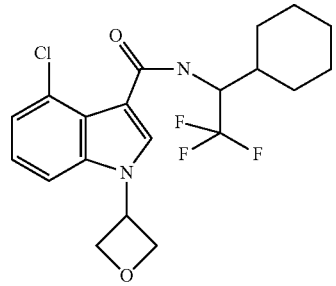 [SMILES: O=C(NC(C1CCCCC1)C(F)(F)F)c1cn(C2COC2)c2cccc(Cl)c12]

The title compound was synthesized according to the procedure described in Example 2 using 4-Chloro-1-oxetan-3-yl-1H-indole-3-carboxylic acid (150.00 mg; 0.60 mmol; 1.00 eq.), 1-Cyclohexyl-2,2,2-trifluoro-ethylamine hydrochloride (149.19 mg; 0.69 mmol; 1.15 eq.), EDC (148.54 mg; 0.77 mmol; 1.30 eq.), Benzotriazol-1-ol (104.70 mg; 0.77 mmol; 1.30 eq.), and Ethyl-diisopropyl-amine (0.29 ml; 1.79 mmol; 3.00 eq.) in N,N-Dimethyl-formamide (3.00 ml) to obtain 4-chloro-N-(1-cyclohexyl-2,2,2-trifluoroethyl)-1-(oxetan-3-yl)-1H-indole-3-carboxamide (84, 34%).

$^1$H NMR (400 MHz, Chloroform-d) δ 8.23 (s, 1H), 7.42 (d, J=8.2 Hz, 1H), 7.36-7.04 (m, 3H), 5.74-5.51 (m, 1H), 5.20 (t, J=7.4 Hz, 2H), 5.07 (m, 2H), 4.89 (pd, J=9.0, 4.3 Hz, 1H), 2.04-1.53 (m, 7H), 1.43-0.99 (m, 4H), [M+H]+: 415.

Example 96: Preparation of 4-chloro-N-(((1R,3R)-1-hydroxy-3-methylcyclohexyl) methyl)-1-(oxetan-3-yl)-1H-indole-3-carboxamide (93)

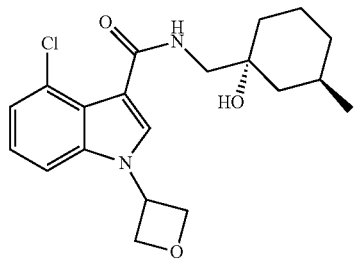 [SMILES: C[C@@H]1CCC[C@](O)(CNC(=O)c2cn(C3COC3)c3cccc(Cl)c23)C1]

To a stirred solution of 4-chloro-1-(oxetan-3-yl)-1H-indole-3-carboxylic acid (0.070 g, 0.27 mmol), HATU (0.116 g, 0.30 mmol) and (1R,3R)-1-(aminomethyl)-3-methylcyclohexanol (0.040 g, 0.27 mmol) in DMF (1.5 mL) was added DIPEA (0.107 g, 0.83 mmol). The mixture was stirred at room temperature overnight. Then the reaction was quenched with water (20 mL), extracted with DCM/methanol (10:1, 30 mL×3). The combined organic layer was washed with water (20 mL×2) and brine (20 mL×2), dried over sodium sulfate, filtered and concentrated in vacuo. The residue was purified by column chromatography on silica gel (DCM:methanol=80:1) to afford 4-chloro-N-(((1R,3R)-1-hydroxy-3-methylcyclohexyl)methyl)-1-(oxetan-3-yl)-1H-indole-3-carboxamide (0.06 mg, 57%) as a white solid.

$^1$H NMR (500 MHz, DMSO-$\delta_6$) δ 8.17 (s, 1H), 7.86 (t, J=7.5 Hz, 1H), 7.56 (dd, J=10.0, 1.5 Hz, 1H), 7.22-7.16 (m, 2H), 5.83-5.77 (m, 1H), 5.05 (t, J=9.0 Hz, 2H), 4.92 (t, J=8.0 Hz, 2H), 4.23 (s, 1H), 3.20 (d, J=7.5 Hz, 2H), 1.73-1.66 (m, 1H), 1.60-1.52 (m, 4H), 1.46-1.43 (m, 1H), 1.25-1.17 (m, 1H), 0.98-0.92 (m, 1H), 0.82 (d, J=8.0 Hz, 3H), 0.77-0.70 (m, 1H) ppm; [M+H]$^+$ 377.1.

Example 97: Preparations of 4-chloro-N-(((1S,3S)-1-hydroxy-3-methylcyclohexyl) methyl)-1-(oxetan-3-yl)-1H-indole-3-carboxamide (90)

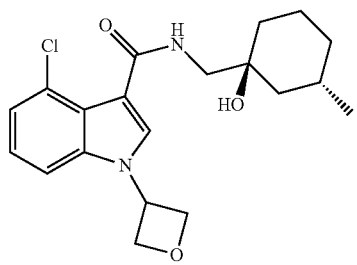 [SMILES: C[C@H]1CCC[C@@](O)(CNC(=O)c2cn(C3COC3)c3cccc(Cl)c23)C1]

The title compound was synthesized according to the procedure described in Example 2 using a mixture of 4-chloro-1-(oxetan-3-yl)-1H-indole-3-carboxylic acid (0.080 g, 0.31 mmol), HOBt (0.047 g, 0.35 mmol), DIPEA (0.123 g, 0.95 mmol), EDCI (0.067 g, 0.35 mmol) and (1S,3S)-1-(aminomethyl)-3-methylcyclohexanol (0.045 g, 0.31 mmol) in DCM to afford 4-chloro-N-(((1S,3S)-1-hydroxy-3-methylcyclohexyl) methyl)-1-(oxetan-3-yl)-1H-indole-3-carboxamide (0.060 g, 50%) as white solid.

$^1$H NMR (500 MHz, DMSO-d$_6$) δ 8.19 (s, 1H), 7.88 (t, J=6.0 Hz, 1H), 7.57 (d, J=8.0 Hz, 1H), 7.23-7.18 (m, 2H), 5.84-5.79 (m, 1H), 5.07 (t, J=7.5 Hz, 2H), 4.93 (t, J=6.5 Hz, 2H), 4.24 (s, 1H), 3.21 (d, J=6.5 Hz, 2H), 1.75-1.70 (m, 1H), 1.64-1.54 (m, 4H), 1.47-1.45 (m, 1H), 1.28-1.20 (m, 1H), 0.99-0.94 (m, 1H), 0.84 (d, J=6.5 Hz, 3H), 0.81-0.72 (m, 1H) ppm; [M+H]$^+$ 377.1

Example 98: 4-chloro-N-((1-hydroxy-3-methylcyclohexyl)methyl)-1-(oxetan-3-yl)-1H-indole-3-carboxamide (83)

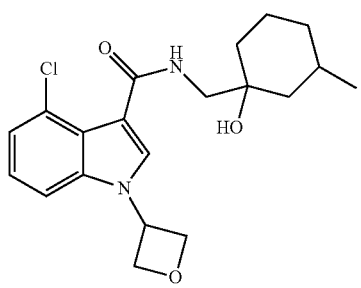 [SMILES: CC1CCCC(O)(CNC(=O)c2cn(C3COC3)c3cccc(Cl)c23)C1]

The title compound was synthesized according to the procedure described in Example 5 using 4-Chloro-1-oxetan-3-yl-1H-indole-3-carboxylic acid (250.00 mg; 0.99 mmol; 1.00 eq.), (HATU) (415.49 mg; 1.09 mmol; 1.10 eq.), DIEA (0.33 ml; 1.99 mmol; 2.00 eq.) and 1-Aminomethyl-3-methyl-cyclohexanol (156.51 mg; 1.09 mmol; 1.10 eq.). The reaction mixture was stirred for 3 h to obtain 4-chloro-N-((1-hydroxy-3-methylcyclohexyl)methyl)-1-(oxetan-3-yl)-1H-indole-3-carboxamide (63 mg, 16.8%).

1H NMR (400 MHz, Chloroform-d) δ 8.13 (s, 1H), 7.39 (dd, J=8.0, 1.2 Hz, 1H), 7.32-7.16 (m, 2H), 5.55 (tt, J=7.5, 6.1 Hz, 1H), 5.17 (t, J=7.4 Hz, 2H), 5.04 (dd, J=7.3, 6.1 Hz, 2H), 3.55-3.45 (m, 2H), 1.84-1.56 (m, 8H), 1.37-1.17 (m, 1H), 1.07-0.76 (d, 4H). [M+H]+ 377

Example 99: Preparation of 4-chloro-N-((3,3-difluorocyclohexyl)methyl)-1-(oxetan-3-yl)-1H-indole-3-carboxamide (69)

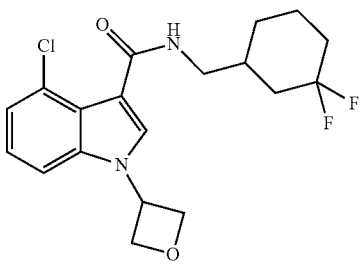 [SMILES: O=C(NCC1CCCC(F)(F)C1)c1cn(C2COC2)c2cccc(Cl)c12]

The title compound was synthesized according to the procedure described in Example 2 using 4-chloro-1-(oxetan-3-yl)-1H-indole-3-carboxylic acid (100.00 mg; 0.40 mmol; 1.00 eq.), (3,3-difluorocyclohexyl)methanamine (91.41 mg; 0.48 mmol; 1.20 eq.), (3-Dimethylamino-propyl)-ethyl-carbodiimide hydrochloride (91.41 mg; 0.48 mmol; 1.20 eq.), Benzotriazol-1-ol (64.43 mg; 0.48 mmol; 1.20 eq.) and DIPEA (0.154 g, 1.19 mmol) in DMF (6.0 mL) (130 mg, 90% yield).

$^1$H NMR (400 MHz, DMSO-d$_6$) δ ppm 8.20 (1H), 8.12 (s, 1H), 7.58 (1H), 7.20 (2H), 5.80 (1H), 5.09 (m, 2H), 4.94

(2H), 3.23-3.15 (2H), 2.12-1.96 (m, 3H), 1.77 (2H), 1.59 (2H), 1.01 (1H). m/z: 383 [M+H].

Example 100: Preparation of 4-chloro-N—(((R)-3,3-difluorocyclohexyl)methyl)-1-(oxetan-3-yl)-1H-indole-3-carboxamide (66)

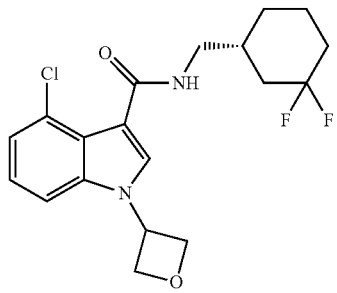 [SMILES: O=C(NC[C@@H]1CCCC(F)(F)C1)c1cn(C2COC2)c2cccc(Cl)c12]

The title compound was separated via chiral column from racemic 4-chloro-N-((3,3-difluorocyclohexyl)methyl)-1-(oxetan-3-yl)-1H-indole-3-carboxamide. Separation: 200 mg of racemic compound was dissolved in 30 mL solvent consisting of MeOH:IPA:ACN=2:3:5; Column: chiralPac IC-H 2-×250 mm; Mobil Phase: 30% 2-methanol containing 0.5% DMEA in CO2; Flow rate: 70 mL/min.

$^1$H NMR (400 MHz, DMSO-d$_6$) δ ppm 8.20 (1H), 8.12 (s, 1H), 7.58 (1H), 7.20 (2H), 5.80 (1H), 5.09 (m, 2H), 4.94 (2H), 3.23-3.15 (2H), 2.12-1.96 (m, 3H), 1.77 (2H), 1.59 (2H), 1.01 (1H). m/z: 383 [M+H]

Example 101: Preparation of 4-chloro-N—(((S)-3,3-difluorocyclohexyl)methyl)-1-(oxetan-3-yl)-1H-indole-3-carboxamide (67)

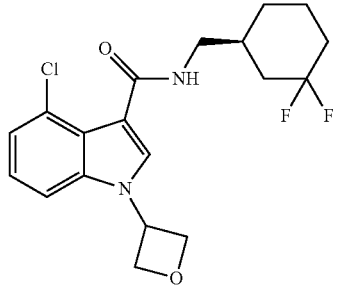 [SMILES: O=C(NC[C@H]1CCCC(F)(F)C1)c1cn(C2COC2)c2cccc(Cl)c12]

The title compound was separated (See example 100) from racemic 4-chloro-N-((3,3-difluorocyclohexyl)methyl)-1-(oxetan-3-yl)-1H-indole-3-carboxamide.

$^1$H NMR (400 MHz, DMSO-d$_6$) δ ppm 8.20 (1H), 8.12 (s, 1H), 7.58 (1H), 7.20 (2H), 5.80 (1H), 5.09 (m, 2H), 4.94 (2H), 3.23-3.15 (2H), 2.12-1.96 (m, 3H), 1.77 (2H), 1.59 (2H), 1.01 (1H). m/z: 383 [M+H]

Example 102: 4-chloro-N-((3,3-difluoro-1-hydroxycyclohexyl)methyl)-1-(oxetan-3-yl)-1H-indole-3-carboxamide (86)

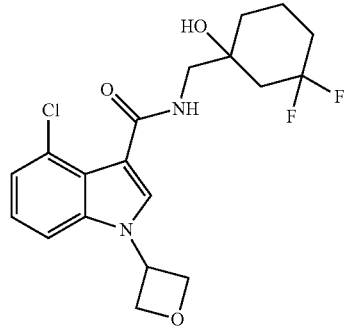 [SMILES: O=C(NCC1(O)CCCC(F)(F)C1)c1cn(C2COC2)c2cccc(Cl)c12]

The title compound was synthesized according to the procedure described in Example 33 using 4-chloro-N-((3,3-difluoro-1-hydroxycyclohexyl)methyl)-1H-indole-3-carboxamide (50.00 mg; 0.20 mmol; 1.00 eq.), 1-(aminomethyl)-3-difluoro cyclo hexanol (36.13 mg; 0.25 mmol; 2.50 eq.) and (Tributyl-lambda5-phosphanylidene)-acetonitrile (147.72 mg; 0.61 mmol; 4.00 eq.) in Toluene (3 mL).

$^1$H NMR (400 MHz, DMSO-d$_6$) δ ppm 8.22 (1H), 8.01 (s, 1H), 7.58 (1H), 7.20 (2H), 5.80 (1H), 5.05 (m, 2H), 4.94 (2H), 4.65 (s, 1H), 3.43 (1H), 3.23 (1H), 2.02-1.96 (m, 3H), 1.77 (2H), 1.59 (2H), 1.51 (1H). m/z: 399 [M+H]

Example 103: (R)-4-chloro-N-((3,3-difluoro-1-hydroxycyclohexyl)methyl)-1-(oxetan-3-yl)-1H-indole-3-carboxamide (84)

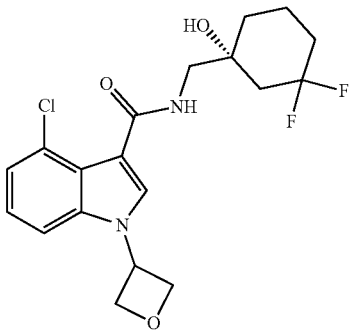 [SMILES: O=C(NC[C@@]1(O)CCCC(F)(F)C1)c1cn(C2COC2)c2cccc(Cl)c12]

The racemic 4-chloro-N-((3,3-difluoro-1-hydroxycyclohexyl)methyl)-1-(oxetan-3-yl)-1H-indole-3-carboxamide was separated via chiral column. Separation: Moblie Phase: Hexane:EtOH:DEA=70:30:0.1; Flow Rate: 1.0 mL/min; Runtime: 25 min. Column: CHIRALPAK AY-H (250×4.6 mm, 5 am).

$^1$H NMR (400 MHz, Chloroform-d) δ 8.07 (d, J=7.6 Hz, 1H), 7.39 (t, J=7.4 Hz, 2H), 7.32-7.06 (m, 1H), 5.56 (d, J=6.9 Hz, 1H), 5.17 (q, J=7.3 Hz, 2H), 5.03 (t, J=6.8 Hz, 2H), 3.78-3.33 (m, 1H), 2.21-2.02 (m, 1H), 1.99-1.74 (m, 4H), 1.65 (q, J=11.5, 9.6 Hz, 5H), 1.37-1.12 (m, 5H). [M+H]$^+$ 399.

Example 104: (S)-4-chloro-N-((3,3-difluoro-1-hydroxycyclohexyl)methyl)-1-(oxetan-3-yl)-1H-indole-3-carboxamide (85)

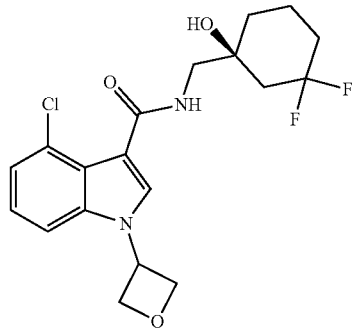 [SMILES: O=C(NC[C@]1(O)CCCC(F)(F)C1)c1cn(C2COC2)c2cccc(Cl)c12]

The racemic 4-chloro-N-((3,3-difluoro-1-hydroxycyclohexyl)methyl)-1-(oxetan-3-yl)-1H-indole-3-carboxamide was separated (See example 103) [M+H]$^+$ 399.

Example 105: Preparation of 4-chloro-N-((4,4-difluoro-1-hydroxycyclohexyl)methyl)-1-(oxetan-3-yl)-1H-indole-3-carboxamide (92)

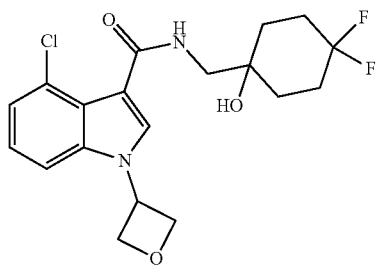 [SMILES: O=C(NCC1(O)CCC(F)(F)CC1)c1cn(C2COC2)c2cccc(Cl)c12]

The title compound was synthesized according to the procedure described in Example 5 using a mixture of 4-chloro-1-(oxetan-3-yl)-1H-indole-3-carboxylic acid (0.070 g, 0.27 mmol), HATU (0.116 g, 0.30 mmol) and 1-(aminomethyl)-4,4-difluorocyclohexanol hydrochloride (0.056 g, 0.27 mmol) and DIPEA (0.107 g, 0.83 mmol) in DMF to afford 4-chloro-N-((4,4-difluoro-1-hydroxycyclohexyl)methyl)-1-(oxetan-3-yl)-1H-indole-3-carboxamide (0.06 mg, 54%) as a white solid.

$^1$H NMR (500 MHz, DMSO-$d_6$) δ 8.19 (s, 1H), 8.05 (t, J=6.0 Hz, 1H), 7.58 (d, J=8.0 Hz, 1H), 7.23-7.18 (m, 2H), 5.85-5.79 (m, 1H), 5.07 (t, J=7.0 Hz, 2H), 4.93 (t, J=7.0 Hz, 2H), 4.73 (s, 1H), 3.35-3.33 (m, 2H), 2.10-1.97 (m, 2H), 1.93-1.88 (m, 2H), 1.67-1.62 (m, 4H) ppm; [M+H]$^+$ 399.1.

Example 106: Preparation of 4-chloro-N-((3,3-difluoro-5-(trifluoromethyl) cyclohexyl) methyl)-1-(oxetan-3-yl)-1H-indole-3-carboxamide (91)

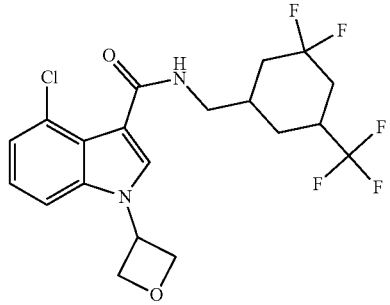 [SMILES: O=C(NCC1CC(C(F)(F)F)CC(F)(F)C1)c1cn(C2COC2)c2cccc(Cl)c12]

The title compound was synthesized according to the procedure described in Example 5 using a mixture of 4-chloro-1-(oxetan-3-yl)-1H-indole-3-carboxylic acid (0.050 g, 0.20 mmol), (3,3-difluoro-5-(trifluoromethyl)cyclohexyl)methanamine (0.043 g, 0.20 mmol), HATU (0.083 g, 0.22 mmol) and DIPEA (0.077 g, 0.60 mmol) in DMF to afford 4-chloro-N-((3,3-difluoro-5-(trifluoromethyl) cyclohexyl)methyl)-1-(oxetan-3-yl)-1H-indole-3-carboxamide (0.030 g, 33%) as white solid.

$^1$H NMR (500 MHz, DMSO-$d_6$) δ 8.26 (t, J=6.0 Hz, 1H), 8.13-8.11 (m, 1H), 7.58 (d, J=8.0 Hz, 1H), 7.23-7.18 (m, 2H), 5.84-5.78 (m, 1H), 5.06 (t, J=7.5 Hz, 2H), 4.93 (t, J=6.5 Hz, 2H), 3.35-3.22 (m, 2H), 2.66-2.64 (m, 1H), 2.23-2.18 (m, 2H), 2.03-1.82 (m, 3H), 1.74-1.61 (m, 1H), 1.26-1.19 (m, 1H) ppm; [M+H]$^+$ 451.1.

Example 107: Preparation of 4-chloro-N-((3,3-difluoro-1-hydroxy-5-methylcyclohexyl)methyl)-1-(oxetan-3-yl)-1H-indole-3-carboxamide (89)

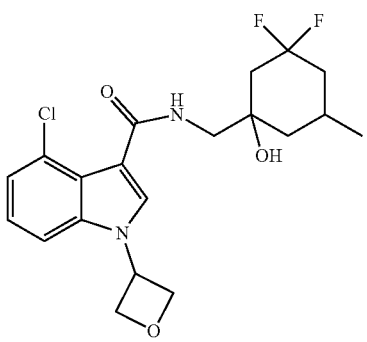 [SMILES: CC1CC(F)(F)CC(O)(CNC(=O)c2cn(C3COC3)c3cccc(Cl)c23)C1]

The title compound was synthesized according to the procedure described in Example 2 using a mixture 4-Chloro-1-oxetan-3-yl-1H-indole-3-carboxylic acid (100.00 mg; 0.40 mmol; 1.00 eq.), (EDCI) (91.41 mg; 0.48 mmol; 1.20 eq.), HOBt (64.4 g, 0.48 mmol), TEA (80.42 mg; 0.79 mmol; 2.00 eq.), and 1-Aminomethyl-3,3-difluoro-5-methyl-cyclohexanol (78.33 mg; 0.44 mmol; 1.10 eq.) to afford 4-chloro-N-((3,3-difluoro-1-hydroxy-5-methylcyclohexyl)methyl)-1-(oxetan-3-yl)-1H-indole-3-carboxamide (40 mg, 24%).

1H NMR (400 MHz, Chloroform-d) δ 8.24-8.09 (m, 1H), 7.41 (d, J=8.0 Hz, 1H), 7.27 (ddd, J=24.3, 13.2, 6.2 Hz, 3H), 5.55 (p, J=7.2 Hz, 1H), 5.18 (t, J=7.6 Hz, 2H), 5.10-4.92 (m, 2H), 3.79 (dd, J=14.7, 6.3 Hz, 1H), 3.51-3.34 (m, 2H), 2.55-2.34 (m, 1H), 2.19-1.66 (m, 5H), 1.52-1.15 (m, 3H), 1.03 (d, J=6.5 Hz, 2H). [M+H]+ 413.

Example 108: Preparation of 4-chloro-1-(oxetan-3-yl)-N-(spiro[2.5]octan-5-ylmethyl)-1H-indole-3-carboxamide (68)

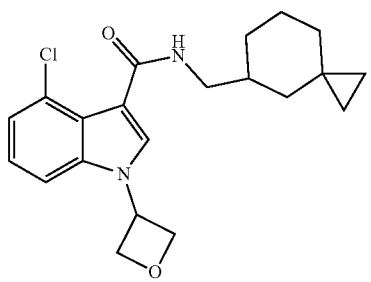 [SMILES: O=C(NCC1CCCC2(CC2)C1)c1cn(C2COC2)c2cccc(Cl)c12]

The title compound was synthesized according to the procedure described in Example 5 using 4-Chloro-1-oxetan-3-yl-1H-indole-3-carboxylic acid (150.00 mg; 0.60 mmol; 1.00 eq.), HATU (249.29 mg; 0.66 mmol; 1.10 eq.), DIEA (0.20 ml; 1.19 mmol; 2.00 eq.) and C-Spiro[2.5]oct-5-yl-methylamine (91.29 mg; 0.66 mmol; 1.10 eq.) to provide 4-chloro-1-(oxetan-3-yl)-N-(spiro[2.5]octan-5-ylmethyl)-1H-indole-3-carboxamide (140 mg, 63%). [M+H]+ 373.

Example 109: Preparation of 4-chloro-N-((5-hydroxyspiro[2.5]octan-5-yl)methyl)-1-(oxetan-3-yl)-1H-indole-3-carboxamide (57)

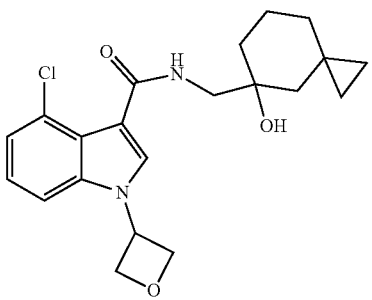 [SMILES: O=C(NCC1(O)CCCC2(CC2)C1)c1cn(C2COC2)c2cccc(Cl)c12]

The title compound was synthesized according to the procedure described in Example 2 using the following: 4-Chloro-1-oxetan-3-yl-1H-indole-3-carboxylic acid (150.00 mg; 0.60 mmol; 1.00 eq.), 5-Aminomethyl-spiro[2.5]octan-5-ol hydrochloride (131.40 mg; 0.69 mmol; 1.15 eq.), EDC (148.54 mg; 0.77 mmol; 1.30 eq.), Benzotriazol-1-ol (104.70 mg; 0.77 mmol; 1.30 eq.) and Ethyl-diisopropyl-amine (0.29 ml; 1.79 mmol; 3.00 eq.) in N,N-Dimethylformamide to provide 4-chloro-N-((5-hydroxyspiro[2.5]octan-5-yl)methyl)-1-(oxetan-3-yl)-1H-indole-3-carboxamide (50 mg, 20%).
¹H NMR (400 MHz, Chloroform-d) δ 8.11 (s, 1H), 7.39 (d, J=8.0 Hz, 1H), 7.33-7.16 (m, 2H), 7.09 (d, J=6.3 Hz, 1H), 5.56 (p, J=6.8 Hz, 1H), 5.12 (dt, J=50.5, 7.0 Hz, 4H), 3.76-3.46 (m, 2H), 1.83-1.53 (m, 6H), 1.48-1.11 (m, 4H), 0.49-0.17 (m, 4H), [M+H]+ 389.

Example 110: Preparation of 4-chloro-N-((1-hydroxy-3-(trifluoromethyl) cyclohexyl)methyl)-1-(oxetan-3-yl)-1H-indole-3-carboxamide (47)

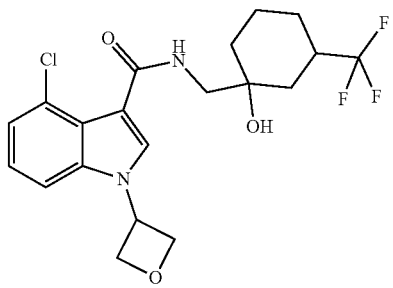 [SMILES: O=C(NCC1(O)CCCC(C(F)(F)F)C1)c1cn(C2COC2)c2cccc(Cl)c12]

The title compound was synthesized according to the procedure described in Example 2 using 4-Chloro-1-oxetan-3-yl-1H-indole-3-carboxylic acid (200.00 mg; 0.79 mmol; 1.00 eq.), 1-Aminomethyl-3-trifluoromethyl-cyclohexanol hydrochloride (213.54 mg; 0.91 mmol; 1.15 eq.), (3-Dimethylamino-propyl)-ethyl-carbodiimide hydrochloride (198.05 mg; 1.03 mmol; 1.30 eq.), Benzotriazol-1-ol (139.60 mg; 1.03 mmol; 1.30 eq.) and Ethyl-diisopropyl-amine (0.39 ml; 2.38 mmol; 3.00 eq.) to afford 4-chloro-N-((1-hydroxy-3-(trifluoromethyl)cyclohexyl)methyl)-1-(oxetan-3-yl)-1H-indole-3-carboxamide (125, 36%).
¹H NMR (400 MHz, Chloroform-d) δ 8.04-7.92 (m, 1H), 7.40-7.26 (m, 2H), 7.23-7.04 (m, 2H), 5.58-5.41 (m, 1H), 5.10 (t, J=7.3 Hz, 2H), 4.95 (q, J=6.7, 6.0 Hz, 2H), 3.62 (dd, J=14.0, 6.3 Hz, 1H), 3.44 (dd, J=14.1, 5.4 Hz, 1H), 2.39-2.15 (m, 1H), 2.39-2.17 (m, 1H), 2.29 (dpd, J=12.8, 8.5, 4.4 Hz, 1H), 2.41-2.15 (m, 1H), 2.11-1.97 (m, 1H), 1.91-1.65 (m, 2H), 1.57-1.02 (m, 4H). [M+H]+: 431

Example 111: Preparation of 4-chloro-N-((4,4-difluoro-1-hydroxy-3-methyl cyclohexyl)methyl)-1-(oxetan-3-yl)-1H-indole-3-carboxamide (46)

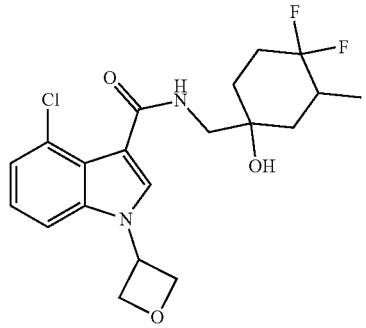 [SMILES: CC1CC(O)(CNC(=O)c2cn(C3COC3)c3cccc(Cl)c23)CCC1(F)F]

The title compound was synthesized according to the procedure described in Example 2 using 4-Chloro-1-oxetan-3-yl-1H-indole-3-carboxylic acid (200.00 mg; 0.79 mmol; 1.00 eq.), 1-Aminomethyl-4,4-difluoro-3-methyl-cyclohexanol hydrochloride (197.10 mg; 0.91 mmol; 1.15 eq.), 3-Dimethylamino-propyl)-ethyl-carbodiimide hydrochloride (198.05 mg; 1.03 mmol; 1.30 eq.), Benzotriazol-1-ol (139.60 mg; 1.03 mmol; 1.30 eq.) and Ethyl-diisopropyl-amine (0.39 ml; 2.38 mmol; 3.00 eq.) in N,N-Dimethylformamide (3.00 ml) to obtain 4-chloro-N-((4,4-difluoro-1- hydroxy-3-methylcyclohexyl)methyl)-1-(oxetan-3-yl)-1H-indole-3-carboxamide (177 mg, 54%).

1H NMR (400 MHz, DMSO-d6) δ 8.25 (s, 1H), 8.04 (t, J=6.2 Hz, 1H), 7.58 (dd, J=7.6, 1.6 Hz, 1H), 7.34-7.07 (m, 2H), 5.91-5.73 (m, 1H), 5.08 (t, J=7.3 Hz, 2H), 4.94 (t, J=6.6 Hz, 2H), 3.64-3.42 (m, 1H), 2.36-1.25 (m, 7H), 0.96 (d, J=6.6 Hz, 3H). [M+H]+: 413

Example 112: Preparation of 4-chloro-1-(oxetan-3-yl)-N-((1-(4-phenylpiperazin-1-yl) cyclohexyl) methyl)-1H-indole-3-carboxamide (51)

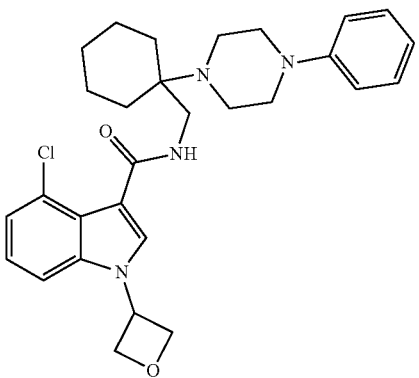 [SMILES: O=C(NCC1(N2CCN(c3ccccc3)CC2)CCCCC1)c1cn(C2COC2)c2cccc(Cl)c12]

The title compound was synthesized according to the procedure described in Example 2 using 4-Chloro-1-oxetan-3-yl-1H-indole-3-carboxylic acid (150.00 mg; 0.60 mmol; 1.00 eq.) C-[1-(4-Phenyl-piperazin-1-yl)-cyclohexyl]-methylamine (187.41 mg; 0.69 mmol; 1.15 eq.), (EDC) (148.54 mg; 0.77 mmol; 1.30 eq.), (104.70 mg; 0.77 mmol; 1.30 eq.) and Ethyl-diisopropyl-amine (0.29 ml; 1.79 mmol; 3.00 eq.) in DMF to give 4-chloro-1-(oxetan-3-yl)-N-((1-(4-phenylpiperazin-1-yl)cyclohexyl)methyl)-1H-indole-3-carboxamide (245, 81%).

1H NMR (400 MHz, Chloroform-d) δ 8.06 (d, J=19.6 Hz, 1H), 7.39 (d, J=7.9 Hz, 1H), 7.35-7.08 (m, 5H), 7.00-6.78 (m, 3H), 5.63-5.46 (m, 1H), 5.18 (t, J=7.4 Hz, 2H), 5.07 (t, J=6.7 Hz, 2H), 3.86-3.61 (m, 2H), 3.34-3.02 (m, 4H), 2.88 (d, J=15.7 Hz, 4H), 1.84-1.41 (m, 10H). [M+H]+: 508

Example 113: Preparation of 4-chloro-1-(oxetan-3-yl)-N-((4-(4-phenylpiperazin-1-yl) tetrahydro-2H-pyran-4-yl)methyl)-1H-indole-3-carboxamide (44)

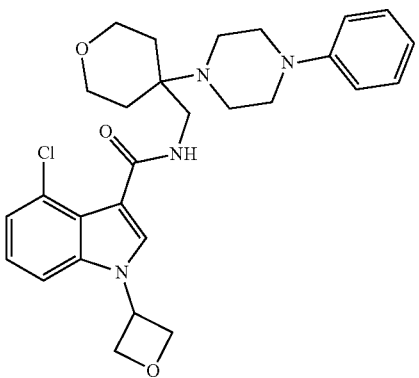 [SMILES: O=C(NCC1(N2CCN(c3ccccc3)CC2)CCOCC1)c1cn(C2COC2)c2cccc(Cl)c12]

The title compound was synthesized according to the procedure described in Example 2 using 4-Chloro-1-oxetan-3-yl-1H-indole-3-carboxylic acid (150.00 mg; 0.60 mmol; 1.00 eq.), C-[4-(4-Phenyl-piperazin-1-yl)-tetrahydro-pyran-4-yl]-methylamine (188.76 mg; 0.69 mmol; 1.15 eq.), (3-Dimethylamino-propyl)-ethyl-carbodiimide hydrochloride (EDC) (148.54 mg; 0.77 mmol; 1.30 eq.), Benzotriazol-1-ol (104.70 mg; 0.77 mmol; 1.30 eq.) and Ethyl-diisopropyl-amine (0.29 ml; 1.79 mmol; 3.00 eq.) to provide the title compound (75 mg, 25%).

¹H NMR (400 MHz, Chloroform-d) δ 8.13 (s, 1H), 7.40 (d, J=7.8 Hz, 1H), 7.33-7.12 (m, 4H), 6.91 (dd, J=21.3, 7.7 Hz, 4H), 5.56 (p, J=6.9 Hz, 1H), 5.18 (t, J=7.4 Hz, 2H), 5.07 (t, J=6.7 Hz, 2H), 4.04-3.63 (m, 6H), 3.20 (t, J=4.6 Hz, 4H), 2.88 (t, J=4.8 Hz, 4H), 1.99 (ddd, J=13.6, 9.8, 4.4 Hz, 2H), 1.70 (s, 2H). [M+H]+: 510

Example 114: Preparation of 4-chloro-N-((4,4-difluorocyclohexyl)methyl)-1-(oxetan-2-ylmethyl)-1H-indole-3-carboxamide (116 MSC2498716)

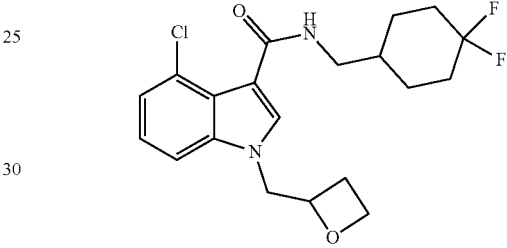

A mixture of 4-chloro-N-((4,4-difluorocyclohexyl) methyl)-1H-indole-3-carboxamide (0.050 g, 0.15 mmol), oxetan-2-ylmethanol (0.027 g, 0.31 mmol), and CMTP (0.074 g, 0.31 mmol) in toluene (2 mL) was stirred under N₂ atmosphere at 110° C. for 3 h. The resulting mixture was concentrated to give a residue, which was purified by pre-TLC (MeOH:DCM=1:10) to afford 4-chloro-N-((4,4-difluorocyclohexyl)methyl)-1-(oxetan-2-ylmethyl)-1H-indole-3-carboxamide (0.040 g, 43%) as a white solid.

¹H NMR (500 MHz, DMSO-d₆) δ 8.13 (t, J=6.0 Hz 1H), 7.71 (s, 1H), 7.60 (d, J=8.0 Hz 1H), 7.18-7.12 (m, 2H), 5.03-4.98 (m, 1H), 4.53-4.40 (m, 3H), 4.33-4.29 (m, 1H), 3.15 (t, J=6.5 Hz, 2H), 2.68-2.61 (m, 1H), 2.36-2.30 (m, 1H), 2.05-1.99 (m, 2H), 1.84-1.78 (m, 4H), 1.28-1.20 (m, 3H) ppm; [M+H]⁺ 397.

Example 115: Preparation of 4-chloro-N-((4,4-difluoro-1-hydroxy cyclohexyl) methyl)-1-(oxetan-2-ylmethyl)-1H-indole-3-carboxamide (115)

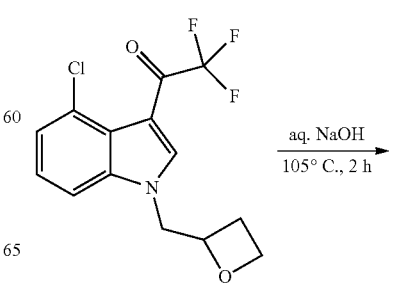

aq. NaOH
105° C., 2 h

-continued

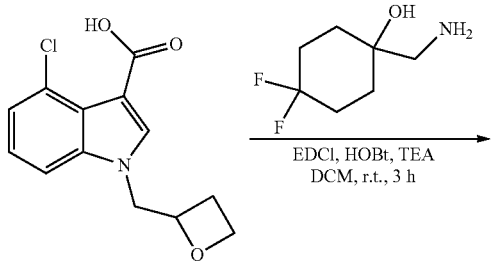

Step 2: Preparation of 4-chloro-N-((4,4-difluoro-1-hydroxycyclohexyl)methyl)-1-(oxetan-2-ylmethyl)-1H-indole-3-carboxamide

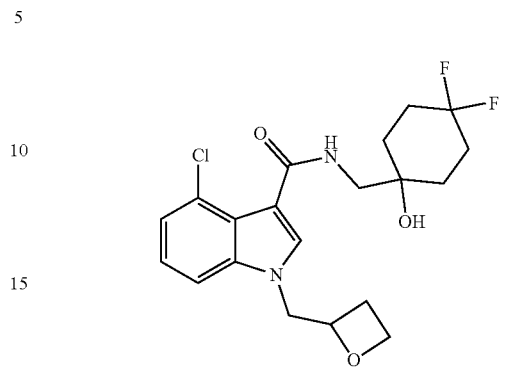

A mixture of 4-chloro-1-(oxetan-2-ylmethyl)-1H-indole-3-carboxylic acid (0.090 g, 0.34 mmol), HOBt (0.0687 mg, 0.51 mmol), EDCI (0.130 g, 0.68 mmol) and TEA (0.138 g, 1.02 mmol) in DCM (2 mL) was stirred at room temperature for 1 h, and 1-(aminomethyl)-4,4-difluorocyclohexanol (0.0819 g, 0.38 mmol) was added. The reaction was stirred at room temperature for 3 h, diluted with DCM (20 ml), washed with water (3×3 mL), dried (Na$_2$SO$_4$) and concentrated in vacuo. The residue was purified by Prep-HPLC to give a white solid (0.060 g, 40.8%).

$^1$H NMR (500 MHz, DMSO-d$_6$) δ 7.98 (t, J=5.5 Hz, 1H), 7.79 (s, 1H), 7.61 (d, J=8.0 Hz, 1H), 7.19 (t, J=7.5 Hz, 1H), 7.15 (d, J=9.0 Hz, 1H), 5.01 (s, 1H), 4.74 (s, 1H), 4.54-4.45 (m, 3H), 4.32-4.29 (m, 1H), 3.32-3.30 (m, 2H), 2.67-2.64 (m, 1H), 2.38-2.32 (m, 1H), 2.09-1.96 (m, 2H), 1.90-1.88 (m, 2H), 1.65 (t, J=8.0 Hz, 4H) ppm; [M+H]$^+$ 413.1.

Example 116: 4-chloro-N-((4,4-difluorocyclohexyl)methyl)-1-(tetrahydrofuran-2-yl)-1H-indole-3-carboxamide (99)

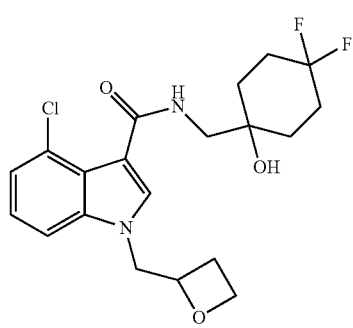

Step 1: Preparation of 4-chloro-1-(oxetan-2-ylmethyl)-1H-indole-3-carboxylic acid

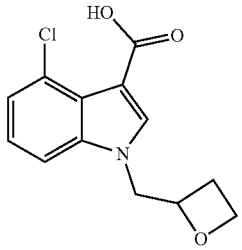 [SMILES: O=C(O)c1cn(CC2CCO2)c2cccc(Cl)c12]

A round-bottom flask was charged with 1-(4-chloro-1-(oxetan-2-ylmethyl)-1H-indol-3-yl)-2,2,2-trifluoroethanone (0.650 g, 2.05 mmol) and 30% aqueous NaOH (6 mL). The mixture was heated to 105° C. for 2 h, and then cooled to room temperature. The mixture was adjusted to pH 3 with conc. HCl, and the precipitate was collected by filtration, dried in vacuo to give 4-chloro-1-(oxetan-2-ylmethyl)-1H-indole-3-carboxylic acid (0.160 g, 29.5%). LCMS m/z: 266.1 [M+H]$^+$.

The title compound was synthesized according to the procedure described in Example 2 using 4-Chloro-1-(tetrahydro-furan-2-yl)-1H-indole-3-carboxylic acid (150.00 mg; 0.56 mmol; 1.00 eq.), C-(4,4-Difluoro-cyclohexyl)-methylamine hydrochloride (120.53 mg; 0.65 mmol; 1.15 eq.), EDC (140.70 mg; 0.73 mmol; 1.30 eq.), Benzotriazol-1-ol (99.17 mg; 0.73 mmol; 1.30 eq.) and Ethyl-diisopropyl-amine (0.28 ml; 1.69 mmol; 3.00 eq.) in N,N-Dimethyl-formamide (3.00 ml) to obtain 4-chloro-N-((4,4-difluorocyclohexyl)methyl)-1-(tetrahydrofuran-2-yl)-1H-indole-3-carboxamide (210 mg, 94%).

¹H NMR (400 MHz, DMSO-d6) δ 8.18 (t, J=6.1 Hz, 1H), 7.77 (s, 1H), 7.59 (d, J=7.8 Hz, 1H), 7.29-7.06 (m, 2H), 6.45-6.24 (m, 1H), 3.99 (dq, J=62.8, 7.5 Hz, 2H), 3.16 (t, J=6.5 Hz, 2H), 2.46-1.95 (m, 6H), 1.93-1.59 (m, 5H), 1.25 (q, J=15.1, 13.6 Hz, 2H), [M+H]⁺ 397.

Example 117: 4-chloro-N-((4,4-difluoro-1-hydroxy-cyclohexyl)methyl)-1-(tetrahydrofuran-2-yl)-1H-indole-3-carboxamide (98)

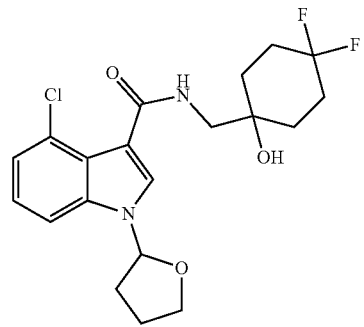 [SMILES: O=C(NCC1(O)CCC(F)(F)CC1)c1cn(C2CCCO2)c2cccc(Cl)c12]

The title compound was synthesized according to the procedure described in Example 2 using 4-Chloro-1-(tetrahydro-furan-2-yl)-1H-indole-3-carboxylic acid (150.00 mg; 0.56 mmol; 1.00 eq.), 1-Aminomethyl-4,4-difluoro-cyclohexanol hydrochloride (130.92 mg; 0.65 mmol; 1.15 eq.), EDC (140.70 mg; 0.73 mmol; 1.30 eq.), Benzotriazol-1-ol (99.17 mg; 0.73 mmol; 1.30 eq.) and Ethyl-diisopropyl-amine (0.28 ml; 1.69 mmol; 3.00 eq.) in N,N-Dimethyl-formamide (3.00 ml) to provide 4-chloro-N-((4,4-difluoro-1-hydroxycyclohexyl)methyl)-1-(tetrahydrofuran-2-yl)-1H-indole-3-carboxamide (210 mg, 90%).

¹H NMR (400 MHz, DMSO-d6) δ 8.06 (t, J=6.3 Hz, 1H), 7.84 (s, 1H), 7.60 (d, J=7.7 Hz, 1H), 7.33-7.08 (m, 2H), 6.36 (t, J=5.2 Hz, 1H), 4.16-3.85 (m, 2H), 2.49-2.26 (m, 3H), 2.21-1.77 (m, 7H), 1.73-1.57 (m, 4H), [M+H]⁺ 413.

Example 118: 4-chloro-N-((4,4-difluoro-1-hydroxy-3-methylcyclohexyl)methyl)-1-(tetrahydrofuran-2-yl)-1H-indole-3-carboxamide (97)

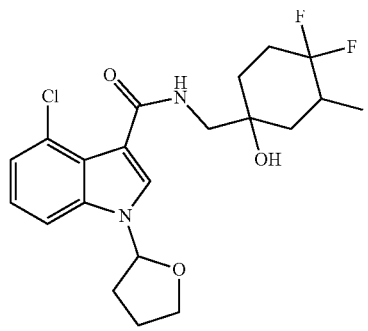 [SMILES: CC1CC(O)(CNC(=O)c2cn(C3CCCO3)c3cccc(Cl)c23)CCC1(F)F]

The title compound was synthesized according to the procedure described in Example 2 using 4-Chloro-1-(tetrahydro-furan-2-yl)-1H-indole-3-carboxylic acid (200.00 mg; 0.75 mmol; 1.00 eq.), 1-Aminomethyl-4,4-difluoro-3-methyl-cyclohexanol hydrochloride (186.70 mg; 0.87 mmol; 1.15 eq.), EDC (187.59 mg; 0.98 mmol; 1.30 eq.), Benzotriazol-1-ol (132.23 mg; 0.98 mmol; 1.30 eq.) and Ethyl-diisopropyl-amine (0.37 ml; 2.26 mmol; 3.00 eq.) in N,N-Dimethyl-formamide (3.00 ml) to obtain 4-chloro-N-((4,4-difluoro-1-hydroxy-3-methylcyclohexyl)methyl)-1-(tetrahydrofuran-2-yl)-1H-indole-3-carboxamide (205, 65%).

¹H NMR (400 MHz, DMSO-d6) δ 8.06 (t, J=6.3 Hz, 1H), 7.89 (s, 1H), 7.61 (d, J=7.5 Hz, 1H), 7.31-7.10 (m, 2H), 6.36 (dd, J=6.7, 3.6 Hz, 1H), 4.84 (s, 1H), 4.00 (m, 2H), 3.63-3.39 (m, 2H), 2.49-1.27 (m, 9H), 0.97 (d, J=6.6 Hz, 3H), [M+H]⁺ 427.

Example 119: 4-chloro-N-(cyclohexylmethyl)-1-(tetrahydrofuran-3-yl)-1H-indole-3-carboxamide (101)

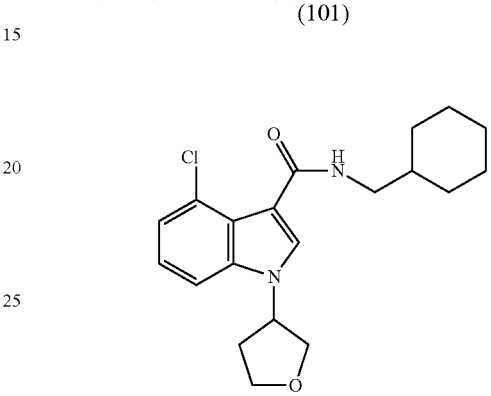

The title compound was synthesized according to the procedure described in Example 2 using 4-Chloro-1-(tetrahydro-furan-3-yl)-1H-indole-3-carboxylic acid (150.00 mg; 0.56 mmol; 1.00 eq.), C-Cyclohexyl-methylamine (73.50 mg; 0.65 mmol; 1.15 eq.), EDC (140.70 mg; 0.73 mmol; 1.30 eq.), Benzotriazol-1-ol (99.17 mg; 0.73 mmol; 1.30 eq.) and Ethyl-diisopropyl-amine (0.28 ml; 1.69 mmol; 3.00 eq.) in N,N-Dimethyl-formamide (3.00 ml) to provide 4-chloro-N-(cyclohexylmethyl)-1-(tetrahydrofuran-3-yl)-1H-indole-3-carboxamide (140 mg, 69%).

¹H NMR (400 MHz, Chloroform-d) δ 7.93 (s, 1H), 7.39 (d, J=7.9 Hz, 1H), 7.22 (dt, J=15.7, 7.7 Hz, 2H), 6.64 (d, J=6.8 Hz, 1H), 5.07 (ddt, J=8.4, 5.9, 3.2 Hz, 1H), 4.28-3.88 (m, 5H), 3.37 (t, J=6.4 Hz, 2H), 2.69-2.42 (m, 1H), 2.25 (tt, J=13.4, 5.8 Hz, 1H), 1.92-1.61 (m, 5H), 1.36-0.94 (m, 5H). [M+H]⁺ 361.

Example 120: Preparation of 4-Chloro-1-(tetrahydro-furan-3-yl)-1H-indole-3-carboxylic acid (3-trifluoromethyl-cyclohexylmethyl)-amide (112)

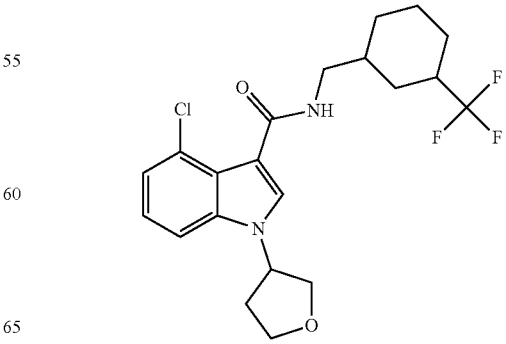

The title compound was synthesized according to the procedure described in Example 5 using 4-Chloro-1-(tetrahydro-furan-3-yl)-1H-indole-3-carboxylic acid (75.00 mg; 0.28 mmol; 1.00 eq.), HATU (214.67 mg; 0.56 mmol; 2.00 eq.), [3-(trifluoromethyl)cyclohexyl]methanamine (53.71 mg; 0.30 mmol; 1.05 eq.) and n,n-diisopropylethylamine (DIPEA) (0.19 ml; 1.13 mmol; 4.00 eq.) in DMF (2.88 ml; 37.30 mmol; 132.13 eq) to afford the desired product 4-Chloro-1-(tetrahydro-furan-3-yl)-1H-indole-3-carboxylic acid (3-trifluoromethyl-cyclohexylmethyl)-amide (75.00 mg; 0.17 mmol)). [M+H]$^+$ 429.2; LC-MS (254 nm) $t_R$=4.39 min; HPLC (254 nm) Purity: 97.53%; $t_R$=97.53 min.

Example 121: Preparation of 4-Chloro-1-(tetrahydro-furan-3-yl)-1H-indole-3-carboxylic acid (1-cyclohexyl-3-hydroxy-propyl)-amide (110)

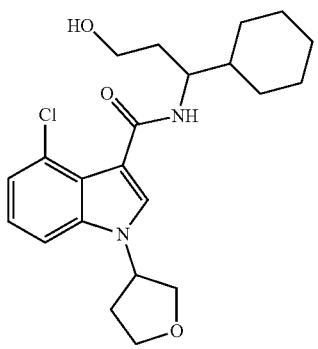 [SMILES: O=C(NC(CCO)C1CCCCC1)c1cn(C2CCOC2)c2cccc(Cl)c12]

The title compound was synthesized according to the procedure described in Example 5 using a mixture of 4-Chloro-1-(tetrahydro-furan-3-yl)-1H-indole-3-carboxylic acid (75.00 mg; 0.28 mmol; 1.00 eq.) and 3-amino-3-cyclohexyl-propan-1-ol (46.61 mg; 0.30 mmol; 1.05 eq.) to afford the desired product 4-Chloro-1-(tetrahydro-furan-3-yl)-1H-indole-3-carboxylic acid (1-cyclohexyl-3-hydroxy-propyl)-amide (19.0 mg; 0.05 mmol). [M+H]$^+$ 405.3 LC-MS (254 nm) $t_R$=3.92 min; HPLC (254 nm) Purity: >99%; $t_R$=4.31 min.

Example 122: Preparation of 4-Chloro-1-(tetrahydro-furan-3-yl)-1H-indole-3-carboxylic acid (2-cyclohexyl-2-dimethylamino-ethyl)-amide (111)

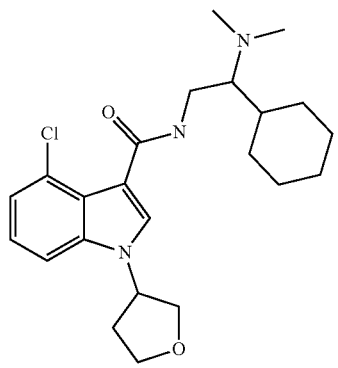 [SMILES: CN(C)C(CNC(=O)c1cn(C2CCOC2)c2cccc(Cl)c12)C1CCCCC1]

The title compound was synthesized according to the procedure described in Example 5 using a mixture of 4-Chloro-1-(tetrahydro-furan-3-yl)-1H-indole-3-carboxylic acid 3 (75.00 mg; 0.28 mmol; 1.00 eq.) and n-(2-amino-1-cyclohexylethyl)-n,n-dimethylamine (50.47 mg; 0.30 mmol; 1.05 eq.) to afford the desired product 4-Chloro-1-(tetrahydro-furan-3-yl)-1H-indole-3-carboxylic acid (2-cyclohexyl-2-dimethylamino-ethyl)-amide (51 mg; 0.12 mmol). [M+H]$^+$ 418.1 LC-MS (254 nm) $t_R$=2.97 min; HPLC (254 nm) Purity: 96.30%; $t_R$=3.37 min.

Example 123: Preparation of 4-Chloro-1-(tetrahydro-furan-3-yl)-1H-indole-3-carboxylic acid ((1R, 4S)-1-bicyclo[2.2.1]hept-2-yl-ethyl)-amide (109)

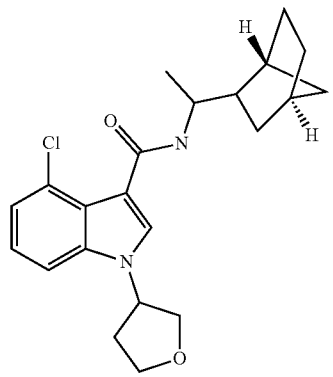 [SMILES: CC(NC(=O)c1cn(C2CCOC2)c2cccc(Cl)c12)C1C[C@H]2CC[C@@H]1C2]

The title compound was synthesized according to the procedure described in Example 5 using a mixture of 4-Chloro-1-(tetrahydro-furan-3-yl)-1H-indole-3-carboxylic acid (75.00 mg; 0.28 mmol; 1.00 eq.) and 1-bicyclo[2.2.1]hept-2-yl-ethylamine hydrochloride (52.08 mg; 0.30 mmol; 1.05 eq.) to afford the desired product 4-Chloro-1-(tetrahydro-furan-3-yl)-1H-indole-3-carboxylic acid ((1R,4S)-1-bicyclo[2.2.1]hept-2-yl-ethyl)-amide (52.0 mg; 0.13 mmol). [M+H]$^+$ 387.1 LC-MS (254 nm) $t_R$=5.56 min; HPLC (254 nm) Purity: >99%; $t_R$=5.10 min.

Example 124: Preparation of 4-Chloro-1-(tetrahydro-furan-3-yl)-1H-indole-3-carboxylic acid (2-cyclopentyl-ethyl)-amide (108)

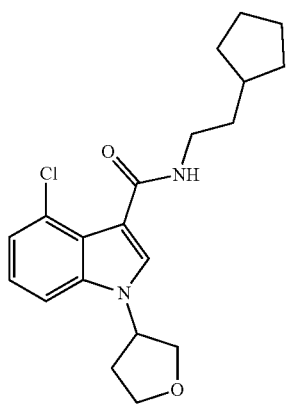 [SMILES: O=C(NCCC1CCCC1)c1cn(C2CCOC2)c2cccc(Cl)c12]

The title compound was synthesized according to the procedure described in Example 5 using a mixture of 4-Chloro-1-(tetrahydro-furan-3-yl)-1H-indole-3-carboxylic acid 3 (75.00 mg; 0.28 mmol; 1.00 eq.) and 2-Cyclopentyl-ethylamine hydrochloride (46.47 mg; 0.31 mmol; 1.10 eq.) to afford the desired product 4-Chloro-1-(tetrahydro-furan-3-yl)-1H-indole-3-carboxylic acid (2-cyclopentyl-ethyl)-amide (40.0 mg; 0.11 mmol). [M+H]$^+$ 361.1 LC-MS (254 nm) $t_R$=4.39 min; HPLC (254 nm) Purity: >99%; $t_R$=4.06 min.

Example 125: Preparation of 4-Chloro-1-(tetra-hydro-furan-3-yl)-1H-indole-3-carboxylic acid (1-hydroxy-3,3-dimethyl-cyclohexylmethyl)-amide (107)

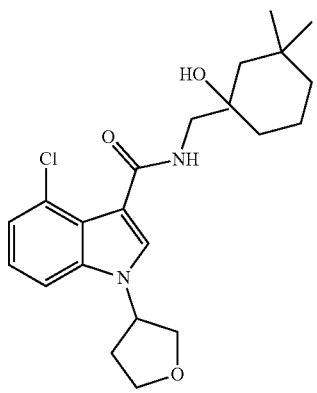

The title compound was synthesized according to the procedure described in Example 5 using a mixture of 4-Chloro-1-(tetrahydro-furan-3-yl)-1H-indole-3-carboxylic acid 3 (75.00 mg; 0.28 mmol; 1.00 eq.) and 1-Aminomethyl-3,3-dimethyl-cyclohexanol hydrochloride (65.62 mg; 0.34 mmol; 1.20 eq.) to afford the desired product 4-Chloro-1-(tetrahydro-furan-3-yl)-1H-indole-3-carboxylic acid (1-hydroxy-3,3-dimethyl-cyclohexylmethyl)-amide (51.0 mg; 0.13 mmol). [M+H]$^+$ 405.2 LC-MS (254 nm) $t_R$=4.10 min; HPLC (254 nm) Purity: 97.80%; $t_R$=4.50 min.

Example 126: Preparation of 4-Chloro-1-(tetra-hydro-furan-3-yl)-1H-indole-3-carboxylic acid (4,4-difluoro-1-hydroxy-3-methyl-cyclohexylmethyl)-amide (106)

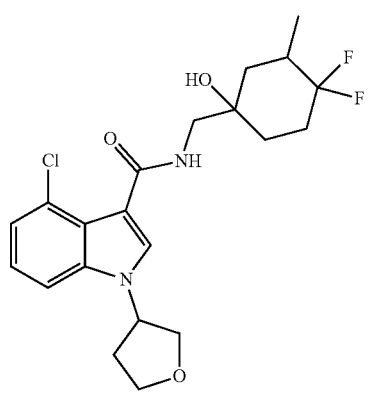 [SMILES: CC1CC(O)(CNC(=O)c2cn(C3CCOC3)c3cccc(Cl)c23)CCC1(F)F]

The title compound was synthesized according to the procedure described in Example 5 using a mixture of 4-Chloro-1-(tetrahydro-furan-3-yl)-1H-indole-3-carboxylic acid (75.00 mg; 0.28 mmol; 1.00 eq.) and 1-Aminomethyl-3,3-dimethyl-cyclohexanol hydrochloride (65.62 mg; 0.34 mmol; 1.20 eq.) to afford the desired product 4-Chloro-1-(tetrahydro-furan-3-yl)-1H-indole-3-carboxylic acid (4,4-difluoro-1-hydroxy-3-methyl-cyclohexylmethyl)-amide (58.0 mg; 0.14 mmol). [M+H]$^+$ 427.1 LC-MS (254 nm) $t_R$=3.72 min; HPLC (254 nm) Purity: 97.07%; $t_R$=4.09 min.

Example 127: Preparation of 4-Chloro-1-(tetra-hydro-furan-3-yl)-1H-indole-3-carboxylic acid (4,4-difluoro-1-hydroxy-cyclohexylmethyl)-amide (104)

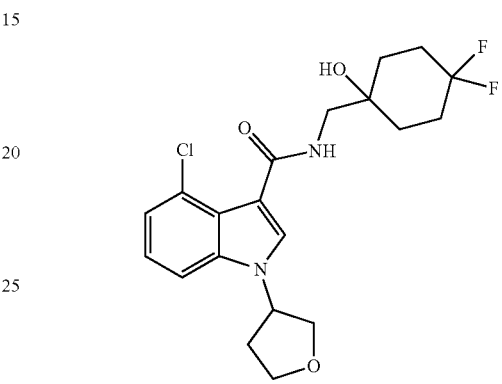

The title compound was synthesized according to the procedure described in Example 5 using a mixture of 4-Chloro-1-(tetrahydro-furan-3-yl)-1H-indole-3-carboxylic acid 3 (75.00 mg; 0.28 mmol; 1.00 eq.) and 1-Aminomethyl-4,4-difluoro-cyclohexanol hydrochloride (68.30 mg; 0.34 mmol; 1.20 eq.) to afford the desired product 4-Chloro-1-(tetrahydro-furan-3-yl)-1H-indole-3-carboxylic acid (4,4-difluoro-1-hydroxy-cyclohexylmethyl)-amide (45.0 mg; 0.11 mmol). [M+H]$^+$ 413.1 LC-MS (254 nm) $t_R$=3.54 min; HPLC (254 nm) Purity: 96.35%; $t_R$=3.82 min.

Example 128: Preparation of 4-Chloro-1-(tetra-hydro-furan-3-yl)-1H-indole-3-carboxylic acid ((1S, 4R)-1-bicyclo[2.2.1]hept-2-ylmethyl)-amide (105)

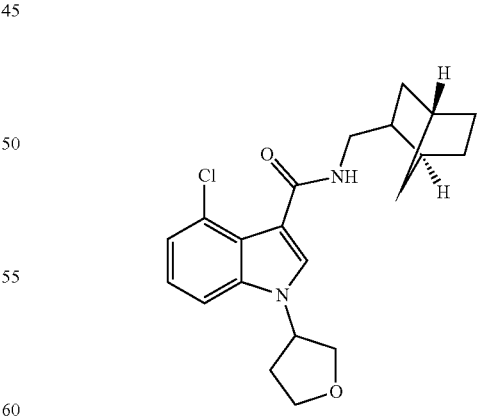

The title compound was synthesized according to the procedure described in Example 5 using a mixture of 4-Chloro-1-(tetrahydro-furan-3-yl)-1H-indole-3-carboxylic acid 3 (75.00 mg; 0.28 mmol; 1.00 eq.) and c-bicyclo[2.2.1]hept-2-yl-methylamine hydrobromide (69.82 mg; 0.34 mmol; 1.20 eq.) to afford the desired product 4-Chloro-1-

(tetrahydro-furan-3-yl)-1H-indole-3-carboxylic acid ((1S, 4R)-1-bicyclo[2.2.1]hept-2-ylmethyl)-amide (62.0 mg; 0.17 mmol). [M+H]⁺ 373.1 LC-MS (254 nm) $t_R$=4.43 min; HPLC (254 nm) Purity: 98.79%; $t_R$=4.88 min.

Example 129: Preparation of 4-Chloro-1-(tetrahydro-furan-3-yl)-1H-indole-3-carboxylic acid (2-cyclopentyl-2-methyl-propyl)-amide (103)

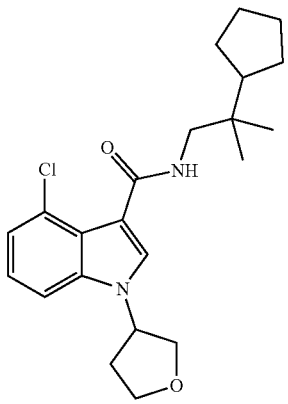 [SMILES: CC(C)(CNC(=O)c1cn(C2CCOC2)c2cccc(Cl)c12)C1CCCC1]

The title compound was synthesized according to the procedure described in Example 5 using a mixture of 4-Chloro-1-(tetrahydro-furan-3-yl)-1H-indole-3-carboxylic acid 3 (75.00 mg; 0.28 mmol; 1.00 eq.) and 2-cyclopentyl-2-methylpropan-1-amine (39.87 mg; 0.28 mmol; 1.00 eq.) to afford the desired product 4-Chloro-1-(tetrahydro-furan-3-yl)-1H-indole-3-carboxylic acid (2-cyclopentyl-2-methyl-propyl)-amide (67.1 mg; 0.17 mmol). [M+H]⁺ 389.2 LC-MS (254 nm) $t_R$=4.87 min; HPLC (254 nm) Purity: >99%; $t_R$=5.41 min.

Example 130: Preparation of 4-Chloro-1-(tetrahydro-furan-3-yl)-1H-indole-3-carboxylic acid (2-cyclopentyl-2-hydroxy-propyl)-amide (102)

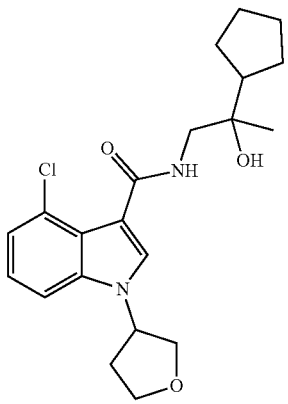 [SMILES: CC(O)(CNC(=O)c1cn(C2CCOC2)c2cccc(Cl)c12)C1CCCC1]

The title compound was synthesized according to the procedure described in Example 5 using a mixture of 4-Chloro-1-(tetrahydro-furan-3-yl)-1H-indole-3-carboxylic acid 3 (75.00 mg; 0.28 mmol; 1.00 eq.) and 1-amino-2-cyclopentylpropan-2-ol (40.43 mg; 0.28 mmol; 1.00 eq.) to afford the desired product 4-Chloro-1-(tetrahydro-furan-3-yl)-1H-indole-3-carboxylic acid (2-cyclopentyl-2-hydroxy-propyl)-amide (48.0 mg; 0.12 mmol). [M+H]⁺ 391.1 LC-MS (254 nm) $t_R$=3.81 min; HPLC (254 nm) Purity: >99%; $t_R$=4.10 min.

Example 131: Preparation of 4-chloro-N-((4,4-difluorocyclohexyl)methyl)-1-(tetrahydrofuran-3-yl)-1H-indole-3-carboxamide (114)

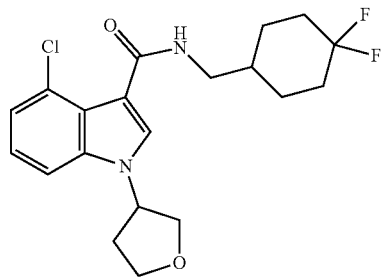 [SMILES: O=C(NCC1CCC(F)(F)CC1)c1cn(C2CCOC2)c2cccc(Cl)c12]

The title compound was synthesized according to the procedure described in Example 33 using tetrahydrofuran-3-ol (0.055 g, 0.62 mmol), 4-chloro-N-((4,4-difluorocyclohexyl)methyl)-1H-indole-3-carboxamide (0.100 g, 0.31 mmol) and cyanomethylenetributylphosphorane (0.296 g, 1.24 mmol) to afford 4-chloro-N-((4,4-difluorocyclohexyl)methyl)-1-(tetrahydrofuran-3-yl)-1H-indole-3-carboxamide (0.045 g, 30%) as white solid.
¹H NMR (500 MHz, DMSO-d₆) δ 8.14 (s, 1H), 7.72 (s, 1H), 7.62 (d, J=7.0 Hz, 1H), 7.21-7.17 (m, 2H), 5.30 (s, 1H), 4.10 (d, J=6.0 Hz, 1H), 3.98-3.95 (m, 2H), 3.84 (d, J=6.0 Hz, 1H), 3.16 (brs, 2H), 2.14 (brs, 1H), 2.03 (brs, 2H), 1.83-1.70 (m, 5H), 1.26-1.24 (m, 2H) ppm; [M+H]⁺ 397.1

Example 132: Preparation of 4-chloro-N-(((1R,3R)-1-hydroxy-3-methyl cyclohexyl)methyl)-1-(tetrahydrofuran-3-yl)-1H-indole-3-carboxamide (113)

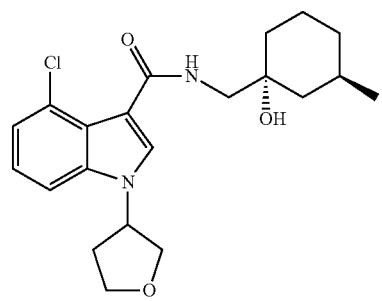 [SMILES: C[C@@H]1CCC[C@](O)(CNC(=O)c2cn(C3CCOC3)c3cccc(Cl)c23)C1]

The title compound was synthesized according to the procedure described in Example 2 using 4-Chloro-1-(tetrahydro-furan-3-yl)-1H-indole-3-carboxylic acid (150.00 mg; 0.56 mmol; 1.00 eq.), (1R,3R)-1-Aminomethyl-3-methylcyclohexanol (92.99 mg; 0.65 mmol; 1.15 eq.), EDCI (140.70 mg; 0.73 mmol; 1.30 eq.), Benzotriazol-1-ol (99.17 mg; 0.73 mmol; 1.30 eq.) and Ethyl-diisopropyl-amine (0.28 ml; 1.69 mmol; 3.00 eq.) in N,N-Dimethyl-formamide (3.00 ml) to obtain 4-chloro-N-(((1R,3R)-1-hydroxy-3-methycyclohexyl)methyl)-1-(tetrahydrofuran-3-yl)-1H-indole-3-carboxamide (167 mg, 76%).

$^1$H NMR (400 MHz, Chloroform-d) δ 8.03 (s, 1H), 7.40 (d, J=7.9 Hz, 1H), 7.24 (dt, J=15.6, 7.6 Hz, 2H), 5.08 (ddt, J=8.7, 6.0, 3.0 Hz, 1H), 4.30-3.91 (m, 4H), 3.57-3.42 (m, 2H), 2.69-2.47 (m, 4H), 2.33-2.15 (m, 1H), 1.89-1.58 (m, 6H), 0.92 (d, J=6.2 Hz, 4H). [M+H]$^+$ 391.

Example 133: Preparation of 4-chloro-N-((1-hydroxy-3-(trifluoromethyl) cyclohexyl)methyl)-1-(tetrahydrofuran-3-yl)-1H-indole-3-carboxamide (100)

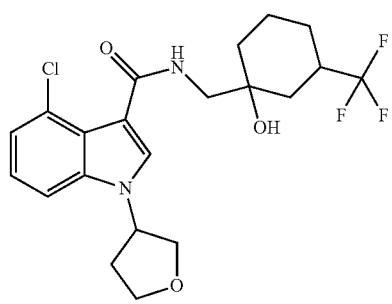 [SMILES: O=C(NCC1(O)CCCC(C(F)(F)F)C1)c1cn(C2CCOC2)c2cccc(Cl)c12]

The title compound was synthesized according to the procedure described in Example 2 using 4-Chloro-1-(tetrahydro-furan-3-yl)-1H-indole-3-carboxylic acid (200.00 mg; 0.75 mmol; 1.00 eq.), 1-Aminomethyl-3-trifluoromethyl-cyclohexanol hydrochloride (202.27 mg; 0.87 mmol; 1.15 eq.), EDC (187.59 mg; 0.98 mmol; 1.30 eq.), Benzotriazol-1-ol (132.23 mg; 0.98 mmol; 1.30 eq.) and Ethyl-diisopropyl-amine (0.37 ml; 2.26 mmol; 3.00 eq.) in N,N-Dimethyl-formamide (3.00 ml) to obtain 4-chloro-N-((1-hydroxy-3-(trifluoromethyl)cyclohexyl)methyl)-1-(tetrahydrofuran-3-yl)-1H-indole-3-carboxamide (40 mg, 13%).

1H NMR (400 MHz, Chloroform-d) δ 7.85 (d, J=9.1 Hz, 1H), 7.40-7.06 (m, 4H), 5.13-4.91 (m, 1H), 4.09 (m, 4H), 3.91 (m, 5.5 Hz, 1H), 3.75-3.30 (m, 2H), 2.66-2.44 (m, 1H), 2.42-1.70 (m, 6H), 1.58-1.09 (m, 4H). [M+H]$^+$ 445.

Example 134: Preparation of 4-chloro-N-((4,4-difluorocyclohexyl)methyl)-1-((tetrahydrofuran-2-yl)methyl)-1H-indole-3-carboxamide (144)

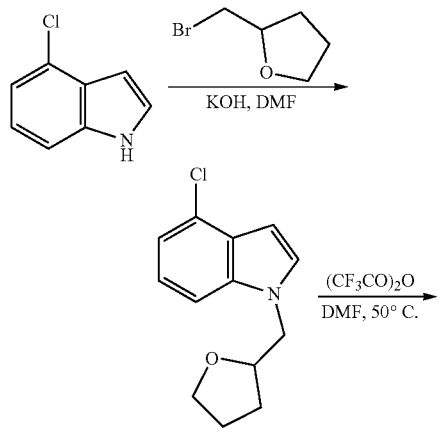

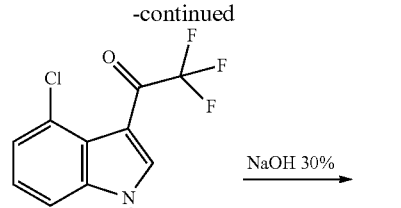

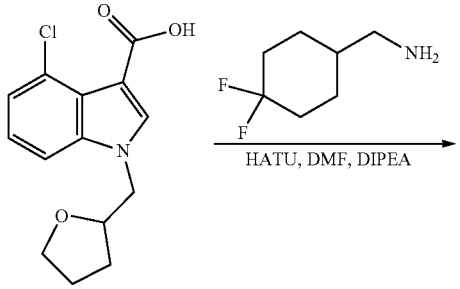

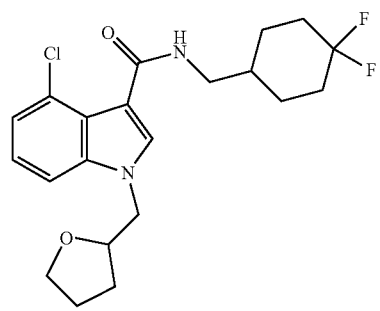

Step 1: Preparation of 4-chloro-1-((tetrahydrofuran-2-yl)methyl)-1H-indole

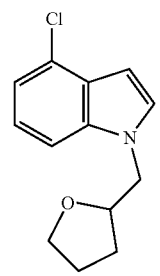 [SMILES: Clc1cccc2c1ccn2CC1CCCO1]

To a stirred solution of 4-chloro-1H-indole (0.500 g, 3.29 mmol) and 2-(bromomethyl)-tetrahydrofuran (0.816 g, 4.94 mmol) in DMF (6 mL) was added KOH (0.739 g, 13.16 mmol) at room temperature. The mixture was heated to 40° C. and stirred for 2.5 h. The mixture was diluted with EtOAc (100 mL) and washed with water (3×30 mL) and dried (Na$_2$SO$_4$) and concentrated in vacuo to give 4-chloro-1-((tetrahydrofuran-2-yl)methyl)-1H-indole (1.17 g, 94%), which was used for the next step without further purification.

Step 2: Preparation of 1-(4-chloro-1-((tetrahydrofuran-2-yl)methyl)-1H-indol-3-yl)-2,2,2-trifluoroethanone

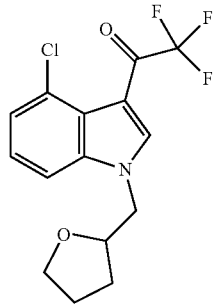 [SMILES: O=C(c1cn(CC2CCCO2)c2cccc(Cl)c12)C(F)(F)F]

To a stirred solution of 4-chloro-1-((tetrahydrofuran-2-yl)methyl)-1H-indole (1.17 g, 4.78 mmol) in DMF (8.0 mL) was added 2,2,2-trifluoroacetic anhydride (4.01 g, 19.12 mmol) at room temperature. After being was stirred at 50° C. for 1 h, the reaction mixture was diluted with EtOAc (100 mL), washed with water (3×30 mL), dried over $Na_2SO_4$) and concentrated in vacuo to give 1-(4-chloro-1-((tetrahydrofuran-2-yl)methyl)-1H-indol-3-yl)-2,2,2-trifluoroethanone (1.5 g, 94%), which was used for the next step without further purification.

Step 3: Preparation of 4-chloro-1-((tetrahydrofuran-2-yl)methyl)-1H-indole-3-carboxylic acid

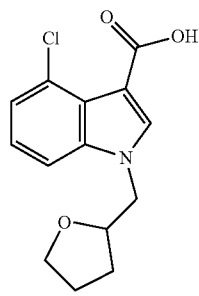 [SMILES: O=C(O)c1cn(CC2CCCO2)c2cccc(Cl)c12]

To a solution of 1-(4-chloro-1-((tetrahydrofuran-2-yl)methyl)-1H-indol-3-yl)-2,2,2-trifluoro ethanone (1.5 g, 4.52 mmol) in water (4.2 mL) was added NaOH (1.81 g, 45.2 mmol). After being stirred at 100° C. for 0.5 h, the reaction mixture was acidified to pH 2 with 1M HCl. The formed precipitate was collected by filtration, washed with water and dried to give 4-chloro-1-((tetrahydrofuran-2-yl)methyl)-1H-indole-3-carboxylic acid (0.700 g, 55.5%) as a white solid.

Step 4: Preparation of 4-chloro-N-((4,4-difluorocyclohexyl)methyl)-1-((tetrahydrofuran-2-yl) methyl)-1H-indole-3-carboxamide

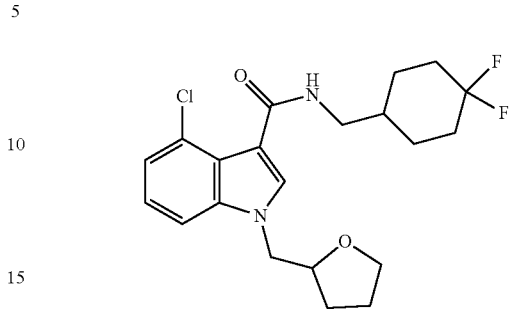

To a solution of 4-chloro-1-((tetrahydrofuran-2-yl)methyl)-1H-indole-3-carboxylic acid (0.200 g, 0.717 mmol) in DMF (2 ml) was added (4,4-difluorocyclohexyl)methanamine (0.117 g, 0.788 mmol), HATU (0.327 g, 0.86 mmol), TEA (0.217 mg, 2.15 mmol) at room temperature. After being was stirred at room temperature for 2 h, the reaction was quenched with water and extracted with DCM/MeOH (10/1, 20 mL×3). The combined extracts were dried over $Na_2SO_4$, filtered and concentrated in vacuum. The residue was purified by pre-HPLC to afford 4-chloro-N-((4,4-difluorocyclohexyl)methyl)-1-((tetrahydrofuran-2-yl)methyl)-1H-indole-3-carboxamide (0.104 g, 35.3%).

$^1$H NMR (500 MHz, DMSO-$d_6$) δ 8.11 (t, J=5.5 Hz, 1H), 7.70 (s, 1H), 7.57 (d, J=7.5 Hz, 1H), 7.18-7.12 (m, 2H), 4.33-4.30 (m, 1H), 4.22-4.13 (m, 2H), 3.76-3.73 (m, 1H), 3.64-3.60 (m, 1H), 3.16-3.14 (m, 2H), 2.03-1.94 (m, 3H), 1.85-1.69 (m, 7H), 1.57-1.53 (m, 1H), 1.26-1.23 (m, 2H) ppm; [M+H]$^+$ 411.1.

Example 135: (S)-4-chloro-N-((4,4-difluorocyclohexyl)methyl)-1-((tetrahydrofuran-2-yl)methyl)-1H-indole-3-carboxamide (132)

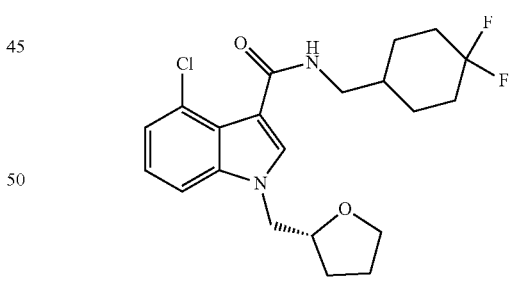

The title compound was separated from 4-chloro-N-((4,4-difluorocyclohexyl) methyl)-1-((tetrahydrofuran-2-yl)methyl)-1H-indole-3-carboxamide by Chiral HPLC. Chiral-HPLC conditions: Co-Solvent: 35% MeOH; Column: OZ-H (4.6*250 mm, 5 um) $CO_2$ Flow Rate: 1.95 mL/min; Co-Solvent Flow Rate: 1.05 mL/min; Total Flow: 3 mL/min.

$^1$H NMR (500 MHz, DMSO-$d_6$) δ 8.09 (t, J=5.5 Hz, 1H), 7.70 (s, 1H), 7.56 (d, J=8.5 Hz, 1H), 7.16 (t, J=8.0 Hz, 1H), 7.12 (d, J=7.5 Hz, 1H), 4.33-4.29 (m, 1H), 4.21-4.11 (m, 2H), 3.74 (q, J=7.0 Hz, 1H), 3.61 (q, J=7.0 Hz, 1H), 3.14 (t, J=6.0 Hz, 2H), 2.03-1.92 (m, 3H), 1.83-1.65 (m, 7H), 1.58-1.51 (m, 1H), 1.28-1.20 (m, 2H) ppm; [M+H]$^+$ 411.1.

Example 136: (R)-4-chloro-N-((4,4-difluorocyclohexyl)methyl)-1-((tetrahydrofuran-2-yl)methyl)-1H-indole-3-carboxamide (135)

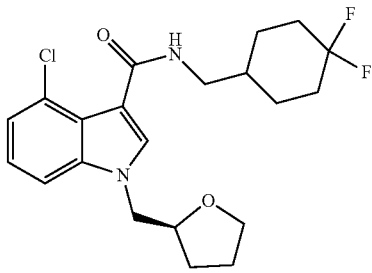 [SMILES: O=C(NCC1CCC(F)(F)CC1)c1cn(C[C@@H]2CCCO2)c2cccc(Cl)c12]

The title compound was separated from 4-chloro-N-((4,4-difluorocyclohexyl) methyl)-1-((tetrahydrofuran-2-yl)methyl)-1H-indole-3-carboxamide by Chiral HPLC.

$^1$H NMR (500 MHz, DMSO-d$_6$) δ 8.09 (t, J=5.5 Hz, 1H), 7.69 (s, 1H), 7.56 (d, J=8.5 Hz, 1H), 7.16 (t, J=8.0 Hz, 1H), 7.12 (d, J=7.0 Hz, 1H), 4.33-4.29 (m, 1H), 4.21-4.11 (m, 2H), 3.74 (q, J=7.5 Hz, 1H), 3.61 (q, J=7.5 Hz, 1H), 3.14 (t, J=6.0 Hz, 2H), 2.05-1.92 (m, 3H), 1.84-1.69 (m, 7H), 1.58-1.51 (m, 1H), 1.28-1.18 (m, 2H) ppm; [M+H]$^+$ 411.1; LC-MS Purity (254 nm): >99%; t$_R$=4.44 min; HPLC Purity (254 nm): >99%; t$_R$=4.74 min; Chiral-HPLC Purity (254 nm): >99%; t$_R$=4.67 min.

Example 137: Preparation of 4-chloro-N-((4,4-difluoro-1-hydroxycyclohexyl)methyl)-1-((tetrahydrofuran-2-yl)methyl)-1H-indole-3-carboxamide (142)

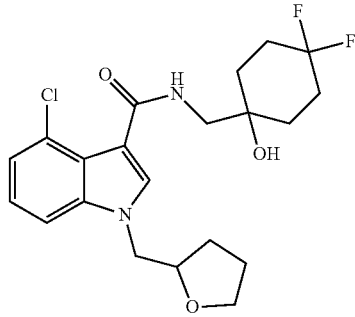 [SMILES: O=C(NCC1(O)CCC(F)(F)CC1)c1cn(CC2CCCO2)c2cccc(Cl)c12]

The title compound was synthesized according to the procedure described in Example 2 using 4-chloro-1-((tetrahydrofuran-2-yl)methyl)-1H-indole-3-carboxylic acid (0.279 g, 1 mmol), HOBt (0.202 g, 1.5 mmol), EDCI (0.382 g, 2 mmol), TEA (0.404 g, 4 mmol) and 1-(aminomethyl)-4,4-difluorocyclohexanol hydrochloride (0.230 g, 1.2 mmol) to give 4-chloro-N-((4,4-difluoro-1-hydroxycyclohexyl)methyl)-1-((tetrahydrofuran-2-yl)methyl)-1H-indole-3-carboxamide (0.320 g, 75%) as a light yellow solid.

(S)-4-chloro-N-((4,4-difluoro-1-hydroxycyclohexyl)methyl)-1-((tetrahydrofuran-2-yl)methyl)-1H-indole-3-carboxamide (0.120 g) and (R)-4-chloro-N-((4,4-di-fluoro-1-hydroxycyclohexyl)methyl)-1-((tetrahydrofuran-2-yl)methyl)-1H-indole-3-carboxamide (0.140 g) were obtained from 4-chloro-N-((4,4-difluoro-1-hydroxycyclohexyl)methyl)-1-((tetrahydrofuran-2-yl)methyl)-1H-indole-3-carboxamide by Chiral HPLC.

Chiral-HPLC conditions: Co-Solvent: 30% MeOH; Column: AD-H (4.6*250 mm, 5 um)

CO$_2$ Flow Rate: 2.1 mL/min; Co-Solvent Flow Rate: 0.9 mL/min; Total Flow: 3 mL/min; Runtime: 9 min.

Example 138: (S)-4-chloro-N-((4,4-difluoro-1-hydroxycyclohexyl)methyl)-1-((tetra hydrofuran-2-yl)methyl)-1H-indole-3-carboxamide (134)

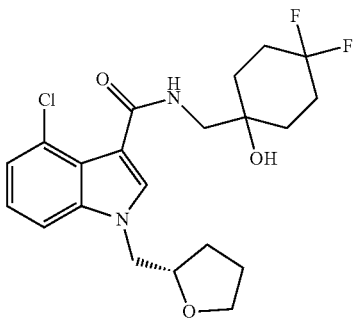 [SMILES: O=C(NCC1(O)CCC(F)(F)CC1)c1cn(C[C@@H]2CCCO2)c2cccc(Cl)c12]

$^1$H NMR (500 MHz, DMSO-d$_6$) δ 7.95 (t, J=6.5 Hz, 1H), 7.78 (s, 1H), 7.58 (d, J=7.0 Hz, 1H), 7.19 (t, J=7.0 Hz, 1H), 7.15 (d, J=7.0 Hz, 1H), 4.75 (s, 1H), 4.35-4.31 (m, 1H), 4.23-4.14 (m, 2H), 3.75 (dd, J=6.5, 14.5 Hz, 1H), 3.62 (d, J=7, 15 Hz, 1H), 3.30 (s, 2H), 2.07-2.03 (m, 1H), 2.01-1.97 (m, 2H), 1.96-1.88 (m, 2H), 1.82-1.76 (m, 2H), 1.65-1.63 (m, 4H), 1.58-1.54 (m, 1H) ppm; [M+H]$^+$ 427.1.

Example 139: (R)-4-chloro-N-((4,4-difluoro-1-hydroxycyclohexyl)methyl)-1-((tetrahydrofuran-2-yl)methyl)-1H-indole-3-carboxamide (MSC2506160) (131)

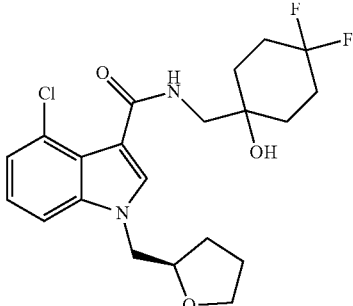

$^1$H NMR (500 MHz, DMSO-d$_6$) δ 7.95 (t, J=6.5 Hz, 1H), 7.78 (s, 1H), 7.58 (d, J=7.0 Hz, 1H), 7.19 (t, J=7.0 Hz, 1H), 7.15 (d, J=7.0 Hz, 1H), 4.75 (s, 1H), 4.35-4.31 (m, 1H), 4.23-4.14 (m, 2H), 3.75 (dd, J=6.5, 14.5 Hz, 1H), 3.62 (d, J=7, 15 Hz, 1H), 3.30 (s, 2H), 2.07-2.03 (m, 1H), 2.01-1.97 (m, 2H), 1.96-1.88 (m, 2H), 1.82-1.76 (m, 2H), 1.65-1.63 (m, 4H), 1.58-1.54 (m, 1H) ppm; [M+H]$^+$ 427.1.

Example 140: 4-chloro-N-((3,3-difluoro-1-hydroxy-cyclohexyl)methyl)-1-((tetrahydrofuran-2-yl)methyl)-1H-indole-3-carboxamide (139)

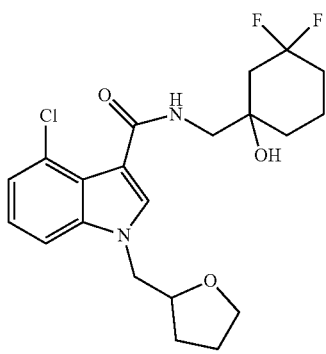 [SMILES: O=C(NCC1(O)CCCC(F)(F)C1)c1cn(CC2CCCO2)c2cccc(Cl)c12]

The title compound was synthesized according to the procedure described in Example 2 using 4-Chloro-1-(tetrahydro-furan-2-ylmethyl)-1H-indole-3-carboxylic acid (150.00 mg; 0.54 mmol; 1.00 eq.), EDC (EDC) (123.36 mg; 0.64 mmol; 1.20 eq.), Triethyl-amine (0.15 ml; 1.07 mmol; 2.00 eq.) and 1-Aminomethyl-3,3-difluoro-cyclohexanol (97.44 mg; 0.59 mmol; 1.10 eq.) to obtain 4-chloro-N-((3,3-difluoro-1-hydroxycyclohexyl)methyl)-1-((tetrahydrofuran-2-yl)methyl)-1H-indole-3-carboxamide (43 mg, 19%).

$^1$H NMR (400 MHz, Methanol-d4) δ 7.83-7.74 (m, 1H), 7.59-7.44 (m, 1H), 7.21 (t, J=5.0 Hz, 2H), 4.49-4.09 (m, 3H), 3.92-3.67 (m, 3H), 3.50 (dd, J=85.1, 13.8 Hz, 2H), 2.20-1.51 (m, 12H), [M+H]$^+$ 427.

Example 141: 4-chloro-N—(((S)-3,3-difluoro-1-hydroxycyclohexyl)methyl)-1-(((S)-tetrahydrofuran-2-yl)methyl)-1H-indole-3-carboxamide (130)

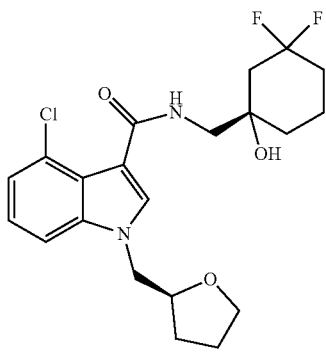 [SMILES: O=C(NC[C@]1(O)CCCC(F)(F)C1)c1cn(C[C@@H]2CCCO2)c2cccc(Cl)c12]

The title compound was separated from 50 mg of the racemic compound 4-chloro-N-((3,3-difluoro-1-hydroxycyclohexyl)methyl)-1-((tetrahydrofuran-2-yl)methyl)-1H-indole-3-carboxamide to obtain 8 mg of the title compound. [M+H]$^+$ 427. Co-Solvent: 30% MeOH; Column: AD-H (4.6*250 mm, 5 um); $CO_2$ Flow Rate: 2.1 mL/min; Co-Solvent Flow Rate: 0.9 mL/min; Total Flow: 3 mL/min; Runtime: 9 min.

Example 142: 4-chloro-N—(((R)-3,3-difluoro-1-hydroxycyclohexyl)methyl)-1-(((S)-tetrahydrofuran-2-yl)methyl)-1H-indole-3-carboxamide (96)

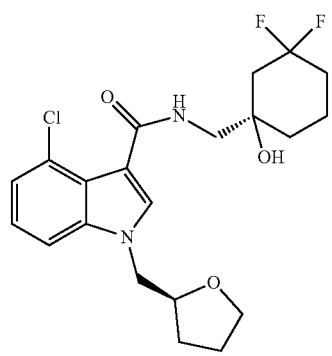 [SMILES: O=C(NC[C@@]1(O)CCCC(F)(F)C1)c1cn(C[C@@H]2CCCO2)c2cccc(Cl)c12]

The title compound was separated from 50 mg of the racemic compound 4-chloro-N-((3,3-difluoro-1-hydroxycyclohexyl)methyl)-1-((tetrahydrofuran-2-yl)methyl)-1H-indole-3-carboxamide to obtain 4 mg of the title compound. [M+H]$^+$ 427. (Separation: See example 141).

Example 143: 4-chloro-N-((3,3-difluoro-1-hydroxycyclohexyl)methyl)-1-(((R)-tetrahydrofuran-2-yl)methyl)-1H-indole-3-carboxamide (133)

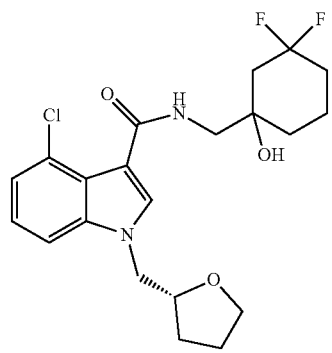 [SMILES: O=C(NCC1(O)CCCC(F)(F)C1)c1cn(C[C@H]2CCCO2)c2cccc(Cl)c12]

The title compound was separated from 50 mg of the racemic compound 4-chloro-N-((3,3-difluoro-1-hydroxycyclohexyl)methyl)-1-((tetrahydrofuran-2-yl)methyl)-1H-indole-3-carboxamide to obtain 7 mg of the title compound. [M+H]$^+$ 427. (Separation: see Example 141).

Example 144: Preparations of 4-chloro-N-(((1R,3R)-1-hydroxy-3-methylcyclohexyl) methyl)-1-((tetrahydrofuran-2-yl)methyl)-1H-indole-3-carboxamide (143)

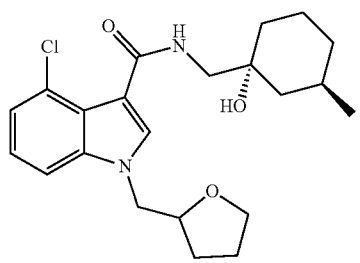 [SMILES: C[C@@H]1CCC[C@](O)(CNC(=O)c2cn(CC3CCCO3)c3cccc(Cl)c23)C1]

The title compound was synthesized according to the procedure described in Example 2 using 4-chloro-1-((tetrahydrofuran-2-yl)methyl)-1H-indole-3-carboxylic acid (0.07 g, 0.25 mmol), (1R,3R)-1-(aminomethyl)-3-methylcyclohexanol (0.045 g, 0.25 mmol), HOBt (0.044 g, 0.30 mmol), EDCI (0.058 g, 0.30 mmol) and triethylamine (0.076 g, 0.75 mmol) in acetonitrile (20 mL) to afford 4-chloro-N-(((1R,3R)-1-hydroxy-3-methylcyclohexyl)methyl)-1-((tetrahydrofuran-2-yl)methyl)-1H-indole-3-carboxamide (0.060 g, 50%) as a white solid.

$^1$HNMR (400 MHz, DMSO-d$_6$,) δ 7.78-7.76 (t, J=4.8 Hz, 2H), 7.58 (d, J=6.4 Hz, 1H), 7.19-7.14 (m, 2H), 4.35-4.32 (m, 1H), 4.27 (s, 1H), 4.24-4.13 (m, 2H), 3.78-3.74 (m, 1H), 3.65-3.60 (m, 1H), 3.21 (d, J=4.8 Hz, 2H), 3.21-3.18 (m, 1H), 2.00-1.94 (m, 1H), 1.82-1.76 (m, 2H), 1.73-1.68 (m, 1H), 1.64-1.52 (m, 5H), 1.47-1.45 (m, 1H), 1.25-1.19 (m, 1H), 0.98-0.93 (t, J=10.2 Hz, 1H), 0.83 (d, J=5.6 Hz, 3H), 0.78-0.72 (m, 1H) ppm; [M+H]$^+$ 405.1.

Example 145: Preparation of 4-chloro-N-(((1S,3S)-1-hydroxy-3-methylcyclohexyl) methyl)-1-((tetrahydrofuran-2-yl)methyl)-1H-indole-3-carboxamide (140)

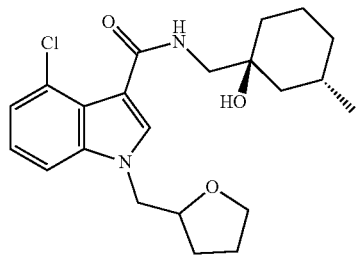 [SMILES: C[C@H]1CCC[C@@](O)(CNC(=O)c2cn(CC3CCCO3)c3cccc(Cl)c23)C1]

The title compound was synthesized according to the procedure described in Example 2 using 4-chloro-1-((tetrahydrofuran-2-yl)methyl)-1H-indole-3-carboxylic acid (0.100 g, 0.358 mmol), EDCI (0.102 g, 0.466 mmol), HOBt (0.0952 mg, 0.466 mmol), TEA (0.15 mL) and (1S,3S)-1-(aminomethyl)-3-methylcyclohexanol (0.0532 g, 0.358 mmol) to obtain 4-chloro-N-(((1S,3S)-1-hydroxy-3-methylcyclohexyl)methyl)-1-((tetrahydrofuran-2-yl)methyl)-1H-indole-3-carboxamide (0.036 g, 21.0%) as a light-yellow solid.

$^1$H NMR (500 MHz, DMSO-d$_6$) δ 7.78 (s, 1H), 7.76 (d, J=6.0 Hz, 1H), 7.58 (d, J=8.5 Hz, 1H), 7.18 (t, J=7.5 Hz, 1H), 7.14 (d, J=7.5 Hz, 1H), 4.33 (m, 1H), 4.27 (s, 1H), 4.23-4.13 (m, 2H), 3.75 (dd, J=7.0, 15.0 Hz, 1H), 3.62 (dd, J=7.0, 15.0 Hz, 1H), 3.30 (s, 1H), 3.21 (d, J=6.0 Hz, 2H), 2.00-1.93 (m, 1H), 1.82-1.76 (m, 2H), 1.60-1.52 (m, 5H), 1.45 (d, J=10.5 Hz, 1H), 1.25-1.19 (m, 1H), 0.95-0.91 (m, 1H), 0.83-0.78 (m, 3H), 0.80-0.74 (m, 1H) ppm; [M+H]$^+$ 405.1.

Example 146: 4-chloro-N-((3,3-difluoro-1-hydroxy-5-methylcyclohexyl)methyl)-1-((tetrahydrofuran-2-yl)methyl)-1H-indole-3-carboxamide (138)

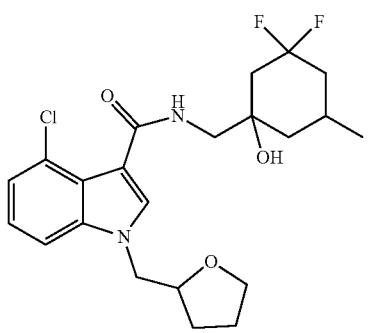 [SMILES: CC1CC(F)(F)CC(O)(CNC(=O)c2cn(CC3CCCO3)c3cccc(Cl)c23)C1]

The title compound was synthesized according to the procedure described in Example 2 using 4-Chloro-1-(tetrahydro-furan-2-ylmethyl)-1H-indole-3-carboxylic acid (500.00 mg; 1.79 mmol; 1.00 eq.), EDC (EDC) (411.20 mg; 2.15 mmol; 1.20 eq.), Triethyl-amine (0.50 ml; 3.58 mmol; 2.00 eq.), Aminomethyl-3,3-difluoro-5-methyl-cyclohexanol (352.37 mg; 1.97 mmol; 1.10 eq.) to provide 4-chloro-N-((3,3-difluoro-1-hydroxy-5-methylcyclohexyl)methyl)-1-((tetrahydrofuran-2-yl)methyl)-1H-indole-3-carboxamide (82, 10%). [M+H]$^+$ 441.

Example 147: Preparation of 4-chloro-N-((3,3-difluoro-5-(trifluoromethyl)cyclo-hexyl)methyl)-1-((tetrahydrofuran-2-yl)methyl)-1H-indole-3-carboxamide (141)

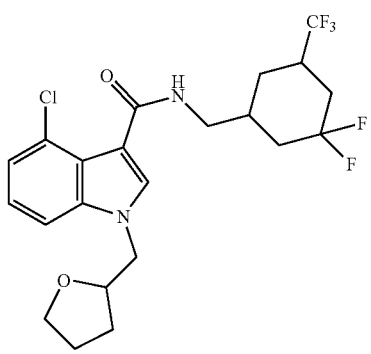 [SMILES: O=C(NCC1CC(C(F)(F)F)CC(F)(F)C1)c1cn(CC2CCCO2)c2cccc(Cl)c12]

The title compound was synthesized according to the procedure described in Example 5 using 4-chloro-1-((tetrahydrofuran-2-yl)methyl)-1H-indole-3-carboxylic acid (0.060 g, 0.214 mmol), (3,3-difluoro-5-(trifluoromethyl)cyclo-hexyl)methanamine (0.0467 g, 0.214 mmol), HATU (0.122 g, 0.322 mmol) and TEA (0.065 g, 0.64 mmol) to afford 4-chloro-N-((3,3-difluoro-5-(trifluoromethyl)cyclohexyl)methyl)-1-((tetrahydrofuran-2-yl)methyl)-1H-indole-3-carboxamide (0.022 g, 21.5%) as a white solid.

¹H NMR (500 MHz, DMSO-d₆) δ 8.20-8.15 (m, 1H), 7.72 (s, 1H), 7.57 (d, J=8.5 Hz, 1H), 7.19-7.13 (m, 2H), 4.36-4.27 (m, 1H), 4.23-4.11 (m, 2H), 3.77-3.68 (m, 1H), 3.64-3.60 (m, 1H), 3.28-3.20 (m, 2H), 2.78-2.64 (m, 1H), 2.33-2.15 (m, 2H), 2.09-1.50 (m, 8H), 1.29-1.09 (m, 1H) ppm; [M+H]⁺ 479.1.

Example 148: 4-chloro-N-((1-hydroxy-3-(trifluoromethyl)cyclohexyl)methyl)-1-((tetrahydrofuran-2-yl)methyl)-1H-indole-3-carboxamide (136)

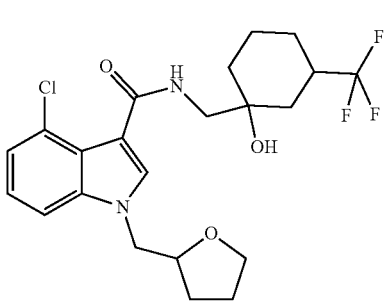 [SMILES: O=C(NCC1(O)CCCC(C(F)(F)F)C1)c1cn(CC2CCCO2)c2cccc(Cl)c12]

The title compound was synthesized according to the procedure described in Example 2 using 4-Chloro-1-(tetrahydro-furan-2-ylmethyl)-1H-indole-3-carboxylic acid (200.00 mg; 0.72 mmol; 1.00 eq.), 1-Aminomethyl-3-trifluoromethyl-cyclohexanol hydrochloride (192.13 mg; 0.82 mmol; 1.15 eq.), EDC (178.19 mg; 0.93 mmol; 1.30 eq.), Benzotriazol-1-ol (125.60 mg; 0.93 mmol; 1.30 eq.) and Ethyl-diisopropyl-amine (0.35 ml; 2.15 mmol; 3.00 eq.) in N,N-Dimethyl-formamide (3.00 ml).

¹H NMR (400 MHz, Chloroform-d) δ 7.76 (s, 1H), 7.42-7.04 (m, 3H), 4.33-3.92 (m, 4H), 3.91-3.32 (m, 5H), 2.27 (q, J=10.1, 9.4 Hz, 1H), 2.07 (d, J=12.9 Hz, 1H), 2.03-1.64 (m, 5H), 1.63-1.00 (m, 5H). [M+H]⁺ 459

Example 149: Preparation of 4-chloro-N-((3-ethyl-1-hydroxycyclohexyl)methyl)-1-((tetrahydrofuran-2-yl)methyl)-1H-indole-3-carboxamide (137)

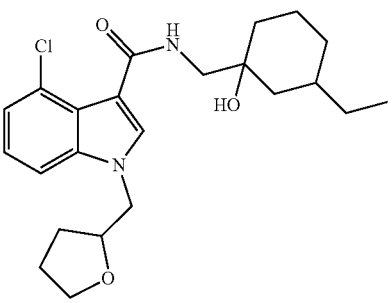 [SMILES: CCC1CCCC(O)(CNC(=O)c2cn(CC3CCCO3)c3cccc(Cl)c23)C1]

The title compound was synthesized according to the procedure described in Example 2 using 4-chloro-1-((tetrahydrofuran-2-yl)methyl)-1H-indole-3-carboxylic acid (50.00 mg; 0.18 mmol; 1.00 eq.), 1-(aminomethyl)-3-ethyl-cyclohexanol (33.19 mg; 0.23 mmol; 1.20 eq.), (3-Dimethylamino-propyl)-ethyl-carbodiimide hydrochloride (45.34 mg; 0.24 mmol; 1.20 eq.) Benzotriazol-1-ol (31.96 mg; 0.24 mmol; 1.20 eq.) and DIPEA (0.093 g, 0.72 mmol) in DMF (2.0 mL).

¹H NMR (400 MHz, DMSO-d₆) δ ppm 7.81 (1H), 7.66 (s, 1H), 7.58 (1H), 7.19 (2H), 4.35 (m, 1H), 4.24 (1H), 4.17 (m, 1H), 3.76 (1H), 3.63 (1H), 3.39 (1H), 1.96 (m, 1H), 1.79 (2H), 1.37 (2H), 1.13 (4H), 0.83 (2H). m/z: 419 [M+H]

Example 150: Preparation of 4-chloro-N-((4,4-difluoro-1-hydroxycyclohexyl) methyl)-1-((tetrahydrofuran-3-yl)methyl)-1H-indole-3-carboxamide (147)

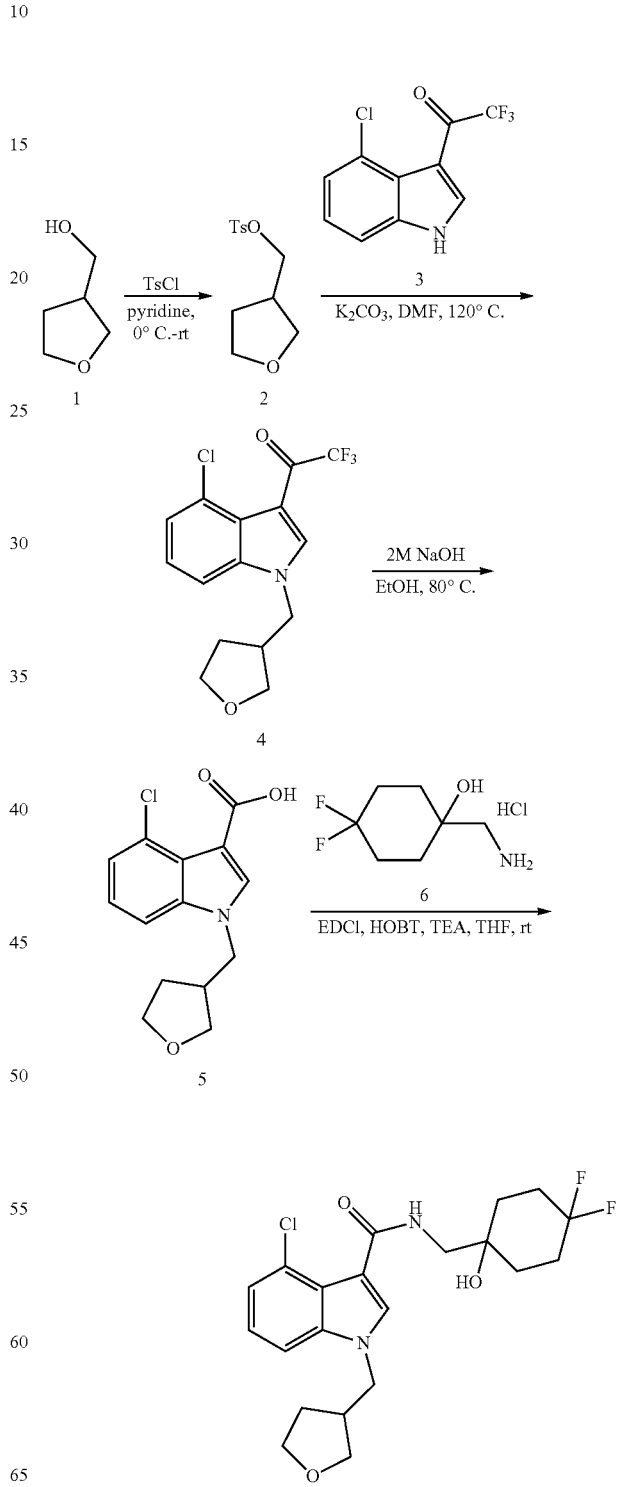

Step 1: Preparation of (tetrahydrofuran-3-yl)methyl 4-methylbenzenesulfonate

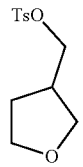

To a stirred solution of (tetrahydrofuran-3-yl)methanol (5.0 g, 49.0 mmol) in pyridine (30 mL) was added TsCl (11.2 g, 58.8 mmol) slowly at 0° C. The reaction mixture was stirred at room temperature overnight. The resulting mixture was diluted with EtOAc (150 mL), washed with saturated aqueous citric acid (100 mL×5) and saturated aqueous NaHCO$_3$ (100 mL×3), dried over Na$_2$SO$_4$, filtered and concentrated in vacuo. The resulting product was purified by column chromatography on silica gel (0-15% EtOAc in petroleum ether) to afford (tetrahydrofuran-3-yl)methyl 4-methylbenzenesulfonate (8.7 g, 69%) as a colorless oil.

Step 2: Preparation of 1-(4-chloro-1-((tetrahydrofuran-3-yl)methyl)-1H-indol-3-yl)-2,2,2-trifluoroethanone

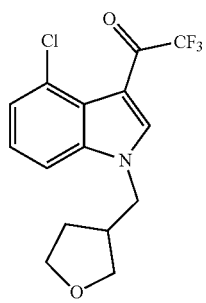 [SMILES: O=C(c1cn(CC2CCOC2)c2cccc(Cl)c12)C(F)(F)F]

A mixture of 1-(4-chloro-1H-indol-3-yl)-2,2,2-trifluoroethanone (2.48 g, 10.0 mmol), (tetrahydrofuran-3-yl)methyl 4-methylbenzenesulfonate (3.07 g, 12.0 mmol) and K$_2$CO$_3$ (4.14 g, 30.0 mmol) in DMF (40 mL) was stirred at 120° C. overnight. The resulting mixture was diluted with EtOAc (150 mL), washed with saturated aqueous NaHCO$_3$ (100 mL×5), dried over Na$_2$SO$_4$, filtered and concentrated in vacuo to afford 1-(4-chloro-1-((tetrahydrofuran-3-yl)methyl)-1H-indol-3-yl)-2,2,2-trifluoroethanone (3.3 g, 100%) as a yellow oil.

Step 3: Preparation of 4-chloro-1-((tetrahydrofuran-3-yl)methyl)-1H-indole-3-carboxylic acid

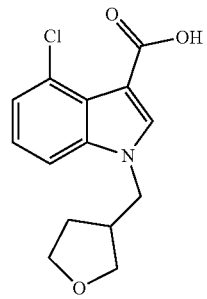 [SMILES: O=C(O)c1cn(CC2CCOC2)c2cccc(Cl)c12]

A mixture of 1-(4-chloro-1-((tetrahydrofuran-3-yl)methyl)-1H-indol-3-yl)-2,2,2-trifluoro-ethanone (3.5 g, 10.6 mmol) and NaOH (30 mL, 2 M) in EtOH (30 mL) was stirred at 80° C. for 2 h. The resulting mixture was concentrated in vacuo, extracted with EtOAc (30 mL), adjusted pH to 4-5, and extracted with EtOAc (50 mL×3). The combined organic layers were washed with brine (50 mL×3), dried over Na$_2$SO$_4$, filtered and concentrated in vacuo to afford the title compound (2.76 g, 90%) as a yellow solid.

Step 4: Preparation of 4-chloro-N-((4,4-difluoro-1-hydroxycyclohexyl)methyl)-1-((tetrahydrofuran-3-yl)methyl)-1H-indole-3-carboxamide

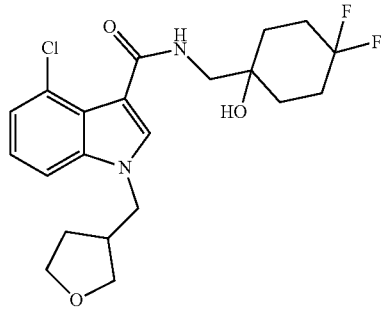 [SMILES: O=C(NCC1(O)CCC(F)(F)CC1)c1cn(CC2CCOC2)c2cccc(Cl)c12]

A mixture of 4-chloro-1-((tetrahydrofuran-3-yl)methyl)-1H-indole-3-carboxylic acid (0.140 g, 0.5 mmol), 1-(aminomethyl)-4,4-difluorocyclohexanol hydrochloride (0.101 g, 0.5 mmol), EDCI (0.144 g, 0.75 mmol), HOBt (0.101 g, 0.75 mmol), TEA (0.253 g, 2.5 mmol) in anhydrous THF (10.0 mL) was stirred at room temperature overnight. The reaction mixture was diluted with saturated NaHCO$_3$ (50 mL) and extracted with EtOAc/THF (20 mL×3). The combined organic layers were washed with brine, dried over Na$_2$SO$_4$, filtered and concentrated to dryness. The residue was purified by re-crystallization from EtOAc/petroleum ether to afford 4-chloro-N-((4,4-difluoro-1-hydroxycyclohexyl)methyl)-1-((tetrahydrofuran-3-yl)methyl)-1H-indole-3-carboxamide (0.120 g, 56%) as a white solid.

$^1$H NMR (500 MHz, DMSO-d$_6$) δ 8.01-7.99 (m, 1H), 7.85 (s, 1H), 7.61-7.59 (m, 1H), 7.22-7.15 (m, 2H), 4.74 (s, 1H), 4.22-4.20 (m, 2H), 3.85-3.82 (m, 1H), 3.67-3.62 (m, 2H), 3.49-3.46 (m, 1H), 3.32-3.31 (m, 1H), 2.77-2.75 (m, 1H), 1.92-1.88 (m, 5H), 1.66-1.62 (m, 5H) ppm; [M+H]$^+$ 427.1.

Example 151: Preparation of 4-chloro-N-((4,4-difluorocyclohexyl)methyl)-1-((tetrahydrofuran-3-yl)methyl)-1H-indole-3-carboxamide (148)

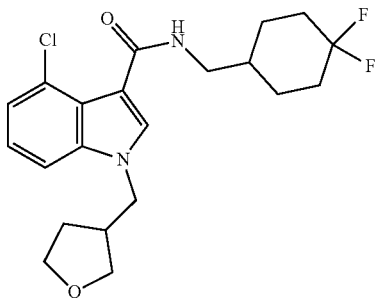 [SMILES: O=C(NCC1CCC(F)(F)CC1)c1cn(CC2CCOC2)c2cccc(Cl)c12]

The title compound was synthesized according to the procedure described in Example 33 using (tetrahydrofuran-3-yl)methanol (0.094 g, 0.92 mmol), 4-chloro-N-((4,4-difluorocyclohexyl)methyl)-1H-indole-3-carboxamide (0.150 g, 0.56 mmol) and CMTP (0.433 g, 1.84 mmol) to afford 4-chloro-N-((4,4-difluorocyclohexyl)methyl)-1-((tetrahydrofuran-3-yl) methyl)-1H-indole-3-carboxamide (0.035 g, 20%) as white solid. $^1$HNMR (500 MHz, DMSO-$d_6$) δ 8.12 (t, J=6.0 Hz, 1H), 7.77 (s, 1H), 7.58 (d, J=6.5 Hz, 1H), 7.19 (t, J=8.0 Hz, 1H), 7.14 (d, J=7.5 Hz, 1H), 4.20-4.19 (m, 2H), 3.86-3.82 (m, 1H), 3.67-3.62 (m, 2H), 3.48-3.45 (m, 1H), 3.15 (t, J=6.5 Hz, 2H), 2.80-2.71 (m, 1H), 2.04-2.02 (m, 2H), 1.92-1.59 (m, 7H), 1.29-1.21 (m, 2H) ppm; [M+H]$^+$ 411.1.

Example 152: Preparation of 4-chloro-N-((3,3-difluoro-1-hydroxycyclohexyl)methyl)-1-((tetrahydrofuran-3-yl)methyl)-1H-indole-3-carboxamide (146)

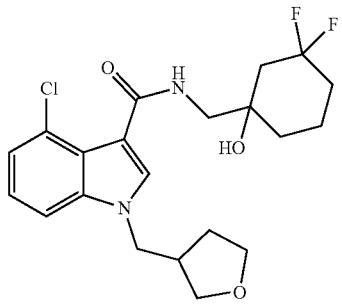 [SMILES: O=C(NCC1(O)CCCC(F)(F)C1)c1cn(CC2CCOC2)c2cccc(Cl)c12]

The title compound was synthesized according to the procedure described in Example 33 using 4-chloro-N-((3,3-difluoro-1-hydroxycyclohexyl)methyl)-1H-indole-3-carboxamide (70.00 mg; 0.28 mmol; 1.00 eq.), (tetrahydrofuran-3-yl)methanol (31.26 mg; 0.31 mmol; 2.50 eq.) and (Tributyl-lambda5-phosphanylidene)-acetonitrile (147.72 mg; 0.61 mmol; 4.00 eq.) in Toluene (3 mL).

$^1$H NMR (400 MHz, DMSO-$d_6$) δ ppm 8.22 (1H), 8.01 (s, 1H), 7.58 (1H), 7.20 (2H), 5.80 (1H), 5.05 (m, 2H), 4.94 (2H), 4.65 (s, 1H), 3.43 (1H), 3.23 (1H), 2.02-1.96 (m, 3H), 1.77 (2H), 1.59 (2H), 1.51 (1H). m/z: 427 [M+H].

Example 153: Preparations of 4-chloro-N-((4,4-difluoro-1-hydroxycyclohexyl) methyl)-1-((tetrahydro-2H-pyran-2-yl)methyl)-1H-indole-3-carboxamide (166)

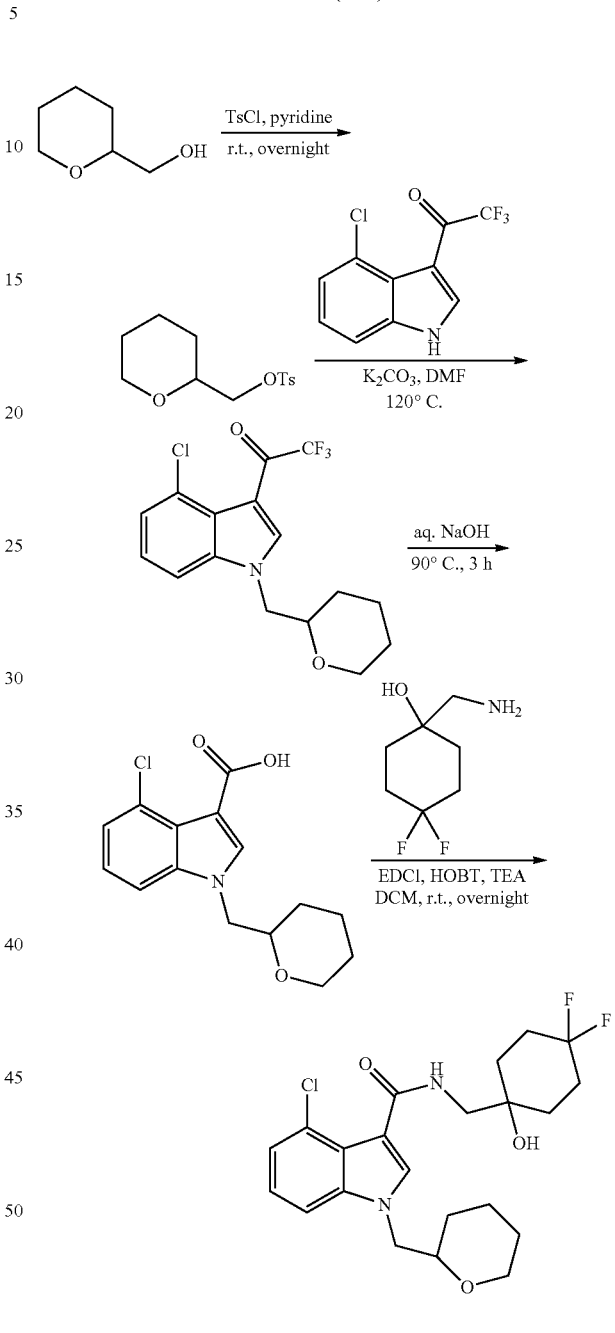

Step 1: Preparation of (tetrahydro-2H-pyran-2-yl)methyl 4-methylbenzenesulfonate

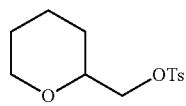 [SMILES: Cc1ccc(S(=O)(=O)OCC2CCCCO2)cc1]

To a solution of (tetrahydro-2H-pyran-2-yl)methanol (2.32 g, 20.0 mmol) in pyridine (15 mL) was added a solution of TsCl (4.58 g, 24.0 mmol) in pyridine (10 mL) dropwise at 0° C. over 30 min. After stirred at room temperature for overnight, the reaction mixture was quenched with 10% aqueous citric acid solution, extracted with EtOAc (20 mL×3). The combined organic phases were dried over $Na_2SO_4$, filtered and concentrated to afford a residue, which was purified by silica column chromatography (petroleum ether:EtOAc=5:1) to give (tetrahydro-2H-pyran-2-yl)methyl 4-methylbenzenesulfonate (3.72 g, 68.7%) as a white solid.

Step 2: Preparation of 1-(4-chloro-1-((tetrahydro-2H-pyran-2-yl)methyl)-1H-indol-3-yl)-2,2,2-trifluoroethanone

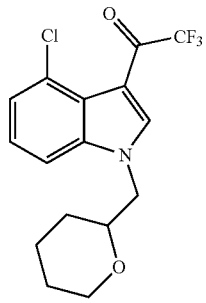 [SMILES: O=C(c1cn(CC2CCCCO2)c2cccc(Cl)c12)C(F)(F)F]

To a stirred solution of 1-(4-chloro-1H-indol-3-yl)-2,2,2-trifluoroethanone (2.0 g, 8.1 mmol) in DMF (20 mL) was added (tetrahydro-2H-pyran-2-yl)methyl 4-methylbenzenesulfonate (2.6 g, 9.7 mmol), $K_2CO_3$ (3.4 g, 24.6 mmol) at room temperature. The resulting reaction mixture was stirred at 120° C. overnight, and then quenched with water and extracted with EtOAc (20 mL×3). The combined organic layers were washed with brine (20 mL×3), dried over $Na_2SO_4$, filtered and concentrated to give 1-(4-chloro-1-((tetrahydro-2H-pyran-2-yl)methyl)-1H-indol-3-yl)-2,2,2-trifluoroethanone (2.2 g, 81%) as red oil.

Step 3: Preparation of 4-chloro-1-((tetrahydro-2H-pyran-2-yl)methyl)-1H-indole-3-carboxylic acid

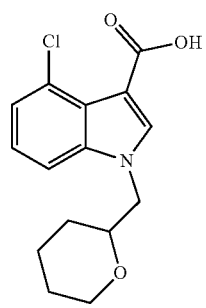 [SMILES: O=C(O)c1cn(CC2CCCCO2)c2cccc(Cl)c12]

To a stirred solution of 1-(4-chloro-1-((tetrahydro-2H-pyran-2-yl)methyl)-1H-indol-3-yl)-2,2,2-trifluoroethanone (2.2 g, 6.4 mmol) in EtOH (20 mL) was added 10% aqueous NaOH (20 mL). The resulting reaction mixture was stirred at 90° C. for 4 hours, and then adjusted to pH 4~5, extracted with EtOAc (40 mL×3). The combined organic layers were dried over $Na_2SO_4$ and filtered. The filtrate was concentrated in vacuo to give 4-chloro-1-((tetrahydro-2H-pyran-2-yl)methyl)-1H-indole-3-carboxylic acid (1.6 g, 87%) as a red solid.

Step 4: Preparation of 4-chloro-N-((4,4-difluoro-1-hydroxycyclohexyl)methyl)-1-((tetrahydro-2H-pyran-2-yl)methyl)-1H-indole-3-carboxamide

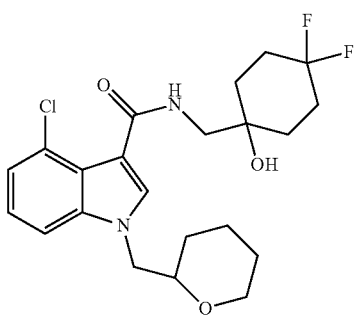 [SMILES: O=C(NCC1(O)CCC(F)(F)CC1)c1cn(CC2CCCCO2)c2cccc(Cl)c12]

A mixture of 4-chloro-N-((4,4-difluoro-1-hydroxycyclohexyl)methyl)-1-((tetrahydro-2H-pyran-2-yl)methyl)-1H-indole-3-carboxamide (0.200 g, 0.68 mmol), 1-(aminomethyl)-4,4-difluorocyclohexanol (0.113 g, 0.68 mmol), HOBt (0.138 g, 1.0 mmol), EDCI (0.196 g, 1.0 mmol) and $Et_3N$ (0.345 g, 3.4 mmol) in DCM (15 mL) was stirred at room temperature overnight, and then diluted with DCM (20 mL). The organic layer was washed with brine (10 mL), dried over $Na_2SO_4$, filtered and concentrated to afford a residue, which was purified by silica column chromatography (petroleum ether:EtOAc=2:1) to give 4-chloro-N-((4,4-difluoro-1-hydroxycyclohexyl)methyl)-1-((tetrahydro-2H-pyran-2-yl)methyl)-1H-indole-3-carboxamide (0.080 g, 27%) as a white solid.
$^1$H NMR (500 MHz, $CDCl_3$) δ 7.91 (s, 1H), 7.35 (d, J=8.0 Hz, 1H), 7.23 (d, J=7.0 Hz, 1H), 7.18 (t, J=8.0 Hz, 2H), 4.16-4.08 (m, 2H), 3.96-3.93 (m, 1H), 3.64-3.61 (m, 1H), 3.55 (d, J=5.5 Hz, 2H), 3.35-3.30 (m, 1H), 2.24-2.12 (m, 2H), 1.97-1.93 (m, 2H), 1.87-1.84 (m, 4H) 1.47-1.42 (m, 5H), 1.33-1.23 (m, 2H), ppm; [M+H]$^+$ 441.2.

Example 154: Preparation of 4-chloro-N-((4,4-difluorocyclohexyl)methyl)-1-((tetrahydro-2H-pyran-2-yl)methyl)-1H-indole-3-carboxamide (167)

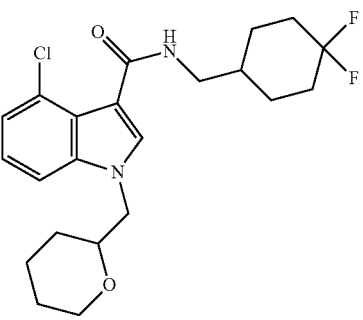 [SMILES: O=C(NCC1CCC(F)(F)CC1)c1cn(CC2CCCCO2)c2cccc(Cl)c12]

The title compound was synthesized according to the procedure described in Example 33 using (tetrahydro-2H-pyran-2-yl)methanol (0.070 g, 0.61 mmol), 4-chloro-N-((4, 4-difluorocyclohexyl)methyl)-1H-indole-3-carboxamide (0.100 g, 0.31 mmol) and cyanomethylenetributylphosphorane (0.296 g, 1.23 mmol) to afford 4-chloro-N-((4,4-difluorocyclohexyl)methyl)-1-((tetrahydro-2H-pyran-2-yl)methyl)-1H-indole-3-carboxamide (0.070 g, 54%) as white solid.

1H NMR (500 MHz, DMSO-$d_6$) δ 8.10 (t, J=6.0 Hz, 1H), 7.66 (s, 1H), 7.55 (d, J=8.5 Hz, 1H), 7.18 (t, J=7.5 Hz, 1H), 7.12 (d, J=8.0 Hz, 1H), 4.26-4.17 (m, 2H), 3.84-3.82 (m, 1H), 3.62-3.60 (m, 1H), 3.30-3.23 (m, 1H), 3.18-3.14 (m, 2H), 2.04-2.00 (m, 2H), 1.85-1.61 (m, 7H), 1.46-1.39 (m, 3H), 1.29-1.17 (m, 3H) ppm; [M+H]$^+$ 424.2.

Example 155: Preparation of 4-chloro-N-((4,4-difluorocyclohexyl)methyl)-1-((tetrahydro-2H-pyran-4-yl)methyl)-1H-indole-3-carboxamide (168)

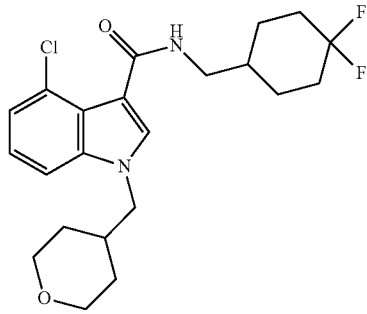 [SMILES: O=C(NCC1CCC(F)(F)CC1)c1cn(CC2CCOCC2)c2cccc(Cl)c12]

The title compound was synthesized according to the procedure described in Example 33 using (tetrahydro-2H-pyran-4-yl)methanol (0.142 g, 1.22 mmol), 4-chloro-N-((4,4-difluorocyclohexyl)methyl)-1H-indole-3-carboxamide (0.200 g, 0.61 mmol) and cyanomethylenetributylphosphorane (0.747 g, 3.06 mmol) to afford 4-chloro-N-((4,4-difluorocyclohexyl)methyl)-1-((tetrahydro-2H-pyran-2-yl)methyl)-1H-indole-3-carboxamide (0.048 g, 18%) as white solid.

$^1$H NMR (500 MHz, DMSO-$d_6$) δ 8.08 (t, J=6.0 Hz, 1H), 7.69 (s, 1H), 7.57 (d, J=8.0 Hz, 1H), 7.17 (t, J=8.0 Hz, 1H), 7.12 (d, J=7.0 Hz, 1H), 4.10 (d, J=7.0 Hz, 2H), 3.83-3.80 (m, 2H), 3.22-3.18 (m, 2H), 3.14 (t, J=6.5 Hz, 2H), 2.07-2.00 (m, 3H), 1.84-1.68 (m, 5H), 1.39-1.19 (m, 6H) ppm; [M+H]$^+$ 425.1.

Example 156: Preparation of 1-((1,4-dioxan-2-yl)methyl)-4-chloro-N-((4,4-difluorocyclohexyl)methyl)-1H-indole-3-carboxamide (150)

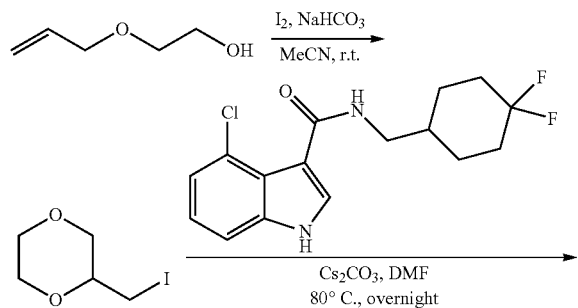

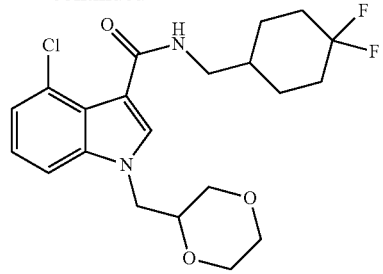

Step 1: Preparation of 2-(iodomethyl)-1,4-dioxane

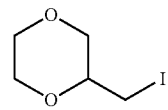

To a solution of 2-(allyloxy)ethanol (1.02 g, 10 mmol) in MeCN (10 mL) was added iodine (3.81 g, 15 mmol), followed by NaHCO$_3$ (1.26 g, 15 mmol) at room temperature. After being stirred at room temperature for 20 h, the resulting reaction mixture was quenched with water, extracted with EtOAc (60 mL). The organic extract was washed with saturated aqueous Na$_2$S$_2$O$_3$ and brine, dried over MgSO$_4$, filtered and concentrated in vacuo. The residue was purified by column chromatography on silica gel (petroleum ether:EtOAc=2:1) to give 2-(iodomethyl)-1,4-dioxane (1.6 g, 70%) as light yellow oil.

Step 2: Preparation of 1-((1,4-dioxan-2-yl)methyl)-4-chloro-N-((4,4-difluorocyclohexyl)methyl)-1H-indole-3-carboxamide

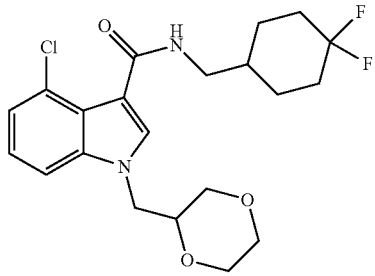 [SMILES: O=C(NCC1CCC(F)(F)CC1)c1cn(CC2COCCO2)c2cccc(Cl)c12]

To a solution of 4-chloro-N-((4,4-difluorocyclohexyl)methyl)-1H-indole-3-carboxamide (0.200 g, 0.613 mmol) in DMF (4 ml) were added 2-(iodomethyl)-1,4-dioxane (0.210 g, 0.920 mmol) and Cs$_2$CO$_3$ (0.599 g, 1.839 mmol). After being stirred at 80° C. overnight, the reaction mixture was diluted with EtOAc (30 mL) and filtered through a Celite pad. The organic phase was washed with water (3×20 mL), dried over Na$_2$SO$_4$ and concentrated in vacuo. The residue was purified by Prep-HPLC to give 1-((1,4-dioxan-2-yl)methyl)-4-chloro-N-((4,4-difluorocyclohexyl)methyl)-1H-indole-3-carboxamide (0.105 g, 40%) as a white solid.

$^1$H NMR (500 MHz, DMSO-$d_6$) δ 8.12 (t, J=6.0 Hz, 1H), 7.76 (s, 1H), 7.56 (d, J=8.0 Hz, 1H), 7.20-7.13 (m, 2H), 4.30-4.17 (m, 2H), 3.86-3.79 (m, 2H), 3.71 (d, J=10.5 Hz,

1H), 3.62 (d, J=10.5 Hz, 1H), 3.52-3.42 (m, 2H), 3.30-3.24 (m, 1H), 3.16-3.14 (m, 2H), 2.04-2.01 (m, 2H), 1.84-1.69 (m, 5H), 1.28-1.20 (m, 2H) ppm; [M+H]+ 427.1.

Example 157: Preparation of 4-chloro-N-((4,4-difluorocyclohexyl)methyl)-1-((4-methylmorpholin-2-yl)methyl)-1H-indole-3-carboxamide (183)

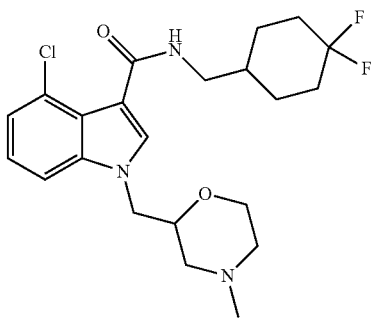 [SMILES: CN1CCOC(Cn2cc(C(=O)NCC3CCC(F)(F)CC3)c3c(Cl)cccc32)C1]

The title compound was synthesized according to the procedure described in Example 33 using 4-chloro-N-((4,4-difluorocyclohexyl)methyl)-1H-indole-3-carboxamide (0.100 g, 0.30 mmol), (4-methylmorpholin-2-yl)methanol (0.098 g, 0.74 mmol) and CMTP (0.286 g, 1.19 mmol) to obtain 4-chloro-N-((4,4-difluoro cyclohexyl) methyl)-1-((4-methylmorpholin-2-yl)methyl)-1H-indole-3-carboxamide (0.056 g, 38%) as a pale yellow solid.

1H NMR (500 MHz, DMSO-d6): δ 8.12 (t, J=6.0 Hz, 1H), 7.67 (s, 1H), 7.56 (d, J=8.0 Hz, 1H), 7.20-7.12 (m, 2H), 4.29-4.24 (m, 2H), 3.76 (d, J=7.0 Hz, 2H), 3.43-3.40 (m, 1H) 3.15 (t, J=6.0 Hz, 2H), 2.73 (d, J=10.5 Hz, 1H), 2.56 (d, J=11.5 Hz, 1H), 2.16 (s, 3H), 2.03-1.93 (m, 3H), 1.85-1.66 (m, 6H), 1.28-1.19 (m, 2H) ppm; [M+Na]+ 440.2.

Example 158: Preparation of 4-chloro-N-((4,4-difluorocyclohexyl)methyl)-1-(1-methylazetidin-3-yl)-1H-indole-3-carboxamide (119)

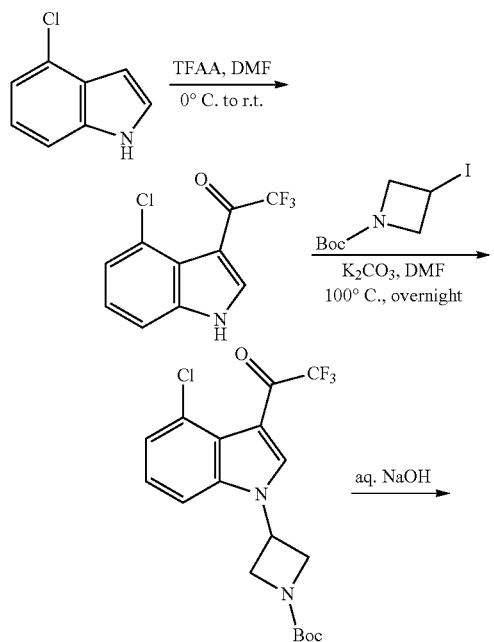

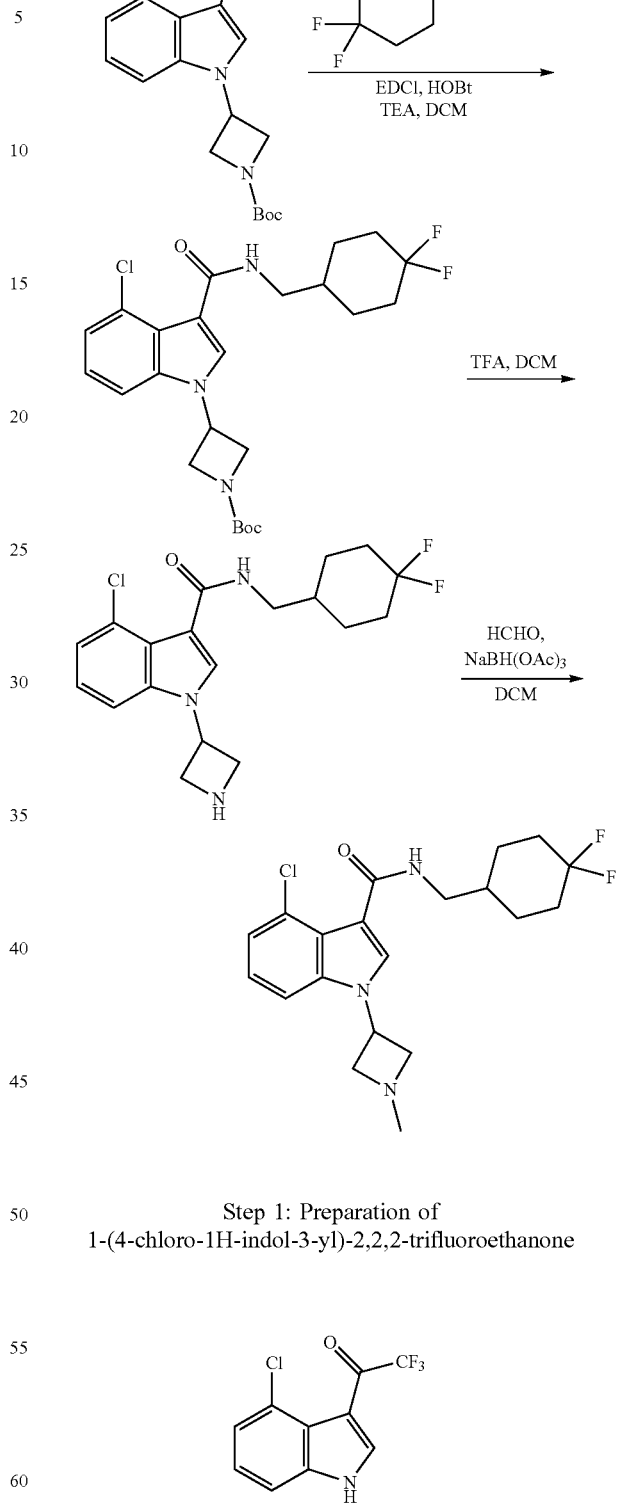

Step 1: Preparation of 1-(4-chloro-1H-indol-3-yl)-2,2,2-trifluoroethanone

To a stirred solution of compound 4-chloro-1H-indole (5.00 g, 32.98 mmol) in DMF (40 mL) was added trifluoroacetic anhydride (6.88 mL, 49.47 mmol) at 0° C. The resulting reaction mixture was stirred at room temperature for 3 h, and was quenched with water (50 mL) and extracted with DCM (200 mL). The separated organic layer was dried over anhydrous sodium sulfate, filtered and concentrated to afford 1-(4-chloro-1H-indol-3-yl)-2,2,2-trifluoroethanone (8.00 g, 95%) as brown oil, which was used for the next step without further purification. LCMS: m/z=248 (M+H)+.

Step 2: Preparation of tert-butyl 3-(4-chloro-3-(2,2,2-trifluoroacetyl)-1H-indol-1-yl)azetidine-1-carboxylate

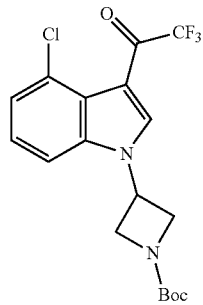 [SMILES: CC(C)(C)OC(=O)N1CC(n2cc(C(=O)C(F)(F)F)c3c(Cl)cccc32)C1]

A mixture of 1-(4-chloro-1H-indol-3-yl)-2,2,2-trifluoroethanone (8.00 g, 32.31 mmol), tert-butyl 3-iodoazetidine-1-carboxylate (10.06 g, 35.54 mmol) and potassium carbonate (13.40 g, 96.93 mmol) in DMF (30 mL) was stirred at 100° C. overnight. After cooled to room temperature, the mixture was quenched with water (50 mL) and extracted with EtOAc (80 mL×3). The combined organic layer was dried with anhydrous sodium sulfate, filtered and concentrated in vacuo. The residue was purified by column chromatography on silica gel (petroleum ether:EtOAc=5:1) to afford tert-butyl 3-(4-chloro-3-(2,2,2-trifluoroacetyl)-1H-indol-1-yl)azetidine-1-carboxylate (9.60 g, 80%) as yellow solid. LCMS: m/z=403.1 (M+H)+.

Step 3: Preparation of 1-(1-(tert-butoxycarbonyl)azetidin-3-yl)-4-chloro-1H-indole-3-carboxylic acid

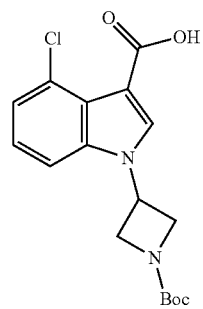 [SMILES: CC(C)(C)OC(=O)N1CC(n2cc(C(=O)O)c3c(Cl)cccc32)C1]

To a stirred solution of tert-butyl 3-(4-chloro-3-(2,2,2-trifluoroacetyl)-1H-indol-1-yl) azetidine-1-carboxylate (9.00 g, 22.34 mmol) in ethanol (160 mL) was added aqueous sodium hydroxide (80 mL, 10%). After stirred at 100° C. for 1 h, the reaction mixture was concentrated in vacuo to remove ethanol. The pH value of the aqueous solution was adjusted to 6 with concentrated hydrochloric acid and extracted with EtOAc (100 mL×3). The combined organic layer was dried over anhydrous sodium sulfate, filtered and concentrated in vacuo. The residue was purified by column chromatography on silica gel (petroleum ether:EtOAc=2:1) to afford 1-(1-(tert-butoxycarbonyl) azetidin-3-yl)-4-chloro-1H-indole-3-carboxylic acid (7.00 g, 82%) as yellow solid. LCMS: m/z=351.1 (M+H)+.

Step 4: Preparation of tert-butyl3-(4-chloro-3-((4,4-difluorocyclohexyl) methyl carbamoyl)-1H-indol-1-yl)azetidine-1-carboxylate

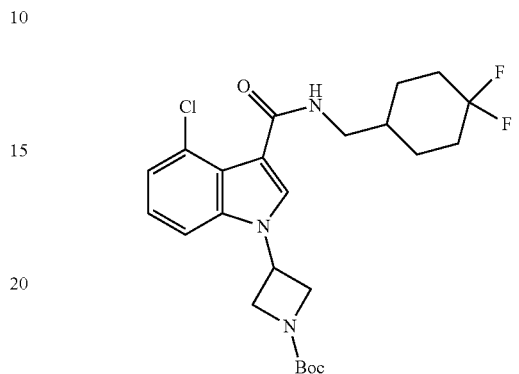

To a stirred solution of 1-(1-(tert-butoxycarbonyl)azetidin-3-yl)-4-chloro-1H-indole-3-carboxylic acid (1.20 g, 3.42 mmol), EDCI (0.852 g, 4.44 mmol) and HOBt (0.600 g, 4.44 mmol) in acetonitrile (30 mL)) was added triethylamine (1.03 g, 10.26 mmol), followed by addition of (4,4-difluorocyclohexyl)methanamine (0.510 g, 3.42 mmol). The reaction was stirred at room temperature overnight, and then it was quenched with water (50 mL) and extracted with DCM (70 mL×3). The combined organic layer was dried over anhydrous magnesium sulfate, filtered and concentrated in vacuo. The residue was purified by column chromatography on silica gel (petroleum ether:EtOAc=2:1) to afford tert-butyl3-(4-chloro-3-((4,4-difluorocyclohexyl)methylcarbamoyl)-1H-indol-1-yl) azetidine-1-carboxylate (1.39 g, 88%) as yellow solid. LCMS: m/z=482.1 (M+1).

Step 5: Preparation of 1-(azetidin-3-yl)-4-chloro-N-((4,4-difluorocyclohexyl)methyl)-1H-indole-3-carboxamide

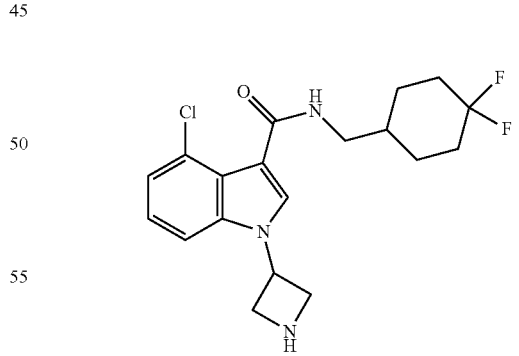

To a stirred solution of tert-butyl3-(4-chloro-3-((4,4-difluorocyclohexyl)methyl carbamoyl)-1H-indol-1-yl) azetidine-1-carboxylate (1.39 g, 2.88 mmol) in DCM (20 mL) was added trifluoroacetic acid (4.0 mL) at 0° C., and the mixture was stirred at the same temperature for 1 h. The reaction was quenched with water (30 mL) and the pH value of the solution was adjusted to 8 with aqueous saturated sodium bicarbonate. The system was extracted with DCM (30 mL×3). The combined organic layer was dried over anhydrous sodium sulfate, filtered and concentrated in vacuo to afford 1-(azetidin-3-yl)-4-chloro-N-((4,4-difluorocyclohexyl)methyl)-1H-indole-3-carboxamide (1.00 g, 91%) as yellow solid. LCMS: m/z=382.1 (M+H)⁺.

Step 6: Preparation of 4-chloro-N-((4,4-difluorocyclohexyl)methyl)-1-(1-methylazetidin-3-yl)-1H-indole-3-carboxamide

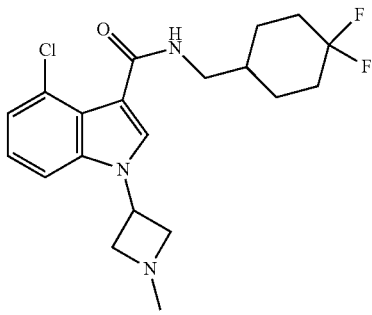 [SMILES: CN1CC(n2cc(C(=O)NCC3CCC(F)(F)CC3)c3c(Cl)cccc32)C1]

To a stirred solution of 1-(azetidin-3-yl)-4-chloro-N-((4,4-difluorocyclohexyl)methyl)-1H-indole-3-carboxamide (0.200 g, 0.52 mmol) in DCM (20 mL) was added formaldehyde (0.5 mL), the mixture was stirred at room temperature for 1 h, then sodium triacetoxyborohydride (0.333 g, 1.57 mmol) was added. The resultant reaction mixture was stirred at room temperature for further 0.5 h, and then it was quenched with water (30 mL) and extracted with DCM (50 mL×3). The combined organic layer was dried over anhydrous sodium sulfate, filtered and concentrated in vacuo. The residue was purified by Pre-TLC (DCM:methanol=10:1) and followed by recrystallization (Hexane:EtOAc=10:1) to afford 4-chloro-N-((4,4-difluorocyclohexyl)methyl)-1-(1-methylazetidin-3-yl)-1H-indole-3-carboxamide (0.045 g, 22%) as white solid.

¹HNMR (400 MHz, DMSO-d₆,) δ 8.16 (t, J=6.0 Hz, 1H), 7.97 (s, 1H), 7.55 (d, J=8.0 Hz, 1H), 7.19-7.14 (m, 2H), 5.15-5.10 (m, 1H), 3.77 (t, J=7.5 Hz, 2H), 3.36-3.34 (m, 2H), 3.16 (t, J=6.5 Hz, 2H), 2.35 (s, 3H), 2.05-1.98 (m, 2H), 1.85-1.69 (m, 5H), 1.28-1.20 (m, 2H) ppm; [M+H]⁺ 396.1.

Example 159: Preparation of 4-chloro-1-(1-cyclopropylazetidin-3-yl)-N-((4,4-difluorocyclohexyl)methyl)-1H-indole-3-carboxamide (171)

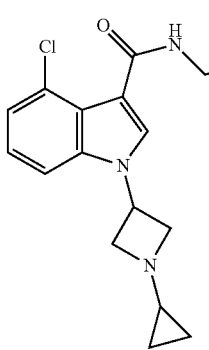

A mixture of 1-(azetidin-3-yl)-4-chloro-N-((4,4-difluorocyclohexyl)methyl)-1H-indole-3-carboxamide (0.400 g, 1.05 mmol), bromocyclopropane (0.383 g, 3.14 mol), potassium carbonate (0.434 g, 3.14 mmol) and sodium iodide (0.156 g, 1.04 mmol) in DMF (3 mL) was stirred at 110° C. overnight. After cooled to room temperature, the reaction was quenched with water (50 mL) and extracted with EtOAc (60 mL×3). The combined organic layer was dried over anhydrous sodium sulfate, filtered and concentrated in vacuo. The residue was purified by pre-TLC (petroleum ether:EtOAc=1:2) to afford 4-chloro-1-(1-cyclopropylazetidin-3-yl)-N-((4,4-difluorocyclohexyl) methyl)-1H-indole-3-carboxamide (0.042 g, 10%) as white solid.

¹HNMR (500 MHz, DMSO-d₆,) δ 8.16 (t, J=4.0 Hz, 1H), 7.98 (s, 1H), 7.57 (d, J=7.5 Hz, 1H), 7.20-7.15 (m, 2H), 5.83-5.75 (m, 1H), 5.25-5.11 (m, 3H), 3.79 (t, J=7.0 Hz, 2H), 3.37-3.36 (m, 2H), 3.16 (t, J=6.5 Hz, 4H), 2.08-1.98 (m, 2H), 1.86-1.66 (m, 5H), 1.29-1.21 (m, 2H) ppm; [M+H]⁺ 422.1.

Example 160: Preparation of 4-chloro-N-((4,4-difluoro-1-hydroxycyclohexyl) methyl)-1-(1-methylazetidin-3-yl)-1H-indole-3-carboxamide (118)

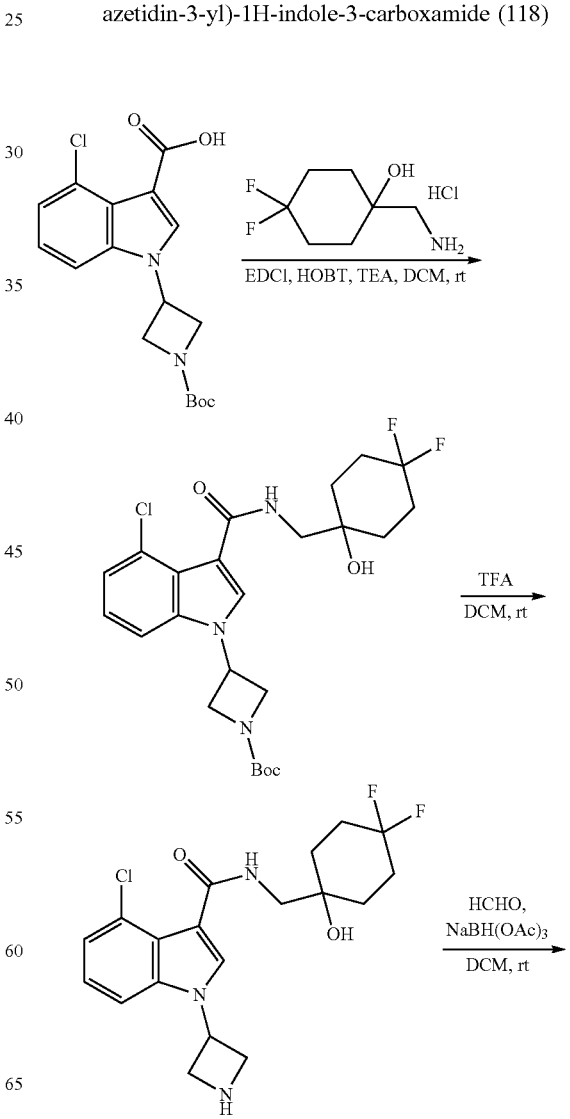

-continued

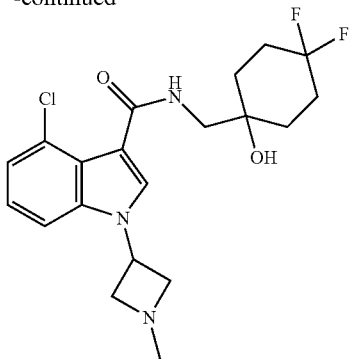

Step 1: Preparation of tert-butyl 3-(4-chloro-3-((4,4-difluoro-1-hydroxycyclohexyl) methyl-carbamoyl)-1H-indol-1-yl)azetidine-1-carboxylate

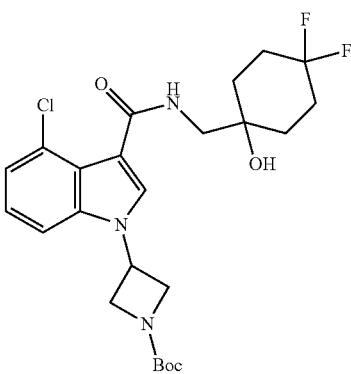 [SMILES: CC(C)(C)OC(=O)N1CC(n2cc(C(=O)NCC3(O)CCC(F)(F)CC3)c3c(Cl)cccc32)C1]

A mixture of 1-(1-(tert-butoxycarbonyl)azetidin-3-yl)-4-chloro-1H-indole-3-carboxylic acid (0.150 g, 0.43 mmol), HATU (0.243 g, 0.64 mmol), DIPEA (0.2 mL) and 1-(aminomethyl)-4,4-difluorocyclohexanol (0.106 g, 0.64 mmol) in DMF (10 mL) was stirred at room temperature overnight. The reaction was quenched with water (20 mL) and extracted with DCM (150 mL). The separated organic layer was dried over MgSO$_4$, filtered, concentrated to give tert-butyl 3-(4-chloro-3-((4,4-difluoro-1-hydroxycyclohexyl)methyl-carbamoyl)-1H-indol-1-yl)azetidine-1-carboxylate (0.180 g, 86%) as a yellow oil.

Step 2: Preparation of 1-(azetidin-3-yl)-4-chloro-N-((4,4-difluoro-1-hydroxy cyclohexyl)methyl)-1H-indole-3-carboxamide

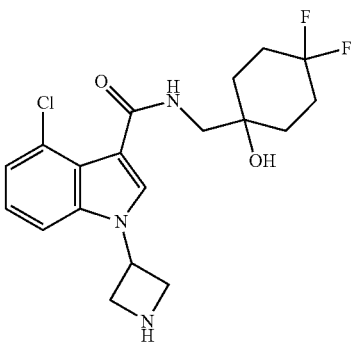 [SMILES: O=C(NCC1(O)CCC(F)(F)CC1)c1cn(C2CNC2)c2cccc(Cl)c12]

To a solution of tert-butyl 3-(4-chloro-3-((4,4-difluoro-1-hydroxycyclohexyl)methyl-carbamoyl)-1H-indol-1-yl)azetidine-1-carboxylate (0.180 g, 0.36 mmol) in DCM (20 mL) was added TFA (4.0 mL) at 0° C. The reaction was stirred at room temperature for 1 h. Then the reaction was quenched with water (20 mL) and the pH of the organic layer was adjusted to 8 with saturated NaHCO$_3$. The separated organic layer was dried over anhydrous Na$_2$SO$_4$, filtered and concentrated to give 1-(azetidin-3-yl)-4-chloro-N-((4,4-difluoro-1-hydroxycyclohexyl)methyl)-1H-indole-3-carboxamide (0.160 g, 95%) as a yellow oil.

Step 3: Preparation of 4-chloro-N-((4,4-difluoro-1-hydroxycyclohexyl)methyl)-1-(1-methylazetidin-3-yl)-1H-indole-3-carboxamide

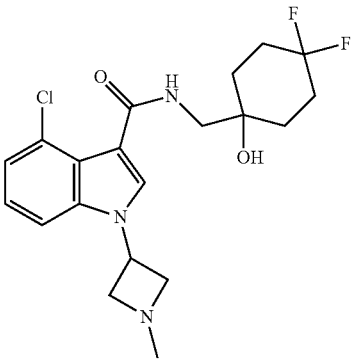 [SMILES: CN1CC(n2cc(C(=O)NCC3(O)CCC(F)(F)CC3)c3c(Cl)cccc32)C1]

To a solution of 1-(azetidin-3-yl)-4-chloro-N-((4,4-difluoro-1-hydroxycyclohexyl) methyl)-1H-indole-3-carboxamide (0.160 g, 0.40 mmol) in DCM (20 mL) was added HCHO (0.5 mL, 37% in H$_2$O). After stirring at room temperature for 1 h, NaBH(OAc)$_3$ (0.333 g, 1.57 mmol) was added. The resultant reaction mixture was stirred at room temperature for another 0.5 h, quenched with water (30 mL) and extracted with DCM (150 mL). The separated organic layer was dried over anhydrous Na$_2$SO$_4$, filtered and concentrated. The residue was purified by Prep-HPLC to give 4-chloro-N-((4,4-difluoro-1-hydroxycyclohexyl)methyl)-1-(1-methylazetidin-3-yl)-1H-indole-3-carboxamide (0.22 g, 14%) as a white solid.

$^1$H NMR (500 MHz, DMSO-d$_6$): δ 8.06-8.03 (m, 2H), 7.57 (d, J=7.5 Hz, 1H), 7.21-7.16 (m, 2H), 5.17-5.12 (m, 1H), 4.75 (s, 1H), 3.80 (t, J=7.5 Hz, 2H), 3.38-3.35 (m, 2H), 3.33-3.32 (m, 2H), 2.36 (s, 3H), 2.06-1.89 (m, 4H), 1.67-1.65 (m, 4H) ppm; [M+H]$^+$ 412.1.

Example 161: Preparations of 4-chloro-N-((4,4-difluorocyclohexyl)methyl)-1-(2-azaspiro[3.3]heptan-6-yl)-1H-indole-3-carboxamide (172)

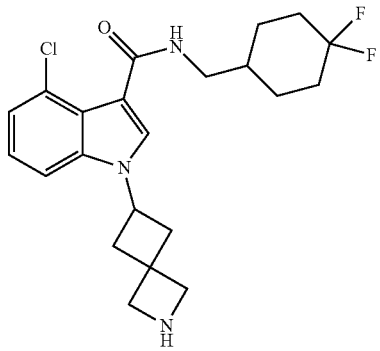 [SMILES: O=C(NCC1CCC(F)(F)CC1)c1cn(C2CC3(CNC3)C2)c2cccc(Cl)c12]

The title compound was synthesized according to the procedure described in Example 33 using 4-Chloro-1H-indole-3-carboxylic acid (4,4-difluoro-cyclohexyl methyl)-amide (50.00 mg; 0.15 mmol; 1.00 eq.), tert-butyl 6-hydroxy-2-azaspiro[3.3]heptane-2-carboxylate (71.29 mg; 0.38 mmol; 2.50 eq.) and (Tributyl-lambda5-phosphanylidene)-acetonitrile (147.72 mg; 0.61 mmol; 4.00 eq.) in Toluene (3 mL).

$^1$H NMR (400 MHz, DMSO-$d_6$) δ 8.88 (s, 1H), 8.10 (1H), 7.92 (s, 1H), 7.50 (1H), 7.15-7.19 (m, 2H), 4.91 (m, 2H), 4.16 (2H), 4.00 (2H), 3.14 (2H), 2.85 (2H), 2.68 (2H), 2.03 (2H), 1.85 (2H), 1.71 (m, 1H), 1.60 (1H), 1.37 (1H), 1.25 (m, 1H), 0.93 (2H). m/z: 422 [M+H].

Example 162: Preparation of (S)-1-(azetidin-2-ylmethyl)-4-chloro-N-((4,4-difluorocyclohexyl)methyl)-1H-indole-3-carboxamide (122)

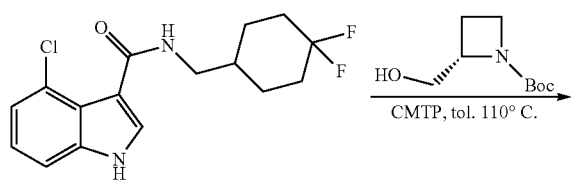

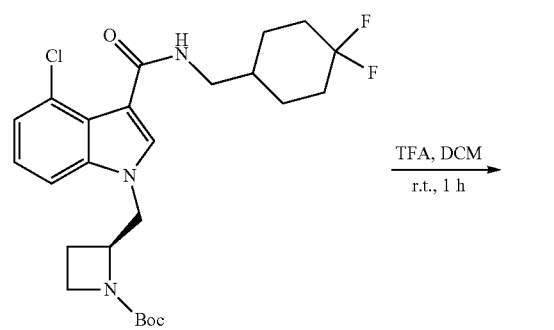

Step 1: Preparation of (S)-tert-butyl 2-((4-chloro-3-((4,4-difluorocyclohexyl) methylcarbamoyl)-1H-indol-1-yl)methyl)azetidine-1-carboxylate

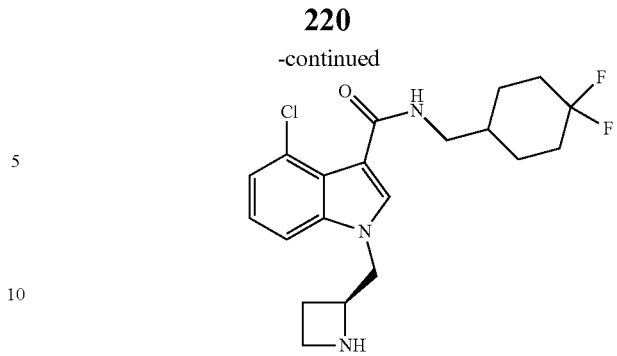

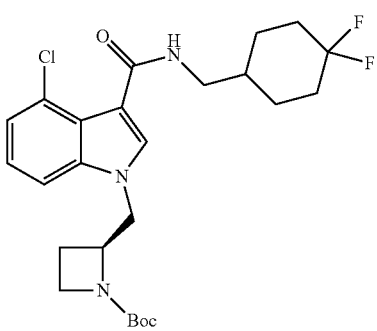 [SMILES: CC(C)(C)OC(=O)N1CC[C@H]1Cn1cc(C(=O)NCC2CCC(F)(F)CC2)c2c(Cl)cccc21]

A mixture of 4-chloro-N-((4,4-difluorocyclohexyl) methyl)-1H-indole-3-carboxamide (0.500 g, 1.53 mmol), (S)-tert-butyl 2-(hydroxymethyl)azetidine-1-carboxylate (0.574 g, 3.06 mmol) and CMTP (1.50 g, 6.12 mmol) in anhydrous toluene (2 mL) was stirred at 110° C. under nitrogen atmosphere for 4 h. After cooled to room temperature, the mixture was quenched water (30 mL) and extracted with EtOAc (20 mL×3). The combined organic layer was dried with anhydrous dried over sodium sulfate, filtered and concentrated in vacuo. The residue was purified by column chromatography on silica gel (petroleum ether:EtOAc=2:1) to afford (S)-tert-butyl2-((4-chloro-3-((4,4-difluorocyclohexyl)methylcarbamoyl)-1H-indol-1-yl)methyl)azetidine-1-carboxylate (0.600 g, 80%) as white solid. LCMS: [M+H]$^+$ 496.1.

Step 2: Preparation of (S)-1-(azetidin-2-ylmethyl)-4-chloro-N-((4,4-difluorocyclohexyl) methyl)-1H-indole-3-carboxamide

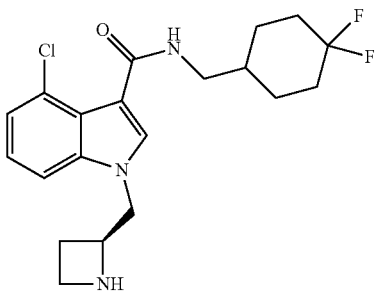 [SMILES: O=C(NCC1CCC(F)(F)CC1)c1cn(C[C@@H]2CCN2)c2cccc(Cl)c12]

To a stirred solution of (S)-tert-butyl2-((4-chloro-3-((4,4-difluorocyclohexyl) methylcarbamoyl)-1H-indol-1-yl) methyl)azetidine-1-carboxylate (0.600 g, 1.20 mmol) in DCM (15 mL) was added trifluoroacetic acid (3 mL) at 0° C., then the reaction was stirred at room temperature for 1 h. The reaction was quenched with water (10 mL) and the pH value of the solution was adjusted to 8 with aqueous saturated sodium bicarbonate, then it was extracted with DCM (20 mL×3). The separated organic layer was dried over anhydrous sodium sulfate, filtered and concentrated in vacuo. The residue was purified by column chromatography on silica gel (DCM:methanol=1:10) to afford (S)-1-(azetidin-2-ylmethyl)-4-chloro-N-((4,4-difluorocyclohexyl) methyl)-1H-indole-3-carboxamide (0.475 g, 91%) as a white solid.

$^1$HNMR (500 MHz, DMSO-$d_6$,) δ 8.07 (t, J=5.5 Hz, 1H), 7.73 (s, 1H), 7.57 (d, J=8.5 Hz, 1H), 7.18-7.11 (m, 2H), 4.27-4.19 (m, 2H), 4.13-4.08 (m, 1H), 3.48-3.39 (m, 1H), 3.17-3.12 (m, 3H), 2.89-2.82 (m, 1H), 2.19-2.13 (m, 1H), 2.07-1.99 (m, 3H), 1.85-1.69 (m, 5H), 1.29-1.21 (m, 2H) ppm; [M+H]$^+$ 396.3.

Example 163: Preparation of (S)-4-chloro-N-((4,4-difluorocyclohexyl)methyl)-1-((1-methylazetidin-2-yl)methyl)-1H-indole-3-carboxamide (151)

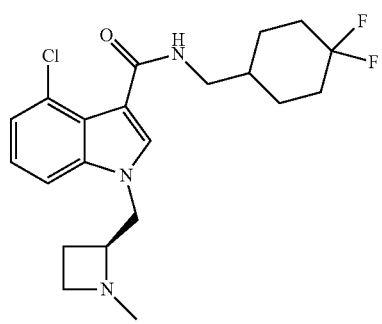 [SMILES: CN1CC[C@H]1Cn1cc(C(=O)NCC2CCC(F)(F)CC2)c2c(Cl)cccc21]

To a stirred solution of (S)-1-(azetidin-2-ylmethyl)-4-chloro-N-((4,4-difluorocyclohexyl) methyl)-1H-indole-3-carboxamide (0.120 g, 0.30 mmol) in DCM (2 mL) was added formaldehyde (0.4 mL). After stirred at room temperature for 1 h, to the mixture was added sodium triacetoxyborohydride (0.190 g, 0.90 mmol). The resulting reaction mixture was stirred at room temperature for further 0.5 h, and then it was quenched with water (10 mL) and extracted with DCM (50 mL×3). The separated organic layer was dried over anhydrous sodium sulfate, filtered and concentrated in vacuo. The residue was purified by column chromatography on silica gel (DCM:methanol=1:10) to afford (S)-4-chloro-N-((4,4-difluorocyclohexyl)methyl)-1-((1-methylazetidin-2-yl)methyl)-1H-indole-3-carboxamide (0.053 g, 42%) as a white solid.

$^1$HNMR (500 MHz, DMSO-$d_6$) δ 8.07 (t, J=5.5 Hz, 1H), 7.70 (s, 1H), 7.56 (d, J=8.0 Hz, 1H), 7.17 (t, J=8.0 Hz, 1H), 7.13 (d, J=7.5 Hz, 1H), 4.25 (d, J=5.0 Hz, 2H), 3.27-3.21 (m, 1H), 3.20-3.14 (m, 3H), 2.67-2.63 (m, 1H), 2.04-1.99 (m, 5H), 1.94-1.89 (m, 1H), 1.85-1.70 (m, 6H), 1.29-1.21 (m, 2H) ppm; [M+H]$^+$ 410.2.

Example 164: Preparation of (R)-1-(azetidin-2-ylmethyl)-4-chloro-N-((4,4-difluorocyclohexyl) methyl)-1H-indole-3-carboxamide (123)

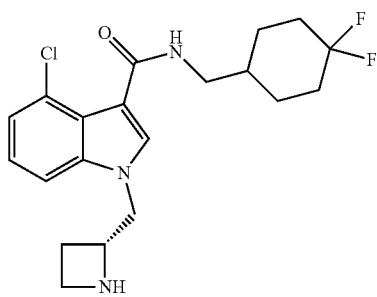 [SMILES: O=C(NCC1CCC(F)(F)CC1)c1cn(C[C@H]2CCN2)c2cccc(Cl)c12]

The title compound was synthesized according to the procedure described in example 162 using 4-Chloro-1H-indole-3-carboxylic acid (4,4-difluoro-cyclohexylmethyl)-amide (85.00 mg; 0.26 mmol; 1.00 eq.), (R)-2-Hydroxymethyl-azetidine-1-carboxylic acid tert-butyl ester (97.41 mg; 0.52 mmol; 2.00 eq.) and (CMTP) (0.27 ml; 1.04 mmol; 4.00 eq.) to provide boc-product which was treated with TFA in DCM to obtain (R)-1-(azetidin-2-ylmethyl)-4-chloro-N-((4, 4-difluorocyclo hexyl) methyl)-1H-indole-3-carboxamide (70 mg, 68%). [M+H]$^+$ 396.

Example 165: Preparation of 4-chloro-N-((4,4-difluorocyclohexyl)methyl)-1-((2-methylazetidin-2-yl) methyl)-1H-indole-3-carboxamide (152)

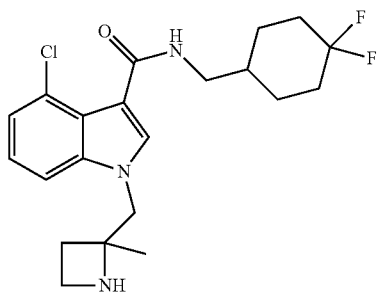 [SMILES: CC1(Cn2cc(C(=O)NCC3CCC(F)(F)CC3)c3c(Cl)cccc32)CCN1]

The title compound was synthesized according to the procedure described in example 162 using 4-Chloro-1H-indole-3-carboxylic acid (4,4-difluoro-cyclohexylmethyl)-amide (200.00 mg; 0.61 mmol; 1.00 eq.), 2-Hydroxymethyl-2-methyl-azetidine-1-carboxylic acid tert-butyl ester (246.37 mg; 1.22 mmol; 2.00 eq.) and (Tributyl-lambda5-phosphanylidene)-acetonitrile (CMTP) (0.48 ml; 1.84 mmol; 3.00 eq.). The boc-protected product was treated with TFA (5 ml) in DCM and the crude was purified on a silica gel columb to get the title compound.

1H NMR (400 MHz, Chloroform-d) δ 8.00 (s, 1H), 7.41 (dd, J=7.9, 1.2 Hz, 1H), 7.20 (dq, J=15.6, 8.3, 7.8 Hz, 2H), 6.92 (t, J=6.1 Hz, 1H), 4.36 (d, J=14.6 Hz, 1H), 4.13 (d, J=14.7 Hz, 1H), 3.66 (q, J=8.4 Hz, 1H), 3.48-3.25 (m, 4H), 2.39 (dt, J=11.2, 8.6 Hz, 1H), 2.23-1.99 (m, 3H), 1.98-1.83 (m, 2H), 1.82-1.56 (m, 4H), 1.50-1.26 (m, 4H). [M+H]$^+$ 410.

Example 166: Preparation of (S)-1-((1-acetylazetidin-2-yl)methyl)-4-chloro-N-((4,4-difluorocyclohexyl)methyl)-1H-indole-3-carboxamide (181)

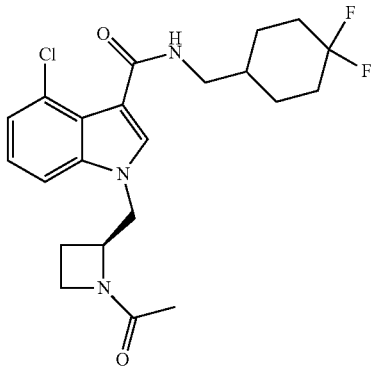 [SMILES: CC(=O)N1CC[C@H]1Cn1cc(C(=O)NCC2CCC(F)(F)CC2)c2c(Cl)cccc21]

To a solution of 1-(S)-1-Azetidin-2-ylmethyl-4-chloro-1H-indole-3-carboxylic acid (4,4-difluoro-cyclohexylmethyl)-amide (100.00 mg; 0.25 mmol; 1.00 eq.) in Dichloromethane (5.00 ml) were added Ethyl-diisopropyl-amine (0.25 ml; 1.52 mmol; 6.00 eq.) and Acetyl chloride (0.05 ml; 0.76 mmol; 3.00 eq.). The reaction mixture was stirred for 1 h at room temperature. Solvent was removed and the crude was purified on Biotage cartridge (10 g) using Ethylacetate-hexane gradient to obtain the title compound as a white solid (100 mg, 90%).

1H NMR (400 MHz, Chloroform-d) δ 7.80 (d, J=2.1 Hz, 1H), 7.46 (d, J=8.0 Hz, 1H), 7.21 (dt, J=15.7, 7.7 Hz, 2H), 6.87 (t, J=6.2 Hz, 1H), 4.73 (h, J=5.1 Hz, 1H), 4.65-4.44 (m, 2H), 3.91 (td, J=8.6, 6.1 Hz, 2H), 3.69 (td, J=8.8, 5.8 Hz, 1H), 3.42 (t, J=6.5 Hz, 2H), 2.37-2.22 (m, 1H), 2.20-2.07 (m, 3H), 2.04-1.87 (m, 3H), 1.84 (s, 2H), 1.81-1.63 (m, 2H), 1.61-1.34 (m, 2H). [M+H]⁺ 438.4

Example 167: Preparation of (S)-4-chloro-N-((4,4-difluorocyclohexyl)methyl)-1-((1-isopropylazetidin-2-yl)methyl)-1H-indole-3-carboxamide (191)

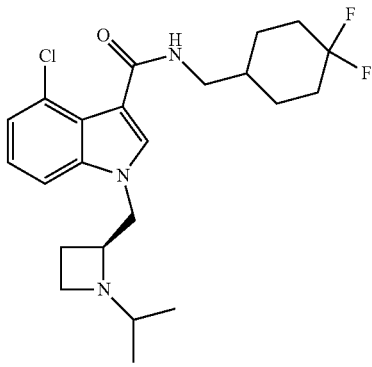 [SMILES: CC(C)N1CC[C@H]1Cn1cc(C(=O)NCC2CCC(F)(F)CC2)c2c(Cl)cccc21]

The title compound was synthesized according to the procedure described in Example 33 using 4-Chloro-1H-indole-3-carboxylic acid (4,4-difluoro-cyclohexyl methyl)-amide (75.00 mg; 0.23 mmol; 1.00 eq.), ((S)-1-Isopropyl-azetidin-2-yl)-methanol (59.31 mg; 0.46 mmol; 2.00 eq.) and (Tributyl-lambda-5-phosphanylidene)-acetonitrile (CMTP) (0.24 ml; 0.92 mmol; 4.00 eq.) [M+H]⁺ 438.

Example 168: Preparation of 1-(azetidin-2-ylmethyl)-4-chloro-N-((3,3-difluoro-1-hydroxycyclohexyl) methyl)-1H-indole-3-carboxamide (124)

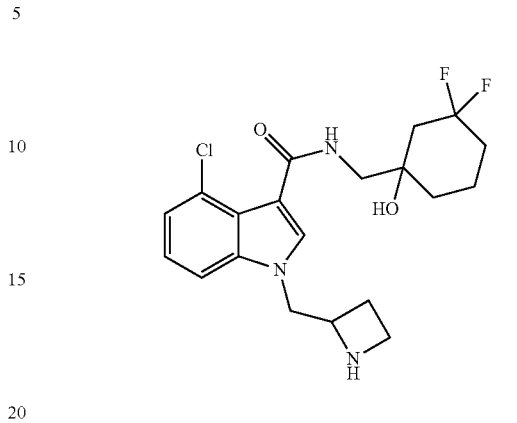

The title compound was synthesized according to the procedure described in Example 33 using 4-chloro-N-((3,3-difluoro-1-hydroxycyclohexyl)methyl)-1H-indole-3-carboxamide (70.00 mg; 0.28 mmol; 1.00 eq.), 2-hydroxymethyl-azetidine-1-carboxylic acid tert-butyl ester (57.36 mg; 0.31 mmol; 2.50 eq.) and (Tributyl-lambda5-phosphanylidene)-acetonitrile (147.72 mg; 0.61 mmol; 4.00 eq.) in Toluene (3 mL).

¹H NMR (400 MHz, DMSO-d₆) δ ppm 8.18 (1H), 7.88 (2H), 7.65 (1H), 7.20 (2H), 4.69 (s, 1H), 4.50 (2H), 3.73 (1H), 3.57 (1H), 3.41 (2H), 3.23 (2H), 2.29 (m, 2H), 2.03 (m, 3H), 1.75 (2H), 1.59 (2H). m/z: 412 [M+H]

Example 169: Preparation of 1-(azetidin-4-ylmethyl)-4-chloro-N-((3,3-difluoro-1-hydroxycyclohexyl) methyl)-1H-indole-3-carboxamide (125)

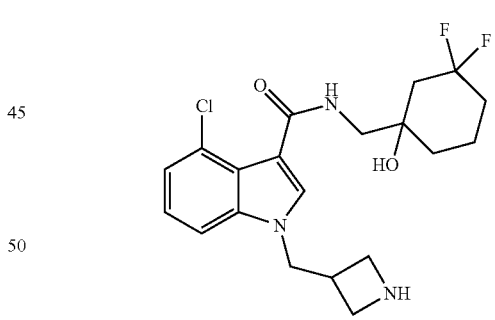

The title compound was synthesized according to the procedure described in Example 33 using 4-chloro-N-((3,3-difluoro-1-hydroxycyclohexyl)methyl)-1H-indole-3-carboxamide (70.00 mg; 0.28 mmol; 1.00 eq.), 3-(hydroxymethyl)-azetidine-1-carboxylic acid tert-butyl ester (57.31 mg; 0.31 mmol; 2.50 eq.) and (Tributyl-lambda5-phosphanylidene)-acetonitrile (147.72 mg; 0.61 mmol; 4.00 eq.) in Toluene (3 mL).

¹H NMR (400 MHz, DMSO-d₆) δ 8.01 (1H), 7.88 (1H), 7.65 (1H), 7.20 (2H), 4.50 (2H), 3.89 (2H), 3.73 (2H), 3.41 (1H), 3.23 (2H), 2.98 (m, 3H), 1.75 (2H), 1.59 (3H). m/z: 412 [M+H].

Example 170: Preparation of (S)-4-chloro-N-((4,4-difluorocyclohexyl)methyl)-1-(pyrrolidin-2-ylmethyl)-1H-indole-3-carboxamide (153)

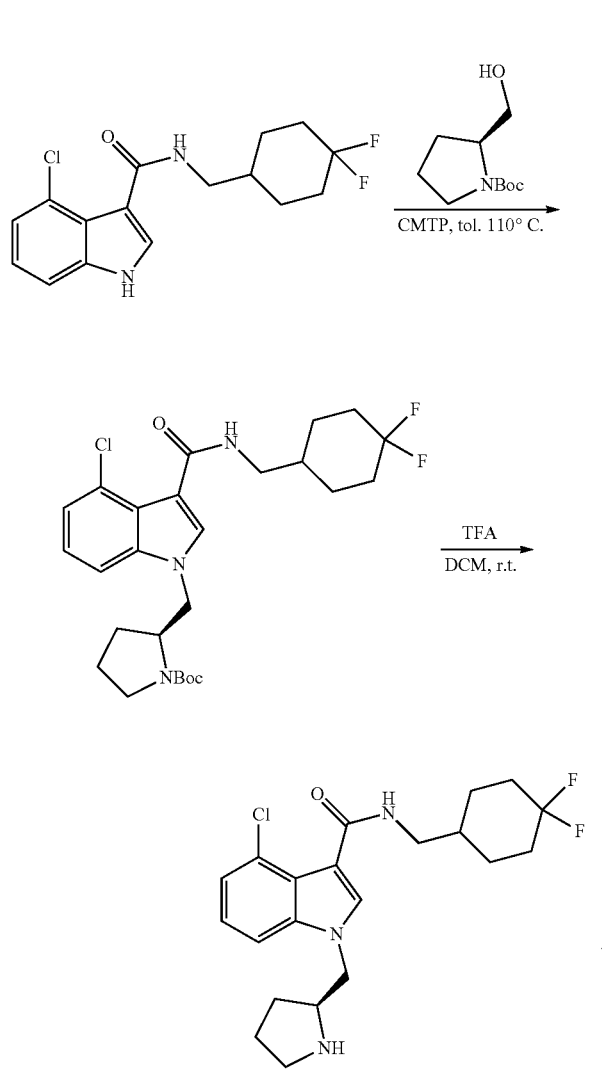

A mixture of 4-chloro-N-((4,4-difluorocyclohexyl)methyl)-1H-indole-3-carboxamide (0.440 g, 1.35 mmol), (S)-tert-butyl 2-(hydroxymethyl)pyrrolidine-1-carboxylate (0.543 g, 2.70 mmol) and CMTP (1.30 g, 5.40 mmol) in anhydrous toluene (4 mL) was stirred at 110° C. for 4 hour under nitrogen. The resulting mixture was concentrated in vacuo to give a residue. A mixture of the residue in DCM (10 ml) and TFA (6 ml) was stirred at r.t. for 2 h. The resulting mixture was concentrated in vacuo, diluted with water, adjusted pH to 9, and extracted with DCM (60 mL×3). The combined organic layers were concentrated in vacuo and purified by prep-HPLC to afford the desired compound as a white solid (0.410 g, 74%).

$^1$H NMR (500 MHz, DMSO-$d_6$): δ 8.06 (t, J=5.8 Hz, 1H), 7.74 (s, 1H), 7.56 (d, J=8.5 Hz, 1H), 7.18-7.12 (m, 2H), 4.13-4.04 (m, 2H), 3.41-3.38 (m, 1H), 3.17-3.15 (m, 2H), 2.83-2.76 (m, 2H), 2.04-2.02 (m, 2H), 1.75-1.59 (m, 8H), 1.36-1.24 (m, 3H) ppm; [M+H]$^+$ 410.1.

Example 171: Preparation of (R)-4-chloro-N-((4,4-difluorocyclohexyl)methyl)-1-(pyrrolidin-2-ylmethyl)-1H-indole-3-carboxamide (154)

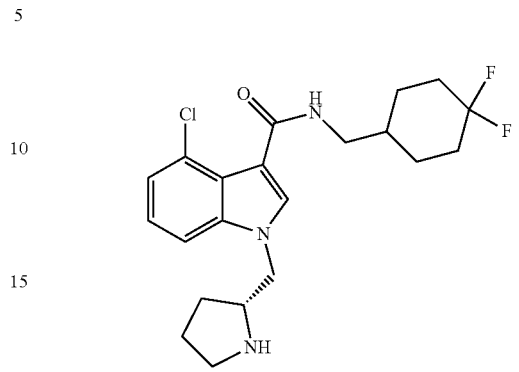

The title compound was synthesized according to the procedure described in Example 170 using 4-chloro-N-((4,4-difluorocyclohexyl)methyl)-1H-indole-3-carboxamide (0.400 g, 1.23 mmol), (R)-tert-butyl 2-(hydroxymethyl) pyrrolidine-1-carboxylate (0.493 g, 2.45 mmol) and CMTP (1.19 g, 4.92 mmol) in anhydrous toluene (4 mL) followed treatment with TFA in DCM to afford the desired compound as a white solid (0.376 g, 76%).

$^1$H NMR (500 MHz, DMSO-$d_6$): δ 8.06 (t, J=5.8 Hz, 1H), 7.74 (s, 1H), 7.56 (d, J=8.5 Hz, 1H), 7.18-7.12 (m, 2H), 4.14-4.06 (m, 2H), 3.41-3.40 (m, 1H), 3.17-3.14 (m, 2H), 2.84-2.77 (m, 2H), 2.04-2.02 (m, 2H) 1.76-1.59 (m, 8H) 1.36-1.24 (m, 3H) ppm; [M+H]$^+$ 410.1.

Example 172: Preparation of 4-chloro-N-((3,3-difluoro-5-methylcyclohexyl)methyl)-1-(pyrrolidin-2-ylmethyl)-1H-indole-3-carboxamide (157)

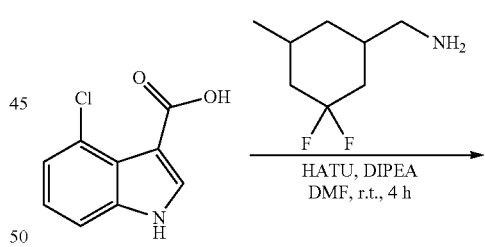

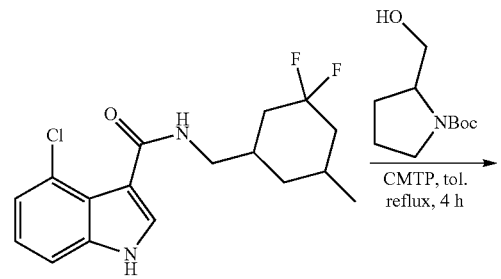

227

-continued

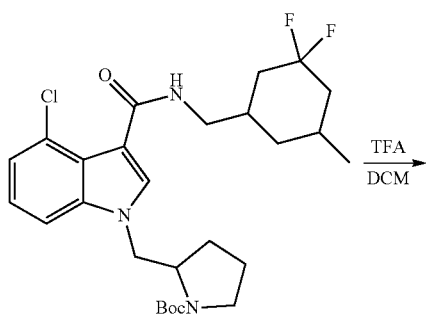

Step 1: Preparation of 4-chloro-N-((3,3-difluoro-5-methylcyclohexyl)methyl)-1H-indole-3-carboxamide

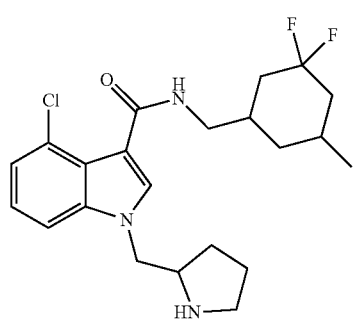

A mixture of 4-chloro-1H-indole-3-carboxylic acid (0.300 g, 1.5 mmol), (3,3-difluoro-5 methylcyclohexyl) methanamine (0.245 g, 1.5 mmol), HATU (0.684 g, 1.8 mmol) and DIPEA (0.387 g, 3.0 mmol) in DMF (15 mL) was stirred at room temperature for 4 h. The mixture was poured into water (15 mL), extracted with EtOAc (40 mL×3). The combined organic layers were dried over Na$_2$SO$_4$, filtered, concentrated and purified by column chromatography on silica gel (petroleum ether:EtOAc=5:1) to give 4-chloro-N-((3,3-difluoro-5-methyl-cyclohexyl)methyl)-1H-indole-3-carboxamide (0.110 g, 22%) as a white solid.

228

Step 2: Preparation of tert-butyl 2-((4-chloro-3-((3,3-difluoro-5-methyl cyclohexyl) methyl carbamoyl)-1H-indol-1-yl)methyl)pyrrolidine-1-carboxylate

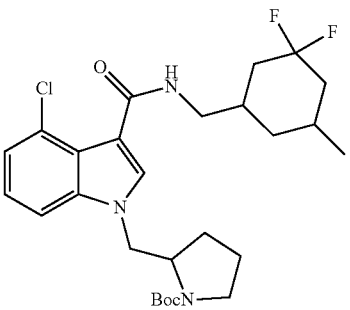

A solution of 4-chloro-N-((3,3-difluoro-5-methylcyclohexyl)methyl)-1H-indole-3-carboxamide (0.110 g, 0.32 mmol), tert-butyl 2-(hydroxymethyl)pyrrolidine-1-carboxylate (0.200 g, 1.0 mmol) and cyanomethylenetributylphosphorane (CMTP) (0.482 g, 2.0 mmol) in toluene (2 mL) was heated at 110° C. under nitrogen for 4 h. The mixture was quenched with water (10 mL) and extracted with EtOAc (10 mL×3). The organic layers were washed with brine, dried over Na$_2$SO$_4$, filtrated and concentrated to give a residue. The residue was purified by column chromatography on silica gel (petroleum ether:EtOAc=5:1) to give tert-butyl2-((4-chloro-3-((3,3-difluoro-5-methylcyclohexyl)methylcarbamoyl)-1H-indol-1-yl)methyl)pyrrolidine-1-carboxylate (0.100 g, 60%) as a white solid.

Step 3: Preparation of 4-chloro-N-((3,3-difluoro-5-methylcyclohexyl)methyl)-1-(pyrrolidin-2-ylmethyl)-1H-indole-3-carboxamide

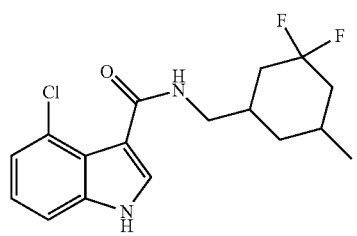 [SMILES: CC1CC(CNC(=O)c2c[nH]c3cccc(Cl)c23)CC(F)(F)C1]

To a solution of 4-chloro-N-((3,3-difluoro-5-methylcyclohexyl)methyl)-1-(pyrrolidin-2-ylmethyl)-1H-indole-3-carboxamide (0.100 g, 0.19 mmol) in DCM (10 mL) was added TFA (10 mL). The reaction mixture was stirred at room temperature for 2 h. The volume was reduced in vacuo to approximately 2 mL. The residue was partitioned between saturated aqueous NaHCO$_3$ (10 mL) and DCM (30 mL). The organic layer was dried over anhydrous Na$_2$SO$_4$, concentrated and purified by Prep-HPLC to give 4-chloro-N-((3,3-difluoro-5-methylcyclohexyl)methyl)-1-(pyrrolidin-2-ylmethyl)-1H-indole-3-carboxamide (0.050 g, 62%) as a white solid.

$^1$H NMR (500 MHz, DMSO-d$_6$) δ 8.08 (t, J=6.0 Hz, 1H), 7.75 (d, J=3.5 Hz, 1H), 7.57 (d, J=8.0 Hz, 1H), 7.17 (t, J=7.5

Hz, 1H), 7.13 (d, J=7.5 Hz, 1H), 4.16-4.12 (m, 1H), 4.07-4.02 (m, 1H), 3.4-3.21 (m, 2H), 3.15-3.09 (m, 1H), 2.85-2.81 (m, 1H), 2.79-2.74 (m, 1H), 2.16 (s, 1H), 2.09-1.97 (m, 3H), 1.79-1.71 (m, 3H), 1.69-1.53 (m, 3H), 1.40-1.31 (m, 2H), 0.99-0.96 (m, 3H) ppm; [M+H]$^+$ 424.1.

Example 173: Preparation of 4-chloro-N-((3,3-difluorocyclohexyl)methyl)-1-(pyrrolidin-2-ylmethyl)-1H-indole-3-carboxamide (156)

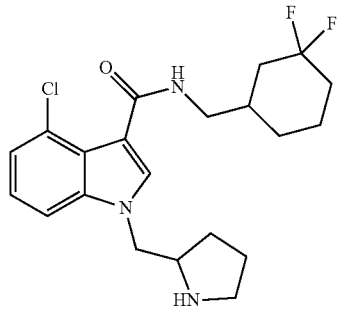 [SMILES: O=C(NCC1CCCC(F)(F)C1)c1cn(CC2CCCN2)c2cccc(Cl)c12]

The title compound was synthesized in line with the procedure described in Example 172 by using 4-chloro-1H-indole-3-carboxylic acid and appropriate amine.

$^1$H NMR (500 MHz, DMSO-d$_6$) δ 8.08 (t, J=6.0 Hz, 1H), 7.76 (s, 1H), 7.57 (d, J=8.0 Hz, 1H), 7.17 (t, J=8.0 Hz, 1H), 7.13 (d, J=7.0 Hz, 1H), 4.16-4.12 (m, 1H), 4.06-4.02 (m, 1H), 3.41-3.37 (m, 1H), 3.24-3.20 (m, 1H), 3.17-3.12 (m, 1H), 2.85-2.80 (m, 1H), 2.79-2.74 (m, 1H), 2.16 (d, J=7.5 Hz, 1H), 1.99 (s, 1H), 1.82-1.63 (m, 6H), 1.61-1.33 (m, 4H), 1.09-1.02 (m, 1H) ppm; [M+H]$^+$ 410.1.

Example 174. 4-chloro-N-((3,3-difluoro-1-hydroxycyclohexyl)methyl)-1-(pyrrolidin-2-ylmethyl)-1H-indole-3-carboxamide (155)

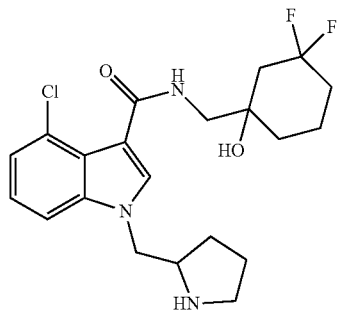 [SMILES: O=C(NCC1(O)CCCC(F)(F)C1)c1cn(CC2CCCN2)c2cccc(Cl)c12]

The title compound was synthesized according to the procedure described in Example 33 using 4-chloro-N-((3,3-difluoro-1-hydroxycyclohexyl)methyl)-1H-indole-3-carboxamide (70.00 mg; 0.28 mmol; 1.00 eq.), 2-hydroxymethyl-pyrrolidine-1-carboxylic acid tert-butyl ester (51.56 mg; 0.31 mmol; 2.50 eq.) and (Tributyl-lambda5-phosphanylidene)-acetonitrile (147.72 mg; 0.61 mmol; 4.00 eq.) in Toluene (3 mL).

$^1$H NMR (400 MHz, DMSO-d$_6$) δ ppm 8.18 (1H), 7.88 (2H), 7.65 (1H), 7.20 (2H), 4.71 (s, 1H), 4.35 (2H), 3.66 (1H), 3.41 (2H), 3.03 (1H), 2.95 (1H), 2.03 (m, 3H), 1.75 (3H), 1.59 (4H). m/z: 426 [M+H]

Example 175: Preparation of 4-chloro-N-((4,4-difluorocyclohexyl)methyl)-1-((1-methylpyrrolidin-2-yl)methyl)-1H-indole-3-carboxamide (158)

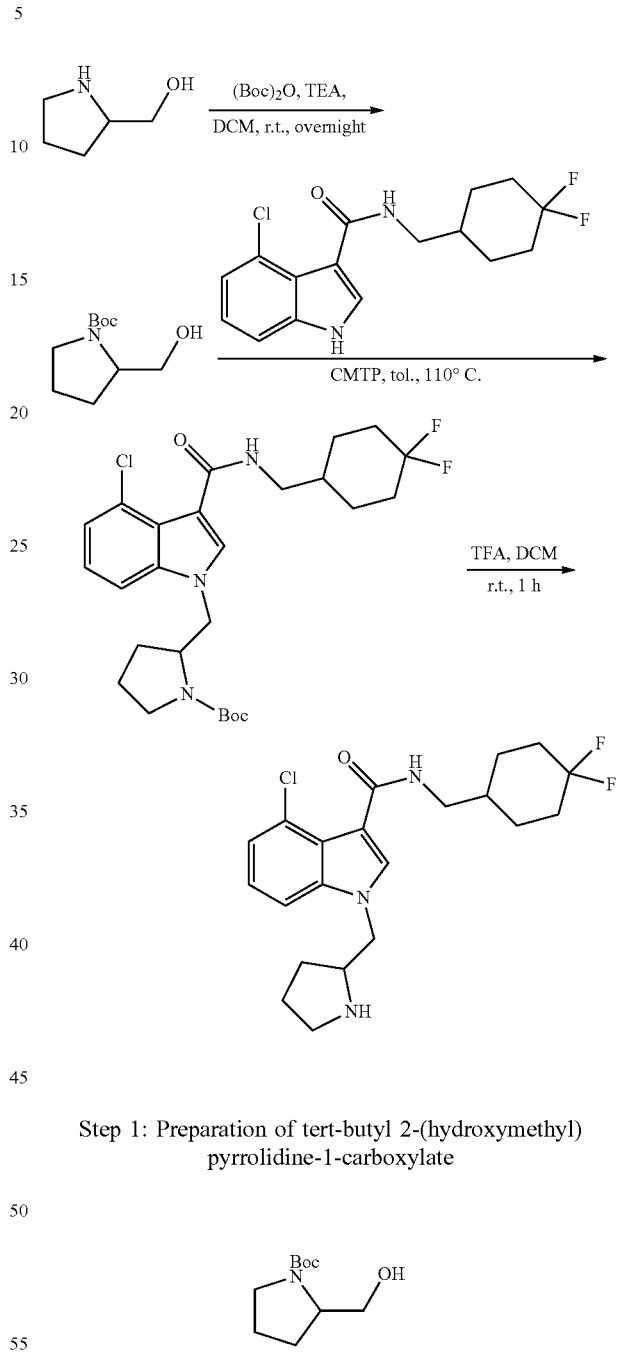

Step 1: Preparation of tert-butyl 2-(hydroxymethyl)pyrrolidine-1-carboxylate

To a stirred mixture of pyrrolidin-2-ylmethanol (0.500 g, 4.95 mmol) and di-tert-butyl dicarbonate (2.16 g, 9.89 mmol) in DCM (10 mL) was added triethylamine (0.751 g, 7.42 mmol). The system was stirred at room temperature overnight. The reaction was quenched with water (10 mL) and extracted with EtOAc (20 mL×3). The combined organic layer was washed with brine (10 mL), dried over anhydrous sodium sulfate, filtered and concentrated in vacuo to afford tert-butyl 2-(hydroxymethyl)pyrrolidine-1-carboxylate (0.900 g, 90%) as light yellow oil.

Step 2: Preparation of tert-butyl 2-((4-chloro-3-((4,4-difluorocyclohexyl) methyl carbamoyl)-1H-indol-1-yl)methyl)pyrrolidine-1-carboxylate

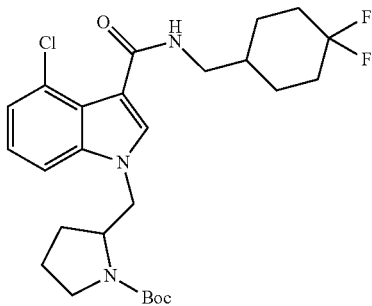 [SMILES: CC(C)(C)OC(=O)N1CCCC1Cn1cc(C(=O)NCC2CCC(F)(F)CC2)c2c(Cl)cccc21]

A mixture of tert-butyl 2-(hydroxymethyl)pyrrolidine-1-carboxylate (0.366 g, 1.82 mmol), 4-chloro-N-((4,4-difluorocyclohexyl)methyl)-1H-indole-3-carboxamide (0.198 g, 0.61 mmol) and CMTP (0.588 g, 2.44 mmol) in toluene (4 mL) was stirred in sealed tube at 110° C. under nitrogen atmosphere for 4 h. The mixture was quenched with water (5 mL) and extracted with EtOAc (10 mL×3). The combined organic layer was washed with brine (15 mL), dried over anhydrous sodium sulfate, filtered and concentrated in vacuo. The residue was purified by column chromatography on silica gel (petroleum ether:EtOAc=2:1) to give tert-butyl 2-((4-chloro-3-((4,4-difluorocyclohexyl) methyl carbamoyl)-1H-indol-1-yl)methyl)pyrrolidine-1-carboxylate (0.800 g, crude) as light yellow solid. LCMS: [M+H]$^+$ 510.1.

Step 3: Preparation of 4-chloro-N-((4,4-difluorocyclohexyl)methyl)-1-(pyrrolidin-2-ylmethyl)-1H-indole-3-carboxamide

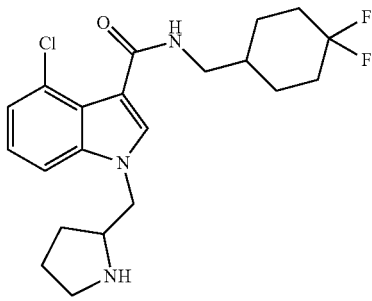 [SMILES: O=C(NCC1CCC(F)(F)CC1)c1cn(CC2CCCN2)c2cccc(Cl)c12]

To a stirred solution of tert-butyl 2-((4-chloro-3-((4,4-difluorocyclohexyl) methylcarbamoyl)-1H-indol-1-yl) methyl)pyrrolidine-1-carboxylate (0.800 g, crude) in DCM (10 mL) was added trifluoroacetic acid (1.5 mL) dropwise. The resulting reaction solution was stirred at room temperature for 1 h, then concentrated in vacuo. The residue was redissolved in DCM (20 mL), washed with aqueous saturated sodium bicarbonate (10 mL×2), brine (10 mL), dried over anhydrous sodium sulfate, filtered and concentrated in vacuo. The residue was purified by column chromatography on silica gel (DCM:methanol=20:1) to afford 4-chloro-N-((4,4-difluorocyclohexyl) methyl)-1-(pyrrolidin-2-ylmethyl)-1H-indole-3-carboxamide (0.100 g, 32%, two steps) as a white solid.

$^1$H NMR (500 MHz, DMSO-d$_6$) δ 8.07 (t, J=6.0 Hz, 1H), 7.75 (s, 1H), 7.57 (d, J=7.5 Hz, 1H), 7.17 (t, J=7.5 Hz, 1H), 7.13 (d, J=7.5 Hz, 1H), 4.19-4.15 (m, 1H), 4.10-4.05 (m, 1H), 3.44-3.42 (m, 2H), 3.16 (t, J=6.0 Hz, 2H), 2.87-2.78 (m, 2H), 2.03-2.02 (m, 2H), 1.85-1.61 (m, 8H), 1.41-1.37 (m, 1H), 1.29-1.24 (m, 2H) ppm; [M+H]$^+$ 410.1.

Example 176: Preparation of 4-chloro-N-((4,4-difluorocyclohexyl)methyl)-1-((1-methylpyrrolidin-2-yl)methyl)-1H-indole-3-carboxamide (170)

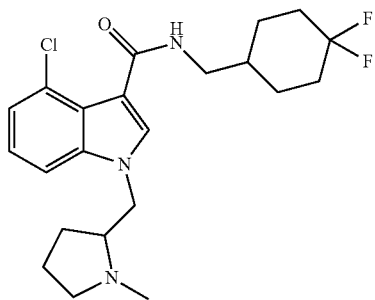 [SMILES: CN1CCCC1Cn1cc(C(=O)NCC2CCC(F)(F)CC2)c2c(Cl)cccc21]

To a stirred solution of 4-chloro-N-((4,4-difluorocyclohexyl)methyl)-1-(pyrrolidin-2-ylmethyl)-1H-indole-3-carboxamide (0.060 g, 0.147 mmol) in DCM (10 mL) was added formaldehyde (0.120 g, 1.47 mmol, 37% in H$_2$O). After the mixture was stirred at room temperature for 1 h, sodium triacetoxyborohydride (0.093 g, 0.44 mmol) was added. The resulting reaction mixture was stirred at room temperature for further 0.5 h, then quenched with water (10 mL) and extracted with DCM (20 mL×3). The combined organic layer was washed with brine (10 mL), dried over anhydrous sodium sulfate, filtered and concentrated in vacuo, the residue was purified by column chromatography on silica gel (DCM:methanol=20:1) to afford 4-chloro-N-((4,4-difluorocyclohexyl)methyl)-1-((1-methylpyrrolidin-2-yl)methyl)-1H-indole-3-carboxamide (0.030 g, 48%) as a white solid.

$^1$H NMR (500 MHz, DMSO-d$_6$) δ 8.08 (t, J=5.5 Hz, 1H), 7.74 (s, 1H), 7.54 (d, J=8.0 Hz, 1H), 7.18 (t, J=8.0 Hz, 1H), 7.13 (d, J=7.5 Hz, 1H), 4.31-4.29 (m, 1H), 4.10-4.06 (m, 1H), 3.16 (t, J=6.5 Hz, 2H), 2.97 (brs, 1H), 2.64-2.59 (m, 1H), 2.26 (s, 3H), 2.19-2.16 (m, 1H), 2.06-2.00 (m, 2H), 1.85-1.70 (m, 6H), 1.60 (brs, 2H), 1.50-1.47 (m, 1H), 1.26-1.24 (m, 2H) ppm; [M+H]$^+$ 424.1.

Example 177: Preparation of (R)-4-chloro-N-((4,4-difluorocyclohexyl)methyl)-1-((1-methyl-5-oxopyrrolidin-2-yl)methyl)-1H-indole-3-carboxamide (182)

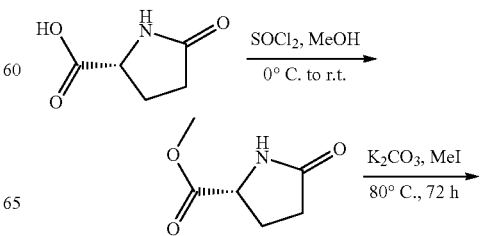

-continued

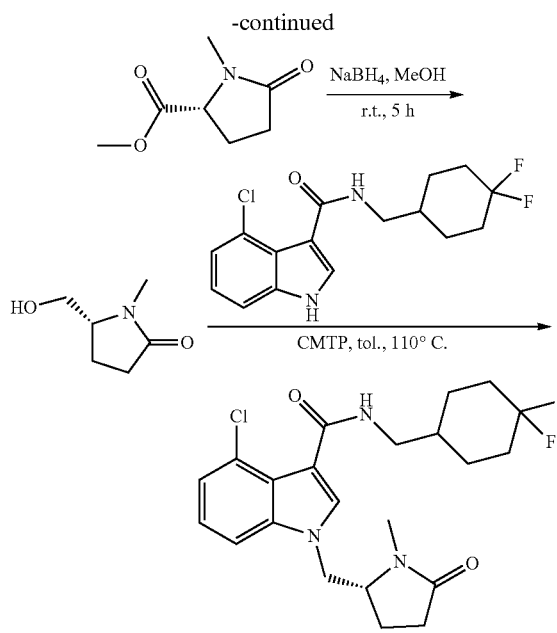

Step 1: Preparation of (R)-methyl 5-oxopyrrolidine-2-carboxylate

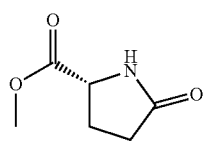

To a mixture of (R)-5-oxopyrrolidine-2-carboxylic acid (10 g, 77 mmol) in MeOH (150 mL) was added dropwise SOCl₂ (10 mL) at 0° C. over 0.5 h. After being stirred at room temperature overnight, the reaction mixture was concentrated and the residue was partitioned between saturated aqueous NaHCO₃ (100 mL) and DCM (250 mL). The separated organic layer was dried over anhydrous Na₂SO₄, filtered and concentrated to give (R)-methyl 5-oxopyrrolidine-2-carboxylate (9.0 g, 91%) as yellow oil.

Step 2: Preparation of (R)-methyl 1-methyl-5-oxopyrrolidine-2-carboxylate

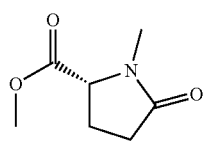

To a mixture of (R)-methyl 5-oxopyrrolidine-2-carboxylate (3.5 g, 24.5 mmol), K₂CO₃ (6.8 g, 49 mmol) in CH₃CN (100 mm) was added CH₃I (6.1 mL, 114 mmol) drop wise at 0° C. After being stirred at 80° C. for 72 h, the reaction mixture was concentrated and the residue was partitioned between water (100 mL) and DCM (350 mL). The separated organic layer was dried over anhydrous Na₂SO₄, filtered and concentrated to give (R)-methyl 1-methyl-5-oxopyrrolidine-2-carboxylate (3.2 g, 84%) as yellow oil.

Step 3: Preparation of (R)-5-(hydroxymethyl)-5-methylpyrrolidin-2-one

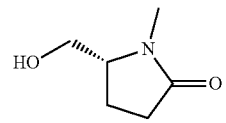

To a solution of (R)-methyl 1-methyl-5-oxopyrrolidine-2-carboxylate (2.5 g, 16 mmol) in MeOH (50 mL) was added NaBH₄ (1.2 g, 32 mmol) in portions at 0° C. After being stirred at room temperature for 5 h, the reaction mixture was concentrated and the residue was partitioned between water (50 mL) and DCM (150 mL). The separated organic layer was dried over Na₂SO₄, filtered, concentrated and purified by column chromatography on silica gel (MeOH:DCM=1:20) to give (R)-5-(hydroxymethyl)-1-methylpyrrolidin-2-one (1.50 g, 72%) as yellow oil.

¹H NMR (400 MHz, DMSO-d₆,) δ 3.86 (m, 1H), 3.62-3.57 (m, 2H), 3.03-2.84 (m, 4H), 2.50-2.43 (m, 1H), 2.34-2.28 (m, 1H), 2.16-2.08 (m, 1H), 2.02-1.95 (m, 1H) ppm.

Step 4: Preparation of (R)-4-chloro-N-((4,4-difluorocyclohexyl)methyl)-1-((1-methyl-5-oxopyrrolidin-2-yl)methyl)-1H-indole-3-carboxamide

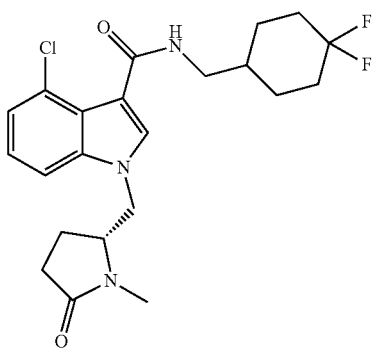 [SMILES: CN1C(=O)CC[C@@H]1Cn1cc(C(=O)NCC2CCC(F)(F)CC2)c2c(Cl)cccc21]

A mixture of (R)-5-(hydroxymethyl)-1-methylpyrrolidin-2-one (0.120 g, 0.92 mmol), 4-chloro-N-((4,4-difluorocyclohexyl)methyl)-1H-indole-3-carboxamide (0.150 g, 0.46 mmol), cyanomethylenetributylphosphorane (CMTP) (0.443 g, 1.84 mmol) in toluene (2 mL) was stirred at 110° C. for 4 h. After being cooled to room temperature, the mixture was partitioned between water (30 mL) and EtOAc (100 mL). The separated organic layer was dried over anhydrous Na₂SO₄, filtered, concentrated and purified by Prep-HPLC to give (R)-4-chloro-N-((4,4-difluorocyclohexyl)methyl)-1-((1-methyl-5-oxopyrrolidin-2-yl)methyl)-1H-indole-3-carboxamide (0.082 g, 41%) as a white solid.

¹H NMR (500 MHz, DMSO-d₆): δ 8.12 (t, J=5.5 Hz, 1H), 7.76 (s, 1H), 7.63 (d, J=8.0 Hz, 1H), 7.23-7.15 (m, 2H), 4.52-4.48 (m, 1H), 4.30-4.26 (m, 1H), 3.98-3.93 (m, 1H), 3.17-3.15 (t, J=6.5 Hz, 2H), 2.67 (s, 3H), 2.22-2.15 (m, 1H), 2.08-1.91 (m, 4H), 1.86-1.65 (m, 6H), 1.29-1.21 (m, 2H) ppm.

Example 178: Preparation of (R)-4-chloro-N-((4,4-difluorocyclohexyl)methyl)-1-((5-oxopyrrolidin-2-yl)methyl)-1H-indole-3-carboxamide (162)

Step 2: Preparation of (R)-4-chloro-N-((4,4-difluorocyclohexyl)methyl)-1-((5-oxopyrrolidin-2-yl)methyl)-1H-indole-3-carboxamide

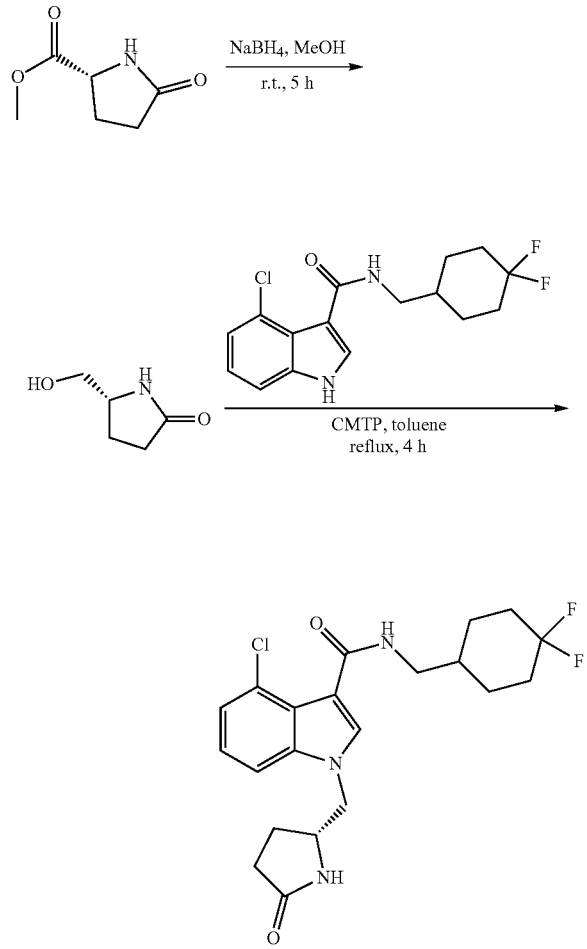

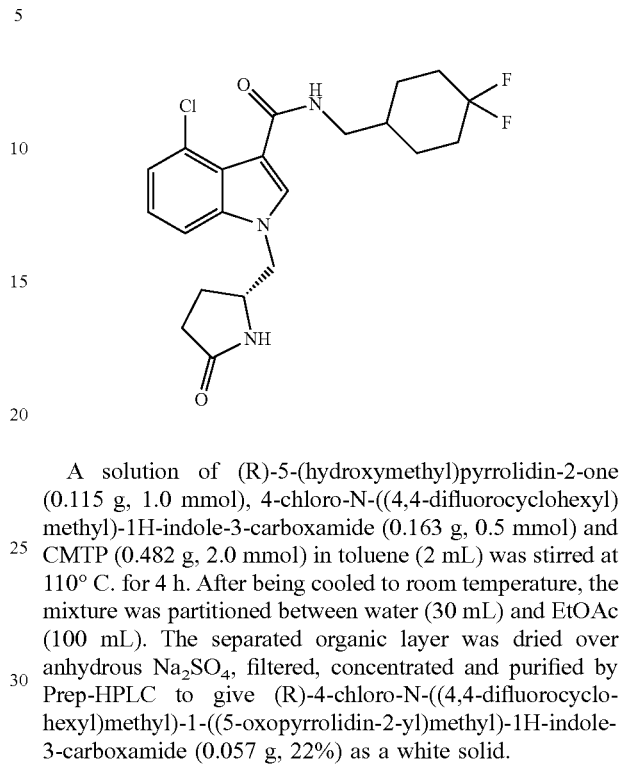

A solution of (R)-5-(hydroxymethyl)pyrrolidin-2-one (0.115 g, 1.0 mmol), 4-chloro-N-((4,4-difluorocyclohexyl)methyl)-1H-indole-3-carboxamide (0.163 g, 0.5 mmol) and CMTP (0.482 g, 2.0 mmol) in toluene (2 mL) was stirred at 110° C. for 4 h. After being cooled to room temperature, the mixture was partitioned between water (30 mL) and EtOAc (100 mL). The separated organic layer was dried over anhydrous $Na_2SO_4$, filtered, concentrated and purified by Prep-HPLC to give (R)-4-chloro-N-((4,4-difluorocyclohexyl)methyl)-1-((5-oxopyrrolidin-2-yl)methyl)-1H-indole-3-carboxamide (0.057 g, 22%) as a white solid.

$^1$H NMR (500 MHz, DMSO-$d_6$) δ 8.09-8.06 (t, J=6.0 Hz, 1H), 7.75 (s, 1H), 7.71 (s, 1H), 7.59 (d, J=8.0 Hz, 1H), 7.21-7.14 (m, 2H), 4.25 (d, J=5.5 Hz, 2H), 3.95-3.93 (m, 1H), 3.18-3.15 (t, J=6.5 Hz, 2H), 2.09-2.00 (m, 5H), 1.86-1.69 (m, 6H), 1.29-1.21 (m, 2H) ppm; [M+H]$^+$ 424.1.

Example 179: Preparation of (S)-4-chloro-N-((4,4-difluoro-1-hydroxy cyclo hexyl)methyl)-1-((1-methylpyrrolidin-2-yl)methyl)-1H-indole-3-carboxamide (169)

Step 1: Preparation of (R)-5-(hydroxymethyl)pyrrolidin-2-one

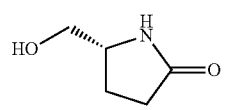

To a solution (R)-methyl 5-oxopyrrolidine-2-carboxylate (6.0 g, 42 mmol) in MeOH (80 mL) was added NaBH$_4$ (3.2 g, 84 mmol) in portions at 0° C. After being stirred at room temperature for 5 h, the reaction mixture was concentrated and the residue was partitioned between water (50 mL) and DCM (150 mL). The separated organic layer was dried over anhydrous $Na_2SO_4$, filtered, concentrated in vacuo. The residue was purified by column chromatography on silica gel (MeOH:DCM=1:10) to give (R)-5-(hydroxymethyl)pyrrolidin-2-one (3.2 g, 73%) as a white solid.

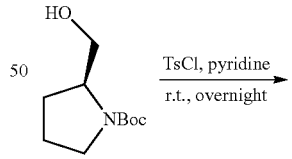

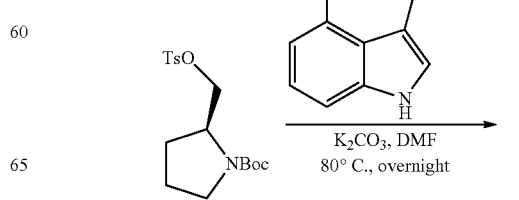

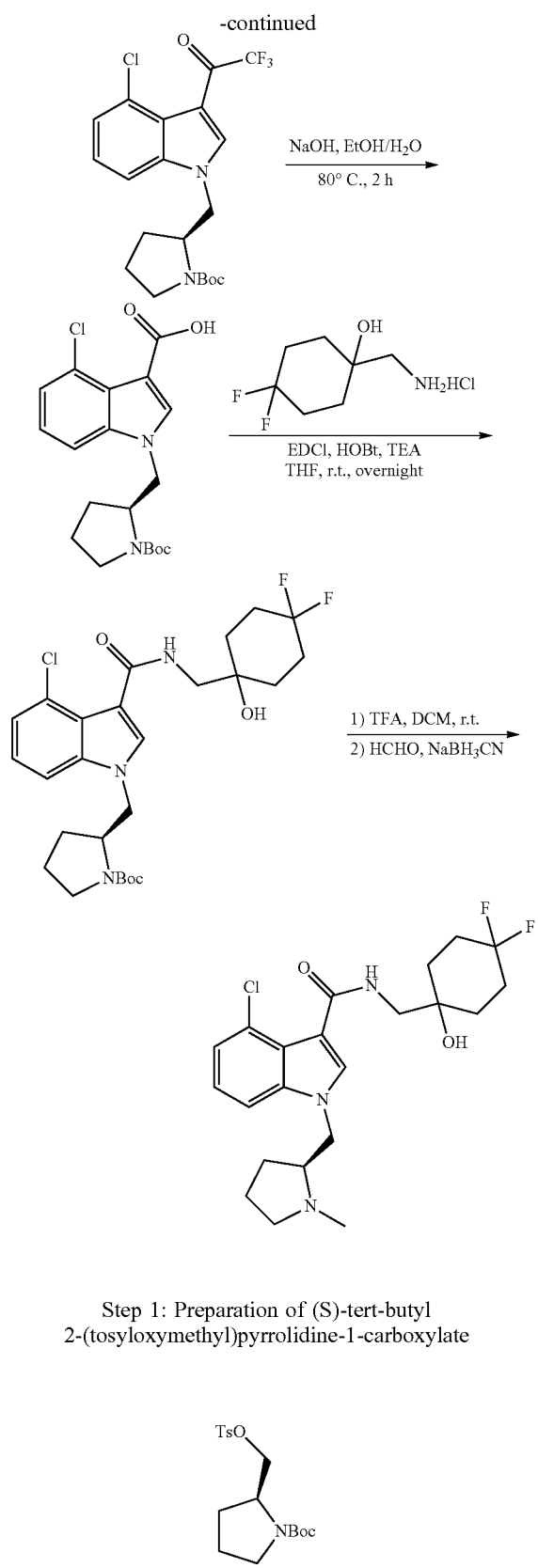

Step 1: Preparation of (S)-tert-butyl 2-(tosyloxymethyl)pyrrolidine-1-carboxylate To a stirred solution of (S)-tert-butyl 2-(hydroxymethyl)pyrrolidine-1-carboxylate (4.02 g, 20.0 mmol) in pyridine (30 mL) was added TsCl (4.58 g, 24.0 mmol) slowly at 0° C. The reaction mixture was stirred at room temperature overnight, diluted with EtOAc (150 mL), washed with saturated aqueous citric acid (100 mL×5) and saturated aqueous NaHCO₃ (100 mL×3), dried over Na₂SO₄, filtered and concentrated in vacuo. The residue was purified by column chromatography on silica gel (0-15% EtOAc in Petroleum Ether) to afford (S)-tert-butyl 2-(tosyloxymethyl)pyrrolidine-1-carboxylate (5.2 g, 73%) as colorless oil.

Step 2: Preparation of (S)-tert-butyl 2-((4-chloro-3-(2,2,2-trifluoroacetyl)-1H-indol-1-yl)methyl)pyrrolidine-1-carboxylate

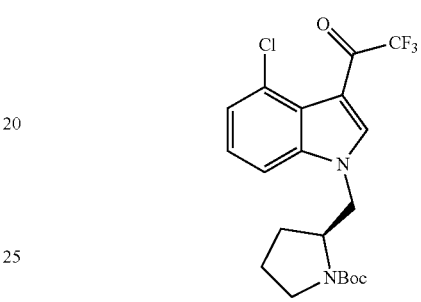

A mixture of 1-(4-chloro-1H-indol-3-yl)-2,2,2-trifluoroethanone (1.24 g, 5.0 mmol), (S)-tert-butyl 2-(tosyloxymethyl)pyrrolidine-1-carboxylate (5.3 g, 15.0 mmol) and K₂CO₃ (8.15 g, 25.0 mmol) in DMF (40 mL) was stirred at 80° C. overnight. The resulting mixture was diluted with EtOAc (150 mL), washed with saturated aqueous NaHCO₃ (100 mL×5), dried over Na₂SO₄, filtered, concentrated in vacuo. The residue was purified by column chromatography on silica gel (0-10% EtOAc in Petroleum Ether) to afford (S)-tert-butyl 2-((4-chloro-3-(2,2,2-trifluoroacetyl)-1H-indol-1-yl)methyl)pyrrolidine-1-carboxylate (1.5 g, 70%) as a white solid.

Step 3: Preparation of (S)-1-((1-(tert-butoxycarbonyl)pyrrolidin-2-yl)methyl)-4-chloro-1H-indole-3-carboxylic acid

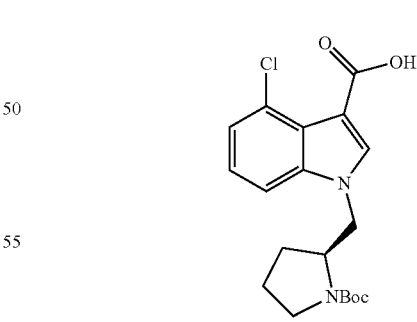

A mixture of (S)-tert-butyl 2-((4-chloro-3-(2,2,2-trifluoroacetyl)-1H-indol-1-yl)methyl)pyrrolidine-1-carboxylate (1.4 g, 3.25 mmol) and NaOH (15 mL, 2 M in H₂O) in EtOH (30 mL) was stirred at 80° C. for 2 h. The resulting mixture was concentrated in vacuo to remove EtOH. The aqueous layer was washed with EtOAc (30 mL), adjusted pH to 4~5, and then extracted with EtOAc (50 mL×3). The combined organic layers were washed with brine (50 mL×3), dried over Na₂SO₄, filtered and concentrated in vacuo to afford (S)-1-((1-(tert-butoxycarbonyl)pyrrolidin-2-yl)methyl)-4-chloro-1H-indole-3-carboxylic acid (1.17 g, 95%) as a white solid.

Step 4: Preparation of (S)-tert-butyl 2-((4-chloro-3-((4,4-difluoro-1-hydroxycyclo hexyl)methylcarbamoyl)-1H-indol-1-yl)methyl)pyrrolidine-1-carboxylate

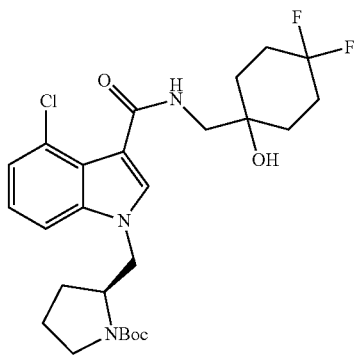 [SMILES: CC(C)(C)OC(=O)N1CCC[C@H]1Cn1cc(C(=O)NCC2(O)CCC(F)(F)CC2)c2c(Cl)cccc21]

A mixture of (S)-1-((1-(tert-butoxycarbonyl)pyrrolidin-2-yl)methyl)-4-chloro-1H-indole-3-carboxylic acid (0.189 g, 0.5 mmol), 1-(aminomethyl)-4,4-difluorocyclohexanol hydrochloride (0.101 g, 0.5 mmol), EDCI (0.144 g, 0.75 mmol), HOBt (0.101 g, 0.75 mmol), TEA (0.253 g, 2.5 mmol) in anhydrous THF (10 mL) was stirred at room temperature overnight. The reaction mixture was diluted with saturated NaHCO₃ (50 mL) and extracted with EtOAc/THF (50 mL×3). The combined organic layers were washed with brine, dried over Na₂SO₄, filtered and concentrated in vacuo. The crude product was purified by re-crystallization from EtOAc/Petroleum Ether to afford (S)-tert-butyl 2-((4-chloro-3-((4,4-difluoro-1-hydroxycyclohexyl)methylcarbamoyl)-1H-indol-1-yl)methyl)pyrrolidine-1-carboxylate (0.172 g, 65%) as a white solid.

Step 5: Preparation of (S)-4-chloro-N-((4,4-difluoro-1-hydroxycyclohexyl)methyl)-1-((1-methyl-pyrrolidin-2-yl)methyl)-1H-indole-3-carboxamide

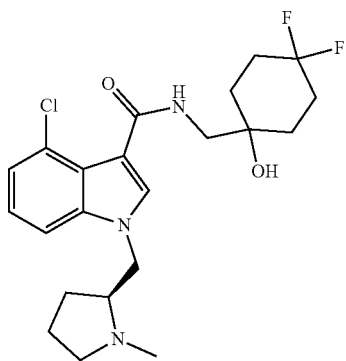 [SMILES: CN1CCC[C@H]1Cn1cc(C(=O)NCC2(O)CCC(F)(F)CC2)c2c(Cl)cccc21]

A mixture of (S)-tert-butyl 2-((4-chloro-3-((4,4-difluoro-1-hydroxycyclohexyl) methylcarbamoyl)-1H-indol-1-yl) methyl)pyrrolidine-1-carboxylate (0.140 g, 0.265 mmol) and TFA (6 mL) in DCM (10 mL) was stirred at room temperature for 2 h. The reaction mixture was concentrated in vacuo to give a residue. A mixture of the residue, HCHO (0.065 g, 0.795 mmol, 37% in H₂O) in DCM (10 mL) was stirred at room temperature for 3 min. followed by the addition of NaBH₃CN (0.050 g, 0.795 mmol). The resulting reaction mixture was stirred at room temperature for 2 h, and then concentrated in vacuo, diluted with aqueous NaHCO₃ (30 mL), and extracted with ethyl acetate (3×30 mL). The combined organic layers were concentrated in vacuo and purified by prep-HPLC to afford (S)-4-chloro-N-((4,4-difluoro-1-hydroxycyclohexyl)methyl)-1-((1-methylpyrrolidin-2-yl)methyl)-1H-indole-3-carboxamide (0.070 g, 60%) as a white solid.

¹H NMR (500 MHz, DMSO-d₆) δ 7.96-7.94 (m, 1H), 7.81 (s, 1H), 7.57-7.55 (m, 1H), 7.21-7.14 (m, 2H), 4.75 (s, 1H), 4.33-4.29 (m, 1H), 4.12-4.07 (m, 1H), 3.32-3.30 (m, 2H), 2.98-2.95 (m, 1H), 2.52-2.50 (m, 1H), 2.25 (s, 3H), 2.18-1.88 (m, 5H), 1.74-1.46 (m, 8H) ppm; [M+H]⁺ 440.1.

Example 180: Preparation of 4-chloro-N-((4,4-difluorocyclohexyl)methyl)-1-((1-isopropylpyrrolidin-2-yl)methyl)-1H-indole-3-carboxamide (196)

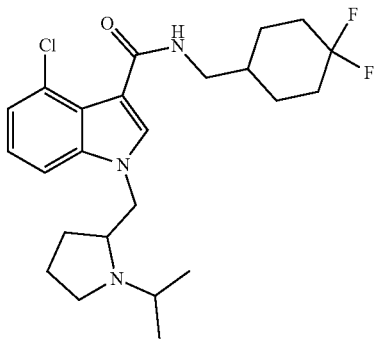 [SMILES: CC(C)N1CCCC1Cn1cc(C(=O)NCC2CCC(F)(F)CC2)c2c(Cl)cccc21]

A mixture of 4-chloro-N-((4,4-difluorocyclohexyl)methyl)-1-(pyrrolidin-2-ylmethyl)-1H-indole-3-carboxamide (0.100 g, 0.24 mmol), acetone (2.0 mL), NaBH₃CN (0.050 g, 0.72 mmol), 4 A molecular sieves (0.050 g) in methanol (2.0 mL) was stirred at 55° C. overnight. The reaction mixture was cooled to room temperature, saturated NaHCO₃ aqueous (30 mL) was added, the mixture was extracted with dichloromethane (20 mL×3). The combined organic layers were dried over MgSO₄, concentrated and purified by pre-HPLC to give 4-chloro-N-((4,4-difluorocyclohexyl)methyl)-1-((1-isopropyl pyrrolidin-2-yl)methyl)-1H-indole-3-carboxamide (0.060 g, 55%) as a white solid.

1H NMR (500 MHz, DMSO-d₆) δ 8.06 (t, J=6.0 Hz, 1H), 7.75 (s, 1H), 7.53 (d, J=8.5 Hz, 1H), 7.20-7.11 (m, 2H), 4.11-3.98 (m, 2H), 3.41 (s, 1H), 3.17-3.14 (m, 3H), 2.82-2.78 (m, 2H), 2.02-2.01 (m, 2H), 1.84-1.69 (m, 5H), 1.59-1.55 (m, 3H), 1.45 (m, 1H), 1.29-1.24 (m, 2H), 1.03 (d, J=6.5 Hz, 3H), 0.92 (d, J=6.5 Hz, 3H) ppm; [M+H]⁺ 452.2.

Example 181: Preparation of 4-chloro-1-((1-cyclo-propylpyrrolidin-2-yl)methyl)-N-((4,4-difluorocyclohexyl)methyl)-1H-indole-3-carboxamide (197)

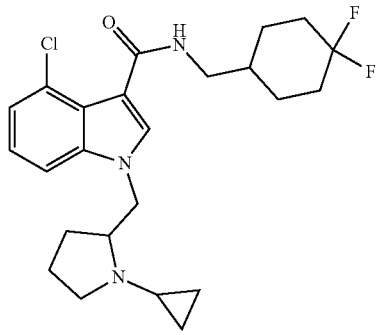 [SMILES: O=C(NCC1CCC(F)(F)CC1)c1cn(CC2CCCN2C2CC2)c2cccc(Cl)c12]

A mixture of 4-chloro-N-((4,4-difluorocyclohexyl)methyl)-1-(pyrrolidin-2-ylmethyl)-1H-indole-3-carboxamide (0.050 g, 0.12 mmol), (1-ethoxycyclopropoxy)trimethylsilane (0.064 g, 0.36 mmol), NaBH$_3$CN (0.015 g, 0.24 mmol), 4 Å molecular sieves (0.045 g), CH$_3$COOH (0.022 g, 0.36 mmol) in methanol (2.0 mL) was stirred at 55° C. overnight. The reaction mixture was cooled to room temperature, saturated NaHCO$_3$ aqueous (30 mL) was added, the mixture was extracted with dichloromethane (20 mL×3). The combined organic layers were dried over MgSO$_4$, concentrated and purified by pre-HPLC to give 4-chloro-1-((1-cyclopropylpyrrolidin-2-yl)methyl)-N-((4,4-difluorocyclohexyl)methyl)-1H-indole-3-carboxamide (0.015 g, 27%) as a yellow solid.

1H NMR (500 MHz, DMSO-d$_6$) δ 8.08 (t, J=6.0 Hz, 1H), 7.75 (s, 1H), 7.51 (d, J=8.0 Hz, 1H), 7.21-7.13 (m, 2H), 4.43-4.38 (m, 1H), 3.99-3.94 (m, 1H), 3.30 (s, 1H), 3.15 (t, J=6.0 Hz, 2H), 3.10-3.00 (m, 2H), 2.04-2.02 (m, 2H), 1.90-1.49 (m, 10H), 1.29-1.19 (m, 2H), 0.53-0.28 (m, 4H) ppm; [M+H]$^+$ 450.1.

Example 182: Preparation of (S)-4-chloro-1-((4,4-difluoro-1-methylpyrrolidin-2-yl) methyl)-N-((4,4-difluorocyclohexyl)methyl)-1H-indole-3-carboxamide (180)

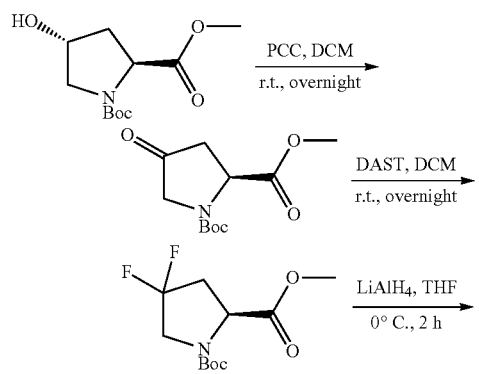

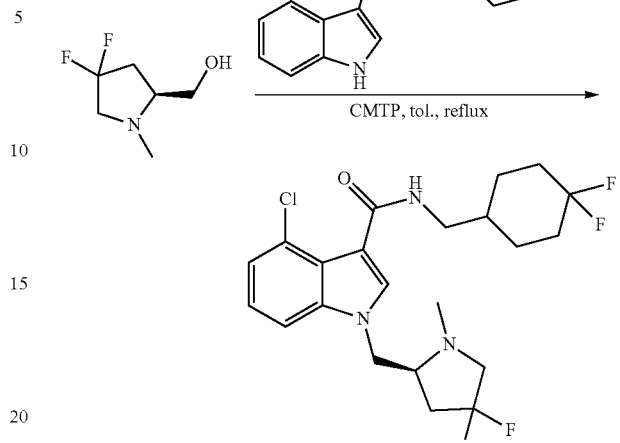

Step 1: Preparation of (S)-1-tert-butyl 2-methyl 4-oxopyrrolidine-1,2-dicarboxylate

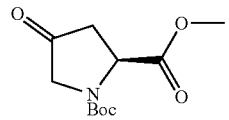 [SMILES: COC(=O)[C@@H]1CC(=O)CN1C(=O)OC(C)(C)C]

To a stirred solution of (2S,4R)-1-tert-butyl 2-methyl 4-hydroxypyrrolidine-1,2-dicarboxy-late (4.0 g, 16.3 mmol) in DCM (100 mL) was added PCC (7.0 g, 32.6 mmol) slowly at 0° C. The reaction mixture was stirred at room temperature overnight, and then filtered and rinsed with DCM (50 mL). The filtrate was concentrated in vacuo and the residue was purified by column chromatograph on silica gel (petroleum ether:EtOAc=5:1) to afford (S)-1-tert-butyl 2-methyl 4-oxopyrrolidine-1,2-dicarboxylate (3.15 g, 79%) as colorless oil.

Step 2: Preparation of (S)-1-tert-butyl 2-methyl 4,4-difluoropyrrolidine-1,2-dicarboxylate

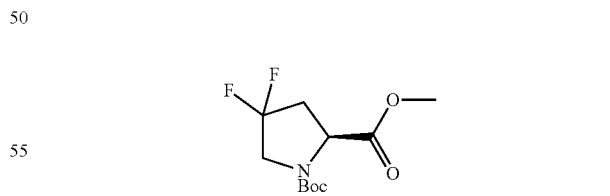

To a stirred solution of (S)-1-tert-butyl 2-methyl 4-oxopyrrolidine-1,2-dicarboxylate (2.9 g, 11.9 mmol) in DCM (20 mL) was added DAST (5.76 g, 35.8 mmol) dropwisely at 0° C. After being stirred at r.t. overnight, the mixture was quenched with water (10 mL) at 0° C., pH was adjusted to 7~8, extracted with DCM (50 mL×3). The organic layers were washed with brine, dried over Na$_2$SO$_4$, filtered, concentrated in vacuo and the residue was purified by column chromatography on silica gel (petroleum ether:EtOAc=10:1)

to afford (S)-1-tert-butyl 2-methyl 4,4-difluoropyrrolidine-1,2-dicarboxylate (2.3 g, 73%) as colorless oil.

Step 3: Preparation of
(S)-(4,4-difluoro-1-methylpyrrolidin-2-yl)methanol

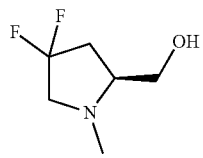

To a stirred solution of LiAlH$_4$ in THF (8.3 mL, 1 M in THF) was added a solution of (S)-1-tert-butyl 2-methyl 4,4-difluoropyrrolidine-1,2-dicarboxylate (2.2 g, 8.3 mmol) in THF (20 mL) dropwise at 0° C. The reaction mixture was stirred for 2 h at 0° C., then quenched by consecutive addition of water (0.3 mL), 15% aqueous NaOH (0.3 mL) and water (1.0 mL). The resulting mixture was filtered through a Celite pad and the filtrate was concentrated in vacuo. The residue was purified by column chromatography on silica gel (petroleum ether:EtOAc=3:1) to give (S)-(4,4-difluoro-1-methylpyrrolidin-2-yl)methanol (0.280 g, 22%) as colorless oil.

Step 4: Preparation of (S)-4-chloro-1-((4,4-difluoro-1-methylpyrrolidin-2-yl)methyl)-N-((4,4-difluorocyclohexyl)methyl)-1H-indole-3-carboxamide

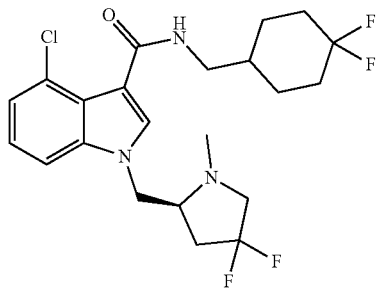 [SMILES: CN1CC(F)(F)C[C@H]1Cn1cc(C(=O)NCC2CCC(F)(F)CC2)c2c(Cl)cccc21]

A mixture of 4-chloro-N-((4,4-difluorocyclohexyl)methyl)-1H-indole-3-carboxamide (0.100 g, 0.31 mmol), (S)-(4,4-difluoro-1-methylpyrrolidin-2-yl)methanol (0.095 g, 0.62 mmol) and cyanomethylenetributylphosphorane (CMTP) (0.296 g, 1.23 mmol) in anhydrous toluene (4 mL) was stirred at 110° C. for 4 h under N$_2$. The resulting mixture was concentrated in vacuo, and the residue was purified by prep-HPLC to afford (S)-4-chloro-1-((4,4-difluoro-1-methylpyrrolidin-2-yl)methyl)-N-((4,4-difluoro cyclohexyl)methyl)-1H-indole-3-carboxamide (0.058 g, 41%) as a white solid.

$^1$H NMR (500 MHz, DMSO-d$_6$) δ 8.12-8.09 (m, 1H), 7.74 (s, 1H), 7.56-7.55 (m, 1H), 7.22-7.14 (m, 2H), 4.49-4.45 (m, 1H), 4.24-4.20 (m, 1H), 3.41-3.35 (m, 1H), 3.17-3.15 (m, 2H), 2.98-2.93 (m, 1H), 2.69-2.60 (m, 1H), 2.33 (s, 3H), 2.30-2.22 (m, 1H), 2.08-1.99 (m, 3H), 1.86-1.70 (m, 5H), 1.29-1.21 (m, 2H) ppm; [M+H]$^+$ 460.1.

Example 183: Preparation of 4-Chloro-1-[1-(2-fluoro-ethyl)-pyrrolidin-2-ylmethyl]-1H-indole-3-carboxylic acid (1-hydroxy-3-methyl-cyclohexylmethyl)-amide (194)

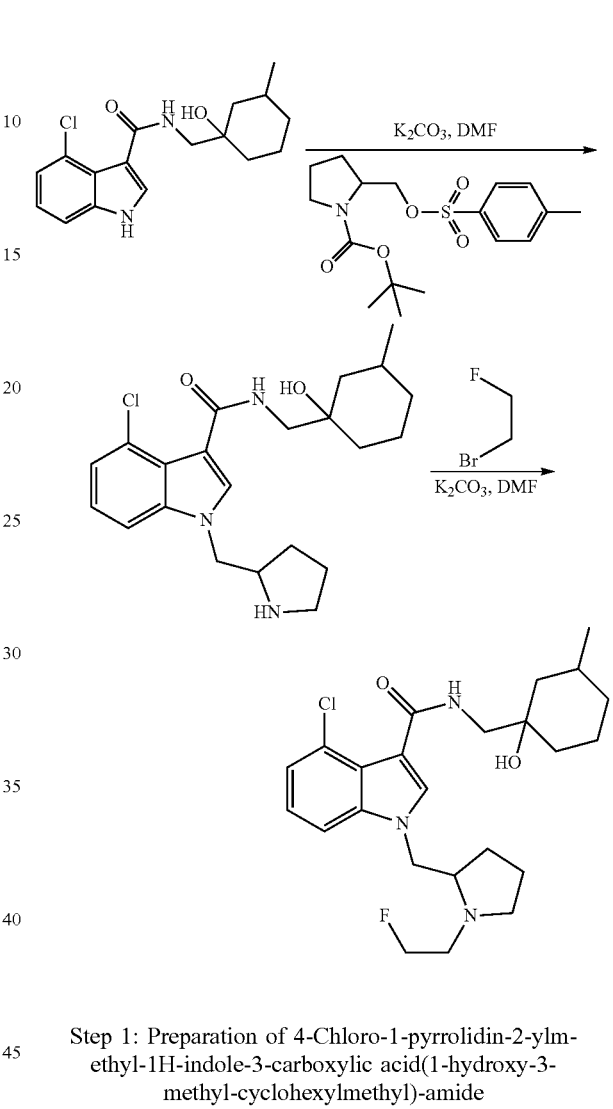

Step 1: Preparation of 4-Chloro-1-pyrrolidin-2-ylmethyl-1H-indole-3-carboxylic acid(1-hydroxy-3-methyl-cyclohexylmethyl)-amide

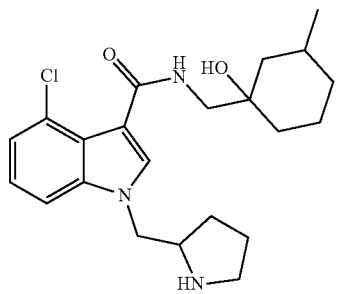 [SMILES: CC1CCCC(O)(CNC(=O)c2cn(CC3CCCN3)c3cccc(Cl)c23)C1]

To a stirred solution of 4-Chloro-1H-indole-3-carboxylic acid (1-hydroxy-3-methyl cyclohexylmethyl)-amide (520 mg, 1.62 mmol, 1.00 eq) in N,N-Dimethyl-formamide (10 mL, 19.23 V) was added K$_2$CO$_3$ (677.45 mg, 4.85 mmol, 3.00 eq) and 2-(Toluene-4-sulfonyloxymethyl)-pyrrolidine- 1-carboxylic acid tert-butyl ester (762.58 mg, 1.94 mmol, 1.20 eq) then the reaction mixture was stirred at 130° C. for 16 h. Completion of the reaction was confirmed by TLC, the reaction mixture was cooled to room temperature, and filtered through celite, washed with ethyl acetate, the filtrate was concentrated under reduced pressure and the crude residue was purified by Prep HPLC to get 4-Chloro-1-pyrrolidin-2-ylmethyl-1H-indole-3-carboxylic acid (1-hydroxy-3-methyl-cyclohexylmethyl)-amide (160 mg, 0.39 mmol, 23.9%) as an off-white solid. [M+H]+ 404.2; LC-MS Purity (254 nm): 97.03%; $t_R$=3.34 min.

Step 2: Preparation of 4-Chloro-1-[1-(2-fluoro-ethyl)-pyrrolidin-2-ylmethyl]-1H-indole-3-carboxylic acid (1-hydroxy-3-methyl-cyclohexylmethyl)-amide

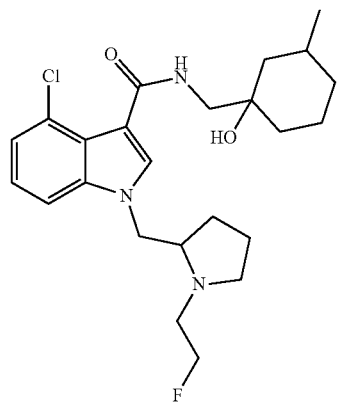 [SMILES: CC1CCCC(O)(CNC(=O)c2cn(CC3CCCN3CCF)c3cccc(Cl)c23)C1]

To a stirred solution of 4-Chloro-1-pyrrolidin-2-ylmethyl-1H-indole-3-carboxylic acid (1-hydroxy-3-methylcyclohexylmethyl)-amide (150 mg, 0.36 mmol, 1.00 eq) in N,N-Dimethyl-formamide (5 ml, 33.33 V) was added $K_2CO_3$ (151.95 mg, 1.09 mmol, 3.00 eq) and 1-Bromo-2-fluoro-ethane (51.70 mg, 0.40 mmol, 1.10 eq) then the reaction mixture was heated in pressure tube at 130° C. for 4 h. After completion of the reaction by TLC, the reaction mixture was cooled to room temperature, and filtered through celite, washed with ethyl acetate, the filtrate was concentrated under reduced pressure to get crude compound which was purified by prep HPLC to get 4-Chloro-1-[1-(2-fluoro-ethyl)-pyrrolidin-2-ylmethyl]-1H-indole-3-carboxylic acid (1-hydroxy-3-methyl-cyclohexylmethyl)-amide (8 mg, 0.02 mmol, 4.8%) as a brown granular solid.

$^1$H NMR (400 MHz, DMSO-$d_6$): δ 7.82 (s, 1H), 7.73 (t, J=6.00 Hz, 1H), 7.57 (dd, J=7.94, 1.08 Hz, 1H), 7.19-7.12 (m, 2H), 4.52 (s, 1H), 4.40 (d, J=2.44 Hz, 1H), 4.22 (d, J=4.76 Hz, 2H), 4.10-4.05 (m, 1H), 3.18 (t, J=4.24 Hz, 2H), 3.08 (d, J=6.76 Hz, 1H), 2.93 (d, J=4.96 Hz, 2H), 2.50-2.49 (m, 2H), 2.28 (d, J=6.88 Hz, 1H), 1.69-1.44 (m, 10H), 1.22 (t, J=3.92 Hz, 2H), 0.82 (d, J=6.60 Hz, 3H), [M+H]+ 450.2.

Example 184: Preparation of 4-chloro-N-((4,4-difluorocyclohexyl)methyl)-1-(pyrrolidin-3-yl)-1H-indole-3-carboxamide (121)

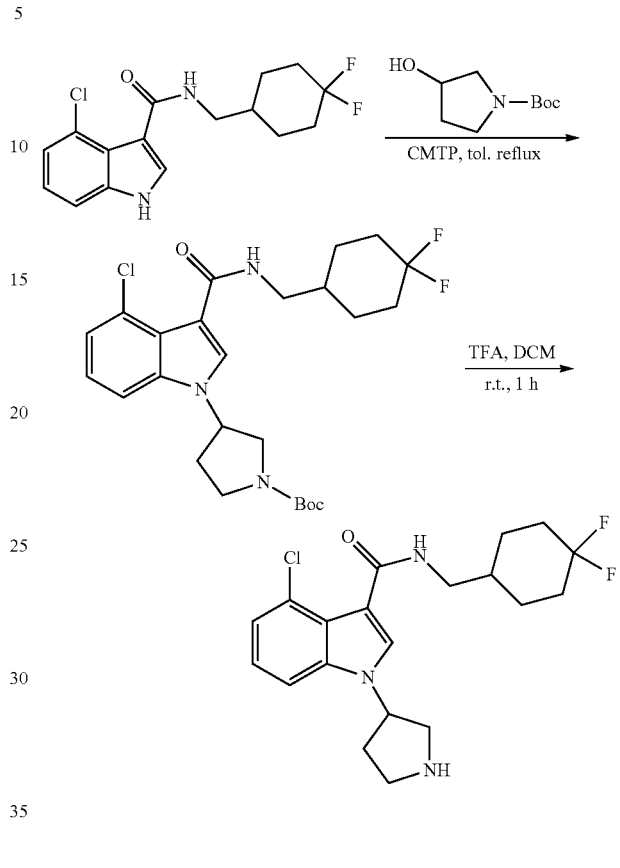

Step 1: Preparation of tert-butyl 3-(4-chloro-3-((4,4-difluorocyclohexyl)methyl carbamoyl)-1H-indol-1-yl)pyrrolidine-1-carboxylate

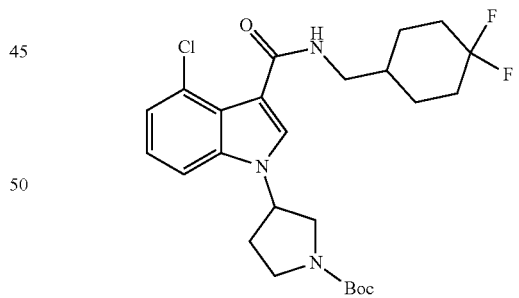

A mixture of tert-butyl 3-hydroxypyrrolidine-1-carboxylate (0.184 g, 0.97 mmol), 4-chloro-N-((4,4-difluorocyclohexyl)methyl)-1H-indole-3-carboxamide (0.160 g, 0.49 mmoL) and CMTP (0.825 g, 1.96 mmol) was stirred in sealed tube at 110° C. for 4 h. The mixture was quenched with water (5 mL) and extracted with EtOAc (10 mL×3). The organic layer was washed with brine, dried over $Na_2SO_4$, filtered and concentrated in vacuo to give tert-butyl 3-(4-chloro-3-((4,4-difluorocyclohexyl)methylcarbamoyl)-1H-indol-1-yl)pyrrolidine-1-carboxylate (0.600 g, crude) as a light yellow solid.

Step 2: Preparation of 4-chloro-N-((4,4-difluorocyclohexyl)methyl)-1-(pyrrolidin-3-yl)-1H-indole-3-carboxamide

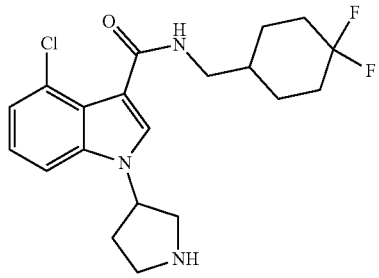 [SMILES: O=C(NCC1CCC(F)(F)CC1)c1cn(C2CCNC2)c2cccc(Cl)c12]

To a stirred solution of tert-butyl 3-(4-chloro-3-((4,4-difluorocyclohexyl) methylcarbamoyl)-1H-indol-1-yl)pyrrolidine-1-carboxylate (0.600 g, crude) in DCM (10 mL) was added TFA (1.5 mL) at room temperature. After stirred at room temperature for 1 h, the reaction was concentrated. The residue was redissolved in DCM (20 mL), washed with saturated aqueous NaHCO$_3$ (10 mL×2), brine (10 mL), dried over Na$_2$SO$_4$ and concentrated to give a residue, which was purified by Pre-HPLC to afford 4-chloro-N-((4,4-difluorocyclohexyl)methyl)-1-(pyrrolidin-3-yl)-1H-indole-3-carboxamide (0.060 g, 31%, two steps) as white solid.
$^1$H NMR (500 MHz, DMSO-d$_6$) δ 7.81-7.75 (m, 2H), 7.56 (t, J=7.5 Hz, 1H), 7.18-7.10 (m, 2H), 5.05-5.00 (m, 1H), 3.28-3.22 (m, 1H), 3.19-3.15 (m, 2H), 3.02-2.88 (m, 4H), 2.34-2.26 (m, 1H), 2.07-1.65 (m, 8H), 1.34-1.26 (m, 2H) ppm; [M+H]$^+$ 396.1.

Example 185: Preparation of 4-chloro-N-((3,3-difluoro-1-hydroxycyclohexyl)methyl)-1-(pyrrolidin-3-yl)-1H-indole-3-carboxamide (120)

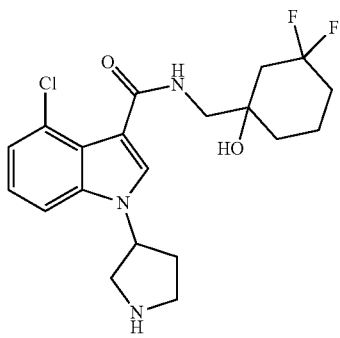 [SMILES: O=C(NCC1(O)CCCC(F)(F)C1)c1cn(C2CCNC2)c2cccc(Cl)c12]

The title compound was synthesized according to the procedure described in Example 33 using 4-chloro-N-((3,3-difluoro-1-hydroxycyclohexyl)methyl)-1H-indole-3-carboxamide (70.00 mg; 0.28 mmol; 1.00 eq.), 3-hydroxypyrrolidine-1-carboxylic acid tert-butyl ester (57.31 mg; 0.31 mmol; 2.50 eq.) and (Tributyl-lambda5-phosphanylidene)-acetonitrile (147.72 mg; 0.61 mmol; 4.00 eq.) in Toluene (3 mL).
$^1$H NMR (400 MHz, DMSO-d$_6$) δ ppm 8.21 (1H), 7.96 (2H), 7.65 (1H), 7.20 (2H), 5.24 (s, 1H), 4.35 (2H), 3.66 (1H), 3.41 (2H), 3.03 (1H), 2.95 (1H), 2.03 (m, 3H), 1.75 (3H), 1.59 (4H). m/z: 412 [M+H]

Example 186. 4-chloro-N-((3,3-difluoro-1-hydroxycyclohexyl)methyl)-1-(pyrrolidin-3-ylmethyl)-1H-indole-3-carboxamide (159)

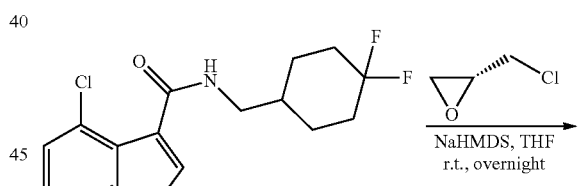

The title compound was synthesized according to the procedure described in Example 33 using 4-chloro-N-((3,3-difluoro-1-hydroxycyclohexyl)methyl)-1H-indole-3-carboxamide (70.00 mg; 0.28 mmol; 1.00 eq.), 3-(hydroxymethyl)-pyrrolidine-1-carboxylic acid tert-butyl ester (61.65 mg; 0.31 mmol; 2.50 eq.) and (Tributyl-lambda5-phosphanylidene)-acetonitrile (147.72 mg; 0.61 mmol; 4.00 eq.) in Toluene (3 mL) by heating at 110° C. for 4 hours. $^1$H NMR (400 MHz, DMSO-d$_6$) δ ppm 8.18 (1H), 7.88 (2H), 7.65 (1H), 7.20 (2H), 4.71 (s, 1H), 4.35 (2H), 3.66 (1H), 3.41 (2H), 3.03 (1H), 2.95 (1H), 2.03 (m, 3H), 1.75 (3H), 1.59 (4H). m/z: 426 [M+H].

Example 187: Preparation of (R)-4-chloro-N-((4,4-difluorocyclohexyl)methyl)-1-((2-oxooxazolidin-5-yl)methyl)-1H-indole-3-carboxamide (126)

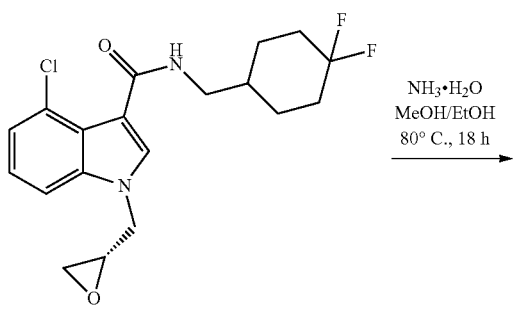

-continued

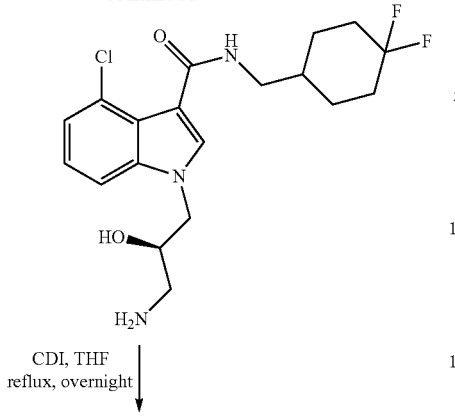

CDI, THF
reflux, overnight

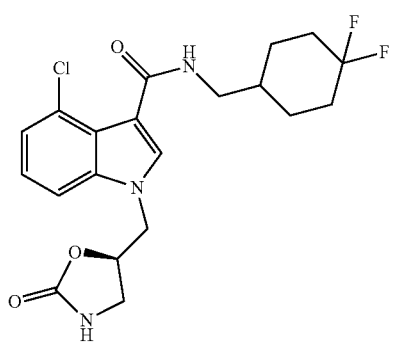

Step 1: Preparation of (S)-4-chloro-N-((4,4-difluorocyclohexyl)methyl)-1-(oxiran-2-ylmethyl)-1H-indole-3-carboxamide To a solution of 4-chloro-N-((4,4-difluorocyclohexyl)methyl)-1H-indole-3-carboxamide (0.300 g, 0.92 mmol) in THF (30 mL) was added NaHMDS (0.93 mL, 0.93 mmol, 1 M in THF) at −78° C. The reaction mixture was stirred at −78° C. for 20 min, then at room temperature for 1 h, (R)-2-(chloromethyl)oxirane (171 mg, 1.86 mmol) was added. After stirred at room temperature for another 18 h, the reaction mixture was quenched with ice-water and extracted with EtOAc (30 mL×3). The separated organic layer was dried over Na₂SO₄, filtered and concentrated. The obtained residue (0.300 g, 84%) was used for the next step without further purification.

Step 2: Preparation of (R)-1-(3-amino-2-hydroxypropyl)-4-chloro-N-((4,4-difluorocyclohexyl)methyl)-1H-indole-3-carboxamide

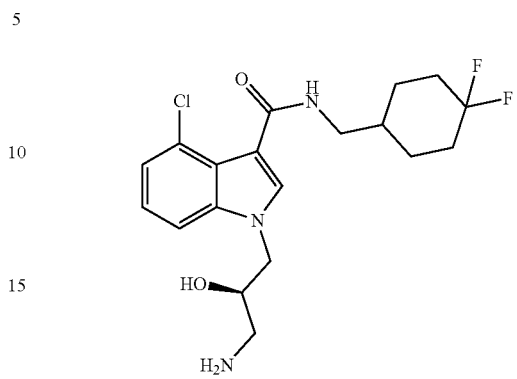

A solution of (S)-4-chloro-N-((4,4-difluorocyclohexyl)methyl)-1-(oxiran-2-ylmethyl)-1H-indole-3-carboxamide (0.300 g, 0.78 mmol) and NH₄OH (8 mL) in MeOH/EtOH (1/1 mL) was stirred at 80° C. for 18 h in sealed tube. After cooled to room temperature, the reaction mixture was concentrated and purified by Pre-HPLC to afford (R)-1-(3-amino-2-hydroxypropyl)-4-chloro-N-((4,4-difluorocyclohexyl)methyl)-1H-indole-3-carboxamide (0.150 g, 48%) as a white solid.
$^1$H NMR (500 MHz, DMSO-$d_6$) δ 8.07 (t, J=5.5 Hz, 1H), 7.70 (d, J=8.0 Hz, 1H), 7.56-7.49 (m, 1H), 7.19-7.12 (m, 2H), 5.04 (s, 1H), 4.33-4.26 (m, 1H), 4.08-4.04 (m, 1H), 3.81-3.70 (m, 1H), 3.17-3.10 (m, 2H), 3.06-3.00 (m, 2H), 2.58-2.53 (m, 2H), 2.04-2.00 (m, 2H), 1.85-1.70 (m, 5H), 1.29-1.21 (m, 2H) ppm; [M+H]⁺ 400.1.

Step 3: Preparation of (R)-4-chloro-N-((4,4-difluorocyclohexyl)methyl)-1-((2-oxooxazolidin-5-yl)methyl)-1H-indole-3-carboxamide

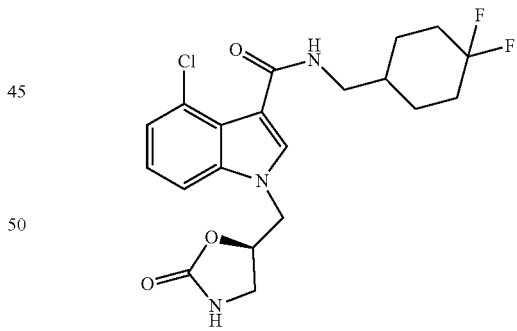

A mixture of (R)-1-(3-amino-2-hydroxypropyl)-4-chloro-N-((4,4-difluorocyclohexyl) methy 1)-1H-indole-3-carboxamide (0.050 g, 0.13 mmol) and CDI (0.081 g, 0.5 mmol) in anhydrous THF (5.0 mL) was refluxed overnight, and then poured into water (15 mL), extracted with EtOAc (30 mL×3). The combined organic layers were dried over Na₂SO₄, filtered and concentrated in vacuo. The residue was purified by Pre-HPLC to afford (R)-4-chloro-N-((4,4-difluorocyclohexyl)methyl)-1-((2-oxooxazolidin-5-yl)methyl)-1H-indole-3-carboxamide (0.020 g, 37%) as a white solid.
$^1$H NMR (500 MHz, DMSO-$d_6$) δ 8.15-8.14 (m, 1H), 7.72 (s, 1H), 7.60 (d, J=8.5 Hz, 1H), 7.21-7.14 (m, 2H), 4.93-4.88 (m, 1H), 4.53-4.45 (m, 2H), 3.60 (t, J=9.0 Hz, 1H), 3.25-3.22 (m, 1H), 3.15 (t, J=6.5 Hz, 2H), 2.08-2.01 (m, 3H), 1.84-1.69 (m, 5H), 1.28-1.20 (m, 2H), ppm; [M+H]+ 425.8.

Example 188: Preparation of 4-chloro-N-((4,4-difluorocyclohexyl)methyl)-1-(piperidin-2-ylmethyl)-1H-indole-3-carboxamide) (173)

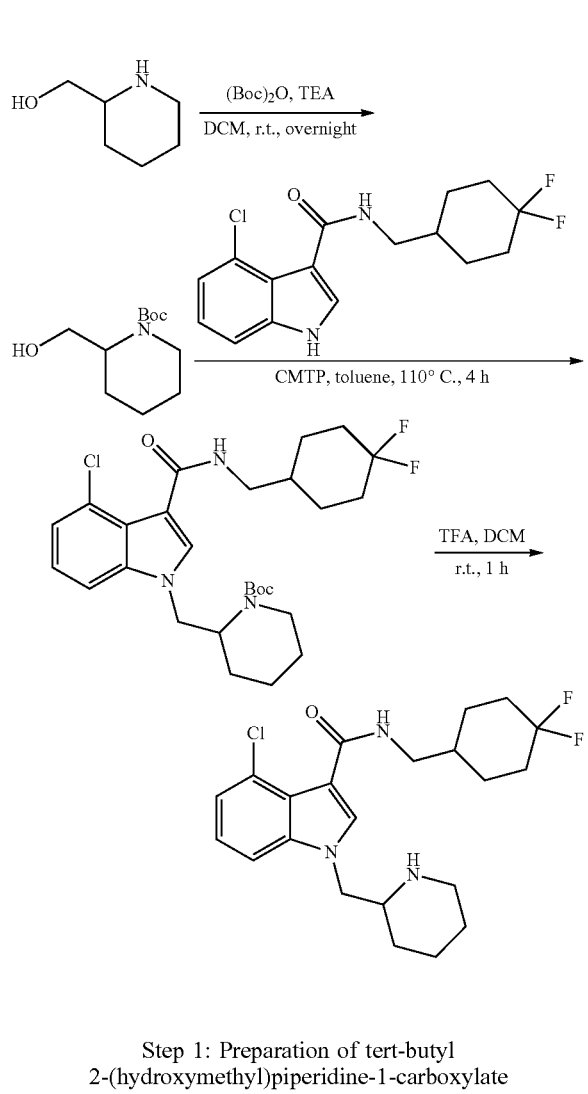

Step 1: Preparation of tert-butyl 2-(hydroxymethyl)piperidine-1-carboxylate

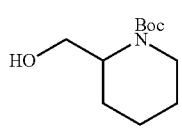

A mixture of piperidin-2-ylmethanol (2.0 g, 16.4 mmol), di-tert-butyl dicarbonate (7.6 g, 34.8 mmoL) and Et₃N (5.28 g, 52.2 mmol, 7.2 mL) in DCM (20 mL) was stirred at room temperature overnight, then quenched with water (20 mL) and extracted with EtOAc (50 mL×3). The combined organic layers were washed with brine, dried over Na₂SO₄, filtered and concentrated in vacuo. The residue was purified by column chromatography on silica gel (petroleum ether:

EtOAc=5:1) to give tert-butyl 2-(hydroxymethyl)piperidine-1-carboxylate (2.3 g, 61%) as white solid.

Step 2: Preparation of tert-butyl 2-((4-chloro-3-((4,4-difluorocyclohexyl)methyl carbamoyl)-1H-indol-1-yl)methyl)piperidine-1-carboxylate

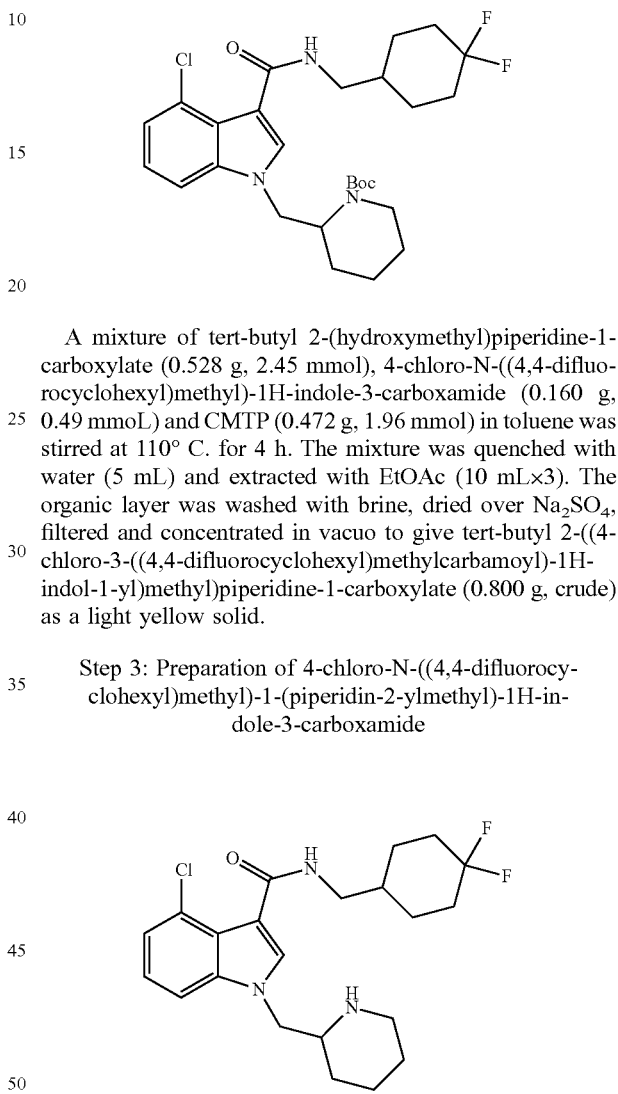

A mixture of tert-butyl 2-(hydroxymethyl)piperidine-1-carboxylate (0.528 g, 2.45 mmol), 4-chloro-N-((4,4-difluorocyclohexyl)methyl)-1H-indole-3-carboxamide (0.160 g, 0.49 mmoL) and CMTP (0.472 g, 1.96 mmol) in toluene was stirred at 110° C. for 4 h. The mixture was quenched with water (5 mL) and extracted with EtOAc (10 mL×3). The organic layer was washed with brine, dried over Na₂SO₄, filtered and concentrated in vacuo to give tert-butyl 2-((4-chloro-3-((4,4-difluorocyclohexyl)methylcarbamoyl)-1H-indol-1-yl)methyl)piperidine-1-carboxylate (0.800 g, crude) as a light yellow solid.

Step 3: Preparation of 4-chloro-N-((4,4-difluorocyclohexyl)methyl)-1-(piperidin-2-ylmethyl)-1H-indole-3-carboxamide To a stirred solution of 2-((4-chloro-3-((4,4-difluorocyclohexyl)methylcarbamoyl)-1H-indol-1-yl)methyl)piperidine-1-carboxylate (0.800 g, crude) in DCM (6 mL) was added TFA (1.5 mL) at room temperature. After stirred at room temperature for 1 h, the reaction was concentrated, the residue was redissolved in DCM (20 mL), washed with saturated aqueous NaHCO₃ (10 mL×2), brine (10 mL), dried over Na₂SO₄ and concentrated to give a residue. The residue was purified by preparative HPLC to afford 4-chloro-N-((4,4-difluorocyclohexyl)methyl)-1-(piperidin-2-ylmethyl)-1H-indole-3-carboxamide (0.036 g, 15%, two steps) as white solid.

¹H NMR (500 MHz, DMSO-d₆) δ 8.09 (t, J=6.0 Hz, 1H), 7.67 (s, 1H), 7.56 (d, J=8.0 Hz, 1H), 7.19-7.12 (m, 2H), 4.10 (d, J=6.5 Hz, 2H), 3.15 (t, J=6.0 Hz, 2H), 2.91 (d, J=6.5 Hz,

1 H), 2.81-2.79 (m, 1H), 2.43-2.40 (m, 1H), 2.04-1.70 (m, 9H), 1.48-1.46 (m, 2H), 1.26-1.23 (m, 4H), 1.07-1.05 (m, 1H) ppm; [M+H]+ 424.1.

Example 189: Preparation of 4-chloro-N-((4,4-difluorocyclohexyl)methyl)-1-(piperidin-3-ylmethyl)-1H-indole-3-carboxamide (174)

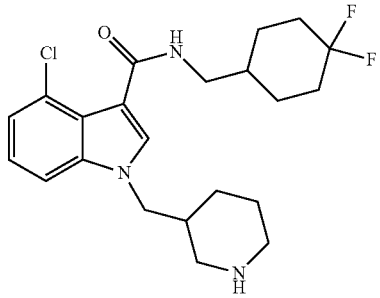 [SMILES: O=C(NCC1CCC(F)(F)CC1)c1cn(CC2CCCNC2)c2cccc(Cl)c12]

The title compound was synthesized according to the procedure described in Example 33 using 4-Chloro-1H-indole-3-carboxylic acid (4,4-difluoro-cyclohexyl methyl)-amide (50.00 mg; 0.15 mmol; 1.00 eq.), 3-hydroxymethyl-piperidine-1-carboxylic acid tert-butyl ester (39.53 mg; 0.38 mmol; 2.50 eq.) and (Tributyl-lambda5-phosphanylidene)-acetonitrile (147.72 mg; 0.61 mmol; 4.00 eq.) in Toluene (3 mL).
$^1$H NMR (400 MHz, DMSO-$d_6$) δ ppm 8.10 (1H), 7.92 (s, 1H), 7.50 (1H), 7.15-7.19 (m, 2H), 4.08 (2H), 3.15 (2H), 2.91 (2H), 2.35 (2H), 2.03 (2H), 1.85 (2H), 1.71 (m, 1H), 1.60 (1H), 1.37 (1H), 1.25 (m, 1H), 0.87 (4H). m/z: 424 [M+H].

Example 190: Preparation of 4-chloro-N-((4,4-difluorocyclohexyl)methyl)-1-(piperidin-4-ylmethyl)-1H-indole-3-carboxamide (175)

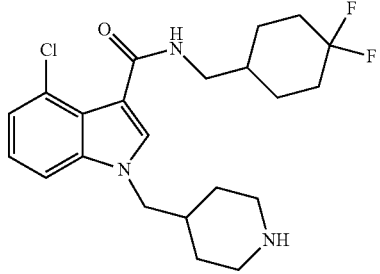 [SMILES: O=C(NCC1CCC(F)(F)CC1)c1cn(CC2CCNCC2)c2cccc(Cl)c12]

The title compound was synthesized according to the procedure described in Example 33 using 4-Chloro-1H-indole-3-carboxylic acid (4,4-difluoro-cyclohexyl methyl)-amide (50.00 mg; 0.15 mmol; 1.00 eq.), 4-hydroxymethyl-piperidine-1-carboxylic acid tert-butyl ester (35.93 mg; 0.38 mmol; 2.50 eq.) and (Tributyl-lambda5-phosphanylidene)-acetonitrile (147.72 mg; 0.61 mmol; 4.00 eq.) in Toluene (3 mL).
$^1$H NMR (400 MHz, DMSO-$d_6$) δ ppm 8.10 (1H), 7.92 (s, 1H), 7.50 (1H), 7.15-7.19 (m, 2H), 4.08 (2H), 3.15 (2H), 2.91 (2H), 2.35 (2H), 2.03 (2H), 1.85 (2H), 1.71 (m, 1H), 1.60 (1H), 1.37 (1H), 1.25 (m, 1H), 0.87 (4H). m/z: 424 [M+H].

Example 191: Preparations of 4-chloro-N-((4,4-difluorocyclohexyl)methyl)-1-(morpholin-3-ylmethyl)-1H-indole-3-carboxamide (164)

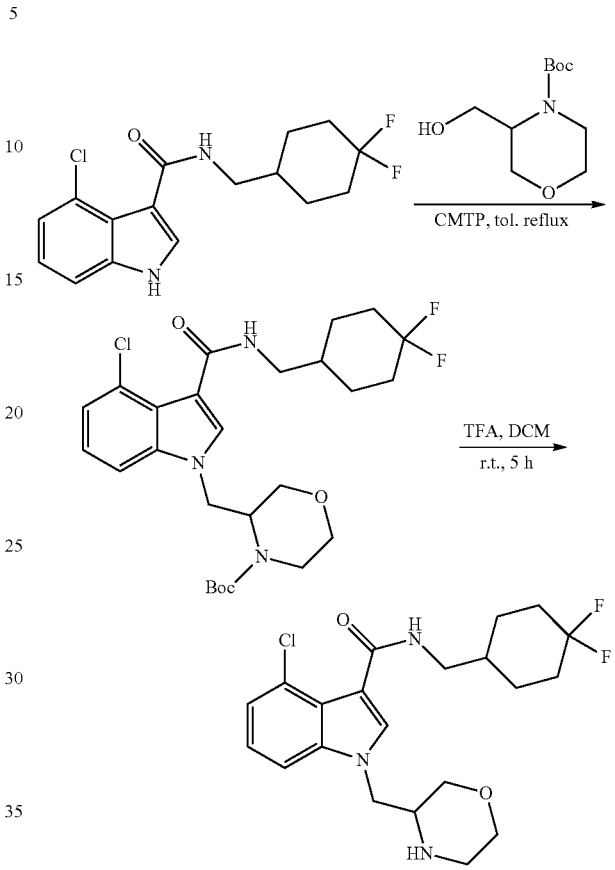

Step 1: Preparation of tert-butyl 3-((4-chloro-3-((4,4-difluorocyclohexyl)methyl carbamoyl)-1H-indol-1-yl)methyl)morpholine-4-carboxylate

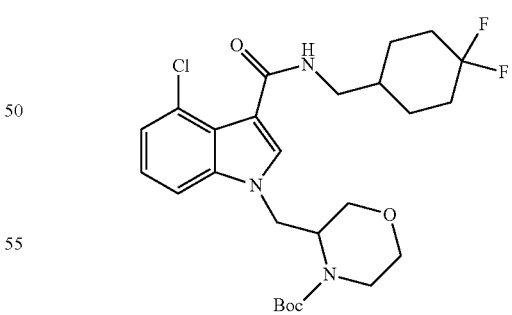

To a mixture of 4-chloro-N-((4,4-difluorocyclohexyl)methyl)-1H-indole-3-carboxamide (0.200 g, 0.61 mmol) and tert-butyl 3-(hydroxymethyl)morpholine-4-carboxylate (0.266 g, 1.22 mmol) in anhydrous toluene (2 mL) was added CMTP (0.591 g, 2.45 mmol) under N2 atmosphere. The reaction mixture was stirred at 110° C. for 4 hours, and then concentrated to dryness and redissolved in EtOAc (10 mL). The organic layer was washed with brine, dried over Na₂SO₄, filtrated and concentrated in vacuo to give a residue, which was used in the next step without further purification.

Step 2: Preparation of 4-chloro-N-((4,4-difluorocyclohexyl)methyl)-1-(morpholin-3-ylmethyl)-1H-indole-3-carboxamide

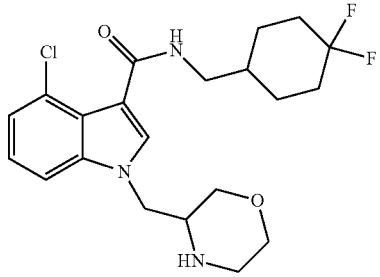 [SMILES: O=C(NCC1CCC(F)(F)CC1)c1cn(CC2COCCN2)c2cccc(Cl)c12]

To a mixture of tert-butyl 3-((4-chloro-3-((4,4-difluorocyclohexyl)methylcarbamoyl)-1H-indol-1-yl)methyl)morpholine-4-carboxylate (0.095 mg, 0.18 mmol) in DCM (10 mL) was added TFA (6 mL). The mixture was stirred at room temperature for 5 hours, quenched with saturated aqueous NaHCO₃ and extracted with DCM (10 mL×3). The organic layer was washed with brine, dried over Na₂SO₄, filtrated and concentrated. The residue was purified by pre-HPLC to give 4-chloro-N-((4,4-difluorocyclohexyl)methyl)-1-(morpholin-3-ylmethyl)-1H-indole-3-carboxamide (0.020 g, 26%) as a light yellow solid.

¹H NMR (500 MHz, CDCl3) δ 7.81 (s, 1H), 7.35 (d, J=7.5 Hz, 1H), 7.24 (d, J=7.0 Hz, 1H), 7.20 (t, J=8.0 Hz, 1H), 6.81 (s, 1H), 4.15-4.03 (m, 2H), 3.83-3.76 (m, 2H), 3.59-3.54 (m, 1H), 3.41 (t, J=6.5 Hz, 2H), 3.35 (t, J=9.0 Hz, 1H), 3.31-3.23 (m, 1H), 2.89-2.80 (m, 2H), 2.13-2.08 (m, 2H), 1.90 (d, J=13.5 Hz, 2H), 1.80-1.67 (m, 4H), 1.44-1.36 (m, 2H) ppm; [M+H]⁺ 426.1.

Example 192: Preparation of 4-chloro-N-((4,4-difluorocyclohexyl)methyl)-1-((4-methylmorpholin-3-yl)methyl)-1H-indole-3-carboxamide (184)

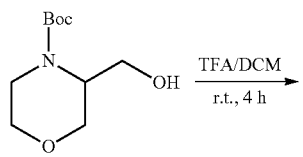

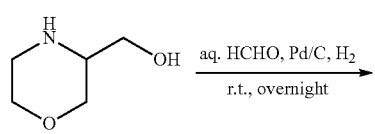

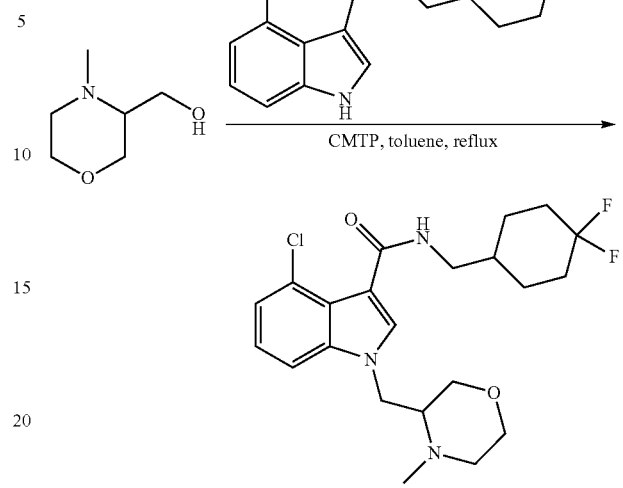

Step 1: Preparation of morpholin-3-ylmethanol

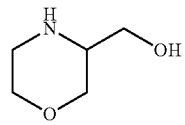

To a mixture of tert-butyl 3-(hydroxymethyl)morpholine-4-carboxylate (1.0 g, 4.6 mmol) in DCM (30 mL) was added TFA (10 mL). The mixture was stirred at room temperature for 3 hours, quenched with saturated aqueous NaHCO₃ and extracted with DCM (30 mL×3). The organic layer was washed with brine, dried over Na₂SO₄, filtrated and concentrated in vacuo to give a residue, which was used in the next step without further purification.

Step 2: Preparation of (4-methylmorpholin-3-yl)methanol

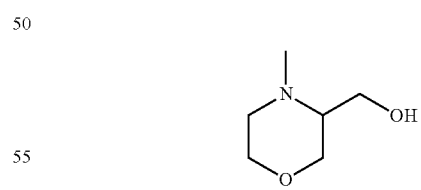

To a mixture of morpholin-3-ylmethanol (0.540 g, 4.6 mmol) in CH3OH (20 mL) was added HCHO (1.86 g, 23 mmol, 37% in H₂O), Pd/C (0.200 g). The mixture was stirred under H₂ (1.0 atm) at room temperature overnight, and then filtered through a Celite pad and the filtrate was concentrated in vacuo. The residue was purified by column chromatography on silica gel (CH3OH:DCM=1:15) to give (4-methylmorpholin-3-yl)methanol (0.130 g, 22%) as a yellow oil.

Step 3: Preparation of 4-chloro-N-((4,4-difluorocyclohexyl)methyl)-1-((4-methyl morpholin-3-yl)methyl)-1H-indole-3-carboxamide

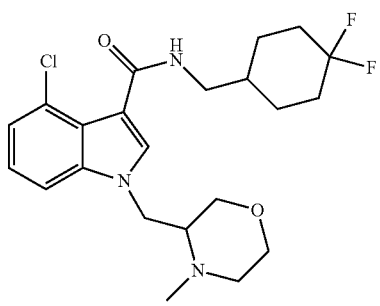 [SMILES: CN1CCOCC1Cn1cc(C(=O)NCC2CCC(F)(F)CC2)c2c(Cl)cccc21]

To a mixture of 4-chloro-N-((4,4-difluorocyclohexyl)methyl)-1H-indole-3-carboxamide (0.134 g, 0.41 mmol) and (4-methylmorpholin-3-yl)methanol (0.054 g, 0.41 mmol) in anhydrous toluene (2 mL) was added CMTP (0.200 g, 0.82 mmol) under $N_2$ atmosphere. The reaction mixture was stirred at 110° C. for 4 hours, concentrated to dryness and redissolved in EtOAc (10 ml). The organic layer was washed with brine, dried over $Na_2SO_4$, filtrated and concentrated. The residue was purified by pre-HPLC to give 4-chloro-N-((4,4-difluorocyclohexyl)methyl)-1-((4-methylmorpholin-3-yl)methyl)-1H-indole-3-carboxamide (0.070 g, 39%) as a white solid.

$^1$H NMR (500 MHz, DMSO-d$_6$) δ 8.13 (t, J=6.0 Hz, 1H), 7.70 (s, 1H), 7.52 (d, J=8.0 Hz, 1H), 7.22-7.14 (m, 2H), 4.55-4.51 (m, 1H), 4.15-4.10 (m, 1H), 3.65 (t, J=6.5 Hz, 1H), 3.50 (m, 2H), 3.35-3.20 (m, 1H), 3.17-3.12 (m, 3H), 2.75-2.72 (m, 1H), 2.55-2.41 (m, 3H), 2.26-2.21 (m, 1H), 2.04-1.99 (m, 2H), 1.85-1.69 (m, 5H), 1.29-1.21 (m, 2H) ppm; [M+H]$^+$ 440.1.

Example 193: Preparation of 4-Chloro-1-(2-methoxy-ethyl)-1H-indole-3-carboxylic acid (2,3-dihydro-benzo[1,4]dioxin-5-yl methyl)-amide (230)

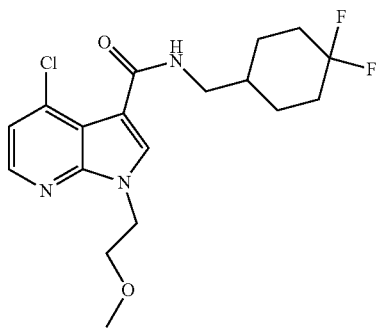 [SMILES: COCCn1cc(C(=O)NCC2CCC(F)(F)CC2)c2c(Cl)ccnc21]

The title compound was synthesized according to the procedure described in Example 2 using 4-Chloro-1-(2-methoxy-ethyl)-1H-pyrrolo[2,3-b]pyridine-3-carboxylic acid (200 mg, 0.68 mmol, 1.00 eq), (4,4-Difluoro-cyclohexyl)-methylamine hydrochloride (192 mg, 1.02 mmol, 1.50 eq), Et$_3$N (0.29 mL, 2.03 mmol, 3.00 eq), Benzotriazol-1-ol (165 mg, 1.02 mmol, 1.50 eq) and EDC (196 mg, 1.02 mmol, 1.50 eq) in dry THF (10 mL, 50 V) to afford 4-Chloro-1-(2-methoxy-ethyl)-1H-pyrrolo[2,3-b]pyridine-3-carboxylic acid (4,4-difluoro cyclohexyl methyl)-amide (130 mg, 0.34 mmol, 51.6%) as a white solid.

$^1$H NMR (400 MHz, DMSO-d$_6$): δ 8.24 (d, J=5.12 Hz, 1H), 8.19 (t, J=6.00 Hz, 1H), 7.95 (s, 1H), 7.27 (d, J=5.12 Hz, 1H), 4.45 (t, J=5.36 Hz, 2H), 3.72 (t, J=5.32 Hz, 2H), 3.23 (s, 3H), 3.15 (t, J=6.32 Hz, 2H), 2.03-2.00 (m, 2H), 1.84-1.81 (m, 3H), 1.77-1.69 (m, 2H), 1.28-1.19 (m, 2H); [M+H]+ 386.2.

Example 194: Preparation of 4-chloro-N-((4,4-difluoro-1-hydroxycyclohexyl) methyl)-1-(2-methoxyethyl)-1H-pyrrolo[2,3-b]pyridine-3-carboxamide (223)

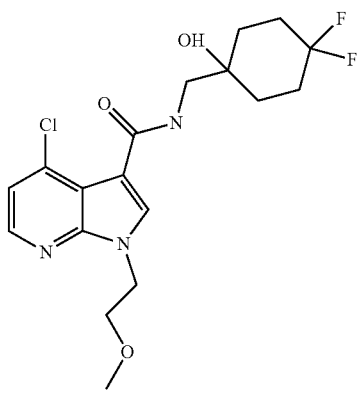 [SMILES: COCCn1cc(C(=O)NCC2(O)CCC(F)(F)CC2)c2c(Cl)ccnc21]

The title compound was synthesized according to the procedure described in Example 33 using 4-Chloro-1H-pyrrolo[2,3-b]pyridine-3-carboxylic acid (4,4-difluoro-1-hydroxy-cyclohexylmethyl)-amide (50.00 mg; 0.15 mmol; 1.00 eq.), 2-methoxy-ethanol (19.28 mg; 0.22 mmol; 1.50 eq.) and (Tributyl-lambda5-phosphanylidene)-acetonitrile (105.32 mg; 0.44 mmol; 3.00 eq.) in Toluene (3 mL).

$^1$H NMR (400 MHz, DMSO-d$_6$) δ ppm 8.26 (1H), 8.09 (m, 1H), 8.05 (1H), 7.31 (s, 1H), 4.77 (m, 1H), 4.47 (2H), 3.74 (2H), 2.62 (3H), 2.09-1.91 (3H), 1.65 (3H). m/z: 402 [M+H].

Example 195: Preparation of 1-Carbamoylmethyl-4-chloro-1H-pyrrolo[2,3-b] pyridine-3-carboxylic acid (4,4-difluoro-1-hydroxy-cyclohexylmethyl)-amide (209)

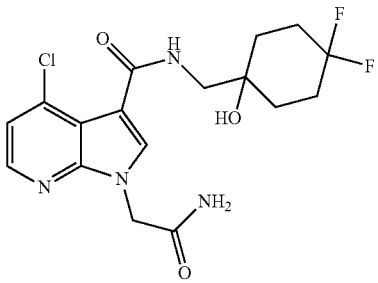 [SMILES: NC(=O)Cn1cc(C(=O)NCC2(O)CCC(F)(F)CC2)c2c(Cl)ccnc21]

The title compound was synthesized according to the procedure described in Example 2 using 1-Carbamoylmethyl-4-chloro-1H-pyrrolo[2,3-b]pyridine-3-carboxylic acid (0.20 g, 0.76 mmol, 1.00 eq), Et$_3$N (0.32 mL, 2.27 mmol, 3.00 eq), 1-Aminomethyl-4,4-difluoro-cyclohexanol (0.15 g, 0.91 mmol, 1.20 eq), EDC (0.29 g, 1.51 mmol, 2.00 eq.) and Benzotriazol-1-ol (0.18 g, 1.13 mmol, 1.50 eq) in dry THF (5 mL, 25 V) to afford 1-Carbamoylmethyl-4-chloro-1H-pyrrolo[2,3-b] pyridine-3-carboxylic acid (4,4-difluoro-1-hydroxy-cyclohexylmethyl)-amide (0.17 g, 0.42 mmol, 55.3%) as a white solid.

$^1$H NMR (400 MHz, DMSO-d$_6$): δ 8.22-8.21 (m, 1H), 8.05-8.01 (m, 2H), 7.67 (s, 1H), 7.29-7.27 (m, 2H), 4.94 (s, 2H), 4.74 (s, 1H), 3.32 (s, 2H), 2.07-1.87 (m, 4H), 1.64-1.62 (m, 4H) ppm; [M+H]+ 401.2.

Example 196: Preparation of 1-Carbamoylmethyl-4-chloro-1H-pyrrolo[2,3-b]pyridine-3-carboxylic acid (4,4-difluorocyclohexylmethyl)-amide (210)

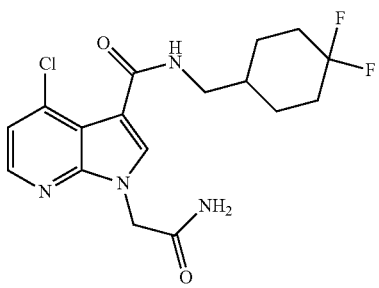 [SMILES: NC(=O)Cn1cc(C(=O)NCC2CCC(F)(F)CC2)c2c(Cl)ccnc21]

The title compound was synthesized according to the procedure described in Example 2 using 1-Carbamoylmethyl-4-chloro-1H-pyrrolo[2,3-b]pyridine-3-carboxylic acid (0.15 g, 0.57 mmol, 1.00 eq) and C-(4,4-Difluoro-cyclohexyl)-methylamine (0.10 g, 0.68 mmol, 1.20 eq) Et$_3$N (0.24 mL, 1.70 mmol, 3.00 eq), EDC (0.22 g, 1.13 mmol, 2.00 eq) and Benzotriazol-1-ol (0.14 g, 0.85 mmol, 1.50 eq) at 0° C., in dry THF (7.50 mL, 50 V) to afford 1-Carbamoylmethyl-4-chloro-1H-pyrrolo[2,3-b]pyridine-3-carboxylic acid (4,4-difluorocyclohexylmethyl)-amide (0.05 g, 0.12 mmol, 21.3%) as a off-white solid.

$^1$H NMR (400 MHz, DMSO-d$_6$): δ 8.21-8.19 (m, 2H), 7.93 (s, 1H), 7.67 (s, 1H), 7.28-7.26 (m, 2H), 4.93 (t, J=6.0 Hz, 2H), 3.13-3.15 (m, 2H), 2.02-2.00 (m, 2H), 1.84-1.81 (m, 3H), 1.77-1.69 (m, 2H), 1.28-1.19 (m, 2H) ppm; [M+H]+ 385.2.

Example 197: Preparation of 1-Carbamoyl methyl-4-chloro-1H-pyrrolo[2,3-b]pyridine-3-carboxylic acid ((1R,3R)-1-hydroxy-3-methyl-cyclohexylmethyl)-amide (214)

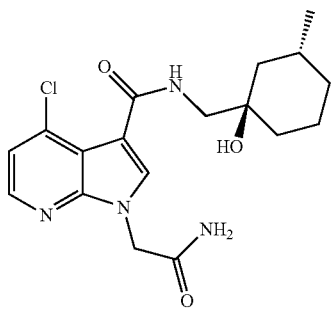 [SMILES: C[C@@H]1CCC[C@](O)(CNC(=O)c2cn(CC(N)=O)c3nccc(Cl)c23)C1]

The title compound was synthesized according to the procedure described in Example 2 using 1-Carbamoylmethyl-4-chloro-1H-pyrrolo[2,3-b] pyridine-3-carboxylic acid (0.15 g, 0.57 mmol, 1.00 eq), (1R,3R)-1-Aminomethyl-3-methyl-cyclohexanol (0.10 g, 0.68 mmol, 1.20 eq), Et$_3$N (0.24 mL, 1.70 mmol, 3.00 eq), (0.22 g, 1.13 mmol, 2.00 eq) and Benzotriazol-1-ol (0.14 g, 0.85 mmol, 1.50 eq) in dry THF (3 mL, 20 V) to afford 1-Carbamoylmethyl-4-chloro-1H-pyrrolo[2,3-b]pyridine-3-carboxylic acid ((1R,3R)-1-hydroxy-3-methyl-cyclohexyl methyl)-amide (0.17 g, 0.44 mmol, 77.2%) as a off-white solid.

$^1$H NMR (400 MHz, DMSO-d$_6$): δ 8.21 (d, J=5.2 Hz, 1H), 7.91 (s, 1H), 7.67 (t, J=Hz, 1H), 7.29 (s, 1H), 4.94 (d, J=Hz, 2H), 4.27 (s, 2H), 3.20 (s, 1H), 1.70-1.43 (m, 6H), 1.23-1.17 (m, 1H), 0.94 (t, J=12.4 Hz, 1H), 0.82 (d, J=6.8 Hz, 3H), 0.76-0.70 (m, 1H) ppm; [M+H]+ 379.2.

Example 198: Preparation of 1-Carbamoyl methyl-4-chloro-1H-pyrrolo[2,3-b]pyridine-3-carboxylic acid ((1S,3S)-1-hydroxy-3-methyl-cyclohexylmethyl)-amide (213)

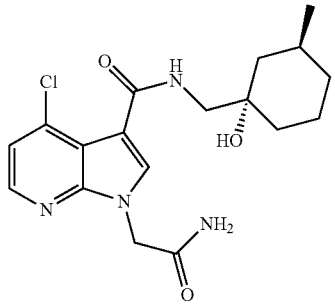 [SMILES: C[C@H]1CCC[C@@](O)(CNC(=O)c2cn(CC(N)=O)c3nccc(Cl)c23)C1]

The title compound was synthesized according to the procedure described in Example 2 using 1-Carbamoylmethyl-4-chloro-1H-pyrrolo[2,3-b]pyridine-3-carboxylic acid (0.15 g, 0.57 mmol, 1.00 eq), (1S,3S)-1-Aminomethyl-3-methyl-cyclohexanol (0.10 g, 0.68 mmol, 1.20 eq), Et$_3$N (0.24 mL, 1.70 mmol, 3 eq), EDC (0.22, g 1.13 mmol, 2.00 eq) and Benzotriazol-1-ol (0.14 g, 0.85 mmol, 1.50 eq) in dry THF (7.5 mL, 50 V) to afford 1-Carbamoyl methyl-4-chloro-1H-pyrrolo[2,3-b]pyridine-3-carboxylic acid ((1S,3S)-1-hydroxy-3-methyl-cyclohexylmethyl)-amide (0.04 g, 0.09 mmol, 15.6%) as a off-white solid.

$^1$H NMR (400 MHz, DMSO-d$_6$) δ 8.22-8.20 (m, 1H), 8.01 (s, 1H), 7.87-7.84 (m, 1H), 7.66 (s, 1H), 7.29-7.27 (m, 2H), 4.93 (s, 2H), 4.26 (s, 1H), 3.21-3.19 (m, 2H), 1.71 (s, 1H), 1.60-1.43 (m, 5H), 1.23-1.17 (m, 1H), 0.97-0.87 (m, 4H), 0.76-0.67 (m, 1H) ppm; [M+H]+ 379.2.

Example 199: Preparation of 1-Carbamoylmethyl-4-chloro-1Hpyrrolo[2,3-b]pyridine-3-carboxylic acid (3,3-difluoro-cyclohexylmethyl)-amide (212)

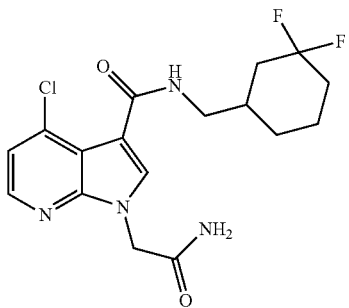 [SMILES: NC(=O)Cn1cc(C(=O)NCC2CCCC(F)(F)C2)c2c(Cl)ccnc21]

The title compound was synthesized according to the procedure described in Example 2 using 1-Carbamoylmethyl-4-chloro-1H-pyrrolo[2,3-b]pyridine-3-carboxylic acid (0.15 g, 0.57 mmol, 1.00 eq), Et₃N (0.24 l, 1.70 mmol, 3.00 eq) and C-(3,3-Difluoro-cyclohexyl)-methylamine hydrochloride (0.13 g, 0.68 mmol, 1.20 eq), EDC (0.22 g, 1.13 mmol, 2.00 eq) and Benzotriazol-1-ol (0.14 g, 0.85 mmol, 1.50 eq) in dry THF (10 mL) to afford 1-Carbamoylmethyl-4-chloro-1Hpyrrolo[2,3-b]pyridine-3-carboxylic acid (3,3-difluoro-cyclohexyl methyl)-amide (0.06 g, 0.14 mmol, 24.8%) as a white solid.

$^1$H NMR (400 MHz, DMSO-$d_6$): δ 8.21-8.20 (m, 2H), 7.95 (s, 1H), 7.67 (s, 1H), 7.28-7.26 (m, 2H), 4.93 (s, 2H), 3.24-3.10 (m, 2H), 1.80-1.22 (m, 6H), 1.09-1.06 (m, 1H) ppm; [M+H]+ 385.2.

Example 200: Preparation of 1-Carbamoylmethyl-4-chloro-1H-pyrrolo[2,3-b]pyridine-3-carboxylic acid (3,3-difluoro-1-hydroxy-cyclohexylmethyl)-amide (211)

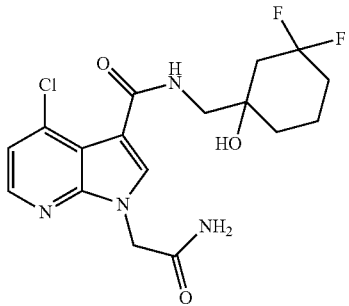 [SMILES: NC(=O)Cn1cc(C(=O)NCC2(O)CCCC(F)(F)C2)c2c(Cl)ccnc21]

The title compound was synthesized according to the procedure described in Example 2 using 1-Carbamoylmethyl-4-chloro-1H-pyrrolo[2,3-b]pyridine-3-carboxylic acid (0.20 g, 0.76 mmol, 1.00 eq), Et₃N (0.24 mL, 1.70 mmol, 3.00 eq) and 1-Aminomethyl-3,3-difluorocyclohexanol hydrochloride (0.18 g, 0.9 mmol, 1.20 eq), EDC (0.29 g, 1.52 mmol, 2.00 eq) and Benzotriazol-1-ol (0.18 g, 1.13 mmol, 1.50 eq) in THF (10 mL) to afford 1-Carbamoylmethyl-4-chloro-1H-pyrrolo [2,3-b]pyridine-3-carboxylic acid (3,3-difluoro-1-hydroxy-cyclohexyl methyl)-amide (0.04 g, 0.11 mmol, 13%) as a white solid.

$^1$H NMR (400 MHz, DMSO-$d_6$): δ 8.22-8.21 (m, 1H), 8.04 (s, 1H), 8.00-7.97 (m, 1H), 7.67 (s, 1H), 7.30-7.27 (m, 2H), 4.94 (s, 2H), 4.69 (s, 1H), 3.41-0.36 (m, 1H), 3.24-3.19 (m, 1H), 2.01-1.89 (m, 3H), 1.75-1.73 (m, 2H), 1.57-1.51 (m, 3H) ppm; [M+H]+ 401.2; LC-MS Purity (254 nm): 96.9%; $t_R$=2.49 min; HPLC Purity (254 nm): 98.2%; $t_R$=2.57 min.

Example 201: Preparation of 4-Chloro-1-oxetan-3-yl-1H-pyrrolo[2,3-b]pyridine-3-carboxylic acid (4,4-difluoro-1-hydroxycyclohexylmethyl)-amide (228)

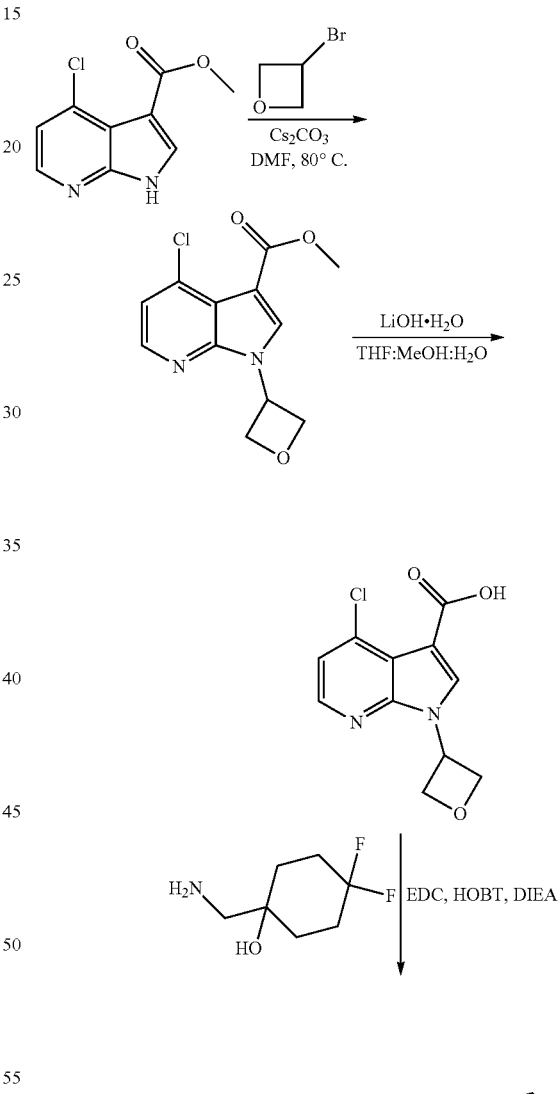

Step 1: Preparation of 4-Chloro-1-oxetan-3-yl-1H-pyrrolo[2,3-b]pyridine-3-carboxylic acid methyl ester

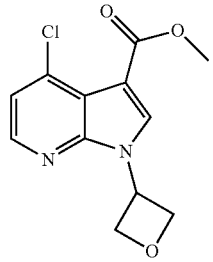 [SMILES: COC(=O)c1cn(C2COC2)c2nccc(Cl)c12]

To a solution of 4-Chloro-1H-pyrrolo[2,3-b]pyridine-3-carboxylic acid methyl ester (500.00 mg; 2.33 mmol; 1.00 eq.) in dry DMF (15 mL, 30 V), and Cesium carbonate (1531.67 mg, 4.65 mmol, 2.00 eq) was added 3-Bromo-oxetane (487.86 mg, 3.49 mmol, 1.50 eq) drop wise at 0° C. and stirred for 18 h at 80° C. Upon completion, monitored by TLC, the reaction mixture was concentrated under reduced pressure and extracted with ethyl acetate. The combined organic layer was washed with water, saturated brine solution, dried over anhydrous sodium sulphate and evaporated under reduced pressure. The crude mass was purified by silica gel column chromatography using 25% Ethyl acetate in petroleum ether as eluent to get the compound 4-Chloro-1-oxetan-3-yl-1H-pyrrolo[2,3-b]pyridine-3-carboxylic acid methyl ester (350 mg, 1.23 mmol, 53.1%) as a off-white solid. $^1$H NMR (400 MHz, DMSO-$d_6$): δ 8.70 (s, 1H), 8.30 (d, J=5.12 Hz, 1H), 7.41 (d, J=5.12 Hz, 1H), 5.99-5.92 (m, 1H), 5.06-4.97 (m, 4H), 3.81 (s, 3H) ppm.

Step 2: Preparation of 4-Chloro-1-oxetan-3-yl-1H-pyrrolo [2,3-b]pyridine-3-carboxylic acid

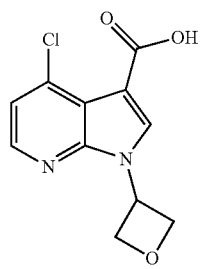 [SMILES: O=C(O)c1cn(C2COC2)c2nccc(Cl)c12]

To a solution of 4-Chloro-1-oxetan-3-yl-1H-pyrrolo[2,3-b]pyridine-3-carboxylic acid methyl ester (350 mg, 1.23 mmol, 1.00 eq) in dry THF (2.00 mL, 26.67 V), Methanol (2.00 mL, 26.67 V) and Water (1.00 mL, 13.33 V), Lithium Hydroxide Monohydrate (22.62 mg, 0.53 mmol, 2.00 eq) was added and stirred for 12 h at RT. Upon completion of reaction, the reaction mixture was concentrated; water was added and acidified with 1.5 N HCl and the solid formed was filtered, washed with water and dried to get 4-Chloro-1-oxetan-3-yl-1H-pyrrolo[2,3-b]pyridine-3-carboxylic acid (250 mg, 0.97 mmol, 78.7%) as a white solid. $^1$H NMR (400 MHz, DMSO-$d_6$): δ 12.33 (brs, 1H), 8.61 (s, 1H), 8.27 (d, J=5.12 Hz, 1H), 7.37 (d, J=5.16 Hz, 1H), 5.98-5.91 (m, 1H), 5.06-5.03 (m, 2H), 5.00-4.97 (m, 2H) ppm.

Example 202: Preparation of 4-Chloro-1-oxetan-3-yl-1H-pyrrolo[2,3-b]pyridine-3-carboxylic acid (4,4-difluoro-1-hydroxycyclohexylmethyl)-amide

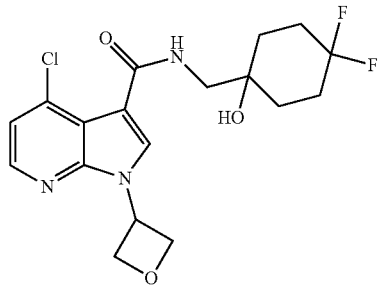 [SMILES: O=C(NCC1(O)CCC(F)(F)CC1)c1cn(C2COC2)c2nccc(Cl)c12]

The title compound was synthesized according to the procedure described in Example 2 using 4-Chloro-1-(2-methoxy-ethyl)-1H-pyrrolo[2,3-b]pyridine-3-carboxylic acid (200 mg, 0.68 mmol, 1.00 eq), (4,4-Difluoro-cyclohexyl)-methylamine hydrochloride (192 mg, 1.02 mmol, 1.50 eq), Et$_3$N (0.29 mL, 2.03 mmol, 3.00 eq), Benzotriazol-1-ol (165 mg, 1.02 mmol, 1.50 eq) and EDC (196 mg, 1.02 mmol, 1.50 eq) in dry THF (10 mL, 50 V) to afford 4-Chloro-1-oxetan-3-yl-1H-pyrrolo[2,3-b]pyridine-3-carboxylic acid (4,4-difluoro-1-hydroxycyclohexylmethyl)-amide (120 mg, 0.30 mmol, 58.5%) as a white solid. $^1$H NMR (400 MHz, DMSO-$d_6$): δ 8.44 (s, 1H), 8.25 (d, J=5.16 Hz, 1H), 8.14 (t, J=6.12 Hz, 1H), 7.32 (d, J=5.12 Hz, 1H), 5.98 (t, J=6.92 Hz, 1H), 5.05-4.97 (m, 4H), 4.71 (s, 1H), 3.31 (s, 2H), 2.07-1.88 (m, 4H), 1.65 (s, 4H), ppm; [M+H]+ 400.2; LC-MS Purity (254 nm): 98.1%; $t_R$=3.15 min; HPLC Purity (254 nm): 97.7%; $t_R$=3.17 min.

Example 203: Preparation of 4-Chloro-1-oxetan-3-yl-1H-pyrrolo[2,3-b]pyridine-3-carboxylic acid ((1S,3S)-1-hydroxy-3-methylcyclohexylmethyl)-amide (221)

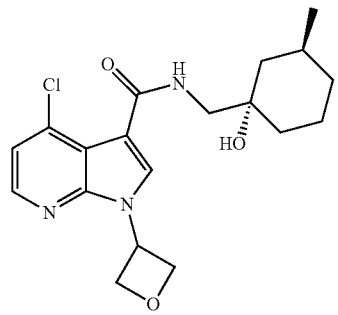 [SMILES: C[C@H]1CCC[C@@](O)(CNC(=O)c2cn(C3COC3)c3nccc(Cl)c23)C1]

The title compound was synthesized according to the procedure described in Example 5 using 4-Chloro-1-oxetan-3-yl-1H-pyrrolo[2,3-b]pyridine-3-carboxylic acid (100 mg, 0.38 mmol, 1.00 eq), Et$_3$N (0.16 mL, 1.13 mmol, 3.00 eq), HATU (295.16 mg, 0.75 mmol, 2.00 eq) and (1S,3S)-1-Aminomethyl-3-methyl-cyclohexanol (66.33 mg, 0.45 mmol, 1.20 eq) in dry DMF (5 mL, 50 V) to afford 4-Chloro-1-oxetan-3-yl-1H-pyrrolo[2,3-b]pyridine-3-carboxylic acid ((1S,3S)-1-hydroxy-3-methyl cyclo hexylmethyl)-amide (30 mg, 0.08 mmol, 20.5%) as a white solid.

¹H NMR (400 MHz, DMSO-d₆): δ 8.44 (s, 1H), 8.25 (d, J=5.16 Hz, 1H), 7.99 (t, J=6.24 Hz, 1H), 7.31 (dd, J=1.16, 5.10 Hz, 1H), 6.00-5.97 (m, 1H), 5.05-4.98 (m, 4H), 4.24 (s, 1H), 3.21 (d, J=5.84 Hz, 2H), 1.72-1.71 (m, 1H), 1.61-1.56 (m, 4H), 1.46-1.44 (m, 1H), 1.24-1.22 (m, 1H), 0.98-0.92 (m, 1H), 0.82 (d, J=6.44 Hz, 3H), 0.77-0.74 (m, 1H); [M+H]+ 378.2.

Example 204: Preparation of 4-Chloro-1-oxetan-3-yl-1H-pyrrolo[2,3-b]pyridine-3-carboxylic acid ((1R,3R)-1-hydroxy-3-methylcyclohexylmethyl)-amide (222)

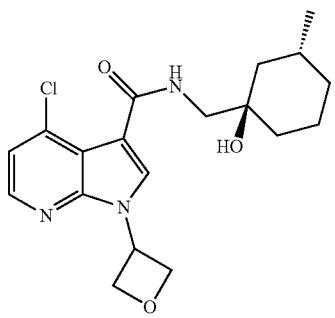 [SMILES: C[C@@H]1CCC[C@](O)(CNC(=O)c2cn(C3COC3)c3nccc(Cl)c23)C1]

The title compound was synthesized according to the procedure described in Example 5 using 4-Chloro-1-oxetan-3-yl-1H-pyrrolo[2,3-b]pyridine-3-carboxylic acid (100 mg, 0.38 mmol, 1.00 eq), Et₃N (0.16 mL, 1.13 mmol, 3.00 eq), HATU (295.16 mg, 0.75 mmol, 2.00 eq) and (1R,3R)-1-Aminomethyl-3-methyl-cyclohexanol (65.39 mg, 0.45 mmol, 1.20 eq) in dry DMF (5 mL, 50 V) to afford 4-Chloro-1-oxetan-3-yl-1H-pyrrolo[2,3-b]pyridine-3-carboxylic acid ((1R,3R)-1-hydroxy-3-methyl cyclohexylmethyl)-amide (30 mg, 0.08 mmol, 20.5%) as a white solid.

¹H NMR (400 MHz, DMSO-d₆): δ 8.44 (s, 1H), 8.24 (d, J=5.12 Hz, 1H), 7.98 (t, J=6.08 Hz, 1H), 7.31 (d, J=5.12 Hz, 1H), 6.02-5.95 (m, 1H), 5.05-4.98 (m, 4H), 4.23 (s, 1H), 3.20 (d, J=6.16 Hz, 2H), 1.72-1.71 (m, 1H), 1.70-1.60 (m, 4H), 1.58-1.55 (m, 1H), 1.25-1.22 (m, 1H), 0.98-0.92 (m, 1H), 0.82 (d, J=6.44 Hz, 3H), 0.77-0.74 (m, 1H) ppm; [M+H]+ 378.2; LC-MS Purity (220 nm): 97.8%; t_R=3.53 min; HPLC Purity (254 nm): 99.5%; t_R=3.52 min.

Example 205: Preparation of 4-chloro-N-((4,4-difluoro-1-hydroxycyclohexyl)methyl)-1-(oxetan-3-ylmethyl)-1H-pyrrolo[2,3-b]pyridine-3-carboxamide (224)

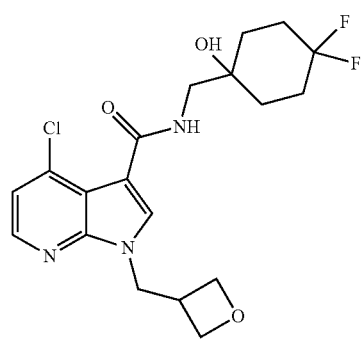 [SMILES: O=C(NCC1(O)CCC(F)(F)CC1)c1cn(CC2COC2)c2nccc(Cl)c12]

The title compound was synthesized according to the procedure described in Example 33 using 4-Chloro-1H-pyrrolo[2,3-b]pyridine-3-carboxylic acid (4,4-difluoro-1-hydroxy-cyclohexylmethyl)-amide (50.00 mg; 0.15 mmol; 1.00 eq.), oxetan-3-yl methanol (20.18 mg; 0.22 mmol; 1.50 eq.) and (Tributyl-lambda5-phosphanylidene)-acetonitrile (105.32 mg; 0.44 mmol; 3.00 eq.) in Toluene (3 mL).

¹H NMR (400 MHz, DMSO-d₆) δ ppm 8.26 (1H), 8.09 (m, 1H), 8.05 (1H), 7.31 (s, 1H), 4.77 (m, 1H), 4.47 (2H), 3.74 (2H), 2.62 (3H), 2.09-1.91 (3H), 1.65 (3H). m/z: 414 [M+H].

Example 206: Preparation of 4-Chloro-1-(tetrahydro-furan-2-ylmethyl)-1H-pyrrolo[2,3-b]pyridine-3-carboxylic acid (4,4-difluoro-cyclohexylmethyl)-amide (227)

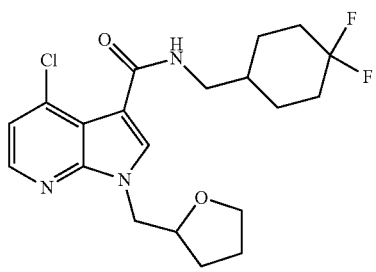 [SMILES: O=C(NCC1CCC(F)(F)CC1)c1cn(CC2CCCO2)c2nccc(Cl)c12]

The title compound was synthesized according to the procedure described in Example 2 using 4-Chloro-1-(tetrahydro-furan-2-ylmethyl)-1H-pyrrolo[2,3-b]pyridine-3-carboxylic acid (150 mg, 0.51 mmol, 1.00 eq), (4,4-Difluoro-cyclohexyl)-methylamine hydrochloride (96 mg, 0.51 mmol, 1.00 eq), Benzotriazol-1-ol (124.57 mg, 0.77 mmol, 1.50 eq), and (3-Dimethylamino-propyl)-ethyl carbodiimide hydrochloride (148 mg, 0.77 mmol, 1.50 eq) in dry THF (25 mL, 166.67 V) as a white solid (130 mg, 0.30 mmol, 58.2%).

¹H NMR (400 MHz, DMSO-d₆): δ 8.23 (d, J=5.12 Hz, 1H), 8.18 (t, J=5.88 Hz, 1H), 7.95 (s, 1H), 7.27 (d, J=5.12 Hz, 1H), 4.35-4.21 (m, 3H), 3.79-3.75 (m, 1H), 3.65-3.59 (m, 1H), 3.15 (t, J=6.40 Hz, 2H), 2.03-2.00 (m, 2H), 1.95-1.90 (m, 1H), 1.82-1.69 (m, 7H), 1.59-1.55 (m, 1H), 1.25-1.23 (m, 2H) ppm; [M+H]+ 412.0; LC-MS Purity (220 nm): 93.6%; t_R=4.18 min; HPLC Purity (254 nm): 93.4%; t_R=4.15 min.

Example 207: Preparation of 4-Chloro-1-(tetrahydro-furan-2-ylmethyl)-1H-pyrrolo [2,3-b]pyridine-3-carboxylic acid ((1S,3S)-1-hydroxy-3-methyl-cyclohexylmethyl)-amide (218)

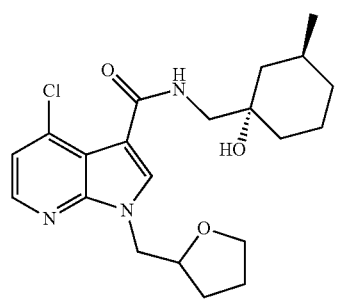 [SMILES: C[C@H]1CCC[C@@](O)(CNC(=O)c2cn(CC3CCCO3)c3nccc(Cl)c23)C1]

The title compound was synthesized according to the procedure described in Example 2 using 4-Chloro-1-(tetra-hydro-furan-2-ylmethyl)-1H-pyrrolo [2,3-b]pyridine-3-carboxylic acid (75 mg, 0.25 mmol, 1.00 eq), (1S,3S)-1-Aminomethyl-3-methyl-cyclohexanol (55.96 mg, 0.38 mmol, 1.50 eq), Benzotriazol-1-ol (62.05 mg, 0.38 mmol, 1.50 eq) and (3-Dimethylamino-propyl)-ethylcarbodiimide hydrochloride (73.80 mg, 0.38 mmol, 1.50 eq) in dry THF (5 mL, 66.67 V) to get 4-Chloro-1-(tetrahydro-furan-2-ylmethyl)-1H-pyrrolo [2,3-b]pyridine-3-carboxylic acid ((1S,3S)-1-hydroxy-3-methyl-cyclohexylmethyl)-amide (30.00 mg, 0.07 mmol, 29.0%) as a off-white solid.

$^1$H NMR (400 MHz, DMSO-d$_6$): δ 8.24 (d, J=5.12 Hz, 1H), 8.02 (s, 1H), 7.89 (t, J=6.08 Hz, 1H), 7.28 (d, J=5.08 Hz, 1H), 4.38-4.21 (m, 4H), 3.79-3.75 (m, 1H), 3.65-3.61 (m, 1H), 3.19 (d, J=6.12 Hz, 2H), 1.94-1.90 (m, 1H), 1.81-1.77 (m, 2H), 1.75-1.73 (m, 1H), 1.61-1.53 (m, 5H), 1.50-1.45 (m, 1H), 1.21-1.20 (m, 1H), 0.97-0.90 (m, 1H), 0.81 (d, J=6.60 Hz, 3H), 0.76-0.72 (m, 1H), ppm; [M+H]+ 406.2; LC-MS Purity (220 nm): 94.1%; t$_R$=3.91 min; HPLC Purity (254 nm): 95.6%; t$_R$=3.88 min.

Example 208: Preparation of 4-Chloro-1-(tetra-hydro-furan-2-ylmethyl)-1H-pyrrolo [2,3-b]pyridine-3-carboxylic acid ((1R,3R)-1-hydroxy-3-methyl-cyclohexylmethyl)-amide (220)

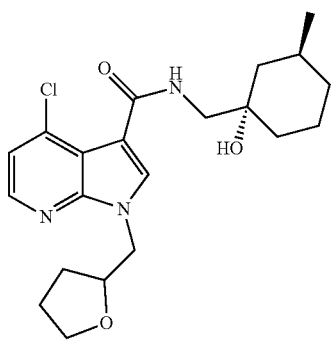 [SMILES: C[C@H]1CCC[C@@](O)(CNC(=O)c2cn(CC3CCCO3)c3nccc(Cl)c23)C1]

The title compound was synthesized according to the procedure described in Example 2 using 4-Chloro-1-(tetra-hydro-furan-2-ylmethyl)-1H-pyrrolo[2,3-b]pyridine-3-carboxylic acid (75 mg, 0.25 mmol, 1.00 eq), (1R,3R)-1-Aminomethyl-3-methyl-cyclohexanol (55.17 mg, 0.38 mmol, 1.50 eq), Benzotriazol-1-ol (62.05 mg, 0.38 mmol, 1.50 eq) and (3-Dimethylamino-propyl)-ethylcarbodiimide hydrochloride (73.80 mg, 0.38 mmol, 1.50 eq) in dry THF (5 mL, 66.67 V) to get 4-Chloro-1-(tetrahydro-furan-2-ylmethyl)-1H-pyrrolo [2,3-b]pyridine-3-carboxylic acid ((1R,3R)-1-hydroxy-3-methyl-cyclohexylmethyl)-amide (30 mg, 0.07 mmol, 29.0%) as a off-white solid.

$^1$H NMR (400 MHz, DMSO-d$_6$): δ 8.24 (d, J=5.08 Hz, 1H), 8.02 (s, 1H), 7.87 (t, J=6.04 Hz, 1H), 7.28 (d, J=5.12 Hz, 1H), 4.35-4.27 (m, 2H), 4.24-4.21 (m, 2H), 3.79-3.76 (m, 1H), 3.65-3.60 (m, 1H), 3.20 (d, J=6.08 Hz, 2H), 1.95-1.91 (m, 1H), 1.83-1.79 (m, 1H), 1.77-1.76 (m, 1H), 1.61-1.50 (m, 5H), 1.45-1.43 (m, 1H), 1.21-1.20 (m, 1H), 0.97-0.94 (m, 1H), 0.82 (d, J=6.60 Hz, 1H), 0.76-0.74 (m, 1H), ppm; [M+H]+ 406.2; LC-MS Purity (220 nm): 94.1%; t$_R$=3.91 min; HPLC Purity (254 nm): 96.6%; t$_R$=3.89 min.

Example 209: Preparation of 4-chloro-N-((4,4-difluoro-1-hydroxycyclohexyl)methyl)-1-((tetrahydro-furan-2-yl)methyl)-1H-pyrrolo[2,3-b]pyridine-3-carboxamide (226)

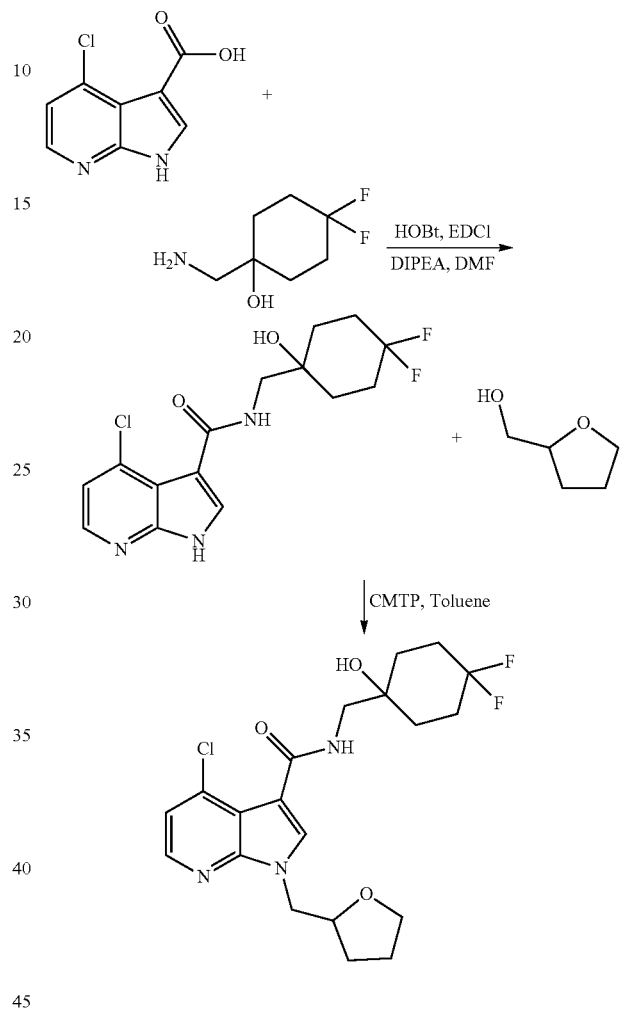

Step 1: Preparation of 4-chloro-N-((4,4-difluoro-1-hydroxycyclohexyl) methyl)-1H-pyrrolo[2,3-b]pyridine-3-carboxamide

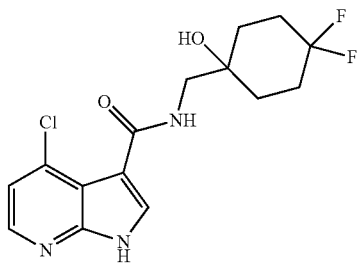 [SMILES: O=C(NCC1(O)CCC(F)(F)CC1)c1c[nH]c2nccc(Cl)c12]

The title compound was synthesized according to the procedure described in Example 2 using 4-Chloro-1H-pyrrolo[2,3-b]pyridine-3-carboxylic acid (500.00 mg; 2.54 mmol; 1.00 eq.), 1-Aminomethyl-4,4-difluoro-cyclohexanol hydrochloride (564.13 mg; 2.80 mmol; 1.10 eq.), (3-Dimethylamino-propyl)-ethyl-carbodiimide hydrochloride (585.08 mg; 3.05 mmol; 1.20 eq.), Benzotriazol-1-ol (412.40 mg; 3.05 mmol; 1.20 eq.) and Ethyl-diisopropylamine (986.13 mg; 7.63 mmol; 3.00 eq.) in DMF (10.0 mL) to provide 4-chloro-N-((4,4-difluoro-1-hydroxy cyclohexyl)methyl)-1H-pyrrolo[2,3-b]pyridine-3-carboxamide (780 mg, 82% yield). m/z: 344 (M+H).

Step 2: Preparation of 4-chloro-N-((4,4-difluoro-1-hydroxycyclohexyl)methyl)-1-((tetrahydrofuran-2-yl)methyl)-1H-pyrrolo[2,3-b]pyridine-3-carboxamide

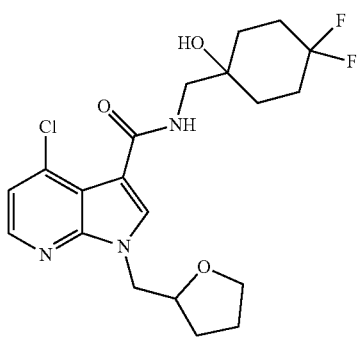 [SMILES: O=C(NCC1(O)CCC(F)(F)CC1)c1cn(CC2CCCO2)c2nccc(Cl)c12]

The title compound was synthesized according to the procedure described in Example 33 using 4-Chloro-1H-pyrrolo[2,3-b]pyridine-3-carboxylic acid (4,4-difluoro-1-hydroxy-cyclohexylmethyl)-amide (50.00 mg; 0.15 mmol; 1.00 eq.), (Tetrahydro-furan-2-yl)-methanol (22.28 mg; 0.22 mmol; 1.50 eq.) and (Tributyl-lambda5-phosphanylidene)-acetonitrile (105.32 mg; 0.44 mmol; 3.00 eq.) in Toluene (3 mL) to provide the desired product (3 mg, 4%).

$^1$H NMR (400 MHz, DMSO-d$_6$) δ ppm 8.26 (1H), 8.11 (s, 1H), 7.31 (1H), 4.74 (1H), 3.83 (1H), 3.65 (1H), 3.53 (1H), 2.85 (1H), 2.02-1.86 (m, 3H), 1.65 (3H). m/z: 428 [M+H].

Example 210: Preparation of 4-Chloro-1-(tetrahydro-furan-3-ylmethyl)-1H-pyrrolo[2,3-b]pyridine-3-carboxylic acid (4,4-difluoro-cyclohexylmethyl)-amide (230)

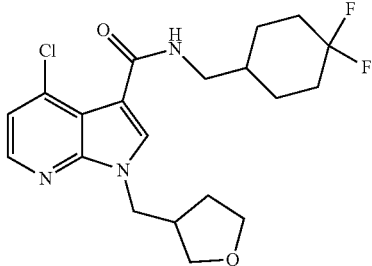 [SMILES: O=C(NCC1CCC(F)(F)CC1)c1cn(CC2CCOC2)c2nccc(Cl)c12]

The title compound was synthesized according to the procedure described in Example 5 using 4-Chloro-1-(tetrahydro-furan-3-ylmethyl)-1H-pyrrolo[2,3-b]pyridine-3-carboxylic acid (100 mg, 0.34 mmol, 1.00 eq) Et$_3$N (0.14 mL, 1.02 mmol, 3.00 eq), 1-[Bis (dimethyl amino)methylene]-1H-1,2,3-triazolo[4,5-b] pyridinium 3-oxidhexafluorophosphate (265.66 mg, 0.68 mmol, 2.00 eq) and C-(4,4-Difluoro-cyclohexyl)-methylamine hydrochloride (75.49 mg, 0.41 mmol, 1.20 eq) in dry DMF (5 mL, 50 V) to afford 4-Chloro-1-(tetrahydro-furan-3-ylmethyl)-1H-pyrrolo[2,3-b]pyridine-3-carboxylic acid (4,4-difluoro-cyclohexylmethyl)-amide (50 mg, 0.12 mmol, 34.8%) as a white solid.

$^1$H NMR (400 MHz, DMSO-d$_6$): δ 8.24 (d, J=5.12 Hz, 1H), 8.20 (t, J=5.80 Hz, 1H), 8.03 (s, 1H), 7.28 (d, J=5.12 Hz, 1H), 4.27 (d, J=7.60 Hz, 2H), 3.81-3.77 (m, 1H), 3.65-3.59 (m, 2H), 3.51-3.48 (m, 1H), 3.15 (t, J=6.32 Hz, 2H), 2.83-2.81 (m, 1H), 2.03-2.00 (m, 2H), 1.90-1.81 (m, 4H), 1.74-1.61 (m, 3H), 1.25-1.22 (m, 2H) ppm; [M+H]+ 412.0; LC-MS Purity (220 nm): 97.1%; t$_R$=4.00 min; HPLC Purity (254 nm): 97.8%; t$_R$=3.97 min.

Example 211: Preparation of 4-chloro-N-((4,4-difluoro-1-hydroxycyclohexyl)methyl)-1-((tetrahydrofuran-3-yl) methyl)-1H-pyrrolo[2,3-b]pyridine-3-carboxamide (225)

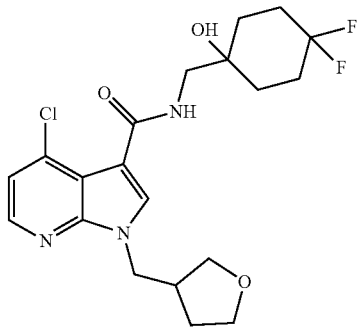 [SMILES: O=C(NCC1(O)CCC(F)(F)CC1)c1cn(CC2CCOC2)c2nccc(Cl)c12]

The title compound was synthesized according to the procedure described in Example 33 using 4-Chloro-1H-pyrrolo[2,3-b]pyridine-3-carboxylic acid (4,4-difluoro-1-hydroxy-cyclohexylmethyl)-amide (50.00 mg; 0.15 mmol; 1.00 eq.), (tetrahydrofuran-3-yl)methanol (22.28 mg; 0.22 mmol; 1.50 eq.) and (Tributyl-lambda5-phosphanylidene)-acetonitrile (105.32 mg; 0.44 mmol; 3.00 eq.) in Toluene (3 mL).

$^1$H NMR (400 MHz, DMSO-d$_6$) δ ppm 8.26 (1H), 8.11 (s, 1H), 7.31 (1H), 4.74 (1H), 3.83 (1H), 3.65 (1H), 3.53 (1H), 2.85 (1H), 2.02-1.86 (m, 3H), 1.65 (3H). m/z: 428 [M+H]

Example 212: (R)-4-chloro-N-((4,4-difluoro-1-hydroxycyclohexyl)methyl)-1-((tetrahydrofuran-3-yl) methyl)-1H-pyrrolo[2,3-b]pyridine-3-carboxamide (215)

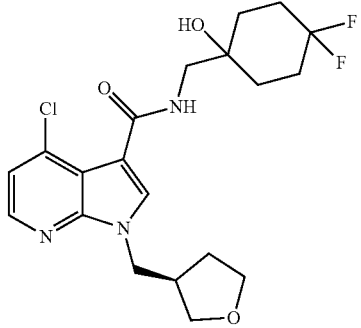 [SMILES: O=C(NCC1(O)CCC(F)(F)CC1)c1cn(C[C@H]2CCOC2)c2nccc(Cl)c12]

The title compound was separated through the chiral column from racemic 4-chloro-N-((4,4-difluoro-1-hydroxycyclohexyl)methyl)-1-((tetrahydrofuran-3-yl)methyl)-1H-pyrrolo[2,3-b]pyridine-3-carboxamide. Moblie Phase: Hexane:EtOH:DEA=70:30:0.1; Flow Rate: 1.0 mL/min; Runtime: 25 min; Column: CHIRALPAK AY-H (250×4.6 mm, 5 am).

$^1$H NMR (400 MHz, DMSO-$d_6$) δ 8.26 (1H), 8.11 (s, 1H), 7.31 (1H), 4.74 (1H), 3.83 (1H), 3.65 (1H), 3.53 (1H), 2.85 (1H), 2.02-1.86 (m, 3H), 1.65 (3H). m/z: 428 [M+H].

Example 213: (S)-4-chloro-N-((4,4-difluoro-1-hydroxycyclohexyl)methyl)-1-((tetra hydrofuran-3-yl)methyl)-1H-pyrrolo[2,3-b]pyridine-3-carboxamide (216)

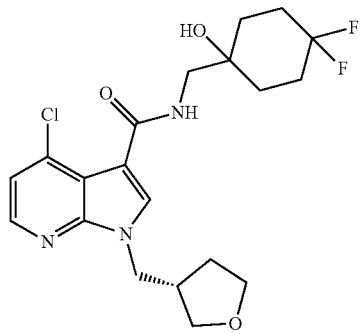 [SMILES: O=C(NCC1(O)CCC(F)(F)CC1)c1cn(C[C@@H]2CCOC2)c2nccc(Cl)c12]

The title compound was separated through the chiral column from racemic 4-chloro-N-((4,4-difluoro-1-hydroxycyclohexyl)methyl)-1-((tetrahydrofuran-3-yl)methyl)-1H-pyrrolo[2,3-b]pyridine-3-carboxamide. (Separation: see Example 212).

$^1$H NMR (400 MHz, DMSO-$d_6$) δ ppm 8.26 (1H), 8.11 (s, 1H), 7.31 (1H), 4.74 (1H), 3.83 (1H), 3.65 (1H), 3.53 (1H), 2.85 (1H), 2.02-1.86 (m, 3H), 1.65 (3H). m/z: 428 [M+H]

Example 214: Preparation of 4-Chloro-1-(tetrahydro-furan-3-ylmethyl)-1H-pyrrolo [2,3-b]pyridine-3-carboxylic acid ((1S,3S)-1-hydroxy-3-methyl-cyclohexylmethyl)-amide (219)

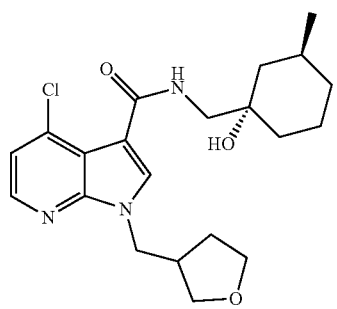 [SMILES: C[C@H]1CCC[C@@](O)(CNC(=O)c2cn(CC3CCOC3)c3nccc(Cl)c23)C1]

The title compound was synthesized according to the procedure described in Example 2 using a mixture of 4-Chloro-1-(tetrahydro-furan-3-ylmethyl)-1H-pyrrolo[2,3-b]pyridine-3-carboxylic acid (75 mg, 0.25 mmol, 1.00 eq), (1S,3S)-1-Aminomethyl-3-methyl-cyclohexanol (55.96 mg, 0.38 mmol, 1.50 eq), Benzotriazol-1-ol (62.05 mg, 0.38 mmol, 1.50 eq) and (3-Dimethylamino-propyl)-ethylcarbodiimide hydrochloride (73.80 mg, 0.38 mmol, 1.50 eq) in dry THF (5 mL, 66.67 V) to get 4-Chloro-1-(tetrahydrofuran-3-ylmethyl)-1H-pyrrolo [2,3-b]pyridine-3-carboxylic acid ((1S,3S)-1-hydroxy-3-methyl-cyclohexylmethyl)-amide (30 mg, 0.07 mmol, 29.0%) as a off-white solid.

$^1$H NMR (400 MHz, DMSO-$d_6$): δ 8.25 (d, J=5.12 Hz, 1H), 8.10 (s, 1H), 7.93 (t, J=5.92 Hz, 1H), 7.28 (d, J=5.12 Hz, 1H), 4.27 (d, J=7.60 Hz, 2H), 4.23 (s, 1H), 3.81-3.77 (m, 1H), 3.65-3.59 (m, 2H), 3.52-3.49 (m, 1H), 3.19 (d, J=6.12 Hz, 2H), 2.83-2.80 (m, 1H), 1.89-1.86 (m, 1H), 1.66-1.61 (m, 1H), 1.60-1.50 (m, 5H), 1.46-1.43 (m, 1H), 1.23-1.20 (m, 1H), 0.97-0.91 (m, 1H), 0.82 (d, J=6.60 Hz, 3H), 0.76-0.73 (m, 1H) ppm; [M+H]+ 406.2; LC-MS Purity (220 nm): 99.7%; $t_R$=3.75 min; HPLC Purity (254 nm): 99.4%; $t_R$=3.73 min.

Example 215: Preparation of 4-Chloro-1-(tetrahydro-furan-3-ylmethyl)-1H-pyrrolo [2,3-b]pyridine-3-carboxylic acid ((1R,3R)-1-hydroxy-3-methyl-cyclohexylmethyl)-amide (217)

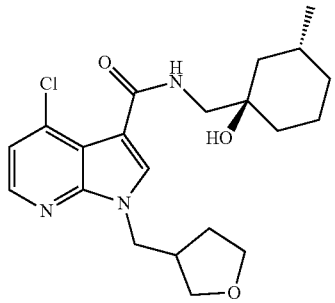 [SMILES: C[C@@H]1CCC[C@](O)(CNC(=O)c2cn(CC3CCOC3)c3nccc(Cl)c23)C1]

The title compound was synthesized according to the procedure described in Example 2 using 4-Chloro-1-(tetrahydro-furan-3-ylmethyl)-1H-pyrrolo[2,3-b] pyridine-3-carboxylic acid (75 mg, 0.25 mmol, 1.00 eq), (1R,3R)-1-Aminomethyl-3-methyl-cyclohexanol (55.17 mg, 0.38 mmol, 1.50 eq), Benzotriazol-1-ol (62.05 mg, 0.38 mmol, 1.50 eq) and (3-Dimethylamino-propyl)-ethyl carbodiimide hydrochloride (73.80 mg, 0.38 mmol, 1.50 eq) in dry THF (5 mL, 66.67 V) to provide 4-Chloro-1-(tetrahydro-furan-3-ylmethyl)-1H-pyrrolo [2,3-b]pyridine-3-carboxylic acid ((1R,3R)-1-hydroxy-3-methyl-cyclohexylmethyl)-amide (30 mg, 0.07 mmol, 29.0%) as a off-white solid.

$^1$H NMR (400 MHz, DMSO-$d_6$): δ 8.25 (d, J=5.12 Hz, 1H), 8.10 (s, 1H), 7.93 (t, J=6.04 Hz, 1H), 7.28 (d, J=5.12 Hz, 1H), 4.27 (d, J=7.56 Hz, 2H), 4.23 (s, 1H), 3.81-3.77 (m, 1H), 3.65-3.59 (m, 2H), 3.52-3.49 (m, 1H), 3.19 (d, J=6.12 Hz, 2H), 2.83-2.80 (m, 1H), 1.90-1.86 (m, 1H), 1.64-1.63 (m, 1H), 1.61-1.50 (m, 5H), 1.46-1.43 (m, 1H), 1.23-1.20 (m, 1H), 0.97-0.91 (m, 1H), 0.82 (d, J=6.60 Hz, 3H), 0.76-0.73 (m, 1H), ppm; [M+H]+ 406.2; LC-MS Purity (220 nm): 99.7%; $t_R$=3.75 min; HPLC Purity (254 nm): 99.4%; $t_R$=3.72 min.

Example 216: Preparation of N-((4,4-difluorocyclohexyl) methyl)-1-(2-hydroxyethyl)-4-(trifluoromethyl)-1H-indole-3-carboxamide (198)

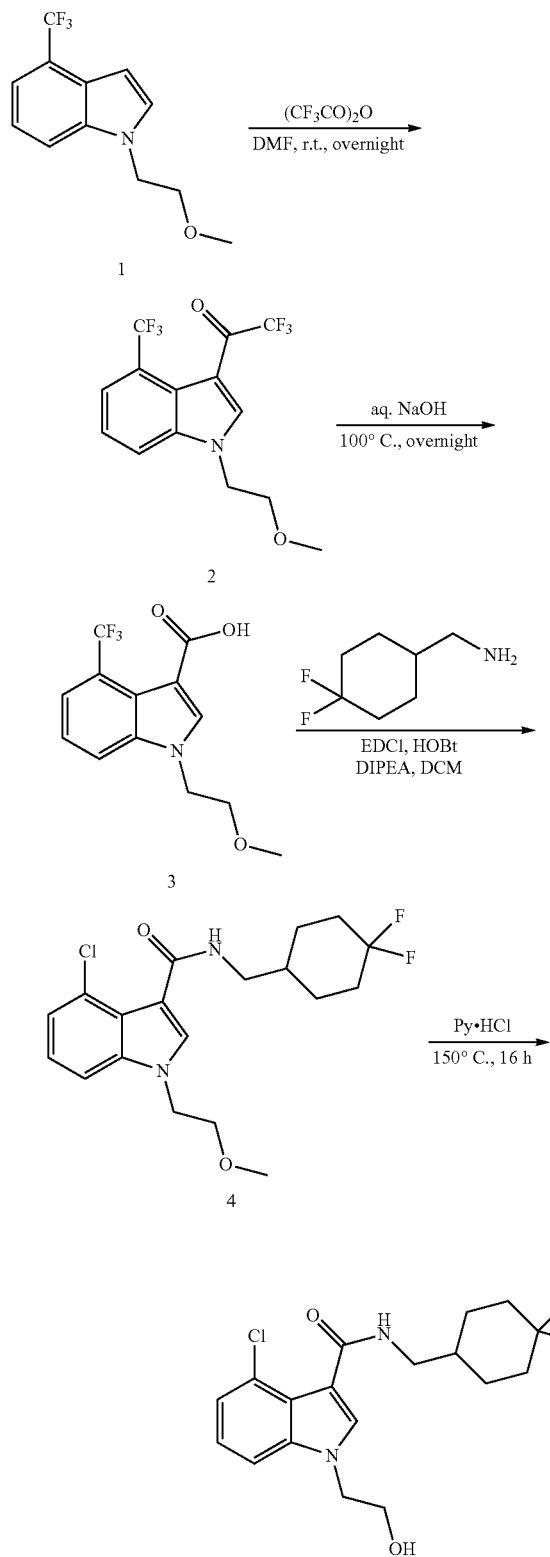

Step 1: Preparation of 2,2,2-trifluoro-1-(1-(2-methoxyethyl)-4-(trifluoromethyl)-1H-indol-3-yl)ethanone

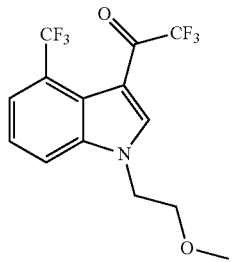 [SMILES: COCCn1cc(C(=O)C(F)(F)F)c2c(C(F)(F)F)cccc21]

To a solution of 1-(2-methoxyethyl)-4-(trifluoromethyl)-1H-indole (0.800 g, 3.3 mmol) in DMF (10.0 mL) was added TFAA (2.1 g, 10 mmol) at room temperature. After stirred at room temperature for 16 h, the reaction mixture was quenched with aqueous $NaHCO_3$, extracted with DCM. The separated organic layer was dried over $MgSO_4$, filtered and concentrated in vacuo to give 2,2,2-trifluoro-1-(1-(2-methoxyethyl)-4-(trifluoromethyl)-1H-indol-3-yl)ethanone (0.90 g, 81%) as a yellow oil.

Step 2: Preparation of 1-(2-methoxyethyl)-4-(trifluoromethyl)-1H-indole-3-carboxylic acid

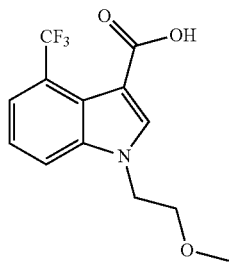 [SMILES: COCCn1cc(C(=O)O)c2c(C(F)(F)F)cccc21]

To a solution of 2,2,2-trifluoro-1-(1-(2-methoxyethyl)-4-(trifluoromethyl)-1H-indol-3-yl)ethanone (0.9 g, 2.65 mmol) in EtOH (5.0 mL) was added 15% aqueous NaOH (4.0 mL) at room temperature. The reaction mixture was stirred at 80° C. for 16 h and then cooled to room temperature. The mixture was washed with ether (25 mL×2) and discarded, and the aqueous layer was adjusted to pH 3 with 4 N HCl, extracted with EtOAc. The separated organic layer was dried over $MgSO_4$, filtered and concentrated in vacuo to give the product 1-(2-methoxyethyl)-4-(trifluoromethyl)-1H-indole-3-carboxylic acid (750 mg, 97%), which was used in the next reaction without further purification.

Step 3: Preparation of N-((4,4-difluorocyclohexyl)methyl)-1-(2-methoxyethyl)-4-(trifluoromethyl)-1H-indole-3-carboxamide (MSC2495502, FR-210)

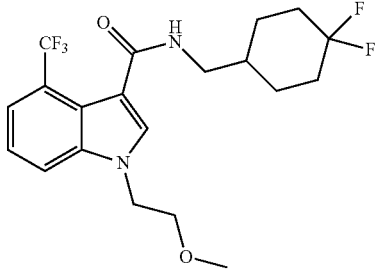 [SMILES: COCCn1cc(C(=O)NCC2CCC(F)(F)CC2)c2c(C(F)(F)F)cccc21]

A mixture of 1-(2-methoxyethyl)-4-(trifluoromethyl)-1H-indole-3-carboxylic acid (0.100 g, 0.35 mmol), (4,4-difluorocyclohexyl)methanamine (0.060 g, 0.4 mmol), HOBt (0.100 g, 0.8 mmol), EDCI (0.140 g, 0.8 mmol) and Et$_3$N (0.100 g, 1.2 mmol) in DMF (3.0 mL) was stirred at room temperature overnight, and then diluted with EtOAc (20 mL). The organic layer was washed with brine (10 mL), dried over MgSO$_4$, filtered and concentrated in vacuo. The residue was purified by prep-TLC (PE:EA=1:1) to give N-((4,4-difluorocyclohexyl)methyl)-1-(2-methoxyethyl)-4-(trifluoromethyl)-1H-indole-3-carboxamide (0.030 g, 20%) as a white solid.

$^1$H NMR (500 MHz, DMSO-d6) δ 8.14 (d, J=5.5 Hz, 1H), 7.89 (d, J=8.0 Hz, 1H), 7.78 (s, 1H), 7.48 (d, J=7.5 Hz, 1H), 7.35 (t, J=8.0 Hz, 1H), 4.45-4.43 (m, 2H), 3.70-3.30 (m, 2H), 3.14 (s, 3H), 3.12-3.11 (m, 2H), 2.06-2.00 (m, 2H), 1.84-1.69 (m, 5H), 1.27-1.18 (m, 2H) ppm; [M+H]+ 418.9.

Step 4: Preparation of N-((4,4-difluorocyclohexyl)methyl)-1-(2-hydroxyethyl)-4-(trifluoromethyl)-1H-indole-3-carboxamide

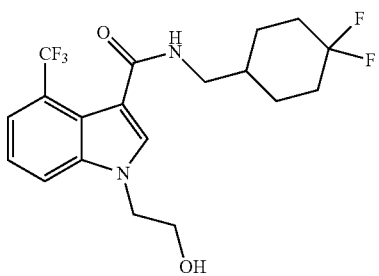 [SMILES: O=C(NCC1CCC(F)(F)CC1)c1cn(CCO)c2cccc(C(F)(F)F)c12]

A mixture of N-((4,4-difluorocyclohexyl)methyl)-1-(2-methoxyethyl)-4-(trifluoromethyl)-1H-indole-3-carboxamide (0.120 g, 0.29 mmol) and pyridine hydrochloride (0.165 g, 1.43 mmol) was stirred at 150° C. for 16 h. After cooled to room temperature, the reaction was quenched with NaHCO$_3$ and extracted with EtOAc. The separated organic layer was dried over MgSO$_4$, filtered and concentrated in vacuo. The residue was purified by prep.-HPLC to give N-((4,4-difluorocyclohexyl)methyl)-1-(2-hydroxyethyl)-4-(trifluoromethyl)-1H-indole-3-carboxamide (0.035 g, 30%) as a white solid.

$^1$H NMR (500 MHz, DMSO-d6) δ 8.11 (d, J=5.0 Hz, 1H), 7.87 (d, J=8.5 Hz, 1H), 7.79 (s, 1H), 7.48 (d, J=8.0 Hz, 1H), 7.34 (t, J=8.0 Hz, 1H), 4.96-4.94 (m, 1H), 4.32-4.30 (m, 2H), 3.75-3.73 (m, 2H), 3.14-3.11 (m, 2H), 2.03-2.00 (m, 2H), 1.84-1.69 (m, 5H), 1.27-1.18 (m, 2H) ppm; [M+Na]+ 427.1.

Example 217

IL-1β Release Assay:

The activation of P2X7 by ATP leads to a fast transient activation of cells resulting in influx of Ca$^{2+}$ followed by conversion of pro-IL-1β to active IL-1β. The functional activity of P2X7 compounds was measured by the release of mature IL-1β in the culture medium of THP-1 cells, detected by sandwich ELISA. Cells were maintained in complete growth medium (RPMI 1640+10% HI-FCS+2 mM L-glutamine+1×PS). Every 3 days, the medium was renewed by diluting the cells 1/3 to 1/4 as cell density did not exceed 0.5 million cells per ml (seeding cell density @ 1×10$^5$/ml). THP-1 cells were harvested from the flask in 50 ml by centrifugation for 3 min at 100 g. The cells were resuspended to 2×10$^5$ cells/ml in medium supplemented with 0.5 μM PMA and incubated. The cells were washed and resuspended to 1.5×10$^5$ cells/ml in medium complemented with 10 ng/ml LPS, and the cells were primed for 4 h at 37° C., 5% CO$_2$. After addition of 20 μL of prediluted test compounds, blank, standard and control reagents, cells were incubated for a further 20 min at 37° C. and stimulated with 0.8 mM BzATP for 30 minutes. The cells were centrifuged, supernatant was collected and the presence of mature IL-1β was detected using Dual human IL-1b kit following manufacturer's instruction. The tetrahydrobenzodiazepine analogs effectively modulated the activity of P2X7 in the cells as measured by the levels of pro-inflammatory cytokine IL-1β, which is released by the activation of P2X7 receptor.

Pore Permeation Assay

Agonist-induced pore formation was determined by measuring cellular uptake of YO PRO fluorescence dye in HEK293 transfected with human P2X7 receptor. A HEK293 cell over expressing human P2X7 was harvested using HQTase reagent to detach the cells from T75 cm flask. The harvested cells are centrifuged @ 1200 rpm for 5 min at room temperature. The viability of cells was determined by Trypan blue dye and the cells are plated @ 10,000 cell/well in 50 ul volume in a 384W BD Poly lysine coated plate and incubated overnight at 37 C. After overnight incubation, the culture medium was replaced with 35 ul/well assay buffer (5 mM KCl, 0.1 mM CaCl2, 5 mM Glucose, 10 mM HEPES buffer pH7.4 containing 125 mM NaCl. The serial dilution of compounds was performed using Bravo liquid handling instrument and the compounds were added using Bravo to the cell assay plate starting at 2.5 uM with three dilutions for 10 points. The positive control inhibitor compound was added to column 23. The plate was shaken slowly on a plate shaker for 10 seconds. The cells were incubated with the compound for 20 minutes at room temperature. After the incubation period, YO PRO dye (1 uM) along with BzATP (10 uM) were added to cells at 10 ul/well. The plate was centrifuged at 1000 rpm for 5 seconds and incubated at room temperature for 30 minutes. The uptake of YO PRO dye into the cells was measured using Envision Fluorescence plate reader instrument (Perkin Elmer).

The data is interpreted according to the following:

| Compound number | hP2X7 IC50 | hTHP-1/IL-ib IC50 |
|---|---|---|
| 1 | C | E |
| 2 | B | B |
| 3 | B | C |
| 4 | B | C |
| 5 | B | C |
| 6 | C | B |
| 7 | A | B |
| 8 | B | C |
| 9 | A | C |
| 10 | B | C |
| 11 | B | |
| 12 | C | D |
| 13 | B | B |
| 14 | B | |
| 15 | B | |
| 16 | D | |
| 17 | B | C |
| 18 | E | E |
| 19 | B | C |
| 20 | B | C |
| 21 | A | B |
| 22 | C | E |
| 23 | E | |
| 24 | D | |
| 25 | D | |
| 26 | E | |
| 27 | E | |
| 28 | E | |
| 29 | C | |
| 30 | B | C |
| 31 | E | |
| 32 | C | D |
| 33 | C | E |
| 34 | C | C |
| 35 | C | C |
| 36 | C | E |
| 37 | B | B |
| 38 | B | C |
| 39 | B | C |
| 40 | B | B |
| 41 | B | A |
| 42 | E | |
| 43 | E | |
| 44 | B | C |
| 45 | E | E |
| 46 | C | |
| 47 | E | |
| 48 | C | C |
| 49 | D | |
| 50 | C | |
| 51 | B | A |
| 52 | D | |
| 53 | B | C |
| 54 | C | |
| 55 | C | |
| 56 | B | C |
| 57 | C | |
| 58 | B | C |
| 59 | B | B |
| 60 | E | |
| 61 | D | |
| 62 | B | B |
| 63 | E | |
| 64 | B | B |
| 65 | B | C |
| 66 | B | C |
| 67 | B | B |
| 68 | A | B |
| 69 | B | C |
| 70 | B | C |
| 71 | E | |
| 72 | D | E |
| 73 | C | D |
| 74 | E | E |
| 75 | A | B |
| 76 | E | |
| 77 | E | |
| 78 | E | |
| 81 | C | D |
| 82 | A | C |
| 83 | A | B |
| 84 | C | C |
| 85 | B | B |
| 86 | B | B |
| 87 | C | E |
| 88 | C | E |
| 89 | C | D |
| 90 | A | B |
| 91 | B | C |
| 92 | B | C |
| 93 | A | B |
| 94 | B | B |
| 95 | B | C |
| 97 | C | |
| 98 | C | C |
| 99 | C | |
| 100 | E | E |
| 101 | C | D |
| 102 | E | |
| 103 | C | |
| 104 | C | |
| 105 | B | C |
| 106 | D | C |
| 107 | B | C |
| 108 | B | C |
| 109 | C | D |
| 110 | C | |
| 111 | E | |
| 112 | B | C |
| 113 | B | B |
| 114 | B | C |
| 115 | C | C |
| 116 | B | B |
| 117 | B | C |
| 118 | D | B |
| 119 | C | C |
| 120 | B | B |
| 121 | B | B |
| 122 | B | B |
| 123 | C | C |
| 124 | B | B |
| 125 | B | B |
| 126 | B | B |
| 127 | B | D |
| 128 | C | C |
| 129 | C | D |
| 130 | B | B |
| 131 | B | B |
| 132 | B | B |
| 133 | B | B |
| 134 | B | C |
| 135 | B | B |
| 136 | E | |
| 137 | C | E |
| 138 | C | C |
| 139 | B | B |
| 140 | B | B |
| 141 | B | B |
| 142 | B | C |
| 143 | B | C |
| 144 | B | C |
| 146 | B | B |
| 147 | B | B |
| 148 | B | B |
| 149 | B | C |
| 150 | B | B |
| 151 | B | B |
| 152 | B | D |
| 153 | A | B |
| 154 | B | B |
| 155 | B | A |

-continued

| Compound number | hP2X7 IC50 | hTHP-1/IL-ib IC50 |
|---|---|---|
| 156 | B | A |
| 157 | B | A |
| 158 | A | A |
| 159 | B | C |
| 160 | C | C |
| 162 | B | B |
| 163 | A | B |
| 164 | C | B |
| 166 | B | B |
| 167 | B | B |
| 168 | B | C |
| 169 | B | B |
| 170 | B | B |
| 171 | C | D |
| 172 | D | |
| 173 | A | A |
| 174 | B | B |
| 175 | C | C |
| 176 | E | E |
| 177 | C | C |
| 178 | B | B |
| 179 | C | C |
| 180 | C | D |
| 181 | C | C |
| 182 | B | B |
| 183 | B | B |
| 184 | C | C |
| 185 | B | B |
| 186 | E | E |
| 187 | B | C |
| 188 | B | B |
| 189 | B | C |
| 190 | C | C |
| 191 | C | E |
| 192 | C | |
| 193 | B | B |
| 194 | | |
| 195 | B | C |
| 196 | B | C |
| 197 | B | B |
| 198 | C | B |
| 199 | C | C |
| 200 | A | B |
| 203 | B | C |
| 205 | A | B |
| 207 | B | C |
| 208 | A | B |

E >1 µM;
D 500-999 nM;
C 101-500 nM;
B 10-100 nM;
A <10 nM.

Example 218. Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

The invention claimed is:
1. A compound of formula III, IV, V or IV:

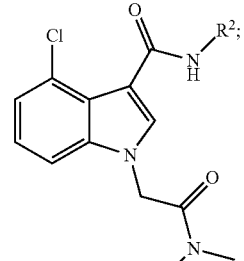

III

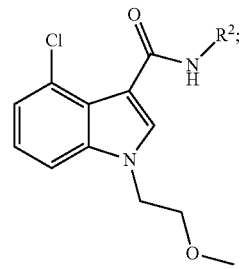

IV

281
-continued
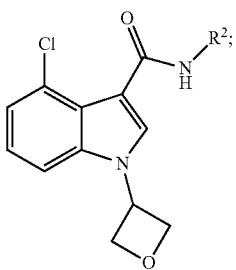
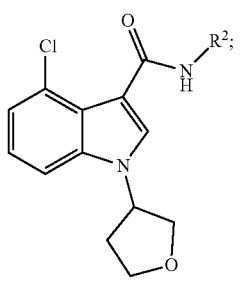
or a pharmaceutically acceptable salt thereof, wherein:
R² is
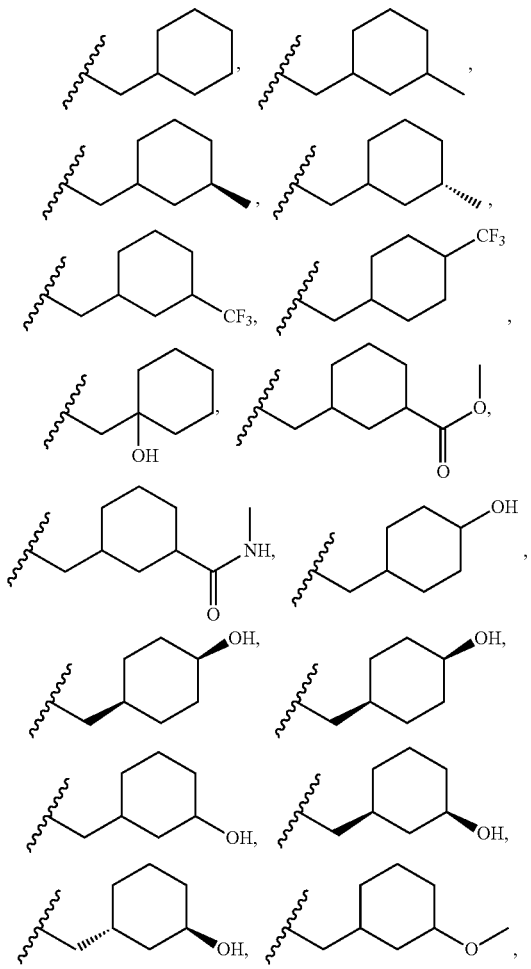
282
-continued
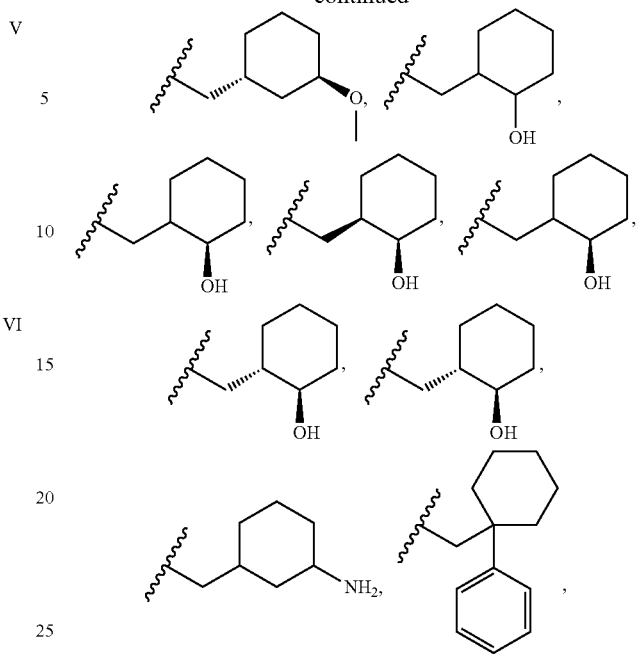
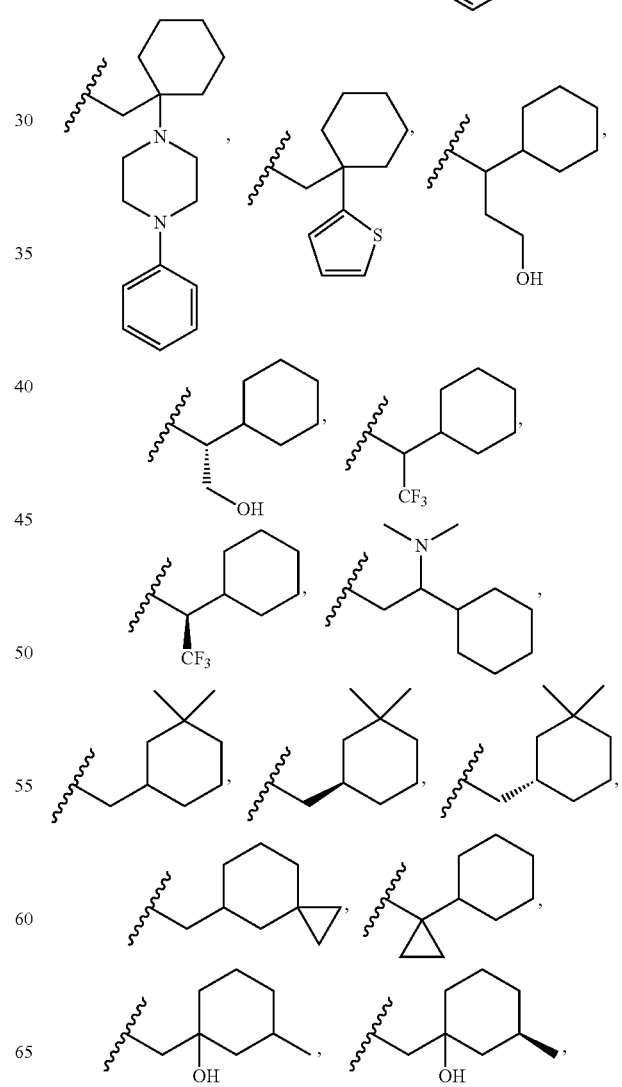

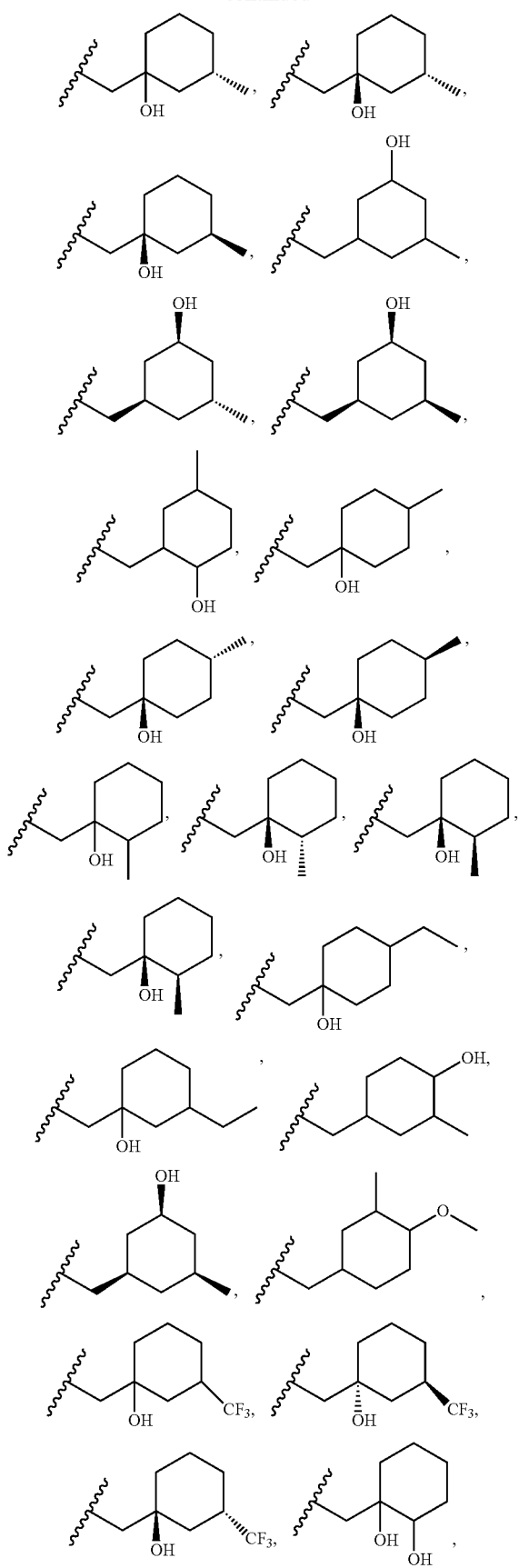
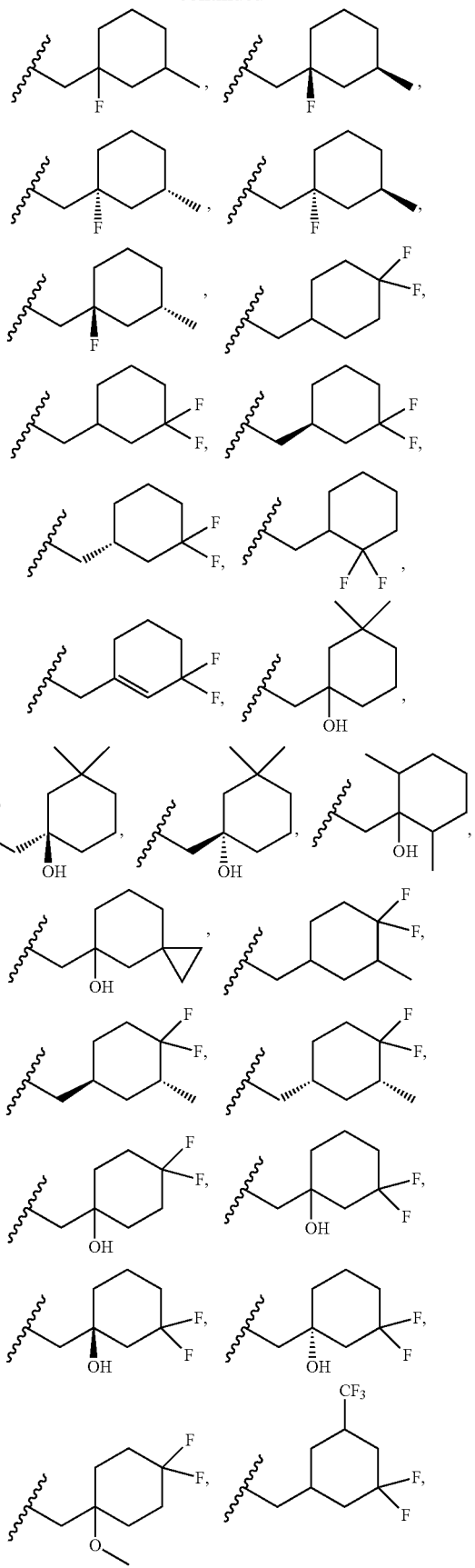

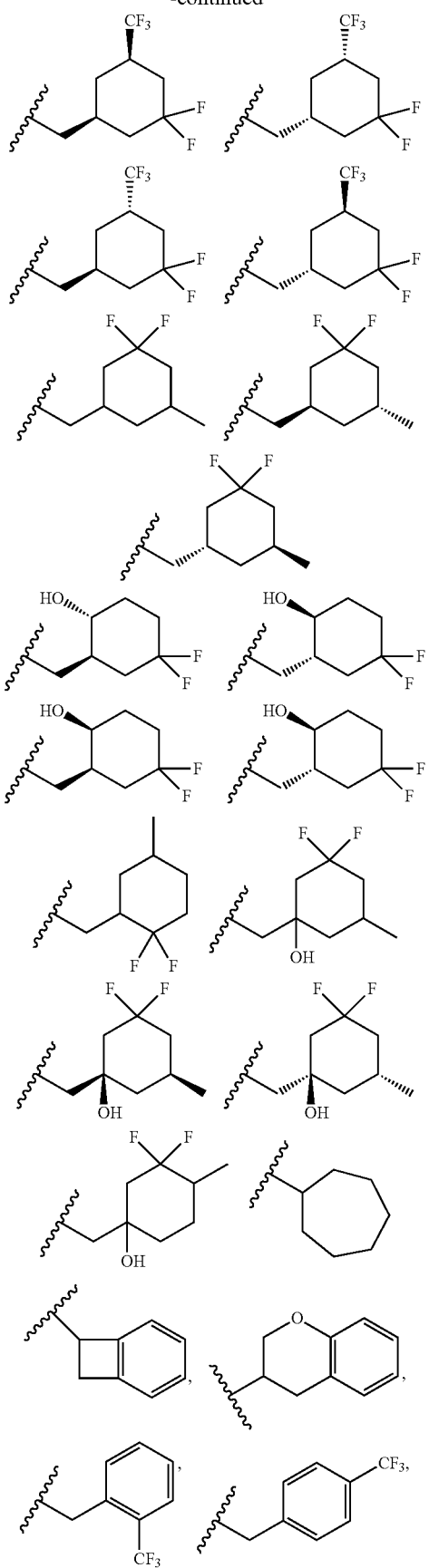
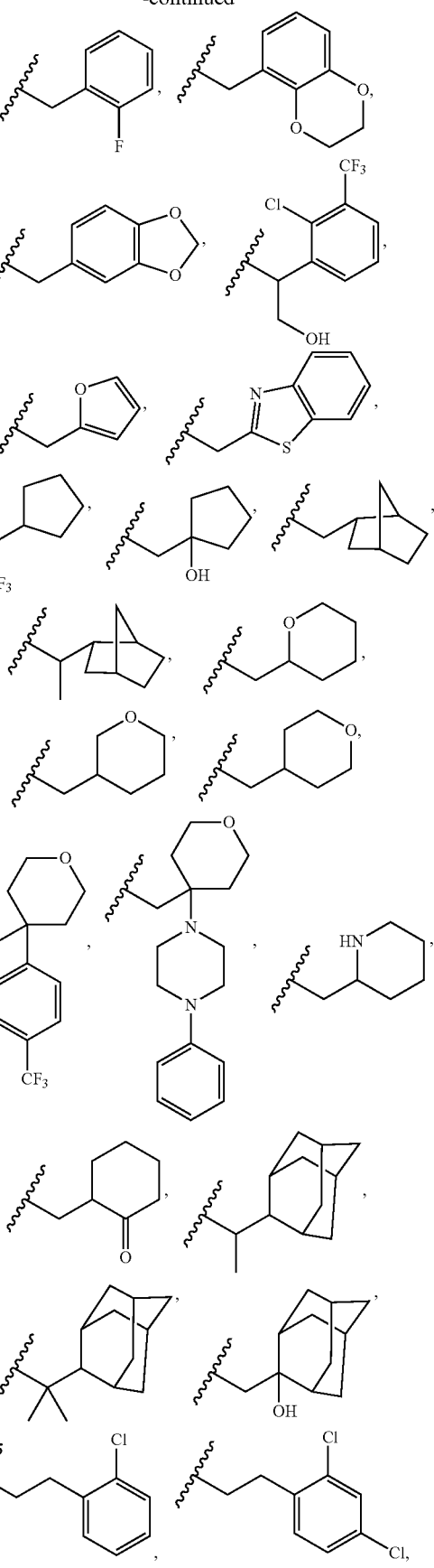

287
-continued

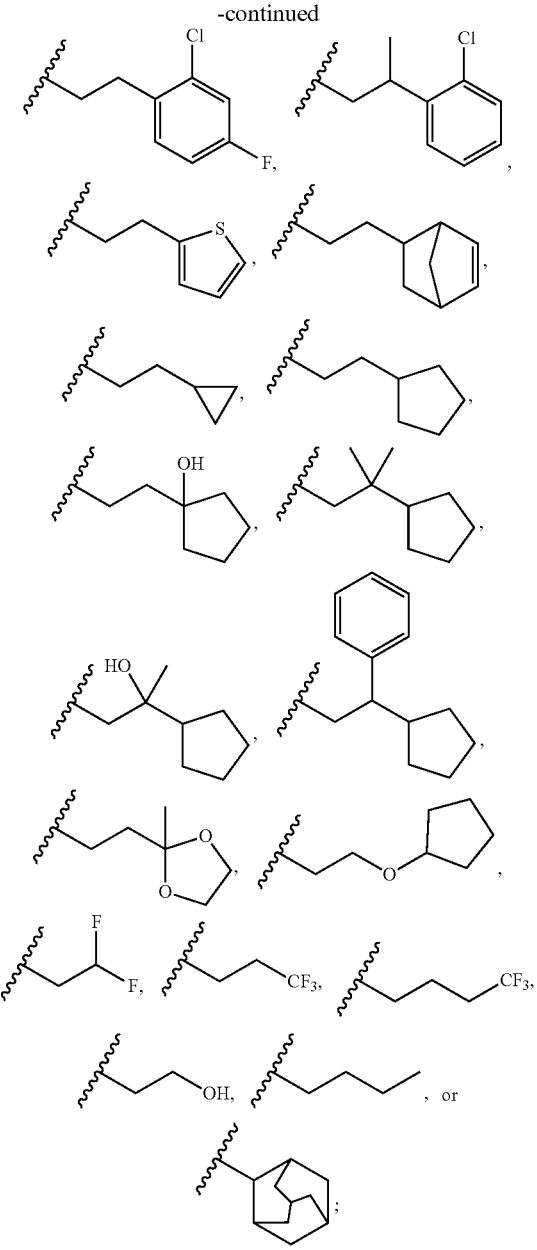

and provided that, if the compound is of formula III, R² is not

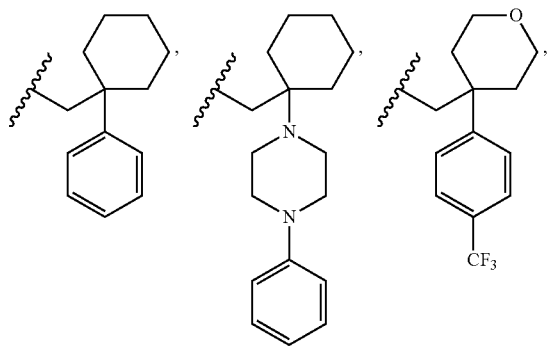

288
-continued

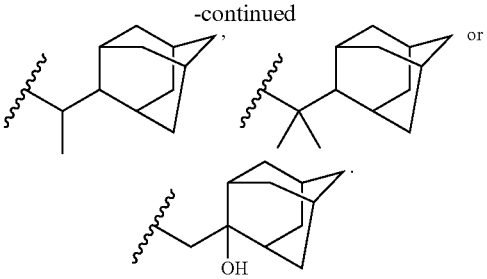

2. The compound of claim 1, which is a compound formula III or a pharmaceutically acceptable salt thereof.

3. The compound of claim 1, which is a compound formula IV or a pharmaceutically acceptable salt thereof.

4. The compound of claim 1, which is a compound formula V or a pharmaceutically acceptable salt thereof.

5. The compound of claim 1, which is a compound formula VI or a pharmaceutically acceptable salt thereof.

6. A pharmaceutical composition comprising a compound of claim 1, and a pharmaceutically acceptable adjuvant, carrier or vehicle.

7. A method for modulating P2X7 activity in a subject or in a biological sample, comprising the step of administering to said subject or contacting said biological sample with a compound of claim 1 or a physiologically acceptable salt thereof.

8. A method for treating a P2X7-mediated disease or disorder in a subject having the disease or disorder, comprising the step of administering to said subject a compound of claim 1.

9. A method for treating a P2X7-mediated disease or disorder, which disease or disorder is: Parkinson's disease; multiple sclerosis (MS); Alzheimer's disease; traumatic brain injury; encephalitis; depression mania; bipolar disease; anxiety; schizophrenia; an eating disorder; a sleep disorder; a cognition disorder; epilepsy; seizure disorder; urinary incontinence; urinary hesitancy; rectal hypersensitivity; fecal incontinence; benign prostatic hypertrophy; inflammatory bowel disease; allergic rhinitis; asthma; reactive airway disease; chronic obstructive pulmonary disease; rheumatoid arthritis; osteoarthritis; myocardial infarction; uveitis; atherosclerosis; or psoriasis; in a subject having the disease or disorder, comprising the step of administering to said subject a compound of claim 1.

10. A method for treating multiple sclerosis in a subject, comprising the step of administering to said subject a compound of claim 1 or a physiologically acceptable salt thereof.

11. A process for manufacturing a compound of claim 1, comprising the steps of:
reacting a compound of formula A:

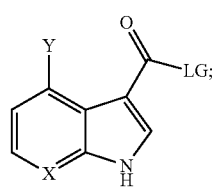

A wherein X is CH and Y is Cl; and wherein LG is group that is able to be displaced;

with a compound of formula LG-R[1];
wherein IV is a group bonded to the nitrogen of the indole ring as in one of formulae III, IV, V or VI;
to yield a compound of formula B:
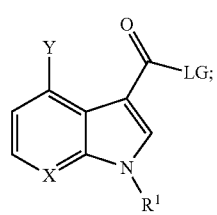
B
and reacting a compound of formula B with a compound of formula $NH_2$—$R^2$;
wherein $R^2$ is as defined in claim 1 to provide the compound.
* * * * *